(12) United States Patent
Dubrow et al.

(10) Patent No.: US 7,579,077 B2
(45) Date of Patent: Aug. 25, 2009

(54) NANOFIBER SURFACES FOR USE IN ENHANCED SURFACE AREA APPLICATIONS

(75) Inventors: Robert Dubrow, San Carlos, CA (US);
Robert Hugh Daniels, Mountain View, CA (US)

(73) Assignee: Nanosys, Inc., Palo Alto, CA (US)

(*) Notice: Subject to any disclaimer, the term of this patent is extended or adjusted under 35 U.S.C. 154(b) by 574 days.

(21) Appl. No.: 10/840,794

(22) Filed: May 5, 2004

(65) Prior Publication Data

US 2006/0159916 A1    Jul. 20, 2006

Related U.S. Application Data

(63) Continuation-in-part of application No. 10/792,402, filed on Mar. 2, 2004.

(60) Provisional application No. 60/468,390, filed on May 6, 2003, provisional application No. 60/468,606, filed on May 5, 2003.

(51) Int. Cl.
*A61F 2/00* (2006.01)
*A61L 15/16* (2006.01)

(52) U.S. Cl. .............. 428/357; 428/364; 428/365; 428/373; 424/422; 424/423; 424/443; 424/444; 977/762; 977/764; 977/773; 977/813; 977/904

(58) Field of Classification Search ......... 424/9.1–9.81, 424/422–437, 443–449; 428/357, 364, 365, 428/373; 977/762, 764, 773, 813–826, 904
See application file for complete search history.

(56) References Cited

U.S. PATENT DOCUMENTS

| 5,196,396 | A | 3/1993 | Lieber |
| 5,252,835 | A | 10/1993 | Lieber et al. |
| 5,840,435 | A | 11/1998 | Lieber et al. |
| 5,897,945 | A | 4/1999 | Lieber et al. |
| 5,976,957 | A | 11/1999 | Westwater et al. |
| 5,997,832 | A | 12/1999 | Lieber et al. |
| 6,036,774 | A | 3/2000 | Lieber et al. |
| 6,099,965 | A | 8/2000 | Tennent et al. |
| 6,106,913 | A | 8/2000 | Scardino et al. |
| 6,130,143 | A | 10/2000 | Westwater et al. |
| 6,159,488 | A * | 12/2000 | Nagler et al. .............. 424/423 |
| 6,159,742 | A | 12/2000 | Lieber et al. |
| 6,190,634 | B1 | 2/2001 | Lieber et al. |

(Continued)

FOREIGN PATENT DOCUMENTS

WO    WO-9918893    4/1999

(Continued)

OTHER PUBLICATIONS

Turner, S. et al., Cell Attachment on Silicon Nanostructures, Nov./Dec. 1997, J. Vac. Sci. Technol. B 15(6) pp. 2848-2854.*

(Continued)

*Primary Examiner*—D. Lawerence Tarazano
*Assistant Examiner*—Matthew D Matzek

(57) ABSTRACT

This invention provides novel nanofiber enhanced surface area substrates and structures comprising such substrates, as well as methods and uses for such substrates.

13 Claims, 68 Drawing Sheets
(31 of 68 Drawing Sheet(s) Filed in Color)

U.S. PATENT DOCUMENTS

| | | | |
|---|---|---|---|
| 6,207,229 | B1 | 3/2001 | Bawendi et al. |
| 6,265,333 | B1 | 7/2001 | Dzenis et al. |
| 6,268,041 | B1 | 7/2001 | Goldstein |
| 6,270,347 | B1 | 8/2001 | Webster et al. |
| 6,274,159 | B1* | 8/2001 | Marotta et al. ............... 424/426 |
| 6,280,390 | B1 | 8/2001 | Akselrod et al. |
| 6,288,390 | B1 | 9/2001 | Siuzdak et al. |
| 6,313,015 | B1 | 11/2001 | Lee et al. |
| 6,322,895 | B1 | 11/2001 | Canham |
| 6,359,288 | B1 | 3/2002 | Ying et al. |
| 6,361,861 | B2 | 3/2002 | Gao et al. |
| 6,362,011 | B1 | 3/2002 | Massey et al. |
| 6,399,177 | B1 | 6/2002 | Fonash et al. |
| 6,666,214 | B2 | 12/2003 | Canham |
| 6,670,179 | B1 | 12/2003 | Mattson et al. |
| 6,720,240 | B2 | 4/2004 | Gole et al. |
| 6,794,196 | B2 | 9/2004 | Fonash et al. |
| 6,811,957 | B1 | 11/2004 | Mau et al. |
| 7,074,294 | B2* | 7/2006 | Dubrow ....................... 156/276 |
| 2002/0037383 | A1 | 3/2002 | Spillman et al. |
| 2002/0049495 | A1 | 4/2002 | Kutryk et al. |
| 2002/0090725 | A1 | 7/2002 | Simpson et al. |
| 2002/0092423 | A1 | 7/2002 | Gillignham et al. |
| 2002/0117659 | A1* | 8/2002 | Lieber et al. .................. 257/14 |
| 2002/0130311 | A1 | 9/2002 | Lieber et al. |
| 2002/0167118 | A1 | 11/2002 | Billiet et al. |
| 2002/0172963 | A1* | 11/2002 | Kelley et al. ..................... 435/6 |
| 2003/0032892 | A1 | 2/2003 | Erlach et al. |
| 2003/0059742 | A1* | 3/2003 | Webster et al. ........... 433/201.1 |
| 2003/0065355 | A1 | 4/2003 | Weber |
| 2003/0089899 | A1 | 5/2003 | Lieber et al. |
| 2003/0093107 | A1 | 5/2003 | Parsonage et al. |
| 2003/0119920 | A1 | 6/2003 | Wang et al. |
| 2003/0189202 | A1* | 10/2003 | Li et al. ........................ 257/14 |
| 2003/0195611 | A1 | 10/2003 | Greenhalgh et al. |
| 2003/0229393 | A1 | 12/2003 | Kutryk et al. |
| 2004/0009598 | A1 | 1/2004 | Hench et al. |
| 2004/0018371 | A1 | 1/2004 | Mao |
| 2004/0023317 | A1 | 2/2004 | Motamedi et al. |
| 2004/0052867 | A1 | 3/2004 | Canham |
| 2004/0076681 | A1 | 4/2004 | Dennis et al. |
| 2004/0106203 | A1* | 6/2004 | Stasiak et al. .................. 436/49 |
| 2004/0115239 | A1 | 6/2004 | Shastri et al. |
| 2004/0258726 | A1* | 12/2004 | Stupp et al. .................. 424/423 |
| 2005/0038498 | A1 | 2/2005 | Dubrow et al. |
| 2005/0096509 | A1 | 5/2005 | Olson |

FOREIGN PATENT DOCUMENTS

| | | |
|---|---|---|
| WO | WO-9940812 | 8/1999 |
| WO | WO-0149776 | 7/2001 |
| WO | WO-03095190 | 11/2003 |
| WO | WO-03097702 | 11/2003 |
| WO | WO-03099951 | 12/2003 |
| WO | WO-03102099 | 12/2003 |
| WO | WO-2004094303 | 11/2004 |
| WO | WO-2005005679 | 1/2005 |

OTHER PUBLICATIONS

Autumn, K. et al., "Adhesive force of a single gecko foot-hair" Nature (2000) 405:681-685.
Chen, I.W. et al., "Sintering dense nanocrystalline ceramics without final-stage grain growth" Nature (2000) 404(6774):168-171.
Choi, H. et al., "Surface-modified silica colloid for diagnostic imaging" J. Colloid Interface Sci (2003) 258(2):435-437.
Cui et al., "Functional nanoscale electronic devices assembled using silicon nanowire building blocks" Science (2001) 291:851-853.
Cui et al., "Nanowire nanosensors for highly sensitive and selective detection of biological and chemical species" Science (2001) 293:1289-1292.
Davis, D.H. et al., "Immobilization of RGD to <111> silicon surfaces for enhanced cell adhesion and proliferation" Biomaterials (2002) 23:4019-4027.
Duan et al., "Single-nanowire electrically driven lasers" Nature (2003) 421:241-245.
Geim, A.K. et al., "Microfabricated adhesive mimicking gecko foot-hair" Nature Materials (2003) 2:461-463.
Greene, L.E. et al., "Low-Temperature Wafer-Scale Production of ZnO Nanowire Arrays" Angew. Chem. Int. Ed. (2003) 42:3031-3034.
Hanekamp C. et al., "Randomized comparison of balloon angioplasty versus silicon carbon-coated stent implantation for de novo lesions in small coronary arteries" Am. J. Cardiol. (2004) 93(10):1233-1237.
Huang, et al., "Integrated optoelectronics assembed from semiconductor nanowires" Abstracts of Papers of the ACS (2002) 224:U308.
Price, R.L. et al., "Nanometer surface roughness increases select osteoblast adhesion on carbon nanofiber compacts" J. Biomed. Mat. Res. (2004) 70A(1):129-138.
Shastri, V.P., "Non-degradable biocompatible polymers in medicine: past, present and future" Curr Pharm. Biotechnol. (2003) 4(5):331-337.
Silva, G.A. et al., "Selective differentiation of neural progenitor cells by high-epitope density nanfibers" Science (2004) 303:1352-1355.
Webster, T.J. et al., "Nano-biotechnology: carbon nanofibres as improved neural and orthopaedic implants" Nanotechnology (2004) 15:48-54.
Webster, T.J. et al., "Increased osteoblast adhesion on nanophase metals: Ti, Ti6A14V, and CoCrMo" Biomaterials (2004) 25:4731-4739.
Xu, H. et al., "Room-temperature preparation and characterization of poly(ethylene glycol)-coated silica nanoparticles for biomedical applications" J. Biomed. Mat. Res. (2003) 66A(4):870-879.
Xu, H. et al., "Strong and bioactive composites containing nano-silica-fused whiskers for bone repair" Biomaterials (2004) 25:4615-4626.
Zhou et al., "Silicon nanowires as chemical sensors" Chem. Phys. Lett. (2003) 369:220-224.

* cited by examiner

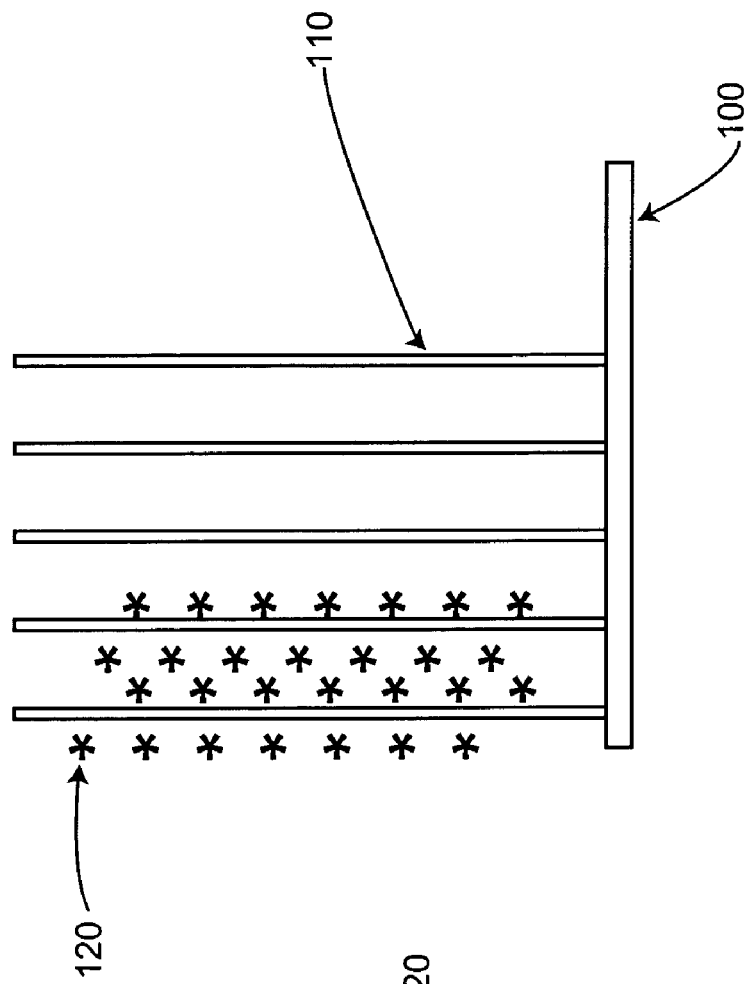
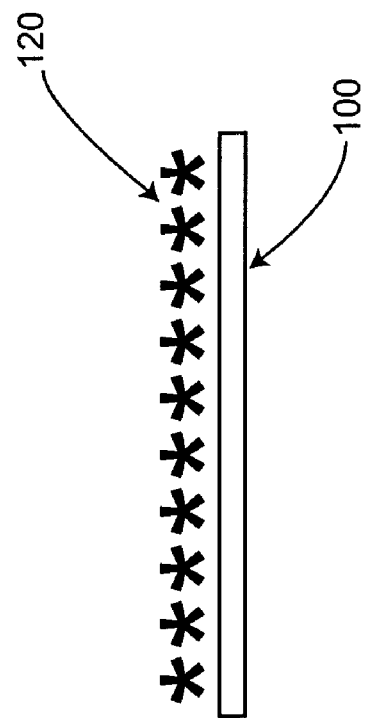
Fig. 1B
Fig. 1A

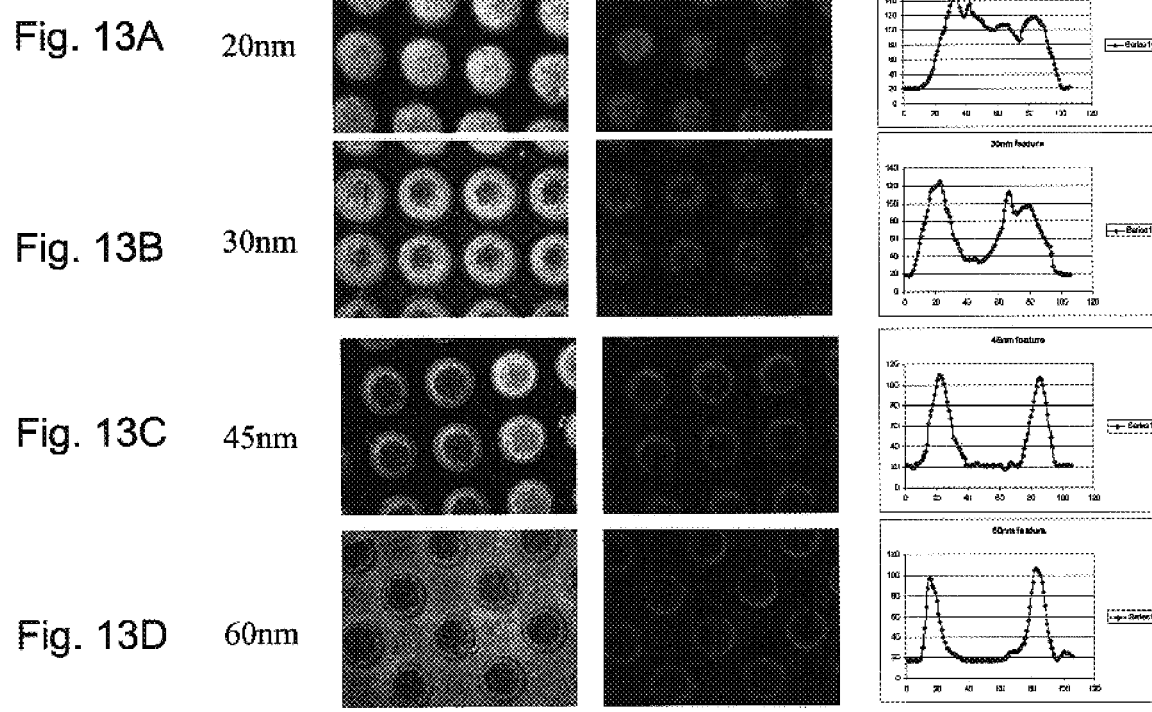
Fig. 13A 20nm
Fig. 13B 30nm
Fig. 13C 45nm
Fig. 13D 60nm

| Time (sec) | Silicon wafer | Nano-wire wafer | Time (sec) | %Wt loss Silicon | %Wt. Loss NW |
|---|---|---|---|---|---|
| 0 | 1.1 | 1 | 0 | 0.0 | 0 |
| 15 | 1.1 | 0.9 | 15 | 0.0 | 10 |
| 30 | 1.1 | 0.8 | 30 | 0.0 | 20 |
| 45 | 1.1 | 0.7 | 45 | 0.0 | 30 |
| 60 | 1.1 | 0.6 | 60 | 0.0 | 40 |
| 75 | | 0.6 | 75 | 0.0 | 40 |
| 90 | | 0.5 | 90 | 0.0 | 50 |
| 105 | | 0.3 | 105 | 0.0 | 70 |
| 120 | 1 | 0.3 | 120 | 9.1 | 70 |
| 135 | | 0.2 | 135 | 9.1 | 80 |
| 150 | | 0 | 150 | 9.1 | 100 |
| 165 | | | 165 | 9.1 | |
| 180 | 0.9 | | 180 | 18.2 | |
| 240 | 0.9 | | 240 | 18.2 | |
| 300 | 0.7 | | 300 | 36.4 | |
| 360 | 0.7 | | 360 | 36.4 | |
| 420 | 0.7 | | 420 | 36.4 | |
| 480 | 0.6 | | 480 | 45.5 | |
| 540 | 0.5 | | 540 | 54.5 | |
| 600 | 0.5 | | 600 | 54.5 | |
| 660 | 0.4 | | 660 | 63.6 | |
| 720 | 0.3 | | 720 | 72.7 | |
| 780 | 0.3 | | 780 | 72.7 | |
| 840 | 0.2 | | 840 | 81.8 | |

Fig. 28B

| SURFACE | Bkgnd (no probe) | +Probe | EXPOSURE TIME (of shown image) | FOLD INCREASE (over planar Si) |
|---|---|---|---|---|
| Glass slide | 28 | 46 | 10sec | 0.7 |
| Planar SiO2 | 11 | 63 | 20sec | 1.0 |
| Wires D (densest) | 56 | 5680 | 0.5sec | 90 |
| Wires B (new) | 30 | 1304 | 2.5sec | 20 |
| Wires C | 36 | 1820 | 0.5sec | 30 |

Fig. 35

NANOFIBER PLANAR

NANOFIBER

NO NANOFIBER

| Spot on plain wafer | Spot wicked onto nanofibers |
|---|---|
| 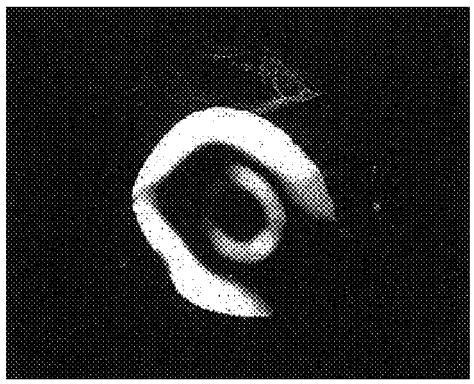 | 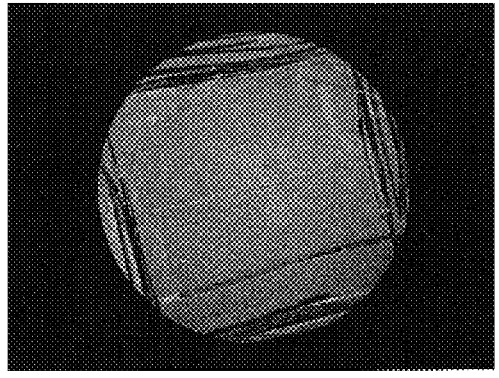 |
| 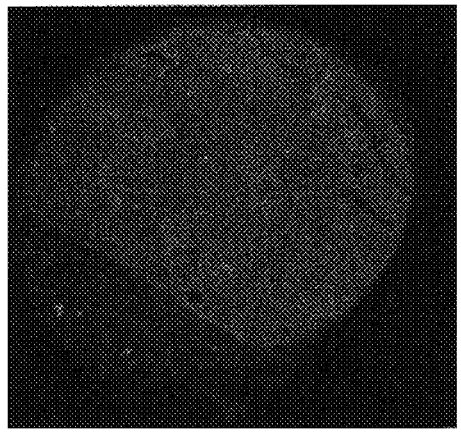 | 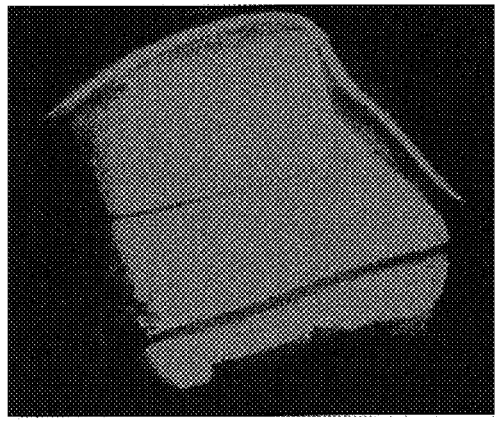 |
Fig. 45

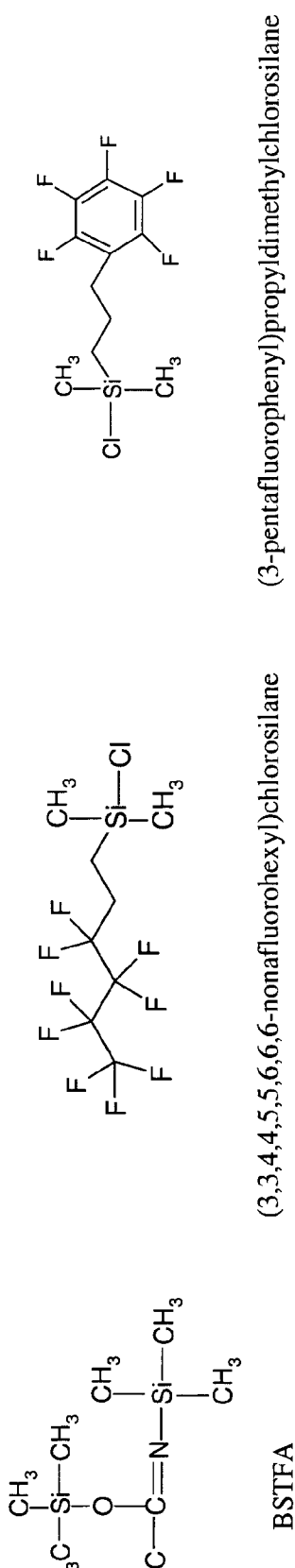
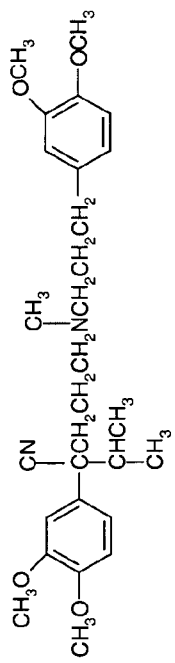
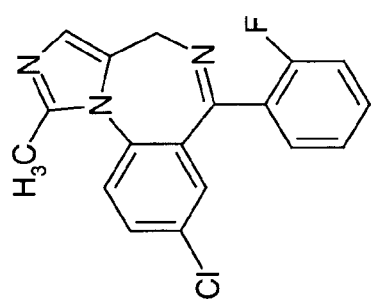
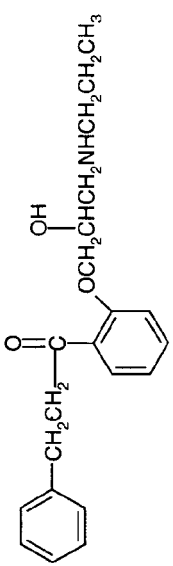
Fig. 51
Fig. 52

A. FHV Digest
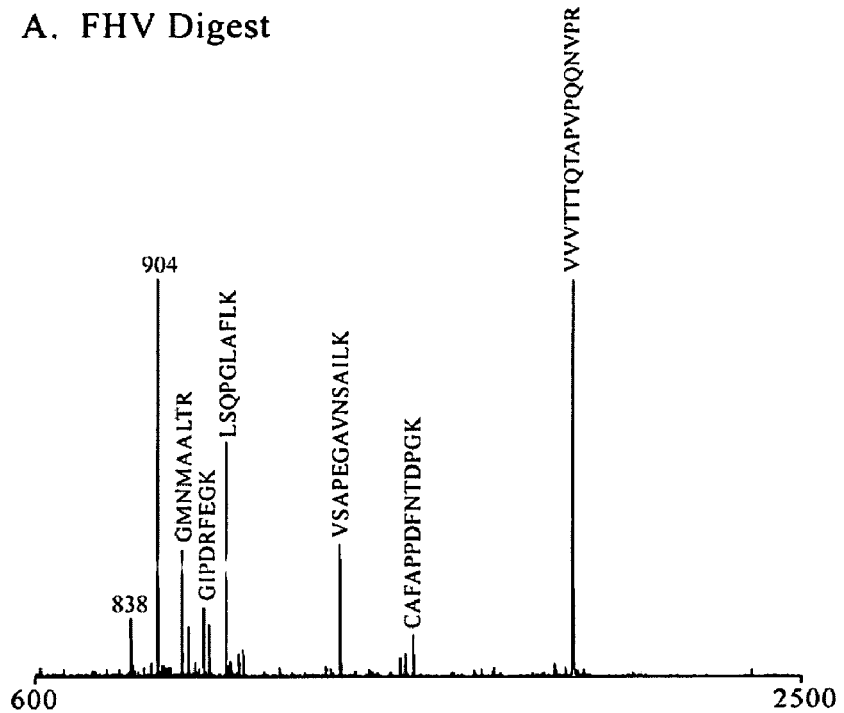
B. BSA Digest
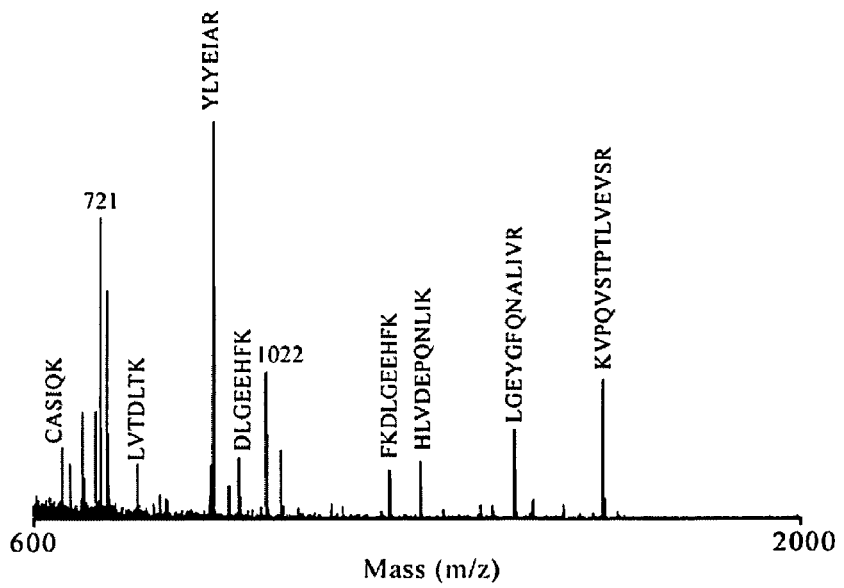
Fig. 60

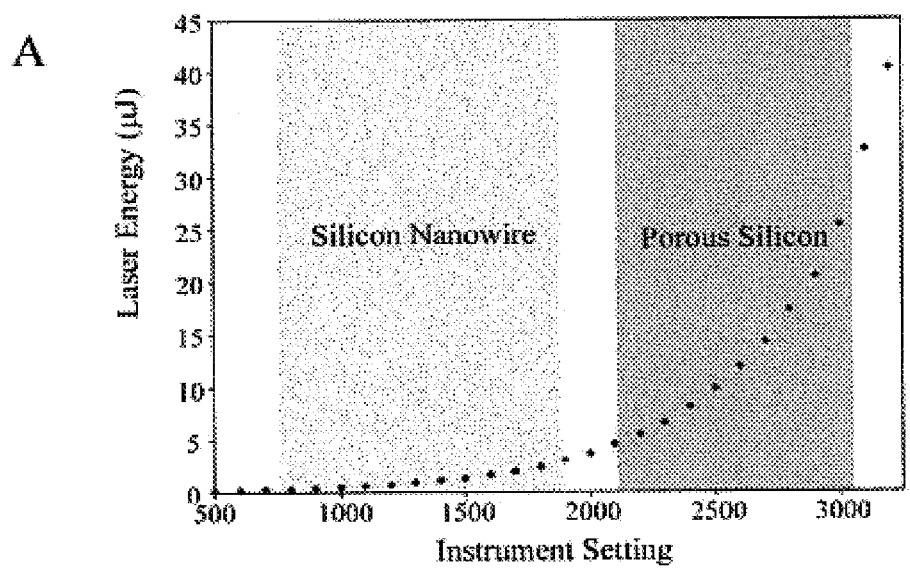
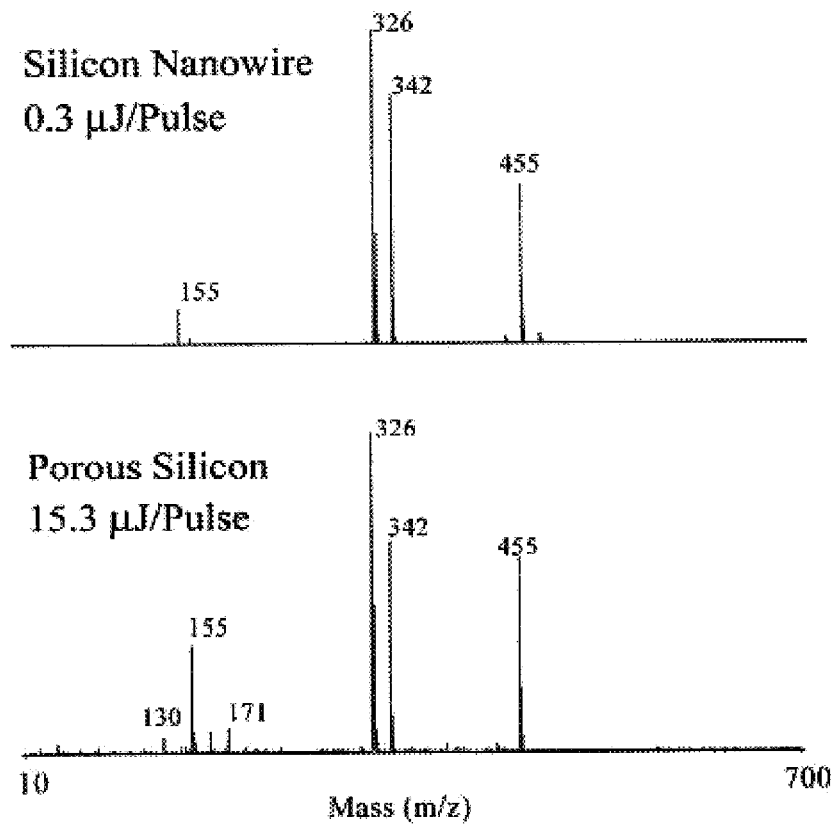
Fig. 61

|   | Background | Avge intensity (Gain 45, Laser power 70) | Saturated binding | Avge intensity (Gain 33, Laser power 70) |
|---|---|---|---|---|
| Native ox | 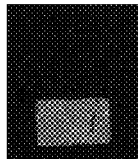 | 4080 |  | 23245 |
| Thermal ox (part) | | 21523 | | 54245 |
| Thermal ox (total) | | 18396 | 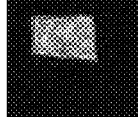 | 51783 |
Fig. 63

DNA Hybridization

- 6500
- 6501
- 6502
- 6503

Protein Binding (IL-6)

- 6504
- 6505
- 6506
- 6507

DNA Hybridization

Protein Detection

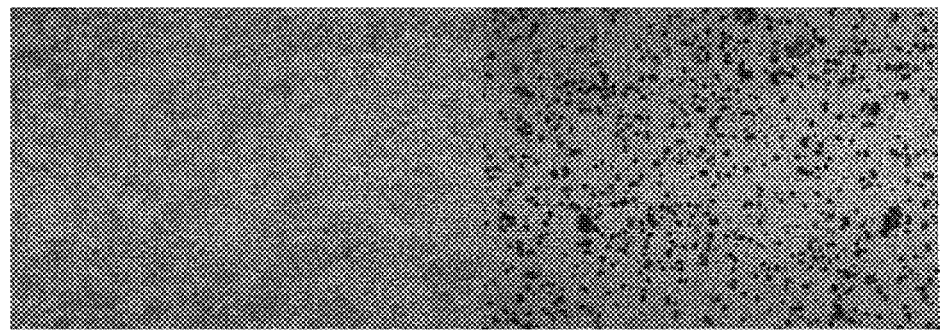
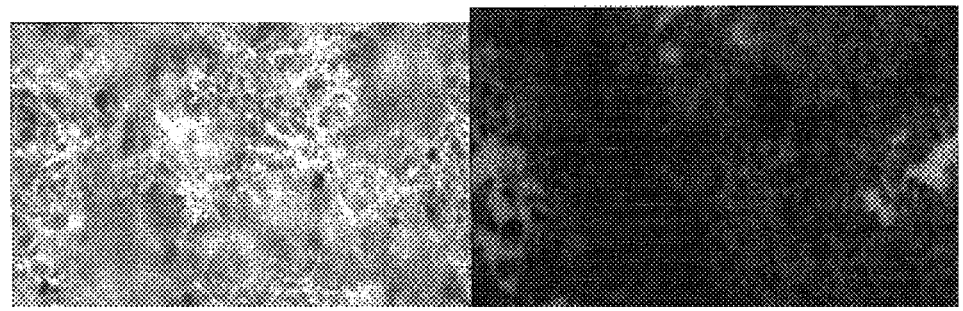
Fig. 72
Fig. 73

NANOFIBER SURFACES FOR USE IN ENHANCED SURFACE AREA APPLICATIONS

CROSS-REFERENCE TO RELATED APPLICATIONS

This application is a continuation-in-part of, and claims benefit of and priority to, U.S. Ser. No. 10/792,402, filed Mar. 2, 2004, and U.S. Provisional Application Nos. 60/468,606 filed May 5, 2003, and 60/468,390 filed May 6, 2003, both entitled "NANOFIBER SURFACES FOR USE IN ENHANCED SURFACE AREA APPLICATIONS." These prior applications are hereby incorporated by reference in their entirety for all purposes.

FIELD OF THE INVENTION

The invention relates primarily to the field of nanotechnology. More specifically, the invention pertains to nanofibers, and nanofiber structures having enhanced surface areas, as well as to the use of such nanofibers and nanofiber structures in various applications.

BACKGROUND OF THE INVENTION

Numerous scientific and commercial processes involve the interaction of one or more compounds (often in liquid form or present in a liquid carrier or the like) with one or more surface area. Such surfaces can be functionalized to perform specific actions, e.g., to bind certain compounds, to indicate the presence of specific compounds, to catalyze specific reactions, to change the relative temperature of compounds/liquids/gasses/etc. that come into contact with the surface, to prevent binding to the surface, to release drugs, etc. For example, common uses of surface/compound interactions include separation columns or filters, heat exchanges, microarray assays, chemical sensors, bio-sensors, medical devices, etc. Other examples are replete throughout the literature and, indeed, throughout everyday usage.

In almost all instances, however, the efficiency or use of such processes and devices is limited, at least in part, by the area of the surface which is in contact with the one or more compound or desired constituent (e.g., the liquid, gas, etc.). This limitation is true in several aspects. First, space limitations are of concern. For example, only a finite number of functional units (e.g., antibodies, catalysts, etc.) can physically exist per unit area of a surface (i.e., within a certain footprint). Thus, the action to be accomplished can be limited by the number of functional units, which is in turn limited by the unit area or footprint of the surface which contains the functional units. One answer to such problems is to increase the unit area or size of the footprint involved. However, besides being inelegant, such response is often problematic due to cost restraints and size limitations imposed on the footprint itself (e.g., the reaction might need to be performed in a limited space in a device, etc.)

Second, such processes and devices are often also limited in terms of resolution or sensitivity. For example, in situations such as detection, the activity allowing detection of a compound or constituent can sometimes be 'weak' or difficult to detect. Alternatively, the compound may only briefly or imperfectly interact with a moiety on the surface (i.e., one involved in the detection process). In such situations, even increasing the footprint size might not be enough to improve detection, since a weak response is still a weak response when spread out over a larger area (i.e., the response per unit area would still be the same). A similar problem can occur in column reactions and can result in faint or diffuse bands.

In a number of conventional or current applications, the surface area of a matrix is increased by providing the material making up the surface with a number of holes or pores. By providing the matrix as a porous solid, rather than just a solid surface, one increases the amount of available surface area without increasing the amount of space that the material occupies (i.e., the footprint size). While such porous configurations do increase the surface area of the matrix, a number of issues arise to limit the effectiveness of such measures. In particular, due to the tortuous and narrow nature of the paths offered by these pores, materials are typically prevented from being actively flowed into contact with the relevant surfaces in the interior of the pores. As a result, materials must drift into contact with these surfaces via diffusion, which is limited by available time, and also by the size of the molecules of interest, e.g., larger molecules diffuse more slowly. Even in cases where porous networks do allow flow-through, the narrow and elongated nature of such networks results in back pressures that typically force materials to flow through less tortuous paths, e.g., around the matrix entirely. Thus, in other words, a third problem often arises in the "path" involved in reactions, etc. For example, in some current traditional separation/detection devices, an analyte needs to wind its way through a complex pathway in order to reach the appropriate detection element or to achieve separation or the like. Such tortuous paths can increase processing times (i.e., decrease throughput).

A final, but not trivial, problem concerns cost. Larger devices/surfaces/structures that are needed, e.g., to allow inclusion of greater numbers of areas or functional units, can be quite expensive.

A welcome addition to the art would be surfaces having enhanced surface areas and structures/devices comprising such, as well as methods of using enhanced area surfaces and devices, which would have the benefits of, e.g., increased functionality per unit area, short and/or non-tortuous processing paths and the like. The current invention provides these and other benefits which will be apparent upon examination of the following.

SUMMARY OF THE INVENTION

In some aspects the current invention comprises a substrate comprising at least a first surface, a plurality of nanofibers attached to the first surface, and, one or more specific moiety attached to one or more member of the plurality of nanofibers. In typical instances, the moiety is an exogenous moiety, e.g., one that is a naturally arising or an un-manipulated oxide layer or the like on the nanofibers. In some embodiments, the nanofibers can comprise an average length of from about 1 micron or less to at least about 500 microns, from about 5 micron or less to at least about 150 microns, from about 10 micron or less to at least about 125 microns, or from about 50 micron or less to at least about 100 microns. Additionally, in some embodiments the nanofibers can comprise an average diameter of from about 5 nm or less to at least about 1 micron, from about 5 nm or less to at least about 500 nm, from about 10 nm or less to at least about 500 nm, from about 20 nm or less to at least about 250 nm, from about 20 nm or less to at least about 200 nm, from about 40 nm or less to at least about 200 nm, from about 50 nm or less to at least about 150 nm, or from about 75 nm or less to at least about 100 nm. Furthermore, in other embodiments, the nanofibers can comprise an average density of from about 0.11 (or about 0.1) nanofiber per square micron or less to at least about 1000 nanofibers per square micron, from about 1 nanofiber per square micron or less to at least about 500 nanofibers per square micron, from about 10 nanofibers per square micron or less to at least about 250 nanofibers per square micron, or from about 50 nanofibers per square micron or less to at least about 100 nanofibers per square micron. In such embodiments the substrates can also have moieties (either specific or nonspecific) which provide one or more interaction site for one or more analyte. In various embodiments, the moiety and the analyte can be, e.g., proteins, peptides, polypeptides, nucleic acids, nucleic acid analogs, metallo-proteins, chemical catalysts, metallic groups, antibodies, ions, ligands, substrates, receptors, biotin, hydrophobic moieties, alkyl chains from about 10 to about 20 carbon atoms in length, phenyl groups, an adhesive enhancing group, and co-factors, etc. In different embodiments, the plurality of nanofibers can be either grown in the place it is to be used, or, it can be grown at another location and transferred to the location it is to be used. In either case, the nanofibers can be either substantially parallel or substantially perpendicular, or a mixture of parallel and perpendicular in relation to the substrate (which can comprise, e.g., silicon, glass, quartz, plastic, ceramic, metal, polymers, TiO, ZnO, ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, PbS, PbSe, PbTe, AlS, AlP, AlSb, $SiO_1$, $SiO_2$, silicon carbide, silicon nitride, polyacrylonitrile (PAN), polyetherketone, polyimide, an aromatic polymer, and an aliphatic polymer, etc.). In yet other embodiments, the moieties can be attached to the nanofibers through a thiol group and there can also be a plurality of nanoparticles dispersed among the plurality of nanofibers.

In other aspects the invention comprises a substrate which comprises a microarray comprising a first and at least a second region (each region comprising at least a first surface and a plurality of nanofibers attached to the first surface and one or more specific moiety attached to one or more member of the plurality of nanofibers). In such embodiments, the first region can comprise a different specific moiety than the second region (or indeed each separate region can comprise different moieties). In some embodiments, such substrates can have at least a third region, which third region separates the first and second regions, and wherein the at least third region comprises a substantially lower density (or even substantially zero) of nanofibers than the first and second regions, thus providing a buffer region having substantially lower density of moiety between the first and second regions. In some embodiments, the first region and at least second region comprise an enhanced surface area, that is from about 2× to about 10,000× or more greater, from about 5× to about 5,000× or more greater, or from about 10× to about 1000× or more greater, or from about 100× to about 750× or more greater, or from about 250× to about 500× or more greater in area than a planar substrate of (substantially) similar footprint dimensions or than an area of the third region of (substantially) similar footprint dimensions. In some embodiments, such third region comprises substantially no nanofibers. In some embodiments, the at least third region (whether or not it comprises a similar, greater, or lesser amount or density of nanofibers than the first and at least second regions) comprises a hydrophobicity/hydrophilicity polarity opposite to a hydrophobicity/hydrophilicity polarity of the nanofibers of the first and at least second regions, thus providing a barrier region between the first and second regions. Such substrates can also comprise wherein the third region comprises nanofibers having one or more hydrophobic or hydrophilic moiety (e.g., a moiety which in of itself is hydrophobic or hydrophilic or is lipophobic or lipophilic or is amphiphobic or amphiphilic or which confers such property upon the nanofibers). Other embodiments comprise wherein the property is super-hydrophobicity, super-lipophobicity or super-amphiphobicity. Such at least third region can optionally comprise a continuous wickable flow-path for one or more fluid, which fluid is contained within the third region by the difference in hydrophobicity/hydrophilicity polarity between the third region and the first and at least second regions.

In some embodiments herein, the substrate(s) can comprise a separation substrate, which substrate comprises at least a first surface, a plurality of nanofibers attached to the first surface, and one or more specific moiety attached to or associated with one or more member of the plurality of nanofibers. In such embodiments the nanofibers and/or the moiety separate (or identify or isolate or the like) one or more analyte from one or more sample. Such substrate(s) optionally comprise an enhanced surface area that is from about 2× to about 10,000× or more greater in area than a substrate of substantially similar footprint dimensions without nanofibers. Such substrate(s) can comprise nanofibers of an average length of from about 1 micron to at least about 200 microns; an average diameter of from about 5 nm to at least about 1 micron; and, an average density of from about 1 nanofiber per square micron to at least about 1000 nanofibers per square micron. The enhanced surface area of such substrates can comprise an enhanced surface area that is from about 5× to about 5000× or more, from about 10× to about 1000× or more, from about 100× to about 750× or more, from about 250× to about 500× or more greater than a planar substrate of substantially similar footprint dimensions. In such substrates, the one or more moiety and/or the one or more material (e.g., that is separated, isolated, identified, etc.) is selected from the group consisting of organic molecules, inorganic molecules, metals, ceramics, proteins, peptides, polypeptides, nucleic acids, nucleic acid analogs, metallo-proteins, chemical catalysts, metallic groups, antibodies, cells, ions, ligands, substrates, receptors, biotin, hydrophobic moieties, alkyl chains from about 10 to about 20 carbon atoms in length, phenyl groups, adhesive enhancing groups, co-factors, etc. The specific moiety can interact specifically or nonspecifically with one or more analyte in the material to be separated, etc. Thus, for example, the moiety can optionally bind to or otherwise identify/separate nonspecifically, e.g., identify/separate, etc. all proteins, all molecules above a certain size/conformation, etc., or can optionally bind to or otherwise identify/separate specifically, e.g., bind/identify/separate/etc. only a specific protein, or a specific antigen on a class of proteins, or a specific nucleic acid sequence, etc. Such substrate(s) can optionally further comprise one or more source of the material(s) to be separated and a fluid delivery device that delivers the one or more material to be separated/isolated/identified/ etc. into contact with the separation substrate.

In other embodiments, the substrates of the invention can comprise part of a mass spectrometry device. Such substrate can comprise a microarray having a first and at least a second region wherein each region comprises at least a first surface and a plurality of nanofibers attached to the first surface. The mass spectrometry analysis can optionally comprise laser desorption ionization, MALDI, SELDI, etc. Such substrate(s) can comprise microarray(s) which have a plurality of regions with each region having at least a first surface and a plurality of nanofibers attached to it. Each region can optionally comprise one or more analyte to be assayed (e.g., through mass-spectrometry). In other embodiments, substantially each region can comprise a different analyte to be assayed. Such analyte(s) can be optionally attached to or associated with one or more member of the plurality of nanofibers, e.g., the analytes can be optionally immobilized and/or dried and/or lyophilized and/or comprised within a matrix. In other embodiments, the analyte(s) is not comprised within a matrix. Other embodiments comprise wherein substantially each region comprises a different analyte to be assayed. The one or more analyte to be analyzed by the mass-spectrometry can optionally be selected from the group consisting of organic molecules, inorganic molecules, metals, ceramics, proteins, peptides, polypeptides, nucleic acids, nucleic acid analogs, metallo-proteins, chemical catalysts, metallic groups, antibodies, cells, ions, ligands, substrates, receptors, biotin, hydrophobic moieties, alkyl chains from about 10 to about 20 carbon atoms in length, phenyl groups, adhesive enhancing groups, co-factors, etc. For such mass-spectrometry substrates, the members of the plurality of nanofibers comprise an average length of from about 1 micron to at least about 200 microns; an average diameter of from about 5 nm to at least about 1 micron; and, an average density of from about 1 nanofiber per square micron to at least about 1000 nanofibers per square micron. Other embodiments comprise wherein the members of the plurality of nanofibers comprise an average diameter of from about 5 nm to at least about 1 micron or more, from about 10 nm to at least about 500 nm or more, from about 20 nm to at least about 250 nm or more, from about 40 nm to at least about 200 nm or more, from about 50 nm to at least about 150 nm or more, or from about 75 nm to at least about 100 nm or more. The enhanced surface area of such substrates can optionally comprises an area that is from about 5× to about 5000× or more greater, from about 10× to about 1000× or more greater, from about 100× to about 750× or more greater, or from about 250× to about 500× or more greater than a planar substrate of substantially similar footprint dimensions. Also such substrates can have a plurality of nanofibers which comprises an average density of from about 0.1 nanofiber per square micron to at least about 1000 or more nanofibers per square micron, from about 1 nanofiber per square micron to at least about 500 or more nanofibers per square micron, from about 10 nanofibers per square micron to at least about 250 or more nanofibers per square micron, or from about 50 nanofibers per square micron to at least about 100 nanofibers per square micron. Such substrates can also optionally further comprise one or more moiety attached to or associated with one or more member of the plurality of nanofibers. Such moiety optionally can provide one or more interaction site for one or more analyte. Each region of the substrate can optionally comprise one or more moiety for specifically or nonspecifically binding one or more analyte. Also substantially each region can comprise a different moiety for binding one or more analyte (e.g., different analytes). The plurality of nanofibers in such substrates optionally can be grown on a second surface (or multiple second surfaces) and transferred to the first surface or optionally the nanofibers can be grown/constructed directly upon the first surface. The substrates and nanofibers of such embodiments can be comprised of material(s) independently selected from the group consisting of: silicon, glass, quartz, plastic, ceramic, metal, polymers, TiO, ZnO, ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, PbS, PbSe, PbTe, AlS, AlP, AlSb, $SiO_1$, $SiO_2$, silicon carbide, silicon nitride, polyacrylonitrile (PAN), polyetherketone, polyimide, an aromatic polymer, an aliphatic polymer, etc.

In yet other embodiments, the substrates of the invention can comprise implantable substrate(s) to be implanted into a subject (e.g., a human, a non-human primate, a mammal, an amphibian, a reptile, a bird, a plant, etc.). Such substrates typically comprise at least a first surface and a plurality of nanofibers attached to the first surface. The plurality of nanofibers can provide a scaffold for tissue attachment of the subject to the first surface. Optionally such substrates can an anti-biofouling surface. The implantable substrates can optionally comprise one or more specific moiety (e.g., hydroxyapatite) and can optionally comprise a coating on one or more nanofiber. In such substrates the nanofibers and/or the substrate can comprise $TiO_x$.

Other embodiments herein comprise substrates comprising drug delivery devices for introduction of one or more substance into a subject (e.g., a human, a non-human primate, a mammal, an amphibian, a reptile, a bird, a plant, etc.). Such substrate typically comprises at least a first surface, a plurality of nanofibers attached to the first surface, and a reservoir of the one or more substance comprised amongst the plurality of nanofibers. The reservoir further can comprises one or more storage matrix. The storage matrix can comprise one or more polymer.

In other aspects the invention comprises a system or device having a substrate comprising at least a first surface; a plurality of nanofibers attached to the first surface; and one or more specific moiety attached to one or more member of the plurality of nanofibers. In some embodiments the moiety is an exogenous moiety. Furthermore, such systems/devices can comprise one or more material delivery system (e.g., wherein the material delivery system delivers one or more material into contact with the first surface, etc.). In some such systems/devices the members of the plurality of nanofibers comprise an average length of from about 1 micron to at least about 200 microns; an average diameter of from about 5 nm to at least about 1 micron; and, an average density of from about 1 nanofiber per square micron to at least about 1000 nanofibers per square micron. Also, in some such systems/devices the one or more moiety provides one or more specific or nonspecific interaction site for one or more analyte. The moiety and the analyte can optionally be selected from the group consisting of organic molecules, inorganic molecules, metals, ceramics, proteins, peptides, polypeptides, nucleic acids, nucleic acid analogs, metallo-proteins, chemical catalysts, metallic groups, antibodies, cells, ions, ligands, substrates, receptors, biotin, hydrophobic moieties, alkyl chains from about 10 to about 20 carbon atoms in length, phenyl groups, adhesive enhancing groups, co-factors, etc.

In yet other aspects the invention comprises a microarray comprising a substrate having a first and at least a second region, each region comprising at least a first surface and a plurality of nanofibers attached to the first surface and one or more moiety (e.g., an exogenous moiety) attached to one or more member of the plurality of nanofibers. In some such embodiments, the first region comprises a different moiety than the at least second region. In yet other embodiments, the microarray comprises at least a third region which separates the first and second regions and which comprises a substantially lower density of nanofibers than the first and second regions. Such third region(s) thus provide a buffer region having substantially lower density of nanofibers between the first and second regions. In some embodiments, the microarrays comprise wherein the first region and the at least second region comprise an enhanced surface area that is from about 2× to about 10,000× or more greater, from about 5× to about 5000× or more greater, from about 10× to about 1000× or more greater, from about 100× to about 750× or more greater, or from about 250× to about 500× or more greater in area than a planar substrate of substantially similar footprint dimensions or than an area of the third region of substantially similar footprint dimensions. In some embodiments, such third region comprises substantially no nanofibers. In some embodiments, the microarrays herein comprise third region(s) that do not comprise a moiety attached to any of the fibers (or substantially all of the nanofibers do not comprise a moiety attached to or associated with them). In yet other embodiments, microarrays herein comprise third region(s) that separate the first and at least second regions and which has nanofibers with a hydrophobicity/hydrophilicity polarity opposite to a hydrophobicity/hydrophilicity polarity of the nanofibers of the first and second regions, thus providing a barrier region between the first and second regions. In such embodiments, the nanofibers of the third region can comprise one or more hydrophobic or hydrophilic moiety. Also, the third region can comprise a continuous wickable flow-path for one or more fluid. Such fluid is contained within the third region by the difference in hydrophobicity/hydrophilicity polarity between the third region and the first and at least second regions.

The invention also comprises methods of identifying the presence of at least a first material in a mixture of the first material and at least a second material. Such methods typically comprise providing a substrate having a first and at least a second region, each region comprising at least a first surface and a plurality of nanofibers attached to the first surface and one or more specific moiety (e.g., an exogenous moiety) attached to one or more member of the plurality of nanofibers. After contacting the mixture with the substrate such moiety interacts with the first material, thus, identifying the presence of the material. In some embodiments, the first region comprises a different specific moiety than the at least second region. Additionally, in some embodiments, the substrate comprises at least a third region which separates the first and second regions and which comprises a substantially lower density of nanofibers than the first and second regions, thus providing a buffer region having substantially lower density of nanofibers between the first and second regions. In some embodiments, such methods further comprise quantifying the presence of the at least first material based on a level of interaction with the one or more moiety.

The invention also comprises microarrays comprised of a first and at least a second region, each region having an enhanced area silicon surface and one or more specific moiety attached to such surface wherein fluorescence from nonspecific binding of one or more analyte to the surface is quenched by proximity to the surface. Also, in such embodiments the fluorescence from specific binding of one or more analyte to the surface is not quenched by proximity to the surface.

The invention also comprises separation systems/devices which have a separation substrate comprising least a first surface, a plurality of nanofibers attached to the first surface, one or more source of one or more material comprising one or more analyte to be separated. Such systems/devices also typically comprise one or more specific moiety (e.g., an exogenous moiety) attached to one or more member of the plurality of nanofibers. The substrates in such systems/devices typically comprise an enhanced surface area of from about 2× to about 10,000× or more greater area than a planar substrate of substantially similar footprint dimensions. Such systems/devices typically comprise nanofibers of an average length of from about 1 micron to at least about 200 microns; an average diameter of from about 5 nm to at least about 1 micron, and an average density of from about 1 nanofiber per square micron to at least about 1000 nanofibers per square micron. The enhanced surface area of such systems/devices typically comprises an area that is from about 5× to about 5000× or more greater, from about 10× to about 1000× or more greater, from about 100× to about 750× or more greater, or from about 250× to about 500× or more greater than a planar substrate of substantially similar footprint dimensions. The moiety(ies) are optionally selected from the group consisting of organic molecules, inorganic molecules, metals, ceramics, proteins, peptides, polypeptides, nucleic acids, nucleic acid analogs, metallo-proteins, chemical catalysts, metallic groups, antibodies, cells, ions, ligands, substrates, receptors, biotin, hydrophobic moieties, alkyl chains from about 10 to about 20 carbon atoms in length, phenyl groups, adhesive enhancing groups, co-factors, etc. Also the specific moiety can interact specifically or nonspecifically with one or more analyte in the material to be separated. Some such systems/devices further comprise a fluid delivery device which delivers the one or more material to be separated into contact with the separation matrix.

The invention also comprises methods to separate at least a first material from a mixture (e.g., of the first material and at least a second material). Such methods comprise providing at least a first surface having a plurality of nanofibers attached thereto and flowing the mixture through the nanofibers, thus separating the first material from the at least second material. Such separations can be based upon a difference in size between the first material and the at least second material, a difference in electrical charge of the first material and the at least second material, etc. In some such embodiments, the plurality of nanofibers further comprise one or more specific moiety (e.g., an exogenous moiety) attached to or associated with one or more member of the plurality of nanofibers. The one or more specific moiety can be specific for one or more aspect of the first material or second material and separation can be based upon selective interaction between the one or more specific moiety of the nanofibers and the one or more aspect of the first or second material.

The invention also includes separation systems/devices having a separation substrate comprising a plurality of nanofibers attached thereto, wherein the substrate comprises an enhanced surface area, which area is from about 2× to about 10,000× or more greater in area than a planar substrate of substantially similar footprint dimensions; one or more source of one or more material to be separated; and, a fluid delivery device. Some embodiments of such systems/devices include wherein members of the plurality of nanofibers comprise an average length of from about 1 micron to at least about 200 microns or more; an average diameter of from about 5 nm to at least about 1 micron or more, and an average density of from about 1 nanofiber per square micron to at least about 1000 nanofibers per square micron or more. In some embodiments the enhanced surface area comprises an area that is from about 5× to about 1000× or more greater, from about 10× to about 1000× or more greater, from about 100× to about 750× or more greater, or from about 250× to about 500× or more greater than a planar substrate of substantially similar footprint dimensions. In some such embodiments the density and/or arrangement of the nanofibers allows separation of one or more analyte from the material based upon one or more of: the size of the analyte, the electrical charge of the analyte, or the conformation of the analyte.

Also included in the invention are separation systems/devices that comprise a separation matrix having a plurality of nanofibers, one or more source of one or more material to be separated, and a fluid delivery device. In some such embodiments, the plurality of nanofibers optionally is not attached to a substrate.

In the various separation systems/devices of the invention, the devices can optionally comprise cylindrical column(s) comprising the plurality of nanofibers. Also, the various separation systems/devices of the invention can include devices that are substantially planar substrates having a plurality of nanofibers. Furthermore, the various separation systems/devices herein optionally can include ones in which one or more of the plurality of nanofibers is crosslinked to one or more other nanofiber of the plurality or in which substantially all members of the plurality of nanofibers are crosslinked to one or more other nanofiber of the plurality.

The invention also includes mass spectrometry systems/devices that comprise a substrate having a first surface with at least a first region comprising a plurality of nanofibers disposed thereon and having at least a first analyte associated therewith. Such mass spectrometry systems/devices also have a laser positioned to direct energy at the at least first region to desorb the first analyte from the first region and a mass spectrometer instrument positioned to receive the at least first analyte desorbed from the substrate. Such mass spectrometry systems/devices can comprise MALDI, SELDI, or other types of mass spectrometry. In some such systems/devices, the substrate comprises a plurality of regions, each one having at least a first surface and a plurality of nanofibers attached thereto. Each such region can optionally comprise one or more analyte to be assayed. In some embodiments, substantially each region comprises a different analyte to be assayed. In the various mass spectrometry systems/devices herein, each region of substrate can comprises one or more moiety (e.g., an exogenous moiety) for specifically or nonspecifically binding one or more analyte. Additionally, the various mass spectrometry systems/devices herein can include wherein substantially each region of the substrate comprises a different moiety for binding one or more analyte. The analytes can optionally be selected from the group consisting of organic molecules, inorganic molecules, metals, ceramics, proteins, peptides, polypeptides, nucleic acids, nucleic acid analogs, metallo-proteins, chemical catalysts, metallic groups, antibodies, cells, ions, ligands, substrates, receptors, biotin, hydrophobic moieties, alkyl chains from about 10 to about 20 carbon atoms in length, phenyl groups, adhesive enhancing groups, co-factors, etc. Additionally, such systems/devices can comprise substrates and/or nanofibers made of, and independently selected from, materials such as, silicon, glass, quartz, plastic, ceramic, metal, polymers, TiO, ZnO, ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, PbS, PbSe, PbTe, AlS, AlP, AlSb, $SiO_1$, $SiO_2$, silicon carbide, silicon nitride, polyacrylonitrile (PAN), polyetherketone, polyimide, an aromatic polymer, an aliphatic polymer, etc. The various mass spectrometry systems/devices herein can include nanofibers that comprise an average diameter of from about 5 nm to at least about 1 micron or more, from about 10 nm to at least about 500 nm or more, from about 20 nm to at least about 250 nm or more, from about 40 nm to at least about 200 nm or more, from about 50 nm to at least about 150 nm or more, or from about 75 nm to at least about 100 nm or more. Additionally, such mass spectrometry systems/devices can include those in which the enhanced surface area comprises an area that is from about 5× to about 5000× or more greater, from about 10× to about 1000× or more greater, from about 100× to about 750× or more greater, or from about 250× to about 500× or more greater than a planar substrate of substantially similar footprint dimensions. Also, the various mass spectrometry systems/devices herein include those in which the plurality of nanofibers comprises an average density of from about 0.1 nanofiber per square micron to at least about 1000 or more nanofibers per square micron, from about 1 nanofiber per square micron to at least about 500 or more nanofibers per square micron, from about 10 nanofiber per square micron to at least about 250 or more nanofibers per square micron, or from about 50 nanofiber per square micron to at least about 100 or more nanofibers per square micron. Some embodiments of such systems devices also in clued those in which members of the plurality of nanofibers comprise an average length of from about 1 micron to at least about 200 microns; an average diameter of from about 5 nm to at least about 1 micron; and, an average density of from about 1 nanofiber per square micron to at least about 1000 nanofibers per square micron. Various mass spectrometry systems/devices herein also include those in which at least first analyte is attached to or associated with one or more member of the plurality of nanofibers (e.g., the analyte is immobilized, is dried, is lyophilized, is comprised within a matrix, etc.). The analyte is also optionally not comprised within a matrix.

The invention also includes methods of performing mass spectrometry by providing a substrate comprising a first surface having at least a first region comprising a plurality of nanofibers disposed thereon and having at least a first analyte associated therewith; providing a laser positioned to direct energy at the at least first region; providing a mass spectrometer instrument positioned to receive the analyte desorbed from the substrate; and desorbing the first analyte from the first region with the energy from the laser. Such methods can include wherein the mass spectrometry analysis is MALDI, wherein the mass spectrometry analysis is SELDI, or wherein the analysis is another form of mass spectrometry. Such methods can include those in which the substrate comprises a plurality of regions, each one having at least a first surface and a plurality of nanofibers attached thereto. Each of such regions can comprises one or more analyte to be assayed and/or substantially each region can comprise a different analyte to be assayed. Also, each region can comprise one or more moiety for specifically or nonspecifically binding one or more analyte. Such analyte is typically attached to or associated with one or more member of the plurality of nanofibers. Thus, the analyte can be immobilized, dried, lyophilized, comprised within a matrix (or not comprised within a matrix), etc.

The current invention also includes implantable devices that can be implanted into a subject (e.g., a human, a non-human primate, a mammal, an amphibian, a reptile, a bird, a plant, etc.), which devices comprises a substrate, having at least a first surface and a plurality of nanofibers attached thereto. Such plurality of nanofibers provides a scaffold for tissue attachment of the subject to the first surface of the device.

Other aspects of the current invention include implantable devices to be implanted into a subject (e.g., a human, a non-human primate, a mammal, an amphibian, a reptile, a bird, a plant, etc.) that provide an anti-biofouling surface. Such devices typically comprise a substrate having at least a first surface, and a plurality of nanofibers thereto.

The various implantable devices of the current invention can include those in which the nanofibers therein comprise one or more specific moiety (e.g., hydroxyapatite). Furthermore, the specific moiety can optionally comprise a coating on one or more nanofiber. In some embodiments, the nanofibers and/or the substrate can comprise $TiO_x$.

The invention also includes methods of providing tissue attachment of a subject to an implantable device. Such methods comprising providing a substrate having at least a first surface and a plurality of nanofibers attached thereto; and implanting or injecting the device into the subject.

The invention also includes methods of suppressing the formation of a biofilm on a medical device in a subject. Such method comprising providing one or more surface of the medical device having a plurality of nanofibers and which surface comes into contact with the subject (e.g., with a tissue or biological material of the subject).

Yet another aspect of the current invention are drug delivery devices for introduction of one or more substance into a subject. Such devices can comprise a substrate having at least a first surface, a plurality of nanofibers attached to the first surface, and a reservoir (e.g., comprising one or more storage matrix, e.g., comprising one or more polymer) of the one or more substance comprised between the members of the plurality of nanofibers.

In yet other aspects, the invention comprises a volatizer (or volatilizer) device having a substrate having at least a first surface; a plurality of nanofibers attached to the first surface; and one or more specific moiety attached to one or more member of the plurality of nanofibers, which moiety comprises an affinity for one or more fluid to be thinly dispersed over and volatilized from the substrate. Such embodiments can also comprise one or more heating source.

Other aspects of the invention include volatizer devices having a substrate (having at least a first surface), a plurality of nanofibers attached to the first surface (wherein one or more fluid is thinly dispersed over and volatized from the substrate), and, a fluid delivery system. Such embodiments can also include, e.g., one or more heating source.

Other aspects of the invention include a method of volatilizing one or more material, by providing a substrate having at least a first surface and a plurality of nanofibers attached to the first surface; providing a fluid delivery system; and, thinly dispersing one or more fluid comprising the material over the substrate. In such embodiments, one or more specific moiety can also be attached to one or more member of the plurality of nanofibers, which moiety comprises an affinity for the one or more fluid.

These and other objects and features of the invention will become more fully apparent when the following detailed description is read in conjunction with the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1, Displays schematic diagrams representing a functionalized planar substrate and a functionalized nanofiber enhanced substrate.

FIGS. 8-14, Display nanofiber arrays of the invention produced through shadow-mask gold film techniques FIG. 15, Displays an example of a nanofiber array of the invention.

FIG. 35, Compares fluorescent signal intensity between hybridization on planar surfaces and nanofiber surfaces.

FIGS. 43-46, Display protein/nucleic acid binding to nanofiber surfaces.

FIG. 51, Displays chemical structures for exemplary derivatization reagents of nanofiber surfaces.

FIG. 52, Displays chemical structures for exemplary compounds analyzed via mass spectroscopy on nanofiber surfaces.

FIGS. 53-55, Display mass spectroscopy analysis of exemplary compounds on nanofiber surfaces.

FIG. 60, Shows laser desorption/ionization from silylated silicon nanowires. FHV digest peptides are SEQ ID NOs:3-8 (from left to right); BSA digest peptides are SEQ ID NOs:9-16 (from left to right).

FIG. 61, Displays a plot of laser energy per pulse against MALDI settings for a laser desorption/ionization analysis using silicon nanowires and porous silicon and a comparison of the laser energy needed to desorb/ionize select small molecules on such platforms.

FIG. 63, Shows quenching of non-specifically bound fluorescence on native versus grown oxides on nanofiber (nanowire) surfaces.

FIG. 72, Displays photographs comparing bacterial growth on planar silicon substrates and nanofiber (nanowire) substrates.

FIG. 73, Shows growth of CHO cells on select areas of a scratched nanofiber substrate.

DETAILED DESCRIPTION

Figure 2:
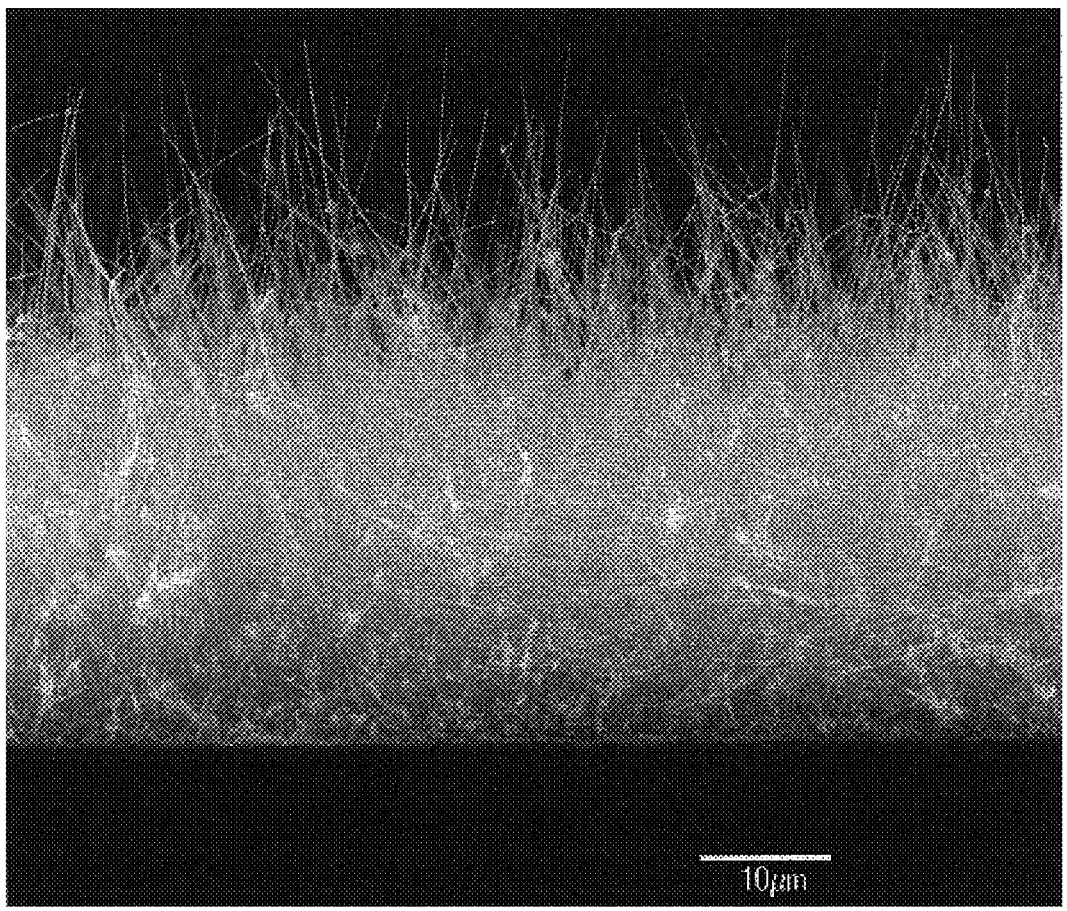
FIG. 2, Displays an electronmicrograph of a representative nanofiber surface.

The current invention comprises a number of different embodiments focused on nanofiber enhanced area surface substrates and uses thereof. As will be apparent upon examination of the present specification, figures, and claims, substrates having such enhanced surface areas present improved and unique aspects that are beneficial in a wide variety of applications ranging from materials science, to medical use, to art. It will be appreciated that enhanced surface areas herein are sometimes labeled as "nanofiber enhanced surface areas" or "NFS" or, alternatively depending upon context, as "nanowire enhanced surface areas" or "NWS." While some illustrations, examples, etc. herein are described in terms of nanowires, unless stated otherwise, other nanofiber constructs herein are also included in various embodiments.

A common factor in the embodiments is the special morphology of nanofiber surfaces (typically silicon oxide nanowires herein, but also encompassing other compositions and forms) which are typically functionalized with one or more moiety. For example, the vastly increased surface area presented by NFS substrates is utilized in, e.g., creation of improved microarray devices, as well as super-hydrophobic surfaces and improved efficiency heat exchangers. In most aspects herein, it is thought that such benefits detailed accrue from the unique morphology of the nanofiber surfaces (especially form the vastly increased surface area) and optionally from the greater concentration of functional units per unit substrate, but the various embodiments herein are not necessarily limited by such theory in their construction, use, or application.

Again, without being bound to a particular theory or mechanism of operation, the concept of the majority of benefits of the invention is believed to operate, at least in part, on the principle that the nanofiber surfaces herein present a greatly enhanced surface area in relation to the same footprint area without nanofibers. In some embodiments, benefits are also thought to arise from the related concept of a non-tortuous path. In other words, various analytes, etc., can access specific moieties, or the like, on the increased surface areas, without having to wind through a convoluted tortuous path as would be the case in more traditional packing materials (e.g., as found in typical separation columns or the like, sol-gel coatings or other conventional membranes or surface coatings).

Numerous additional nanofiber applications related to concepts herein can be found in, e.g., U.S. Application No. 60/466,229, filed Apr. 28, 2003 both filed Apr. 27, 2004, both entitled "Super-Hydrophobic Surfaces, Methods of Their Construction and Uses Therefor"; U.S. Application Nos. 60/463,766, filed Apr. 17, 2003 and Ser. No. 10/661,381, filed Sep. 12, 2003,(filed Apr. 16, 2004), U.S. application Ser. No. 10/825,861, filed Apr. 16, 2004, Taiwanese Application No. 93110667 filed Apr. 16, 2004, filed Apr. 19, 2004, and U.S. application Ser. No. 10/828,100, filed Apr. 19, 2004, all entitled "Structures, Systems and Methods for Joining Articles and Materials and Uses Therefor"; U.S. application Ser. No. 60/549,711, filed Mar. 2, 2004, entitled "Medical Device Applications of Nanostructured Surfaces"; and U.S. Application No. 60/541,463, filed Feb. 2, 2004, entitled "Porous Substrates, Articles, Systems and Compositions Comprising Nanofibers and Methods of Their Use and Production," all of which are incorporated herein by reference in their entirety for all purposes.

I) Characteristics of Nanofiber Surface Substrates

As noted previously, increased surface area is a property that is sought after in many fields (e.g., in substrates for assays or separation column matrices). For example, fields such as tribology and those involving separations and adsorbents are quite concerned with maximizing surface areas. The current invention offers surfaces and applications having increased or enhanced surface areas (i.e., increased or enhanced in relation to structures or surfaces without nanofibers).

A "nanofiber enhanced surface area" herein corresponds to a substrate comprising a plurality of nanofibers (e.g., nanowires, nanotubes, etc.) attached to the substrate so that the surface area within a certain "footprint" of the substrate is increased relative to the surface area within the same footprint without the nanofibers. In typical embodiments herein, the nanofibers (and often the substrate) are composed of silicon oxides. It will be noted that such compositions convey a number of benefits in certain embodiments herein. Also, in many preferred embodiments herein, one or more of the plurality of nanofibers is functionalized with one or more moiety.

See below. However, it will also be noted that the current invention is not specifically limited by the composition of the nanofibers or substrate, unless otherwise noted.

Thus, as an illustrative, but not limiting, example, FIGS. 1 and 2 present schematic and actual representations of nanofiber enhanced surface area substrates of the invention. FIG. 1a represents a non-enhanced surface area substrate comprising a finite number of functional units (e.g., moieties such as catalysts, antibodies, etc.), 120. As can be seen, only a certain number of functional units fit within a footprint on the substrate, 100. FIG. 1b, however, presents one possible embodiment of the current invention. The substrate in 1b presents the same footprint as that of 1a, but because of the number of nanofibers, 110, the surface area is greatly increased and, thus, the number of functional units, 120, (in embodiments comprising such) are greatly increased as well. FIG. 2 displays a photomicrograph of an enhanced surface area nanofiber substrate. It will be noted that the number and shape and distribution of the nanofibers allows ample opportunity for multi-functionalization, etc. Again, it is to be emphasized that such examples are merely to illustrate of the myriad possible embodiments of the current invention.

Another benefit of many embodiments of the current invention involves the issue of non-tortuous pathways. In a many applications involving steps such as filtration or separation via column, etc., the surface area of typical matrices is increased by providing holes or pores of the appropriate size in the matrices. The holes/pores provide a greater amount of surface area to come into contact with, e.g., liquids or the like that are passed through the column. However, the pores create tortuous and narrow pathways for analytes to travel through the matrices. Thus, if analytes are to reach an appropriate moiety (e.g., a specific antibody, ligand, etc.) they must travel this gauntlet to do so. In other words, the analytes, etc. are typically prevented from being actively flowed into contact with the relevant surfaces in the interior of the pores. Because of this, the analytes have to "drift" into contact with the appropriate surface or moiety via diffusion. In turn, the diffusion is limited by available time (i.e., how quickly the analyte is being forced, or is moving, through the device), and by the size of the molecules of interest, e.g., larger molecules diffuse more slowly. Typically, higher pressures must also be used to force analytes through such tortuous pathways as well. Pressures can typically force materials to flow through less tortuous paths, e.g., around the matrix entirely. As will be greatly appreciated therefore, another benefit of the current invention is that, in many embodiments, it presents a needed increased surface area (e.g., thus providing a greater number of moieties specific for analytes, etc.), but without forcing the analytes to wind their way through a difficult tortuous path.

The various embodiments of the current invention are adaptable to, and useful for, a great number of different applications. For example, as explained in more detail below, various permutations of the invention can be used in, e.g., binding applications (e.g., microarrays and the like), separations (e.g., HPLC or other similar column separations), bioscaffolds (e.g., as a base for cell culture and/or medical implants, optionally which resist formation of biofilms, etc.), and controlled release matrices, etc. Other uses and embodiments are examined herein.

As will be appreciated by those of skill in the art, in numerous materials the surface properties can provide a great deal of the functionality or use of the material. For example, in various types of molecular separations, the selectivity is provided by interaction of the surface of the column or packing material with the appropriate analytes. Thus, embodiments herein comprise numerous uses of NFS substrates of the invention in various separation procedures and the like. For example, as explained below, the current invention finds application in separation columns (e.g., HPLC, capillary electrophoresis, etc.) as well as thin film separations and the like.

Also, as explained in greater detail below, another aspect of the current invention is its use in DNA arrays (and other similar nucleotide and/or protein assays) where, typically, flat glass slides are used. In the current invention, by coating a surface with nanofibers (e.g., by growing nanofibers thereon) and then spotting or arranging the array on the coated surface, the surface area density, and thus sensitivity, can be increased dramatically without sacrificing hybridization time (as would occur with tortuous path porous coatings, etc.).

In other embodiments, amplified detection of cells or tissue is optionally achieved with metal-terminated nanofibers. In such embodiments, the surface of the fibers is coated with any number of fluorescent molecules. The gold tip optionally has a binding molecule specific to a desired target. Thus, the fiber acts as an arrow targeted at the surface. In usage, many of the nanofibers could "hit" the target and allow detection (i.e., through fluorescence, or, optionally, through other detection means, if the nanofiber is so modified). In yet other embodiments, it will be appreciated that properties such as surface lubricity and wetability are also dramatically altered on a wide variety of materials through creation of an enhanced area nanowire surface.

Examined in more detail below, are other beneficial uses of various embodiments of the current invention. For example, the distinct morphology of the nanofiber surfaces herein can be utilized in numerous biomedical applications such as scaffolding for growth of cell culture (both in vitro and in vivo). In vivo uses can include, e.g., aids in bone formation, etc. Additionally, the surface morphology of some of the embodiments produces surfaces that are resistant to biofilm formation and/or bacterial/microorganismal colonization. Other possible biomedical uses herein, include, e.g., controlled release matrices of drugs, etc. See below.

As also will be appreciated by those of skill in the art, many aspects of the current invention are optionally variable (e.g., surface chemistries on the nanofibers, surface chemistries on any end of the nanofibers or on the substrate surface, etc.). Specific illustration of various modifications, etc. herein, should therefore not be taken as limiting the current invention. Also, it will be appreciated that the length to thickness ratio of the nanofibers herein is optionally varied, as is, e.g., the composition of the nanofibers. Furthermore, a variety of methods can be employed to bring the fibers in contact with surfaces. Additionally, while many embodiments herein comprise nanofibers that are specifically functionalized in one or more ways, e.g., through attachment of moieties or functional groups to the nanofibers, other embodiments comprise nanofibers which are not functionalized. For example, some enhanced surface areas of the invention can comprise, e.g., filters for purification, or the like, based upon molecule size, which are comprised of nanofibers that are not functionalized to particular analytes to be filtered.

II) Nanofibers and Nanofiber Construction

In typical embodiments herein the surfaces (i.e., the nanofiber enhanced area surfaces) and the nanofibers themselves can optionally comprise any number of materials. The actual composition of the surfaces and the nanofibers is based upon a number of possible factors. Such factors can include, for example, the intended use of the enhanced area surfaces, the conditions under which they will be used (e.g., temperature, pH, presence of light (e.g., UV), atmosphere, etc.), the reactions for which they will be used (e.g., separations, bioassays, etc.), the durability of the surfaces and the cost, etc. The ductility and breaking strength of nanowires will vary depending on, e.g., their composition. For example, ceramic ZnO wires can be more brittle than silicon or glass nanowires, while carbon nanotubes may have a higher tensile strength.

As explained more fully below, some possible materials used to construct the nanofibers and nanofiber enhanced surfaces herein, include, e.g., silicon, ZnO, TiO, carbon, carbon nanotubes, glass, and quartz. See below. The nanofibers of the invention are also optionally coated or functionalized, e.g., to enhance or add specific properties. For example, polymers, ceramics or small molecules can optionally be used as coating materials. The optional coatings can impart characteristics such as water resistance, improved mechanical or electrical properties or specificities for certain analytes. Additionally, specific moieties or functional groups can also be attached to or associated with the nanofibers herein.

Of course, it will be appreciated that the current invention is not limited by recitation of particular nanofiber and/or substrate compositions, and that, unless otherwise stated, any of a number of other materials are optionally used in different embodiments herein. Additionally, the materials used to comprise the nanofibers can optionally be the same as the material used to comprise the substrate surfaces or they can be different from the materials used to construct the substrate surfaces.

In yet other embodiments herein, the nanofibers involved can optionally comprise various physical conformations such as, e.g., nanotubules (e.g., hollow-cored structures), etc. A variety of nanofiber types are optionally used in this invention including carbon nanotubes, metallic nanotubes, metals and ceramics.

It is to be understood that this invention is not limited to particular configurations, which can, of course, vary (e.g., different combinations of nanofibers and substrates and optional moieties, etc. which are optionally present in a range of lengths, densities, etc.). It is also to be understood that the terminology used herein is for the purpose of describing particular embodiments only, and is not intended to be limiting. As used in this specification and the appended claims, the singular forms "a," "an," and "the" include plural referents unless the context clearly dictates otherwise. Thus, for example, reference to "a nanofiber" optionally includes a plurality of such nanofibers, and the like. Unless defined otherwise, all scientific and technical terms are understood to have the same meaning as commonly used in the art to which they pertain. For the purpose of the present invention, additional specific terms are defined throughout.

A) Nanofibers

The term "nanofiber" as used herein, refers to a nanostructure typically characterized by at least one physical dimension less than about 1000 nm, less than about 500 nm, less than about 250 nm, less than about 150 nm, less than about 100 nm, less than about 50 nm, less than about 25 nm or even less than about 10 nm or 5 nm. In many cases, the region or characteristic dimension will be along the smallest axis of the structure.

Nanofibers of this invention typically have one principle axis that is longer than the other two principle axes and, thus, have an aspect ratio greater than one, an aspect ratio of 2 or greater, an aspect ratio greater than about 10, an aspect ratio greater than about 20, or an aspect ratio greater than about 100, 200, 500, 1000, or 2000. In certain embodiments, nanofibers herein have a substantially uniform diameter. In some embodiments, the diameter shows a variance less than about 20%, less than about 10%, less than about 5%, or less than about 1% over the region of greatest variability and over a linear dimension of at least 5 nm, at least 10 nm, at least 20 nm, or at least 50 nm. Typically the diameter is evaluated away from the ends of the nanofiber (e.g. over the central 20%, 40%, 50%, or 80% of the nanofiber). In yet other embodiments, the nanofibers herein have a non-uniform diameter (i.e., they vary in diameter along their length). For example, a wide range of diameters could be desirable due to cost considerations and/or to create a more random surface. Also in certain embodiments, the nanofibers of this invention are substantially crystalline and/or substantially monocrystalline.

It will be appreciated that the term nanofiber, can optionally include such structures as, e.g., nanowires, nanowhiskers, semi-conducting nanofibers, carbon and/or boron nanotubes or nanotubules and the like. Also, nanostructures having smaller aspect ratios (e.g., than those described above), such as nanorods, nanotetrapods, nanoposts and the like are also optionally included within the nanofiber definition herein (in certain embodiments). Examples of such other optionally included nanostructures can be found, e.g., in published PCT Application No. WO 03/054953 and the references discussed therein, all of which are incorporated herein by reference in their entirety for all purposes.

The nanofibers of this invention can be substantially homogeneous in material properties, or in certain embodiments they are heterogeneous (e.g. nanofiber heterostructures) and can be fabricated from essentially any convenient material or materials. The nanofibers can comprise "pure" materials, substantially pure materials, doped materials and the like and can include insulators, conductors, and semiconductors. Additionally, while some illustrative nanofibers herein are comprised of silicon (or silicon oxides), as explained above, they optionally can be comprised of any of a number of different materials, unless otherwise stated. Composition of nanofibers can vary depending upon a number of factors, e.g., specific functionalization (if any) to be associated with or attached to the nanofibers, durability, cost, conditions of use, etc. The composition of nanofibers is quite well known to those of skill in the art. As will be appreciated by such skilled persons, the nanofibers of the invention can, thus, be composed of any of a myriad of possible substances (or combinations thereof). Some embodiments herein comprise nanofibers composed of one or more organic or inorganic compound or material. Any recitation of specific nanofiber compositions herein should not be taken as necessarily limiting.

Additionally, the nanofibers of the invention are optionally constructed through any of a number of different methods, and examples listed herein should not be taken as necessarily limiting. Thus, nanofibers constructed through means not specifically described herein, but which fall within the parameters as set forth herein are still nanofibers of the invention and/or are used with the methods of the invention.

In a general sense, the nanofibers of the current invention often (but not exclusively) comprise long thin protuberances (e.g., fibers, nanowires, nanotubules, etc.) grown from a solid, optionally planar, substrate. Of course, in some embodiments herein the nanofibers are deposited onto their ultimate substrates, e.g., the fibers are detached from the substrate on which they are grown and attached to a second substrate. The second substrate need not be planar and, in fact, can comprise a myriad of three-dimensional conformations, as can the substrate on which the nanofibers were grown originally. In some embodiments herein, the substrates are flexible. Also, as explained in greater detail below, nanofibers of the invention can be grown/constructed in, or upon, variously configured surfaces, e.g., within capillary tubes, etc. See infra.

In various embodiments herein, the nanofibers involved are optionally grown on a first substrate and then subsequently transferred to a second substrate which is to have the enhanced surface area. Such embodiments are particularly useful in situations wherein the substrate desired needs to be flexible or conforming to a particular three-dimensional shape that is not readily subjected to direct application or growth of nanofibers thereon. For example, nanofibers can be grown on such rigid surfaces as, e.g., silicon wafers or other similar substrates. The nanofibers thus grown can then optionally be transferred to a flexible backing such as, e.g., rubber or the like. Again, it will be appreciated, however, that the invention is not limited to particular nanofiber or substrate compositions. For example, nanofibers are optionally gown on any of a variety of different surfaces, including, e.g., flexible foils such as aluminum or the like. Additionally, for high temperature growth processes, any metal, ceramic or other thermally stable material is optionally used as a substrate on which to grow nanofibers of the invention. Furthermore, low temperature synthesis methods such as solution phase methods can be utilized in conjunction with an even wider variety of substrates on which to grow nanofibers. For example, flexible polymer substrates and other similar substances are optionally used as substrates for nanofiber growth/attachment.

As one example, the growth of nanofibers on a surface using a gold catalyst has been demonstrated in the literature. Applications targeted for such fibers are based on harvesting them from the substrate and then assembling them into devices. However, in many other embodiments herein, the nanofibers involved in enhanced surface areas are grown in place. Available methods, such as growing nanofibers from gold colloids deposited on surfaces are, thus, optionally used herein. The end product that results is the substrate upon which the fibers are grown (i.e., with an enhanced surface area due to the nanofibers). As will be appreciated, specific embodiments and uses herein, unless stated otherwise, can optionally comprise nanofibers grown in the place of their use and/or through nanofibers grown elsewhere, which are harvested and transferred to the place of their use. For example, many embodiments herein relate to leaving the fibers intact on the growth substrate and taking advantage of the unique properties the fibers impart on the substrate. Other embodiments relate to growth of fibers on a first substrate and transfer of the fibers to a second substrate to take advantage of the unique properties that the fibers impart on the second substrate.

For example, if nanofibers of the invention were grown on, e.g., a non-flexible substrate (e.g., such as some types of silicon wafers) they could be transferred from such non-flexible substrate to a flexible substrate (e.g., such as rubber or a woven layer material). Again, as will be apparent to those of skill in the art, the nanofibers herein could optionally be grown on a flexible substrate to start with, but different desired parameters may influence such decisions.

A variety of methods may be employed in transferring nanofibers from a surface upon which they are fabricated to another surface. For example, nanofibers may be harvested into a liquid suspension, e.g., ethanol, which is then coated onto another surface. Additionally, nanofibers from a first surface (e.g., ones grown on the first surface or which have been transferred to the first surface) can optionally be "harvested" by applying a sticky coating or material to the nanofibers and then peeling such coating/material away from the first surface. The sticky coating/material is then optionally placed against a second surface to deposit the nanofibers. Examples of sticky coatings/materials which are optionally used for such transfer include, but are not limited to, e.g., tape (e.g., 3M Scotch® tape), magnetic strips, curing adhesives (e.g., epoxies, rubber cement, etc.), etc. The nanofibers could be removed from the growth substrate, mixed into a plastic, and then surface of such plastic could be ablated or etched away to expose the fibers.

The actual nanofiber constructions of the invention are optionally complex. For example, FIG. 2 is a photomicrograph of a typical nanofiber construction. As can be seen in FIG. 2, the nanofibers form a complex three-dimensional pattern. The interlacing and variable heights, curves, bends, etc. form a surface which greatly increases the surface area per unit substrate (e.g., as compared with a surface without nanofibers). Of course, in other embodiments herein, it should be apparent that the nanofibers need not be as complex as, e.g., those shown in FIG. 2. Thus, in many embodiments herein, the nanofibers are "straight" and do not tend to bend, curve, or curl. Additionally, in some embodiments, such straight or non-curling fibers are tiled (or substantially most of such nanofibers are), e.g., at a desired orientation or angle, etc. However, such straight nanofibers are still encompassed within the current invention. In either case, the nanofibers present a non-tortuous, greatly enhanced surface area.

B) Functionalization

Some embodiments of the invention comprise nanofiber and nanofiber enhanced area surfaces in which the fibers include one or more functional moiety (e.g., a chemically reactive group) attached to or associated with them. Functionalized nanofibers are optionally used in many different embodiments, e.g., to confer specificity for desired analytes in reactions such as separations or bio-assays, etc. Beneficially, typical embodiments of enhanced surface areas herein are comprised of silicon oxides, which are conveniently modified with a large variety of moieties. Of course, other embodiments herein are comprised of other nanofiber compositions (e.g., polymers, ceramics, metals that are coated by CVD or sol-gel sputtering, etc.) which are also optionally functionalized for specific purposes. Those of skill in the art will be familiar with numerous functionalizations and functionalization techniques which are optionally used herein (e.g., similar to those used in construction of separation columns, bio-assays, etc.).

For example, details regarding relevant moiety and other chemistries, as well as methods for construction/use of such, can be found, e.g., in Hermanson *Bioconjugate Techniques* Academic Press (1996), Kirk-Othmer *Concise Encyclopedia of Chemical Technology* (1999) Fourth Edition by Grayson et al. (ed.) John Wiley & Sons, Inc., New York and in Kirk-Othmer *Encyclopedia of Chemical Technology* Fourth Edition (1998 and 2000) by Grayson et al. (ed.) Wiley Interscience (print edition)/John Wiley & Sons, Inc. (e-format). Further relevant information can be found in *CRC Handbook of Chemistry and Physics* (2003) $83^{rd}$ edition by CRC Press. Details on conductive and other coatings, which can also be incorporated onto nanofibers of the invention by plasma methods and the like can be found in H. S. Nalwa (ed.), *Handbook of Organic Conductive Molecules and Polymers*, John Wiley & Sons 1997. See also, ORGANIC SPECIES THAT FACILITATE CHARGE TRANSFER TO/FROM NANOCRYSTALS U.S. Ser. No. 60/452,232 filed Mar. 4, 2003 by Whiteford et al. Details regarding organic chemistry, relevant for, e.g., coupling of additional moieties to a functionalized surface of nanofibers can be found, e.g., in Greene (1981) *Protective Groups in Organic Synthesis*, John Wiley and Sons, New York, as well as in Schmidt (1996) *Organic Chemistry* Mosby, St Louis, Mo., and March's *Advanced Organic Chemistry Reactions, Mechanisms and Structure*, Fifth Edition (2000) Smith and March, Wiley Interscience New York ISBN 0-471-58589-0, filed Apr. 27, 2004, entitled "Super-hydrophobic Surfaces, Methods of Their Construction and Uses Therefor." Those of skill in the art will be familiar with many other related references and techniques amenable for functionalization of NFS herein.

Thus, again as will be appreciated, the substrates involved, the nanofibers involved (e.g., attached to, or deposited upon, the substrates), and any optional functionalization of the nanofibers and/or substrates, and the like can be optionally varied in various embodiments. For example, the length, diameter, conformation and density of the fibers can be varied, as can the composition of the fibers and their surface chemistry.

C) Density and Related Issues

In terms of density, it will be appreciated that by including more nanofibers emanating from a surface, one automatically increases the amount of surface area that is extended from the basic underlying substrate. This, thus, increases the amount of intimate contact area between the surface and any analyte, etc. coming into contact with the nanofiber surfaces. As explained in more detail below, the embodiments herein optionally comprise a density of nanofibers on a surface of from about 0.1 to about 1000 or more nanofibers per micrometer$^2$ of the substrate surface. Again, here too, it will be appreciated that such density depends upon factors such as the diameter of the individual nanofibers, etc. See below. The nanowire density influences the enhanced surface area, since a greater number of nanofibers will tend to increase the overall amount of area of the surface. Therefore, the density of the nanofibers herein typically has a bearing on the intended use of the enhanced surface area materials because such density is a factor in the overall area of the surface.

For example, an illustrative typical flat planar substrate, e.g., a silicon oxide chip or a glass slide, can comprise 10,000 possible binding sites for an analyte or 10,000 possible functionalization sites, etc. per square micron (i.e., within a square micron footprint). However, if such a substrate surface were coated with nanofibers, then the available surface area would be much greater. In some embodiments herein each nanofiber on a surface comprises about 1 square micron in surface area (i.e., the sides and tip of each nanofiber present that much surface area). If a comparable square micron of substrate comprised from 10 to about 100 nanofibers per square micron, the available surface area is thus 10 to 100 times greater than a plain flat surface. Therefore, in the current illustration, an enhanced surface area would have 100,000 to 10,000,000 possible binding sites, functionalization sites, etc. per square micron footprint. It will be appreciated that the density of nanofibers on a substrate is influenced by, e.g., the diameter of the nanofibers and any functionalization of such fibers, etc.

Different embodiments of the invention comprise a range of such different densities (i.e., number of nanofibers per unit area of a substrate to which nanofibers are attached). The number of nanofibers per unit area can optionally range from about 1 nanofiber per 10 micron$^2$ up to about 200 or more nanofibers per micron$^2$; from about 1 nanofiber per micron$^2$ up to about 150 or more nanofibers per micron$^2$; from about 10 nanofibers per micron$^2$ up to about 100 or more nanofibers per micron$^2$; or from about 25 nanofibers per micron$^2$ up to about 75 or more nanofibers per micron$^2$. In yet other embodiments, the density can optionally range from about 1 to 3 nanowires per square micron to up to approximately 2,500 or more nanowires per square micron.

In terms of individual fiber dimensions, it will be appreciated that by increasing the thickness or diameter of each individual fiber, one will again, automatically increase the overall area of the fiber and, thus, the overall area of the substrate. The diameter of nanofibers herein can be controlled through, e.g., choice of compositions and growth conditions of the nanofibers, addition of moieties, coatings or the like, etc. Preferred fiber thicknesses are optionally between from about 5 nm up to about 1 micron or more (e.g., 5 microns); from about 10 nm to about 750 nanometers or more; from about 25 nm to about 500 nanometers or more; from about 50 nm to about 250 nanometers or more, or from about 75 nm to about 100 nanometers or more. In some embodiments, the nanofibers comprise a diameter of approximately 40 nm.

In addition to diameter, surface area of nanofibers (and therefore surface area of a substrate to which the nanofibers are attached) also is influenced by length of the nanofibers. Of course, it will also be understood that for some fiber materials, increasing length may yield increasing fragility. Accordingly, preferred fiber lengths will typically be between about 2 microns up to about 1 mm or more; from about 10 microns to about 500 micrometers or more; from about 25 microns to about 250 microns or more; or from about 50 microns to about 100 microns or more. Some embodiments comprise nanofibers of approximately 50 microns in length while yet other embodiments can comprise lengths of from about 0.5 microns to about 10 microns. Some embodiments herein comprise nanofibers of approximately 40 nm in diameter and approximately 50 microns in length.

Nanofibers herein can present a variety of aspect ratios. Thus, nanofiber diameter can comprise, e.g., from about 5 nm up to about 1 micron or more (e.g., 5 microns); from about 10 nm to about 750 nanometers or more; from about 25 nm to about 500 nanometers or more; from about 50 nm to about 250 nanometers or more, or from about 75 nm to about 100 nanometers or more, while the lengths of such nanofibers can comprise, e.g., from about 2 microns (e.g., 0.5 microns) up to about 1 mm or more; from about 10 microns to about 500 micrometers or more; from about 25 microns to about 250 microns or more; or from about 50 microns to about 100 microns or more Fibers that are, at least in part, elevated above a surface are particularly preferred, e.g., where at least a portion of the fibers in the fiber surface are elevated at least 10 nm, or even at least 100 nm above a surface, in order to provide enhanced surface area available for contact with, e.g., an analyte, etc.

Again, as seen in FIG. 2, the nanofibers optionally form a complex three-dimensional structure. The degree of such complexity depends in part upon, e.g., the length of the nanofibers, the diameter of the nanofibers, the length:diameter aspect ratio of the nanofibers, moieties (if any) attached to the nanofibers, and the growth conditions of the nanofibers, etc. The bending, interlacing, etc. of nanofibers, which help affect the degree of enhanced surface area available, are optionally manipulated through, e.g., control of the number of nanofibers per unit area as well as through the diameter of the nanofibers, the length and the composition of the nanofibers, etc. Thus, it will be appreciated that enhanced surface area of nanofiber substrates herein is optionally controlled through manipulation of these and other parameters. It will also be appreciated that the degree of "tortuous-ness" of any path an analyte takes through or past a nanofiber substrate of the invention can also be influenced by such factors.

Also, in some, but not all, embodiments herein, the nanofibers of the invention comprise bent, curved, or even curled forms. As can be appreciated, if a single nanofiber snakes or coils over a surface (but is still just a single fiber per unit area bound to a first surface), the fiber can still provide an enhanced surface area due to its length, etc.

D) Nanofiber Construction

As will be appreciated, the current invention is not limited by the means of construction of the nanofibers herein. For example, while some of the nanofibers herein are composed of silicon, the use of silicon should not be construed as necessarily limiting. The formation of nanofibers is possible through a number of different approaches that are well known to those of skill in the art, all of which are amenable to embodiments of the current invention.

Typical embodiments herein can be used with various methods of nanostructure fabrication, as will be known by those skilled in the art, as well as methods mentioned or described herein. In other words, a variety of methods for making nanofibers and nanofiber containing structures have been described and can be adapted for use in various of the methods, systems and devices of the invention.

The nanofibers can be fabricated of essentially any convenient material (e.g., a semiconducting material, a ferroelectric material, a metal, ceramic, polymers, etc.) and can comprise essentially a single material or can be heterostructures. For example, the nanofibers can comprise a semiconducting material, for example a material comprising a first element selected from group 2 or from group 12 of the periodic table and a second element selected from group 16 (e.g., ZnS, ZnO, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and like materials); a material comprising a first element selected from group 13 and a second element selected from group 15 (e.g., GaN, GaP, GaAs, GaSb, InN, InP, InAs, InSb, and like materials); a material comprising a group 14 element (Ge, Si, and like materials); a material such as PbS, PbSe, PbTe, AlS, AlP, and AlSb; or an alloy or a mixture thereof.

In some embodiments herein, the nanofibers are optionally comprised of silicon or a silicon oxide. It will be understood by one of skill in the art that the term "silicon oxide" as used herein can be understood to refer to silicon at any level of oxidation. Thus, the term silicon oxide can refer to the chemical structure $SiO_x$, wherein x is between 0 and 2 inclusive. In other embodiments, the nanofibers can comprise, e.g., silicon, glass, quartz, plastic, metal, polymers, TiO, ZnO, ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, PbS, PbSe, PbTe, AlS, AlP, AlSb, $SiO_1$, $SiO_2$, silicon carbide, silicon nitride, polyacrylonitrile (PAN), polymethylmethacrylate (PMMA), polydimethylsiloxane (PDMS), poly(ethylene terephthalate) (PETG), polyaniline, metal-organic polymers, polycarbonate, organic polymers, polyetherketone, polyimide, aromatic polymers, aliphatic polymers, polyvinyl alcohol, polystyrene, polyester, polyamide, and combinations thereof.

It will be appreciated that in some embodiments, the nanofibers can comprise the same material as one or more substrate surface (e.g., a surface to which the nanofibers are attached or associated), while in other embodiments, the nanofibers comprise a different material than the substrate surface. Additionally, the substrate surfaces can optionally comprise any one or more of the same materials or types of materials as do the nanofibers (e.g., such as the materials illustrated herein).

As previously stated, some, but by no means all, embodiments herein comprise silicon nanofibers. Common methods for making silicon nanofibers include vapor liquid solid growth (VLS), laser ablation (laser catalytic growth) and thermal evaporation. See, for example, Morales et al. (1998) "A Laser Ablation Method for the Synthesis of Crystalline Semiconductor Nanowires" Science 279, 208-211 (1998). In one example approach, a hybrid pulsed laser ablation/chemical vapor deposition (PLA-CVD) process for the synthesis of semiconductor nanofibers with longitudinally ordered heterostructures, and variations thereof, can be used. See, Wu et al. (2002) "Block-by-Block Growth of Single-Crystalline Si/SiGe Superlattice Nanowires," Nano Letters Vol. 2:83-86.

In general, multiple methods of making nanofibers have been described and can be applied in the methods, systems and devices herein. In addition to Morales et al. and Wu et al. (above), see, for example, Lieber et al. (2001) "Carbide Nanomaterials" U.S. Pat. No. 6,190,634 B1; Lieber et al. (2000) "Nanometer Scale Microscopy Probes" U.S. Pat. No. 6,159,742; Lieber et al. (2000) "Method of Producing Metal Oxide Nanorods" U.S. Pat. No. 6,036,774; Lieber et al. (1999) "Metal Oxide Nanorods" U.S. Pat. No. 5,897,945; Lieber et al. (1999) "Preparation of Carbide Nanorods" U.S. Pat. No. 5,997,832; Lieber et al. (1998) "Covalent Carbon Nitride Material Comprising $C_2N$ and Formation Method" U.S. Pat. No. 5,840,435; Thess, et al. (1996) "Crystalline Ropes of Metallic Carbon Nanotubes" Science 273:483-486; Lieber et al. (1993) "Method of Making a Superconducting Fullerene Composition By Reacting a Fullerene with an Alloy Containing Alkali Metal" U.S. Pat. No. 5,196,396; and Lieber et al. (1993) "Machining Oxide Thin Films with an Atomic Force Microscope: Pattern and Object Formation on the Nanometer Scale" U.S. Pat. No. 5,252,835. Recently, one dimensional semiconductor heterostructure nanocrystals, have been described. See, e.g., Bjork et al. (2002) "One-dimensional Steeplechase for Electrons Realized" Nano Letters Vol. 2:86-90.

It should be noted that some references herein, while not specific to nanofibers, are optionally still applicable to the invention. For example, background issues of construction conditions and the like are applicable between nanofibers and other nanostructures (e.g., nanocrystals, etc.).

In another approach which is optionally used to construct nanofibers of the invention, synthetic procedures to prepare individual nanofibers on surfaces and in bulk are described, for example, by Kong, et al. (1998) "Synthesis of Individual Single-Walled Carbon Nanotubes on Patterned Silicon Wafers," Nature 395:878-881, and Kong, et al. (1998) "Chemical Vapor Deposition of Methane for Single-Walled Carbon Nanotubes," Chem. Phys. Lett. 292:567-574.

In yet another approach, substrates and self assembling monolayer (SAM) forming materials can be used, e.g., along with microcontact printing techniques to make nanofibers, such as those described by Schon, Meng, and Bao, "Self-assembled monolayer organic field-effect transistors," Nature 413:713 (2001); Zhou et al. (1997) "Nanoscale Metal/Self-Assembled Monolayer/Metal Heterostructures," Applied Physics Letters 71:611; and WO 96/29629 (Whitesides, et al., published Jun. 26, 1996).

In some embodiments herein, nanofibers (e.g., nanowires) can be synthesized using a metallic catalyst. A benefit of such embodiments allows use of unique materials suitable for surface modifications to create enhanced properties. A unique property of such nanofibers is that they are capped at one end with a catalyst, typically gold. This catalyst end can optionally be functionalized using, e.g., thiol chemistry without affecting the rest of the wire, thus, making it capable of bonding to an appropriate surface. In such embodiments, the result of such functionalization, etc., is to make a surface with end-linked nanofibers. These resulting "fuzzy" surfaces, therefore, have increased surface areas (i.e., in relation to the surfaces without the nanofibers) and other unique properties. In some such embodiments, the surface of the nanowire and/or the target substrate surface is optionally chemically modified (typically, but not necessarily, without affecting the gold tip) in order to give a wide range of properties useful in many applications.

In other embodiments, to slightly increase or enhance a surface area, the nanofibers are optionally laid "flat" (e.g., substantially parallel to the substrate surface) by chemical or electrostatic interaction on surfaces, instead of end-linking the nanofibers to the substrate. In yet other embodiments herein, techniques involve coating the base surface with functional groups which repel the polarity on the nanofiber so that the fibers do not lay on the surface but are end-linked.

Synthesis of nanostructures, e.g., nanocrystals, of various compositions as can be included and/or utilized in the embodiments of the present invention, is described in, e.g., Peng et al. (2000) "Shape control of CdSe nanocrystals" *Nature* 404:59-61; Puntes et al. (2001) "Colloidal nanocrystal shape and size control: The case of cobalt" *Science* 291:2115-2117; U.S. Pat. No. 6,306,736 to Alivisatos et al. (Oct. 23, 2001) entitled "Process for forming shaped group III-V semiconductor nanocrystals, and product formed using process"; U.S. Pat. No. 6,225,198 to Alivisatos et al. (May 1, 2001) entitled "Process for forming shaped group II-VI semiconductor nanocrystals, and product formed using process"; U.S. Pat. No. 5,505,928 to Alivisatos et al. (Apr. 9, 1996) entitled "Preparation of III-V semiconductor nanocrystals"; U.S. Pat. No. 5,751,018 to Alivisatos et al. (May 12, 1998) entitled "Semiconductor nanocrystals covalently bound to solid inorganic surfaces using self-assembled monolayers"; U.S. Pat. No. 6,048,616 to Gallagher et al. (Apr. 11, 2000) entitled "Encapsulated quantum sized doped semiconductor particles and method of manufacturing same"; and U.S. Pat. No. 5,990,479 to Weiss et al. (Nov. 23, 1999) entitled "Organo luminescent semiconductor nanocrystal probes for biological applications and process for making and using such probes."

Additional information on growth of nanofibers, such as nanowires, having various aspect ratios, including nanofibers with controlled diameters, is described in, e.g., Gudiksen et al. (2000) "Diameter-selective synthesis of semiconductor nanowires" *J. Am. Chem. Soc.* 122:8801-8802; Cui et al. (2001) "Diameter-controlled synthesis of single-crystal silicon nanowires" *Appl. Phys. Lett.* 78:2214-2216; Gudiksen et al. (2001) "Synthetic control of the diameter and length of single crystal semiconductor nanowires" *J. Phys. Chem. B* 105:4062-4064; Morales et al. (1998) "A laser ablation method for the synthesis of crystalline semiconductor nanowires" *Science* 279:208-211; Duan et al. (2000) "General synthesis of compound semiconductor nanowires" *Adv. Mater.* 12:298-302; Cui et al. (2000) "Doping and electrical transport in silicon nanowires" *J. Phys. Chem. B* 104:5213-5216; Peng et al. (2000), supra; Puntes et al. (2001), supra; U.S. Pat. No. 6,225,198 to Alivisatos et al., supra; U.S. Pat. No. 6,036,774 to Lieber et al. (Mar. 14, 2000) entitled "Method of producing metal oxide nanorods"; U.S. Pat. No. 5,897,945 to Lieber et al. (Apr. 27, 1999) entitled "Metal oxide nanorods"; U.S. Pat. No. 5,997,832 to Lieber et al. (Dec. 7, 1999) "Preparation of carbide nanorods"; Urbau et al. (2002) "Synthesis of single-crystalline perovskite nanowires composed of barium titanate and strontium titanate" *J. Am. Chem. Soc.*, 124:1186; Yun et al. (2002) "Ferroelectric Properties of Individual Barium Titanate Nanowires Investigated by Scanned Probe Microscopy" *Nano Letters* 2, 447; and published PCT application nos. WO 02/17362, and WO 02/080280.

Growth of branched nanofibers (e.g., nanotetrapods, tripods, bipods, and branched tetrapods) is described in, e.g., Jun et al. (2001) "Controlled synthesis of multi-armed CdS nanorod architectures using monosurfactant system" *J. Am. Chem. Soc.* 123:5150-5151; and Manna et al. (2000) "Synthesis of Soluble and Processable Rod-, Arrow-, Teardrop-, and Tetrapod-Shaped CdSe Nanocrystals" *J. Am. Chem. Soc.* 122:12700-12706. Synthesis of nanoparticles is described in, e.g., U.S. Pat. No. 5,690,807 to Clark Jr. et al. (Nov. 25, 1997) entitled "Method for producing semiconductor particles"; U.S. Pat. No. 6,136,156 to El-Shall, et al. (Oct. 24, 2000) entitled "Nanoparticles of silicon oxide alloys"; U.S. Pat. No. 6,413,489 to Ying et al. (Jul. 2, 2002) entitled "Synthesis of nanometer-sized particles by reverse micelle mediated techniques"; and Liu et al. (2001) "Sol-Gel Synthesis of Free-Standing Ferroelectric Lead Zirconate Titanate Nanoparticles" *J. Am. Chem. Soc.* 123:4344. Synthesis of nanoparticles is also described in the above citations for growth of nanocrystals, and nanofibers such as nanowires, branched nanowires, etc.

Synthesis of core-shell nanofibers, e.g., nanostructure heterostructures, is described in, e.g., Peng et al. (1997) "Epitaxial growth of highly luminescent CdSe/CdS core/shell nanocrystals with photostability and electronic accessibility" *J. Am. Chem. Soc.* 119:7019-7029; Dabbousi et al. (1997) "(CdSe)ZnS core-shell quantum dots: Synthesis and characterization of a size series of highly luminescent nanocrystallites" *J. Phys. Chem. B* 101:9463-9475; Manna et al. (2002) "Epitaxial growth and photochemical annealing of graded CdS/ZnS shells on colloidal CdSe nanorods" *J. Am. Chem. Soc.* 124:7136-7145; and Cao et al. (2000) "Growth and properties of semiconductor core/shell nanocrystals with InAs cores" *J. Am. Chem. Soc.* 122:9692-9702. Similar approaches can be applied to growth of other core-shell nanostructures. See, for example, U.S. Pat. No. 6,207,229 (Mar. 27, 2001) and U.S. Pat. No. 6,322,901 (Nov. 27, 2001) to Bawendi et al. entitled "Highly luminescent color-selective materials."

Growth of homogeneous populations of nanofibers, including nanofibers heterostructures in which different materials are distributed at different locations along the long axis of the nanofibers is described in, e.g., published PCT application Nos. WO 02/17362, and WO 02/080280; Gudiksen et al. (2002) "Growth of nanowire superlattice structures for nanoscale photonics and electronics" *Nature* 415:617-620; Bjork et al. (2002) "One-dimensional steeplechase for electrons realized" *Nano Letters* 2:86-90; Wu et al. (2002) "Block-by-block growth of single-crystalline Si/SiGe superlattice nanowires" *Nano Letters* 2, 83-86; and U.S. patent application 60/370,095 (Apr. 2, 2002) to Empedocles entitled "Nanowire heterostructures for encoding information." Similar approaches can be applied to growth of other heterostructures and applied to the various methods and systems herein.

In some embodiments the nanofibers used to create enhanced surface areas can be comprised of nitride (e.g., AlN, GaN, SiN, BN) or carbide (e.g., SiC, TiC, Tungsten carbide, boron carbide) in order to create nanofibers with high strength and durability. Alternatively, such nitrides/carbides are used as hard coatings on lower strength (e.g., silicon or ZnO) nanofibers. While the dimensions of silicon nanofibers are excellent for many applications requiring enhanced surface area (e.g., see, throughout and "Structures, Systems and Methods for Joining Articles and Materials and Uses Therefore," filed Apr. 17, 2003, U.S. Ser. No. 60/463,766, etc.) other applications require nanofibers that are less brittle and which break less easily. Therefore, some embodiments herein take advantage of materials such as nitrides and carbides which have higher bond strengths than, e.g., Si, $SiO_2$ or ZnO. The nitrides and carbides are optionally used as coatings to strengthen the weaker nanofibers or even as nanofibers themselves.

Carbides and nitrides can be applied as coatings to low strength fibers by deposition techniques such as sputtering and plasma processes. In some embodiments, to achieve high strength nanocoatings of carbide and nitride coatings, a random grain orientation and/or amorphous phase are grown to avoid crack propagation. Optimum conformal coating of the nanofibers can optionally be achieved if the fibers are growing perpendicular to a substrate surface. The hard coating for fibers in such orientation also acts to enhance the adhesion of the fibers to the substrate. For fibers that are randomly oriented, the coating is preferential to the upper layer of fibers.

Low temperature processes for creation of silicon nanofibers are achieved by the decomposition of silane at about 400° C. in the presence of a gold catalyst. However, as previously stated, silicon nanofibers are too brittle for some applications to form a durable nanofiber matrix (e.g., an enhanced surface area). Thus, formation and use of, e.g., SiN is optionally utilized in some embodiments herein. In those embodiments, $NH_3$, which has decomposition at about 300° C., is used to combine with silane to form SiN nanofibers (also by using a gold catalyst). Other catalytic surfaces to form such nanofibers can include, e.g., Ti, Fe, etc.

Forming carbide and nitride nanofibers directly from a melt can sometimes be challenging since the temperature of the liquid phase is typically greater than 1000° C. However, a nanofiber can be grown by combining the metal component with the vapor phase. For example, GaN and SiC nanofibers have been grown (see, e.g., Peidong, Lieber, supra) by exposing Ga melt to $NH_3$ (for GaN) and graphite with silane (SiC). Similar concepts are optionally used to form other types of carbide and nitride nanofibers by combing metal-organic vapor species, e.g., tungsten carbolic [W(CO)6] on a carbon surface to form tungsten carbide (WC), or titanium dimethoxy dineodecanoate on a carbon surface to form TiC. It will be appreciated that in such embodiments, the temperature, pressure, power of the sputtering and the CVD process are all optionally varied depending upon, e.g., the specific parameters desired in the end nanofibers. Additionally, several types of metal organic precursors and catalytic surfaces used to form the nanofibers, as well as, the core materials for the nanofibers (e.g., Si, ZnO, etc.) and the substrates containing the nanofibers, are all also variable from one embodiment to another depending upon, e.g., the specific enhanced nanofiber surface area to be constructed.

Some embodiments herein comprise methods for improving the density and control of nanowire growth as they relate to generating a nanostructured surface coating of substrates. Such methods include repetitive cycling of nanowire synthesis and gold fill deposition to make "nano-trees" as well as the co-evaporation of material that will not form a silicon eutectic, thus, disrupting nucleation and causing smaller wire formation Such methods are utilized in the creation of ultra-high capacity surface based structures through nanofiber growth technology for, e.g., diagnostic arrays, adhesion promotion between surfaces, non-fouling surfaces, filtration, etc.). Use of single-step metal film type process in creation of nanofibers limits the ability to control the starting metal film thickness, surface roughness, etc., and, thus, the ability of control nucleation from the surface.

In some embodiments of nanofiber enhanced surfaces it can be desirable to produce multibranched nanofibers. Such multibranched nanofibers could allow an even greater increase in surface area than would occur with non-branched nanofiber surfaces. To produce multibranched nanofibers gold film is optionally deposited onto a nanofiber surface (i.e., one that has already grown nanofibers). When placed in a furnace, fibers perpendicular to the original growth direction can result, thus, generating branches on the original nanofibers. Colloidal metal particles can optionally be used instead of gold film to give greater control of the nucleation and branch formation. The cycle of branching optionally could be repeated multiple times, e.g., with different film thicknesses, different colloid sizes, or different synthesis times, to generate additional branches having varied dimensions. Eventually, the branches between adjacent nanofibers could optionally touch and generate an interconnected network. Sintering is optionally used to improve the binding of the fine branches.

In yet other embodiments, it is desirable to form finer nanofibers (e.g., nanowires). To accomplish this, some embodiments herein optionally use a non-alloy forming material during gold or other alloy forming metal evaporation. Such material, when introduced in a small percentage can optionally disrupt the metal film to allow it to form smaller droplets during wire growth and, thus, correspondingly finer wires.

Such approaches can allow improved control of nanofiber formation and allow generation of finer and more numerous nanofibers from a slightly thicker initial metal film layer. In applications such as nanoarrays, etc., the improved control can optionally improve the signal ratio from the nanofibers to the planar surface or just add a greater degree of control. Possible materials for use in finer nanofiber construction include, e.g., Ti, $Al_2O_3$ and $SiO_2$.

In yet other embodiments, post processing steps such as vapor deposition of glass can allow for greater anchoring or mechanical adhesion and interconnection between nanofibers, thus, improving mechanical robustness in applications requiring additional strength as well as increasing the overall surface to volume of the nanostructure surface.

The present invention can be used with structures that may fall outside of the size range of typical nanostructures. For example, Haraguchi et al. (U.S. Pat. No. 5,332,910) describes nanowhiskers which are optionally used herein. Semi-conductor whiskers are also described by Haraguchi et al. (1994) "Polarization Dependence of Light Emitted from GaAs p-n junctions in quantum wire crystals" *J. Appl. Phys.* 75(8): 4220-4225; Hiruma et al. (1993) "GaAs Free Standing Quantum Sized Wires," *J. Appl. Phys.* 74(5):3162-3171; Haraguchi et al. (1996) "Self Organized Fabrication of Planar GaAs Nanowhisker Arrays"; and Yazawa (1993) "Semiconductor Nanowhiskers" *Adv. Mater.* 5(78):577-579. Such nanowhiskers are optionally nanofibers of the invention. While the above references (and other references herein) are optionally used for construction and determination of parameters of nanofibers of the invention, those of skill in the art will be familiar with other methods of nanofiber construction/design, etc. which can also be amenable to the methods and devices herein.

III) Exemplary Embodiments of Nanofiber Enhanced Surface Area Substrates

While modification of surfaces to enhance their properties is a standard process, this invention covers the fabrication, e.g., growth or placement, of nanofibers (and optionally modification of such fibers with moieties) on the surface of articles for performance enhancement. In regard to growth of nanofibers in place, examples include the growth of silicon nanofibers on a glass substrate to increase its surface area. Many surfaces and shapes are optionally coated with nanofibers to increase their surface area including, e.g., optical lenses; the inside of tubes (e.g., for separations) or the outside of tubes (e.g., for catheters, etc.); flat surfaces such as glass; or particles such as those present in HPLC packings. Thus, for example, enhanced glass or other separating material would be capable of adsorbing more molecules in applications such as DNA arrays or immunoassays. See below. The invention also includes embodiments wherein nanofibers are grown inside of, e.g., a capillary to form a high surface area separation matrix for capillary chromatography. See below. Yet other embodiments include nanofibers grown in place to enhance the insulation properties of window glass by reducing convection at its surface. Additionally, a Velcro®-like surface is also made by growing a very dense web of nanofibers on one surface (optionally constraining it physically during growth) to make loops and a less dense surface that provides hooks on the other surface. Nanofiber surfaces optionally have tremendously higher bond strengths with adhesives due to the increased surface area that can become entwined with the adhesive. For this and other nanofiber adhesion methods, see, e.g., "Structures, Systems and Methods for Joining Articles and Materials and Uses Therefore," filed April 17, U.S. Ser. No. 60/463,766 and "Structures, Systems and Methods for Joining Articles and Materials and Uses Therefore," filed Sep. 12, 2003, both of which are incorporated herein in their entirety for all purposes. Other embodiments herein comprise the use of the nanofiber surfaces of the invention as bioscaffolds for, e.g., high density cell culture and increased interaction and bonding of medical implants through use of nanofiber enhanced area surfaces. A number of further examples of uses of nanofiber surfaces, e.g., in medical applications, etc., and which can utilize aspects of the current invention and aspects of which the current invention can utilize can be found in, e.g., U.S. Ser. No. 60/549,711 filed Mar. 2, 2004 entitled "Medical Device Applications of Nanostructured Surfaces"; U.S. Ser. No. 60/541,463, filed Feb. 2, 2004 entitled "Porous Substrates, Articles, Systems and Compositions Comprising Nanofibers and Methods of Their Use and Production"; U.S. Ser. No. 60/466,229, filed Apr. 28, 2003, and Ser. No. 10/833,944 filed Apr. 27, 2004, both entitled "Super-hydrophobic Surfaces, Methods of Their Construction and Uses Therefor," and U.S. application Ser. Nos. 10/661,381, filed Sep. 12, 2003 and 60/463,766, filed Apr. 17, 2003 and Ser. No. 10/825,861 (filed Apr. 16, 2004) and Ser. No. 10/828,100 (filed Apr. 19, 2004) all entitled "Structures, Systems and Methods for Joining Articles and Materials and Uses Therefor," all of which are incorporated herein in their entirety for all purposes. Even though macrofiber surfaces (usually formed by abrasion or depositions) are more common than nanofiber ones, they do not have a comparable surface area to a nanofiber surface herein.

It should be appreciated that specific embodiments and illustrations herein of uses or devices, etc. which comprise nanofiber enhanced surface areas should not be construed as necessarily limiting. In other words, the current invention is illustrated by the descriptions herein, but is not constrained by individual specifics of the descriptions unless specifically stated. The above embodiments are illustrative of various uses/applications of the enhanced surface area nanofiber surfaces and constructs thereof. Again, the enumeration of specific embodiments herein is not to be taken as necessarily limiting on other uses/applications which comprise the enhanced surface area nanofiber structures of the current invention.

Not only are nanofiber enhanced surface area applications useful for traditional activities (e.g., filtering, assays, etc.), but nanofibers densely arranged on a surface also exhibit novel characteristics that can enable applications that are otherwise impossible or impractical. For example, the nanofibers can be treated to prevent wetting by various solvents (hydrophobicity, in the case of water as the solvent) or to enhance wetting (e.g., hydrophilicity). Thus, illustrative embodiments of uses for nanofiber enhanced surface area materials can include, e.g., super-hydrophobically (or more generally lyophobically or liquidphobically or lipophobically or amphiphobically) treated materials, gas-to-liquid exchangers (e.g., artificial lungs), platen printing, non-fouling boilers or heat exchangers, anti-icing surfaces, e.g., for aircraft or the like, barrier layers for waste ponds and underground tanks to prevent underground toxic plumes, building material additives (e.g., shingles, siding, subterranean concrete), etc. See, e.g., "Super-Hydrophobic Surfaces, Methods of Their Construction and Uses Therefor," filed Apr. 28, 2003, U.S. Ser. No. 60/466,229, and Ser. No. 10/833,944 filed Apr. 27, 2004, all of which are incorporated herein in their entirety for all purposes. Alternatively, hydrophilically treated nanofiber enhanced area materials can include, e.g., high-efficiency volatizers (evaporators) and high-efficiency condensers, etc.

Other applications of the current invention optionally utilize a layer of gas trapped between a liquid and the substrate surface (i.e., a gas layer amongst and between the nanofibers). For example, gas-to-liquid exchange between the two phases can optionally occur. In some embodiments, the enhanced surface area nanofiber substrate comprises a porous layer, thus gas flow on the side of the substrate opposite the liquid can diffuse through the substrate and nanofiber layer to reach the liquid. In embodiments wherein the substrate is gas impermeable, gas flow can be parallel to the surface of the nanofiber substrate and "flow" between the nanofibers (i.e., between the liquid and the substrate surface). Applications optionally include, e.g., artificial lungs (e.g., blood as the liquid and air or oxygen as the gas diffusing in), chemical reactors, bioreactors (e.g., with $O_2$ and $CO_2$ as the diffusing species), sewage disposal, etc.

In other embodiments herein, hydrophilically treated enhanced surface area materials tend to wet thoroughly and immediately. It will be appreciated, and is illustrated in more detail below, that even non-functionalized nanofiber surface area substrates display a wicking effect. See below. The fibers within the wetted area are optionally made of a material which has a much higher thermal conductivity than the liquid. This optionally provides a mechanism for greater thermal fluxes than would occur on a flat surface (i.e., one that does not have an enhanced surface area).

For example, it is contemplated that evaporation of liquids, e.g., in high-efficiency volatizers, with humidifiers, etc. can use such enhanced surface areas. Nanofiber covered surfaces (i.e., enhanced surface areas) with an optional affinity for the substance to be evaporated and a means of transferring heat to the nanowires are thought to be ideal for this purpose. Heat transfer can be conductive, e.g., through the substrate, or radiative. Heat can be also generated within the nanofiber layer itself, e.g., by chemical reaction with catalyst coated nanofibers. Applications can optionally include combustors in gas turbines or steam powerplants, space heaters, and chemical reactors. In some typical embodiments herein the structure of the nanofiber substrates, even when not functionalized with, e.g., hydrophilic moieties, acts as an effective wick for liquids placed upon the substrate. Example 1 below, displays a graph comparing the wicking of water on a planar silicon surface against that on a nanofiber enhanced surface area substrate of the invention. As can be seen, wicking occurs much more rapidly with the substrates of the invention. As will be gathered from the representative examples herein, such property can be utilized to, e.g., quickly apply coatings of materials upon a surface that are, in typical embodiments, several microns deep and of an even thickness. Such spreading is done without additional mechanical means and occurs as a function of the surface morphology of the substrates.

Evaporation of liquids can also be useful for cooling. High efficiency heat exchangers are contemplated to transfer heat into the evaporating liquid, such as occurs in the evaporator in an air conditioner or steam powerplant.

The same property that makes evaporation efficient on a nanofiber covered surface makes condensation efficient there as well. The difference is that heat is removed from the condensing liquid. Applications again include air conditioning or steam powerplants or other high efficiency condensers. Of course, it will be appreciated that the wicking abilities, hydrophobic/hydrophilic properties, heat transfer, etc. of nanofiber enhanced surfaces are equally applicable to other embodiments herein (e.g., see below).

A) Micro-Patterning of Enhanced Surface Area Substrates

In some embodiments, the invention comprises methods to selectively modify or create enhanced surface area substrates as well as such enhanced substrates themselves and devices comprising the same. As will be appreciated, e.g., and as is described herein, such methods and devices are applicable to a wide range of uses and can be created in any of a number of ways (several of which are illustrated herein). For example, in some embodiments, the invention comprises methods to selectively modify or create a substrate surface such that the probability of placing nanoscopic wires/tubes across pre-positioned metal electrodes is increased.

As will be appreciated, the enhanced surface areas provided by surfaces containing grown nanofibers can provide significant advantages as, e.g., substrates for biological arrays. One advantage arises due to increased density of probes in a given region of substrate. However, because of the enhanced wicking capability of grown nanofiber enhanced surfaces, the application of chemistry to link specific bio-molecules, etc. to defined regions in a congruous lawn of nanofibers is sometimes difficult to control. Therefore, some embodiments herein comprise methods that can allow spatially controlled chemistry to be applied to nanofiber enhanced surfaces. Such control can facilitate the utility of enhanced nanofiber surfaces in real applications.

Several approaches are included in the embodiments herein for selectively patterning areas of nanofiber growth or placement on substrates so as to generate spatially defined regions to apply specific chemistry. In such approaches, the term "substrate" relates to the material upon which the fibers are grown (or, in some embodiments, placed or deposited upon). In different situations, substrates are optionally comprised of, e.g., silicon wafer, glass, quartz, or any other material appropriate for VLS based nanowire growth or the like. For example, substrates and nanofibers upon them can be independently composed of, e.g., silicon, glass, quartz, plastic, ceramic, metal, polymers, TiO, ZnO, ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, PbS, PbSe, PbTe, AlS, AlP, AlSb, $SiO_1$, $SiO_2$, silicon carbide, silicon nitride, polyacrylonitrile (PAN), polyetherketone, polyimide, aromatic polymers, aliphatic polymers, etc. See also, above. Those of skill in the art will be familiar with other possible nanofiber materials.

In some embodiments herein, micro-patterning of enhanced surface area substrates is optionally created by lithographically applying planar regions of gold to a substrate as the standard growth initiator through use of conventional lithographic approaches which are well known to those of skill in the art. Nanofibers (e.g., VLS nanowires) are then grown, e.g., in the manner of Peidong Yang, *Advanced Materials*, Vol. 13, No. 2, January 2001.

In other embodiments, the arrays can be created by chemically precoating a substrate through conventional lithographic approaches so that deposition of gold colloids is controlled prior to growth of nanofibers (e.g., by selective patterning of thiol groups on the substrate surface). In yet other embodiments, nanofibers are optionally pre-grown in a conventional manner well known to those of skill in the art (e.g., see above) and then selectively attached to or placed upon regions of the substrate where the spatially defined pattern is required.

Figure 3:
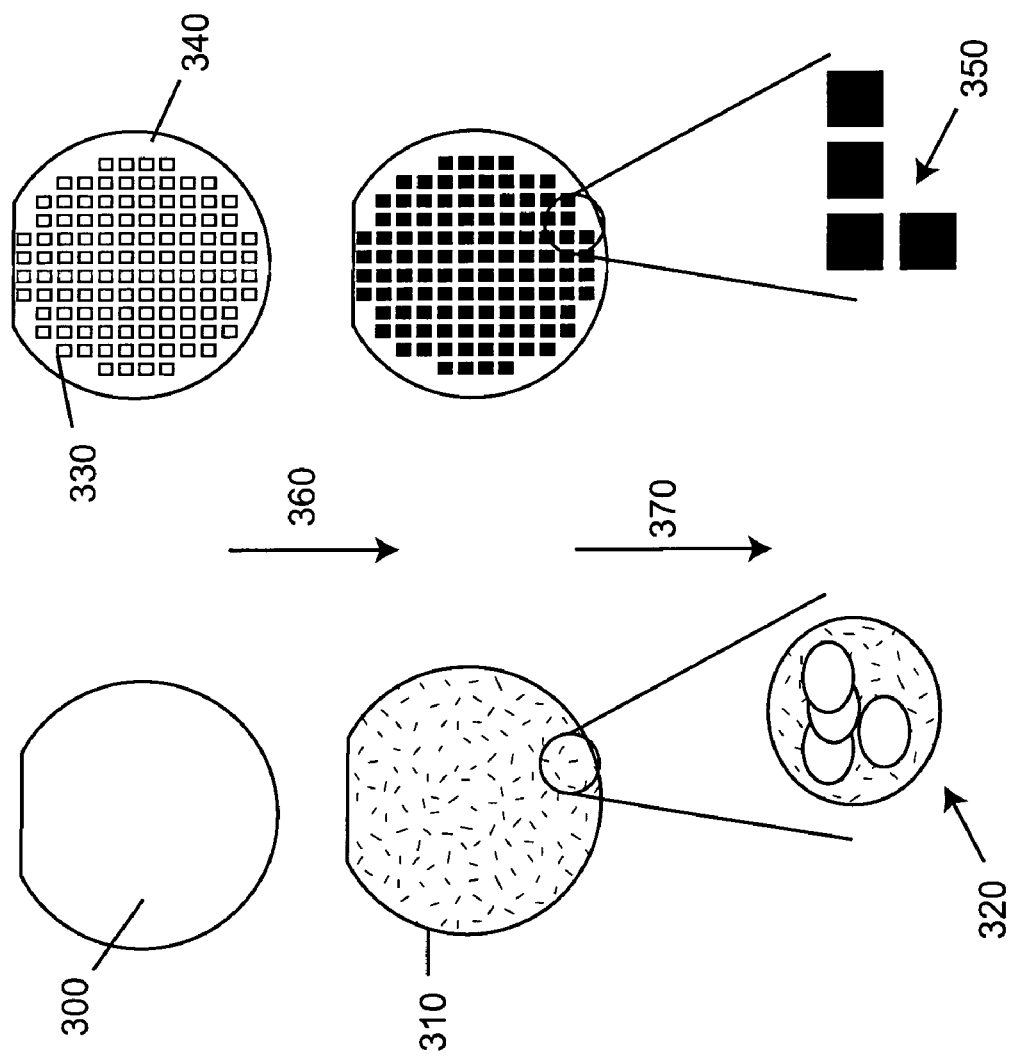
FIG. 3, Presents diagrams comparing unpatterned and patterned (microarrayed) nanofiber surfaces.

Of course, in yet other embodiments, "lawns" of nanofibers forming an enhanced surface area substrate are selectively patterned through removal of nanofibers in preselected areas. FIG. 3 schematically displays the concepts of selective micropatterning of enhanced surface area substrates. Thus, as can be seen in FIG. 3, enhanced surface area substrates that are not patterned can often experience wicking of analytes, etc. deposited upon the nanofibers. In FIG. 3, a surface having randomly disturbed gold, 300, results in nanofibers covering its entire substrate, 310. When nanofibers are grown, 360, such can result in unpredictable fluid wicking, 320, which, in turn, can be sometimes undesirable when the appropriate chemistry/bio-molecule is applied, 370. In contrast, enhanced surface area substrates that are micropatterned (or even nano-patterned) do not experience uncontrolled wicking of analytes, etc. because such wicking is contained within isolated regions of nanofibers (i.e., the wicking is stopped by empty regions upon the substrate surface). Thus, in FIG. 3, a substrate with a pre-patterned gold pattern, 330, and a hydrophobic surface, 340, will result in well defined surface coverage, 350. It will be appreciated that FIG. 3 is only one example of patterned arrays of the invention. Thus, other arrays can optionally comprise nanofiber lawns that have areas selectively cleared of nanofibers (thus, creating nanofiber islands, etc.) or can have nanofibers only grown or deposited in certain selected areas (or any combinations thereof). Those of skill in the art will be aware of numerous other patterns, etc. of arrays which can optionally be within embodiments herein. Additionally, as will also be appreciated, while "microarray," "micropatterned" and similar terms are used for the various embodiments throughout, the nanofiber enhanced surfaces of the invention can also comprise "milliarrays" and be "millipatterned," can comprise "nanoarrays" and be "nanopatterned," etc. Thus, while the text and claims herein typically describe patterning in terms of "micro" features, "nano" features as well as other sized features are also within purview of the current invention.

In yet other embodiments herein, nanofiber surfaces (e.g., congruous lawns of nanofibers) are optionally coated with a moiety, e.g., a hydrophobic moiety, a hydrophilic moiety, an amphiphobic moiety, an amphiphilic moiety, a lipophobic moiety, a lipophilic moiety, etc. In other words, the entire surface of the nanofiber lawn is treated/functionalized with such moiety. The functionalized lawn can then be selectively treated to remove the moiety in only selected locations (e.g., where it is desirous to attach other molecules such as DNA, proteins, etc.). One method to selectively treat the functionalized nanofibers is to selectively expose the lawn to, e.g., UV light (done in embodiments wherein the moiety comprises a photo-labile moiety and will, thus, be degraded by the light while leaving the nanofiber intact and without the moiety). In yet other embodiments, a hydrophilic lawn is treated/functionalized to create hydrophobic regions (i.e., the mirror image of the above). Appropriate molecules, etc. are then placed in desired locations upon the microarrays produced.

No matter their format or manner of construction, the patterned nanofiber arrays of the invention are adaptable to a wide range of possible uses and applications. Those of skill in the art will be quite familiar with a broad range of arrays such as nucleic acid arrays (e.g., DNA, RNA, etc.), protein arrays, or arrays comprising other biological or chemical moieties. For example, the nanofiber arrays herein are optionally used with protein arrays for applications with mass-spectrometry. See below. Recently, several applications (e.g., by Ciphergen Biosystems, Fremont, Calif.) have been developed for use of protein arrays and various of mass-spectrometry variations, such as surface-enhanced laser desorption ionization (SELDI), matrix assisted laser desorption/ionization (MALDI), and the like. Proteins can, thus, be "stored" on a chip or wafer and conveniently characterized through SELDI or MALDI, etc. See, e.g., www.ciphergen.com. Nanofiber arrays of the invention are contemplated to be used with those and similar techniques. Those of skill in the art will be familiar with other types of mass spectrometry analysis which can optionally utilize the microarrays and other features of the current invention. Again, those of skill in the art will appreciate that the possible uses/applications of nanofiber arrays, whether DNA, protein, or other moiety, are quite broad and that specific recitation of particular uses/embodiments herein should not necessarily be taken as limiting.

While, certain methods of patterning, substrate/nanofiber composition and the like are illustrated herein, it will again be appreciated that such are illustrative of the range of methods included in the invention. Thus, such parameters can be changed and still come within the range of the invention. For example, as illustrated above, micropatterning of enhanced surface areas is optionally accomplished in any of a number of ways (e.g., lithographic deposition, laser ablation of nanofiber elements, etc.), all of which are encompassed herein.

i) Patterned Microarrays and Devices

Existing substrates for fluorescent microarray applications (as well as other types of microarray applications, e.g., radioactive, chemiluminescent, etc.) have many limitations. Limitations can include, e.g., poor sensitivity, low dynamic range, variable spot uniformity and large feature sizes on mechanically spotted arrays. Despite these limitations, the fluorescent microarray has become a major tool for large scale genomic analyses and the emerging proteomic industry. Thus far, attempts to introduce new substrates have been unsuccessful, largely because of reduced kinetic performance and the requirements for major changes to the basic array fabrication and analysis infrastructure. The current invention, however, comprises embodiments having nano-enabled microarray substrates that can overcome limitations facing existing microarrays and which are optionally compatible with existing typical hybridization protocols, as well as array fabrication and analysis infrastructures and are optionally used for a wide range of microarray purposes (e.g., can be used with proteins, nucleic acids, ligands, receptors, etc., basically all possible moieties available to other current microarray methods).

The market for both large scale genomic and proteomic analyses has grown dramatically over recent years and is expected to grow further as more information is gained about the role of genetic sequence variations and expression patterns in development and disease. DNA microarrays have already become a major tool in both basic research on the genetic basis of disease and in target identification and validation in drug discovery efforts. Furthermore, it is likely that in the future microarrays will significantly impact the areas of molecular diagnostics and pharmacogenomics that are currently dominated by costly service driven genomic analyses such as sequencing or in situ hybridization. Additionally, the current drive to simultaneously analyze molecular differences at the level of protein expression will further expand the utility of the microarray format into the field of proteomics. Therefore, any technology, such as that of the present invention, that can improve the performance, cost, utility and quality of microarray experiments without significantly altering the existing methodologies and analytical processes is quite desirable. Currently, there are two major formats of microarrays that are widely used for genomic analyses (primarily for expression analysis but increasingly for genotyping as well).

The first of the current microarrays protocols is "in situ synthesized oligonucleotide arrays." Popular examples of such pre-arrayed chips (e.g., those of Affymetrix, Santa Clara, Calif.) are synthesized with oligonucleotide probes on the chip and arrayed with small feature sizes (e.g., 18×18 um) of a high density. Such chips are fabricated through a process analogous to the lithographic approaches for microchip fabrication. By applying photomasks to a substrate coated with chemical precursors that can be sequentially deprotected by exposure to light, complex high density arrays of oligonucleotides can be synthesized in a well characterized manner. Although expensive, these arrays are widely used when simultaneous analyses of whole genomes are required using well characterized arrays. Other popular technologies (e.g., those of Agilent Technologies, Palo Alto, Calif.) also have a method of in situ synthesis of oligonucleotide arrays utilizing chemical deprotection methods and inkjet technology as the means of delivering each nucleotide to the desired location. This method has been less accepted than the lithographic approach, probably due to the ease at which feature sizes can be reduced by employing lithography and the subsequent quality of small features. The advantage of in situ synthesized arrays is the high density and quality of the arrayed oligonucleotides. However, these fabrication methods are costly and hence impractical for many applications, and neither full length cDNA probes or proteins are compatible with this methodology. Furthermore, the fundamental limits of dynamic range and signal per unit area on planar glass substrates has become a significant issue as feature sizes are reduced.

The second of the current methods used to construct microarrays comprises "spotted arrays." These arrays are fabricated on various substrates (including glass slides, membranes and polymer gels) by the mechanical deposition of presynthesized oligonucleotide probes or cDNA. This spotting approach can use chemical linkage steps or simple adsorption of the DNA to appropriately treated surfaces. There are two main ways to deposit the probes, either by contact printing (most common for "home-made" arrays due to the cost) and non-contact printing (e.g., ink-jet or piezo electric) where smaller volumes can be applied. However, the cost of the spotters needed restricts their use primarily to pre-made arrays. The size of features on these spotted arrays (especially pin-printing) is larger than for the lithographically synthesized arrays and the density of features is lower. Spotted arrays are generally less expensive and are commonly fabricated by the end-user using precoated slides or membranes and robotic microarray spotters. Additionally, protein based arrays also use a spotted fabrication approach. Thus, technologies that improve DNA spotted arrays may have a concomitant benefit for the fabrication of protein arrays as well.

As mentioned above, certain improvements to enhance the efficacy and utility of both microarray formats is desired. For example, enhancing the dynamic range of both types of microarray is desirable. Currently, the dynamic range of these assays is less than three orders of magnitude and is dominated by background fluorescence of the stained array slide on the low end and by saturation of binding sites on the microarray spots on the high end. Thus, there is often an under-representation of the magnitude of change in differentially expressed genes being screened on a microarray. For example, in order to pick up changes in expression of genes for which the mRNA copy number in the cell is low, currently it is often necessary to amplify the RNA before hybridization to the array. For RNA species that are present at much higher concentrations in the cell, this amplification results in the production of saturating levels of nucleotide. Thus, changes in the levels of these more highly expressed RNA species will be underestimated from the array data. Therefore, to accurately quantify expression level changes determined in microarray experiments, time consuming methods such as quantitative PCR are often carried out to confirm or better quantify changes seen on microarrays.

Figure 4:
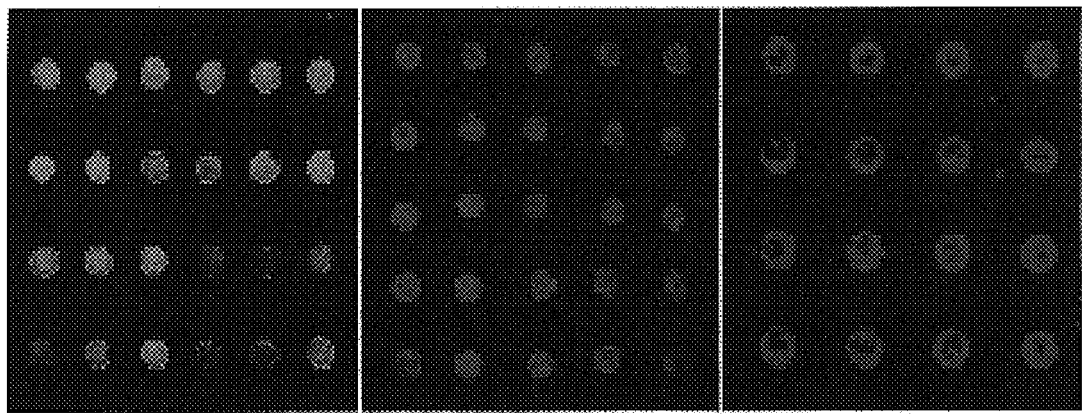
FIG. 4, Displays the variability of DNA distributed within spotting on traditional DNA arrays.

Yet another drawback for specifically spotted arrays on planar surfaces, is the quality of the feature on the substrate. The two major issues involved in quality are spot uniformity and feature size. The tendency of spotted array features to be non-uniform (especially home fabricated versions) restricts accurate analysis of their results. See, e.g., FIG. 4 which shows non-homogeneity within spotted array features on planar surfaces (here, spotted DNA). As can be seen, the fluorescence intensity, thus indicating DNA distribution, is uneven and inconsistent within the spots. Furthermore, the large feature size (driven by the accuracy of the spotting tool and the wetting properties of the substrate material) limits the density of the spotted array. Typically feature sizes of between 150 um and 500 um diameter are achievable for the most common pin spotters at a pitch of around 500 um, while ink-jet printed arrays currently achieve about 80-150 um diameter.

Embodiments of the invention described herein address such problems as dynamic range, array density and spotting uniformity. Nanofiber enhanced surface area microarrays of the invention are optionally patterned, etc. for the applications noted above. There are several methods under development for increasing the effective surface area and performance of microarray substrates. However, the nanowire enhanced substrates herein are superior to other approaches for increasing surface area, for several reasons; e.g., most other attempts at improving the substrate for microarrays have involved the deposition of three-dimensional polymer matrices on glass or have used etched microchannels in the glass itself. Porous gels such as Codelink™ slides (Amersham BioSciences, Piscataway, N.J.) or Hydrogel™ (Perkin Elmer, Wellesley, Mass.) are generally only suitable for spotting approaches and they suffer from diffusion issues that can lead to slower hybridization/wash times or difficulty in controlling spot size. More elaborate attempts to reduce hybridization volumes/times by having microchannels etched in thicker segments of glass require fundamental changes to the current process of microarray analysis and also increase costs of array fabrication.

Thus, as will be appreciated, increasing the possible signal per unit area (as is done with nanofiber enhanced surface area substrates of the invention) extends the dynamic range of microarrays at the high end and allows more complete data to be acquired from a single experiment. Additionally, increasing the signal per unit area facilitates reduction in feature sizes, which is another desirable development for lithographically synthesized arrays.

The common factor shared by both current array formats described above (as well as many embodiments of the current invention) is the adoption of fluorescent labeling of targets as the preferred method of detection. Typical fluorescent arrays are read by fluorescent array scanners which either image entire arrays or confocally scan the array using a laser to excite the fluorescent spots. Currently, the major formats of microarray technology detect the binding of labeled targets, e.g., fluorescently labeled targets, to probe molecules immobilized on flat glass surfaces. However, as noted previously, planar substrates (without nanofibers) limit the existing technology in terms of the amount of detectable signal per unit area and in the uniformity and size of spotted probes.

ii) Nanofiber Tracks/Channels as Substrates for Lateral Flow Based Assays

In some embodiments of the invention, methods to pattern nanofiber surfaces can optionally result in, or produce, "channels" or "tracks" on a planar surface. Applications can, thus, utilize the wickable properties of nanofiber enhanced surfaces to allow, e.g., liquid flow, sample separation and target capture in a lateral flow format.

As demonstrated throughout, the enhanced surface areas provided by surfaces containing grown nanofibers (e.g., nanowires) provide significant advantages as substrates for myriad purposes such as biological binding assays. The increased density of probes possible in a given region of nanofiber enhanced substrate increases the sensitivity and robustness of such assays. In addition, as explained elsewhere herein, because of the enhanced wicking capability of nanofiber enhanced surfaces (e.g., grown in situ or deposited nanofibers, e.g., nanofibers packed into such things as microchannels, microtroughs, microditches, etc.), the application of a solution in any region of an enhanced area will lead to the rapid dispersion of the solution in the nanofiber filed area until the solution fills the space between the nanofibers (i.e. the interstitial space). If the nanofiber surface is patterned in a manner to encourage such flow in a directed fashion from a point where a sample is applied, then such patterned surface can optionally be utilized in lateral flow based binding assays. Thus, targets present in a sample applied to such patterned nanofiber surfaces can bind to or with one or more probe that is linked or associated (e.g., bound upon a nanofiber) at some defined spot along the tracks/channels of nanofibers.

In accordance with its usage in other contexts herein, the term "substrate" relates to the material upon which the nanofibers are grown or placed/deposited (e.g., a silicon wafer, glass, quartz, or any other material appropriate for nanofiber patterning and growth, see above). Methods of patterning nanofiber enhanced surfaces (e.g., to produce the tracks/channels) are described throughout. For example, many techniques described for use in other micro-patterned arrays herein are also applicable to creation of channel/track patterns as well. Thus, laser ablation, photo-lithography, mechanical scraping, etc. can all be used to construct the channel/track areas of the embodiment. Those of skill in the art will also be familiar with related methods of patterning which are optionally used in the current embodiment.

Figure 5A:
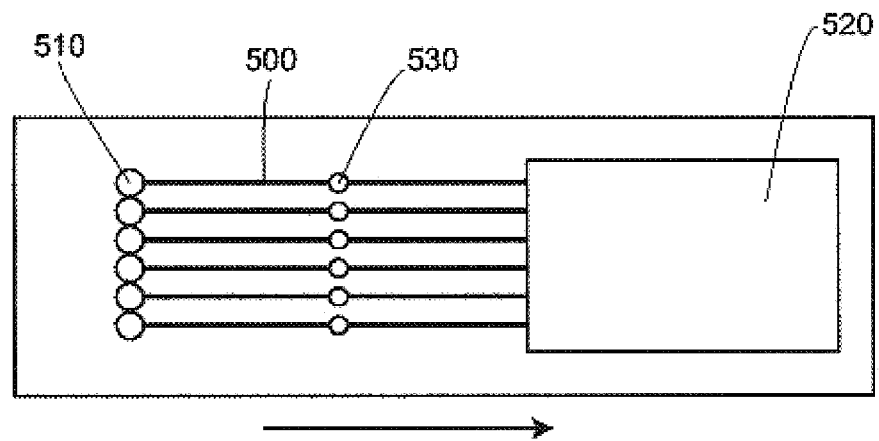
FIG. 5, Panels A-C, Displays exemplary arrangements of patterned nanofiber wicking tracks/channels.
Figure 5B:
Figure 5C:
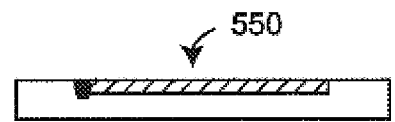

Patterning of nanofiber surfaces herein for wicking based assays can involve numerous different nanofiber track/channel arrangements depending upon, e.g., the specific parameters of the uses involved (e.g., number and type of analytes, conditions of the assay(s), etc.). FIG. 5 shows a sample arrangement of nanofiber wicking tracks/channels. However, such arrangements are for exemplary purposes only and should not be construed as necessarily limiting. As can be seen in FIG. 5A six tracks/channels, 500, comprised of nanofiber enhanced surface areas are in fluid communication with sample deposition areas, 510 (also optionally comprising nanofiber enhanced surface area) and a system for drawing solution(s) through the nanofiber tracks/channels. The arrow indicates the direction of flow. Such drawing or wicking system can optionally comprise a large field or area of nanofiber enhanced surface area which acts as a large wicking pad to draw solutions through the tracks/channels (e.g., 520 in FIG. 5). Optional immobilized probes, 530, are also possible features. FIGS. 5B and 5C also display sample side views of a nanofiber enhanced surface having a track and a recessed channel respectfully. Element 540 in FIG. 5B equates with the tracks/channels, 500 in FIG. 5A, with the tracks on top of the substrate. In FIG. 5C, element 550 represents a recessed channel and sample well and equates with 500 in FIG. 5C.

Figure 6A:
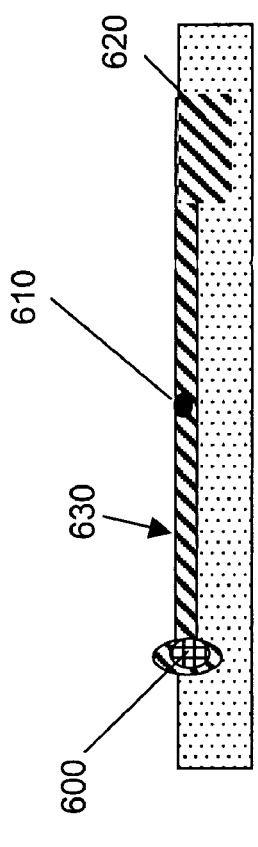
FIG. 6, Displays a schematic of an exemplary nanofiber wicking arrangement.
Figure 6B:
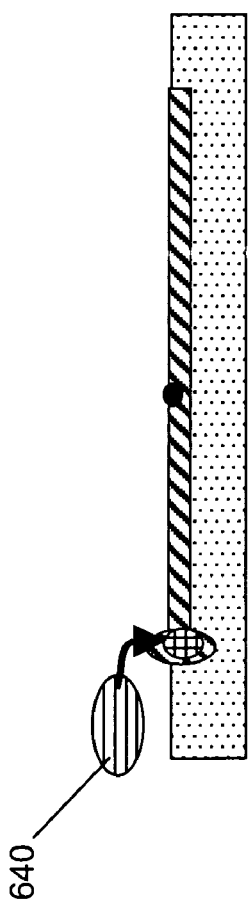
Figure 6C:
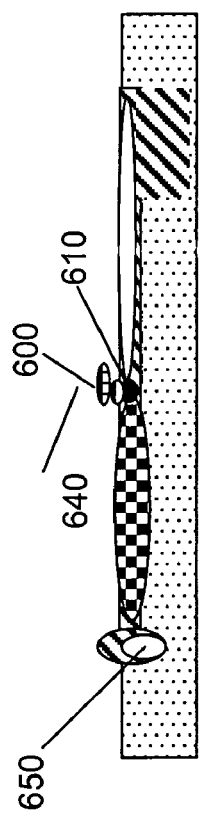
Figure 6D:
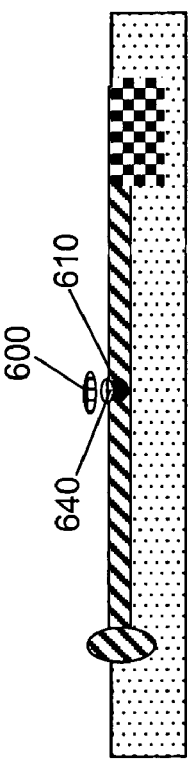

In a typical application, a sample solution (e.g., containing one or more target to be detected) can be applied at one end of a track or channel while at the other end of the track/channel a material/system encourages forward progress of the solution through the track/channel. The material or system that encourages the forward progress of the solution can comprise, e.g. a larger filed of nanofibers or alternative wicking matter. Those of skill in the art will be familiar with techniques and materials, e.g., those utilized in chromatographic wicking applications and various microfluidic devices, which are capable of use in the current embodiments. The sample applied to the track/channel is typically followed by a volume of solution (either with or without the target(s) to be detected) to allow continued flow of the solution. Probe(s) specific for the particular target(s) in the sample solution can be immobilized at particular locations along the tracks/channels herein. See, e.g., 530 in FIG. 5. In many instances, a secondary labeling tag (e.g., a fluorescent or calorimetric tag, etc.) can optionally be present in the solution or in a solution that is wicked through the track/channel after the solution comprising the target. Alternatively, such tag can be attached, e.g., via a matrix, at the start of the track/channel and then released into the flow of the solution. In any case, the secondary tag in solution can wash over the previously bound target (i.e., the target that was present in the sample) that is immobilized on the nanofiber surface. Alternatively, in some embodiments the target can interact with the probe without the addition of any additional tag. Thus, the interaction of target in the solution and probe upon the nanofiber surface can produce an indication (e.g., fluorescent, calorimetric, radiometric, etc.) that allows detection/monitoring of the interaction. Finally the surface can be examined to determine the presence or absence of the target (e.g., detection of fluorescent tag). FIG. 6 displays schematic representations of an exemplary assay scheme showing application of a sample in solution to a track/channel followed by wicking through of a label, washing of the sample/label and detection of the bound sample/label (e.g., an exemplary lateral flow assay carried out on nanofiber tracks). In FIG. 6, a labeled secondary detection reagent on a sample pad, 600, and an immobilized capture probe, 610, are within nanofiber channel, 630, attached to wick reservoir, 620. A target or sample, 640, is applied to the sample pad in FIG. 6B. As the assay proceeds in 6C, solution, 650 wicks through the nanofibers and the target and secondary detection reagent are immobilized at the capture probe site. In FIG. 6D, the sample has completely wicked through the track leaving immobilized detection reagent that can be quantified. Again, the above is an exemplary arrange of a lateral flow assay carried out on nanofiber tracks and should not be taken as necessarily limiting on the myriad of other possible arrangements and configurations that are possible with such assays and which are encompassed within the current invention.

As explained herein, for this and other many embodiments of the invention, the probe can be any molecule of interest (e.g., DNA, protein, organic molecules, inorganic molecules, metals, ceramics, peptides, polypeptides, nucleic acids, nucleic acid analogs, metallo-proteins, chemical catalysts, metallic groups, antibodies, cells, ions, ligands, substrates, receptors, biotin, hydrophobic moieties, alkyl chains from about 10 to about 20 carbon atoms in length, phenyl groups, adhesive enhancing groups, and co-factors, etc.) that has an affinity for one or more molecule(s) that could be present in a sample to be analyzed. The probe is optionally immobilized at some point on, or within, the nanofiber surface in such a fashion as to be capable of capturing a target molecule that flows past. The sample to be assayed can be any solution containing a target(s) of interest (e.g., DNA, protein, small organic molecules, etc.) that can be subsequently captured by the specific probe. In some applications (e.g., if the sample were whole blood) the nanofiber surface can also act as a separations media for the constituents of the sample.

It will be appreciated that, as in the other embodiments herein, many aspects of the embodiments can be changed without straying from the claimed invention. For example, the method(s) by which the nanofiber surfaces are patterned can be changed, as can the number and dimensions of the tracks/channels. Additionally, the density, composition, etc. of the nanofibers in the nanofiber enhanced surface can also be varied. Also, as will be appreciated, the assays in the embodiments herein are optionally used for any of a large number of different probe/target combinations (e.g., DNA-DNA, antibody-protein, etc.). Further examples are discussed in other embodiments herein and are equally applicable in the current examples. Those of skill in the art will be familiar with a large number of well characterized methods and types of various probe/target combinations which can be incorporated into versions of the current embodiments. Additionally, the detection methods/systems used to detect any target in an assayed sample is also variable.

The illustrations in Example 2 demonstrate the binding of a soluble analyte (target) to a probe that is immobilized within a nanofiber track and the use of wicking properties of the nanofiber tracks to produce sample flow.

ii) Components and Construction of Nanofiber Enhanced Surface Area Microarrays

As described previously, NFS embodiments herein are optionally constructed of any of a number of different substrates. Thus, as will be appreciated, creation and use of micropatterned arrays of nanofiber enhanced surface area substrates can optionally utilize any of a number of different nanofiber/substrate components. However, in typical embodiments, the arrays are based upon the ability to control and pattern the growth of $SiO_2$ coated, nanometer diameter nanofibers on the surface of a typically planar substrate. The silicon oxide nanofibers provide dramatic increases in effective surface area and yet retain the basic chemical characteristics desired for surface functionalization and assay development. In some embodiments, the nanowire-enhanced substrates optionally achieve a 100-fold increase in signal intensity per unit area in relation to a more traditional non-nanofiber array. Furthermore, in yet other embodiments, feature sizes on spotted arrays are decreased to well below currently achievable levels while, at the same time, the uniformity of the spotted probe is increased.

Preferred embodiments herein comprise a novel microarray substrate formed from a thin, but dense film of $SiO_2$ coated silicon nanofibers. In typical embodiments, such nanofibers comprise one or more functional moiety. Such nanofibers dramatically increase the effective binding surface area of the substrate material without having to, e.g., generate pores which would decrease binding kinetics or increase the depth of field of detection. Thus, traditional array scanners can be used for detection with devices of the invention. The nano-structured surfaces also provide multiple advantages over conventional microarray substrates by providing a significantly enhanced surface area; improving feature uniformity on spotted arrays and allowing for much smaller features to be printed (due to the increased signal per unit area); maintaining binding and washing kinetics equivalent to a flat glass surface; and, not necessarily requiring any changes to the analytical instrumentation, chemistries or microarray protocols for either high density lithographically printed or spotted arrays.

In various optional embodiments herein, the microarrays of the invention (comprised of enhanced surface area materials) are optimized in terms of fiber density, fiber length and diameter and fiber surface properties in regard to signal intensity, binding kinetics and assay dynamic range. Other embodiments comprise methods for applying defined spot sizes to enhanced nanowire surfaces, e.g., both by limited volumetric approaches and by chemically patterning the surface of the nanowire substrate to define the spot size. See below. In yet other embodiments, proteins attached to nanowire substrates optionally demonstrate equally beneficial surfaces for protein binding applications, as compared with conventional glass substrates (i.e., ones without nanofiber enhanced surface areas). Also, as is illustrated below, in many embodiments, the nanofiber enhanced surface area substrates of the invention allow for clearly and uniformly defined spot formation. In other embodiments, the enhanced surface area microarrays comprise increased intensity per unit area (thus, providing a path to significant reduction in feature sizes of all array formats) as compared with traditional planar microarrays. Also, a typical feature of some embodiments herein is increased dynamic range (thus, providing better data from a single microarray experiment and expanding the utility of this important analytical tool) as compared with traditional microarrays. Reduced spot size for mechanically spotted arrays is an optional feature of some embodiments of the invention as well and, thus, increases the achievable feature density because of this more flexible approach to array fabrication. Finally, embodiments of the invention can often provide a more uniform spot size on mechanically spotted arrays (thus increasing the quality of data and accuracy of data analysis) as compared with planar microarrays.

Figure 7:
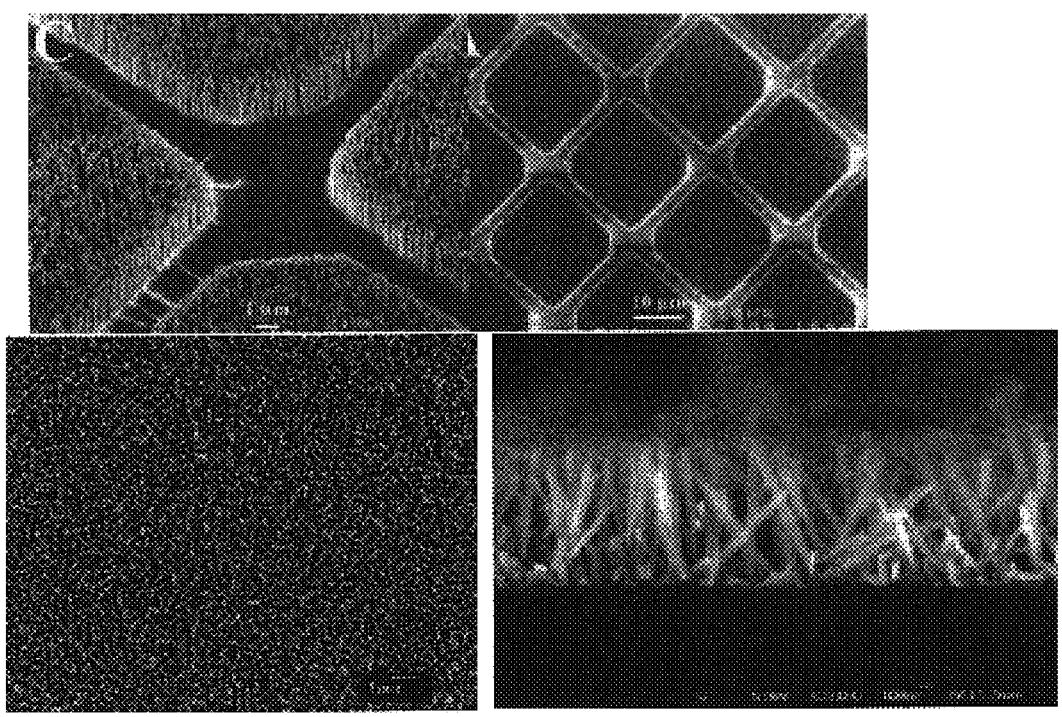
FIG. 7, Displays electronmicrograph images of typical nanofiber surfaces.

As explained in greater detail below, the technology described herein is based on the ability to grow nanometer scale wires of defined diameter and length on various surfaces. In Example 3, FIG. 7 shows an example of how a bottom up approach to assembling these materials provides a unique, "extreme" surface with very high surface to volume ratios and yet without the complex etched architecture of other (top down) strategies for increasing surface area to volume (e.g. etched silicon). FIG. 7 shows SEM views of top and side views of a typical nanofiber surface, both patterned and unpatterned. The silicon nanofibers were grown out from a silicon wafer and the surfaces were therefore compatible with standard glass modification chemistries, etc. Those of skill in the art will appreciate the breadth of possible modifications to such materials. Although discussion herein primarily focuses on silicon wafers as the substrate for nanowire growth, the process can potentially be conducted on a wide variety of substrates that can have planar or complex geometries. For example, this process can also be done at low temperatures on plastic substrates. Substrates can be completely covered, patterned, or have nanofibers in specific locations. Nanofibers are optionally made from a wide variety of materials as well as grown on various substrates. Again, however, typical embodiments herein focus on controlling the various growth parameters of silicon nanowires on silicon oxide wafers or glass slide substrates.

In various embodiments herein, it is contemplated to use conventional $SiO_2$-based chemistries to link DNA probes to nanofiber-enhanced surfaces and detect subsequent hybridization of fluorescently labeled targets. Also, optimization of the materials in terms of density, diameter, and length to provide an enhancement in signal intensity per unit area of two orders of magnitude (or 3 orders, or more, or 4 orders or more, or 5 orders or more, or 10 orders or more) with no concomitant loss in binding kinetics or relative increase in background is also contemplated.

Because nanofibers in such embodiments are each coated with a thin layer of $SiO_2$, the material comprising the nanofiber is compatible with existing surface modification strategies and also with the existing infrastructure for spotting and analyzing microarrays. Those of skill in the art should be familiar with a number of such different surface modifications. Such material has several unique properties over and above the enhanced surface area aspects herein. For example, nanofiber surfaces treated with a hydrophilic surface chemistry result in a highly hydrophilic mesh that wicks solutions very homogeneously throughout the surface, thus providing a perfect matrix for homogenous array spotting. Additionally, even untreated typical NFS surfaces display a high level of such wicking. Specific moieties which increase hydrophilicity of the nanofibers surfaces are also optionally added in some embodiments. See, e.g., Ser. No. 10/833,944, filed Apr. 27, 2004, entitled "Super-Hydrophobic Surfaces, Methods of Their Construction and Uses Therefor." Conversely, a hydrophobic surface treatment can also render the surface super-hydrophobic, excluding water completely and thus restricting solutions to predefined regions. The combination of these two qualities provides a mechanism for generating an exemplary spotting substrate.

In contrast to other recent attempts to improve microarrays, the current invention (in several embodiments) comprises a thin ~10 um layer of nanofibers applied to a substrate which, although massively increasing the surface area, does not require a modification to the depth of field of fluorescent array scanners and thus will not change the ability to analyze bound fluorescence by conventional scanners or other aspects of standard array methodology. The enhanced area substrates herein incorporate a robust and well defined surface of nanofibers that results in a significant increase in surface area but with the retention of standard glass surface chemistry and no reduction in binding kinetics or changes in nonspecific binding. In various embodiments, this increased surface area can be optimized to increase both dynamic range and signal intensity per unit area by, e.g., two orders of magnitude or more. The superior surface properties of the nanofiber-enhanced surface also optionally allows far more homogenous spotting of a predefined region using standard spotting techniques.

Furthermore, methods for pre-defining nanofiber enhanced features on standard microarray slide geometries to provide improved platforms for more uniform spotted arrays with reduced feature size is contemplated herein, e.g., a uniformly spotted array with 50 um diameter features fabricated with a traditional pin-printing system, or even spotted feature sizes and hence array densities to approach those of the synthesized arrays of sub 25 micron diameter spots (e.g., 15 micron spots, 10 micron spots, 5 micron spots, 1 micron spots, etc.).

Figure 8B:
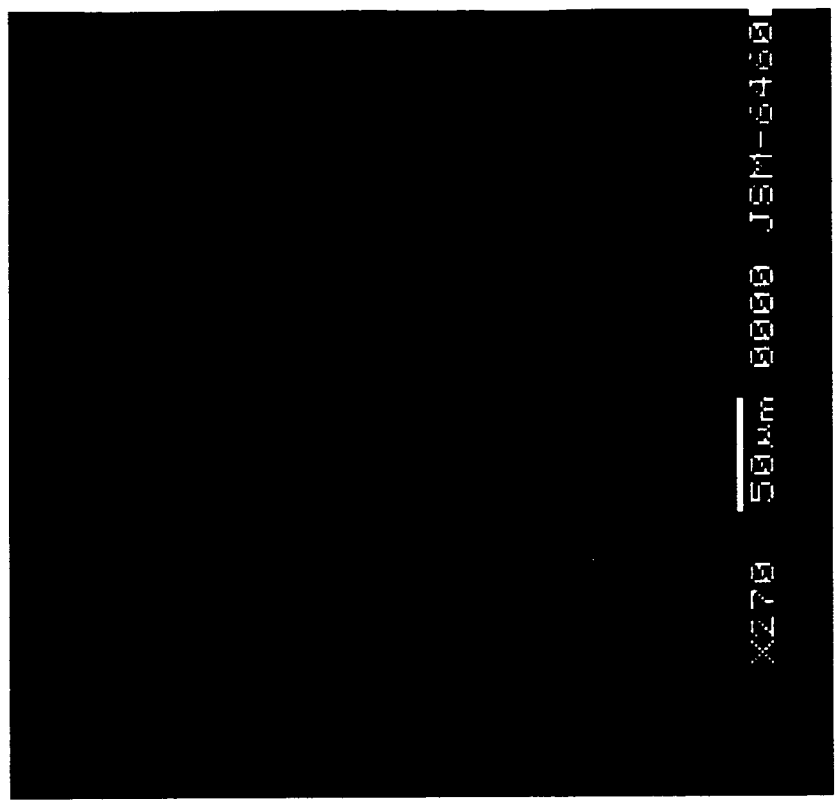
Figure 8A:
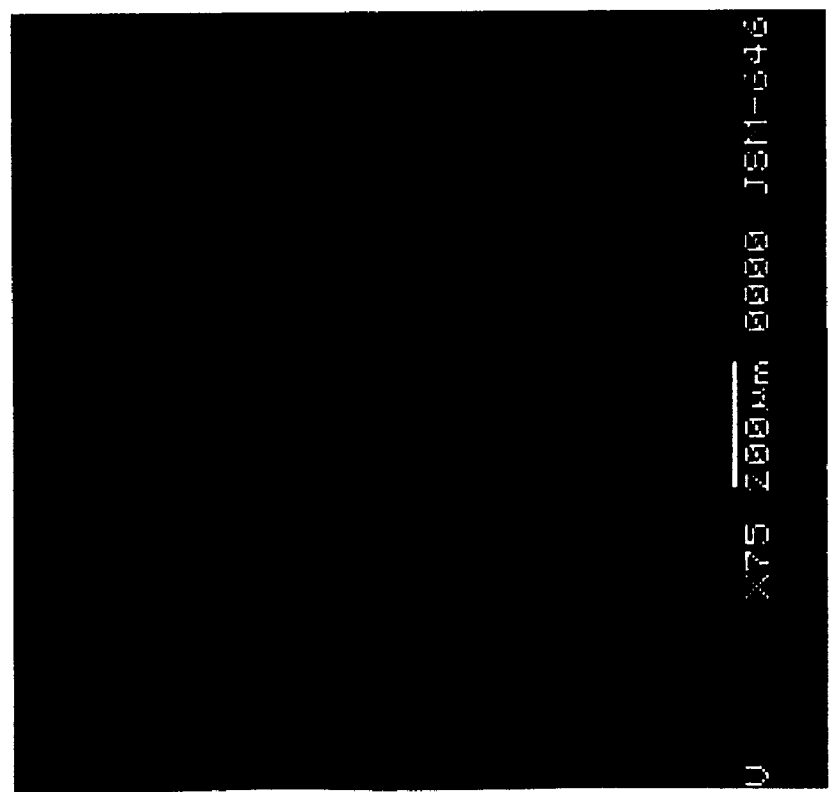
Figure 9A:
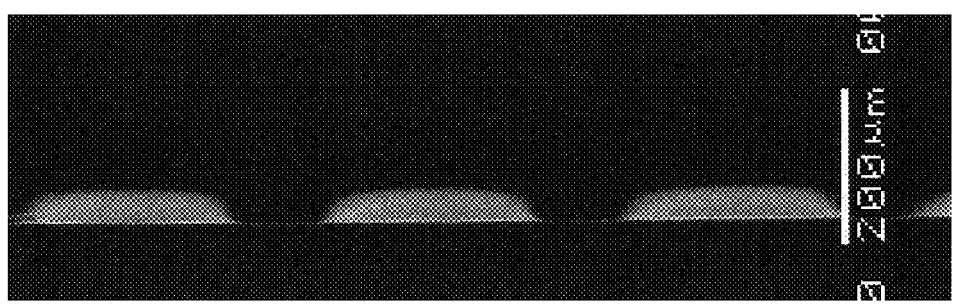
Figure 9B:
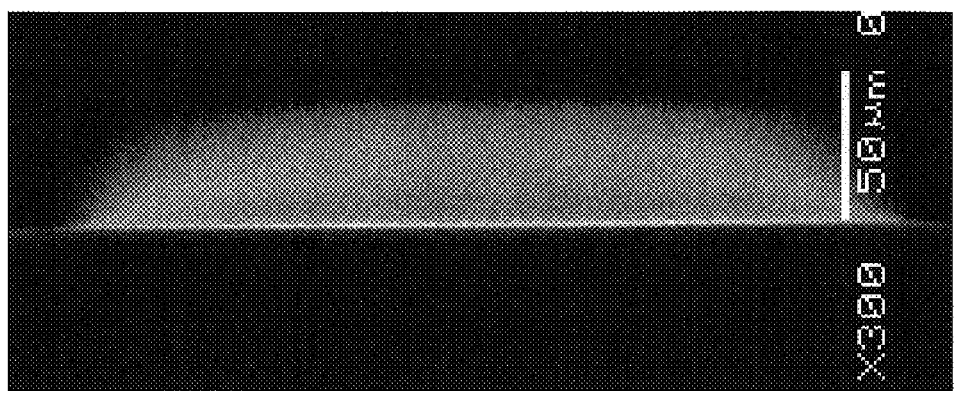
Figure 10A:
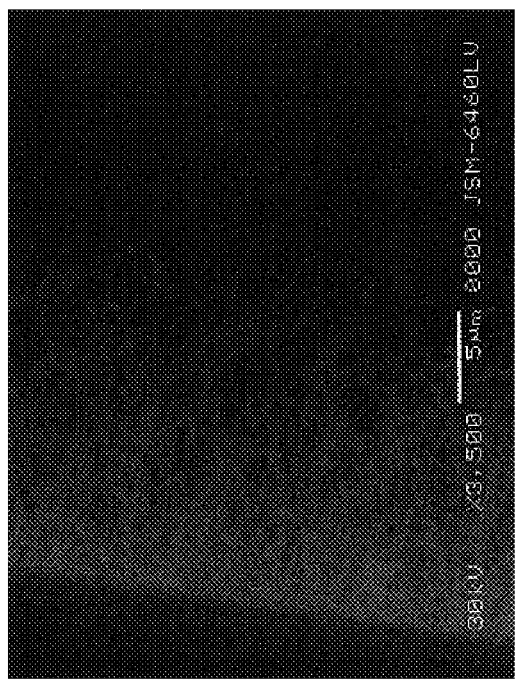
Figure 10B:
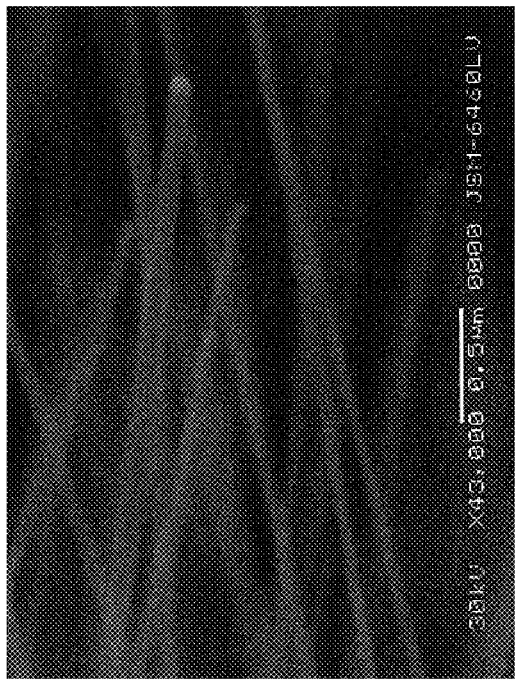

One possible procedure useful for production of well-defined patterns of nanofiber arrays involves shadow masking of gold films. Of course, it will be appreciated that gold-film techniques are also amenable to production of nanofiber surfaces in embodiments herein which do not involve arrays. Shadow masking of gold films can provide well-defined features with surface area increases that are at least equivalent to those produced through colloidal processes. Examples of nanofiber arrays produced by masking process can be seen in Example 3 and FIGS. 8 through 14. In the example and the figures, a stainless steel mask having holes was used with standard silicon/silicon oxide wafers to produce a patterned nanofiber array. From 20 to 60 nm of gold was sputtered onto the silicon wafers through the mask to produce the defined nanofiber areas. The nanofibers (here nanowires) were grown to procedures standard in the art. FIG. 8 shows well-defined nanofiber pattern areas created using a shadow mask and 40 nm gold deposition. FIG. 9 shows side views of similar discrete nanofiber areas.

Figure 11:
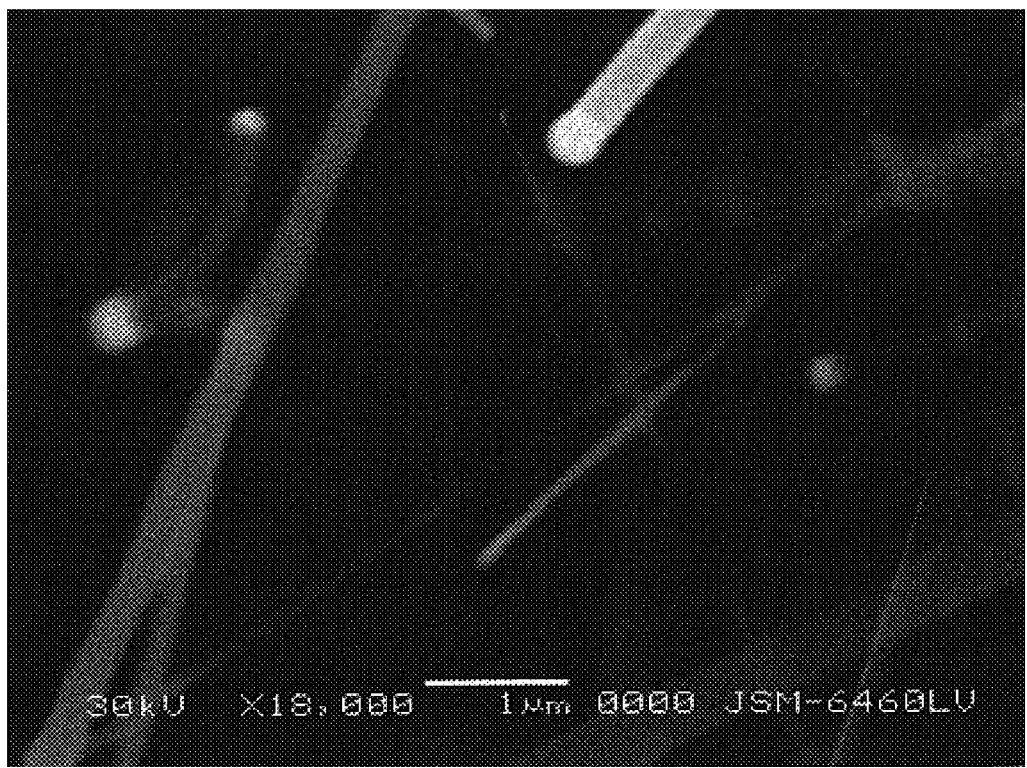

As also seen in Example 3, based on fluorescent measurements, thinner deposits of gold film (e.g., 20 nm) typically give thinner, more uniform diameter nanofibers with surface areas equivalent to other nanofiber growth methods (e.g., standard gold colloid deposition methods). For example, FIG. 10 displays nanofibers that are fairly uniform (e.g., 50 to 100 nm) that were created through use of a 20 nm gold film deposit. Additionally, FIG. 11 shows that gold film thickness of between 30 and 60 nm generates a wide nanofiber size distribution with many nanofibers within the 50 um range. Thus, optimization of gold film thickness to manipulate the nanofiber surface areas (e.g., within the arrays) and nanofiber homogeneity within those areas are features of the invention.

Figure 14A:
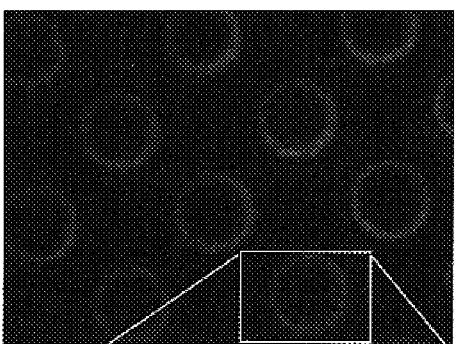
Figure 14B:
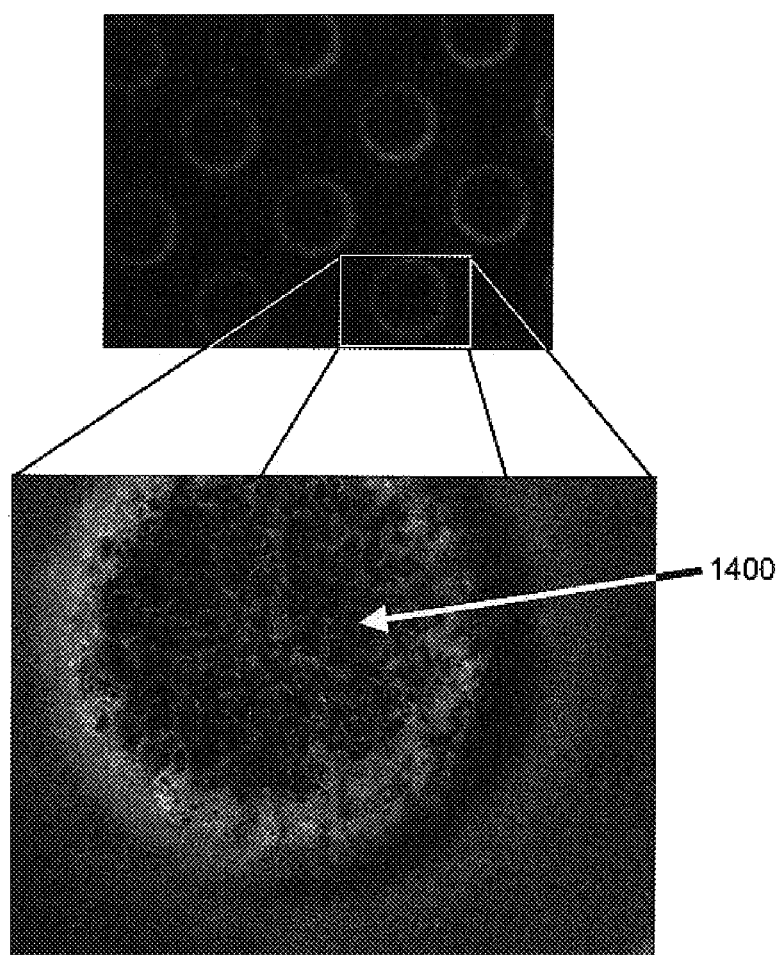

Analysis of shadow-mask produced nanofiber arrays by fluorescent intensity and light microscopy reveals a great deal of heterogeneity in terms of feature resolution between the nanofiber areas and the substrate background. Features produced using a 20 nm gold film showed a 25-fold increase over planar areas (i.e., those areas without nanofibers or with comparatively much fewer nanofibers), which is better than the average colloidal synthesis production method results. Through variation of feature sizes in the masks used and in the depth of the gold deposit used, the sharpness or definition of the nanofiber arrays can be manipulated. Thus, in Example 3, FIG. 12 displays light and FL-microscopy of two sample nanofiber arrays (both using 20 nm gold film). See Example 3. FIG. 13 also shows exemplary possible variations achievable through manipulation of gold film thicknesses in regard to feature homogeneity. FIG. 14 displays that through manipulation of the gold film used in nanofiber construction, nanofiber features on a substrate can produce "doughnut" intensity profiles (e.g., similar to the effect seen with analyte drops in traditional microarray technologies) which are believed to be due to large, thick nanofibers in the central portion of the features, 1400.

Figure 15:
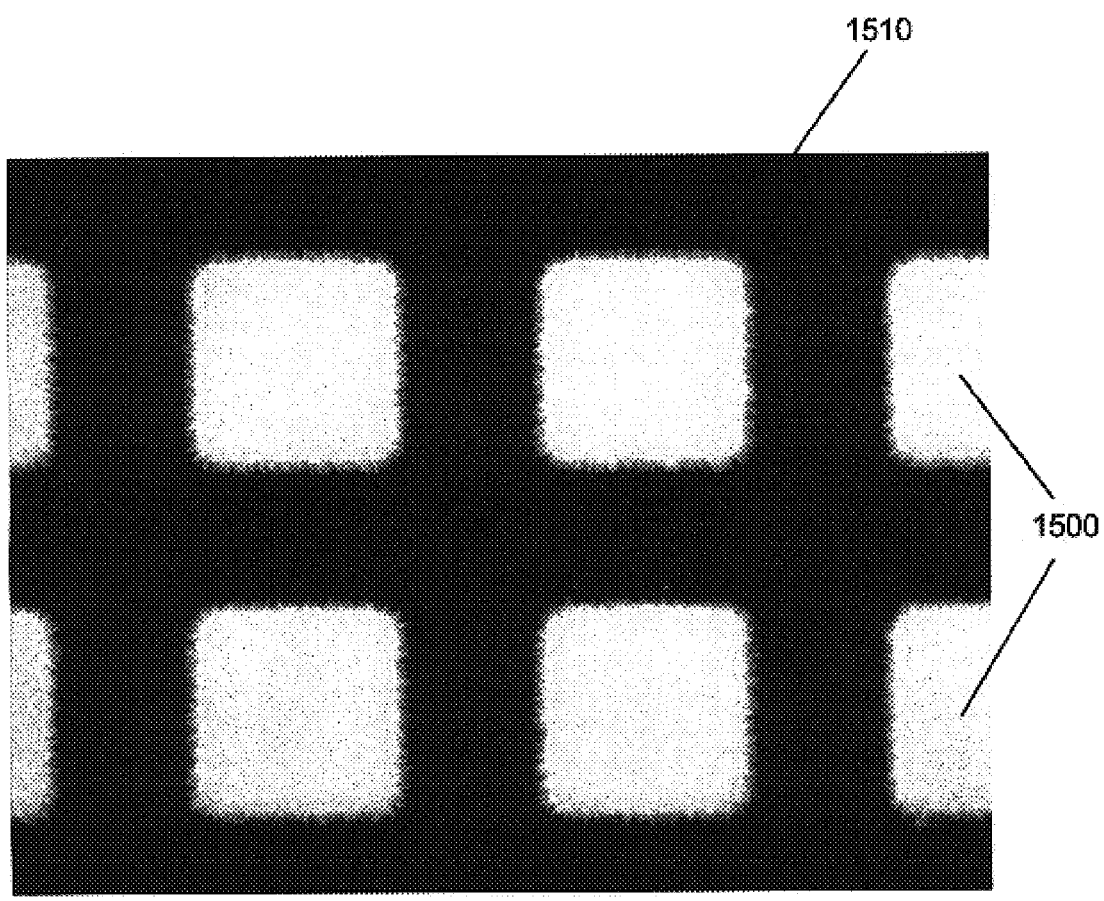
Figure 16A:
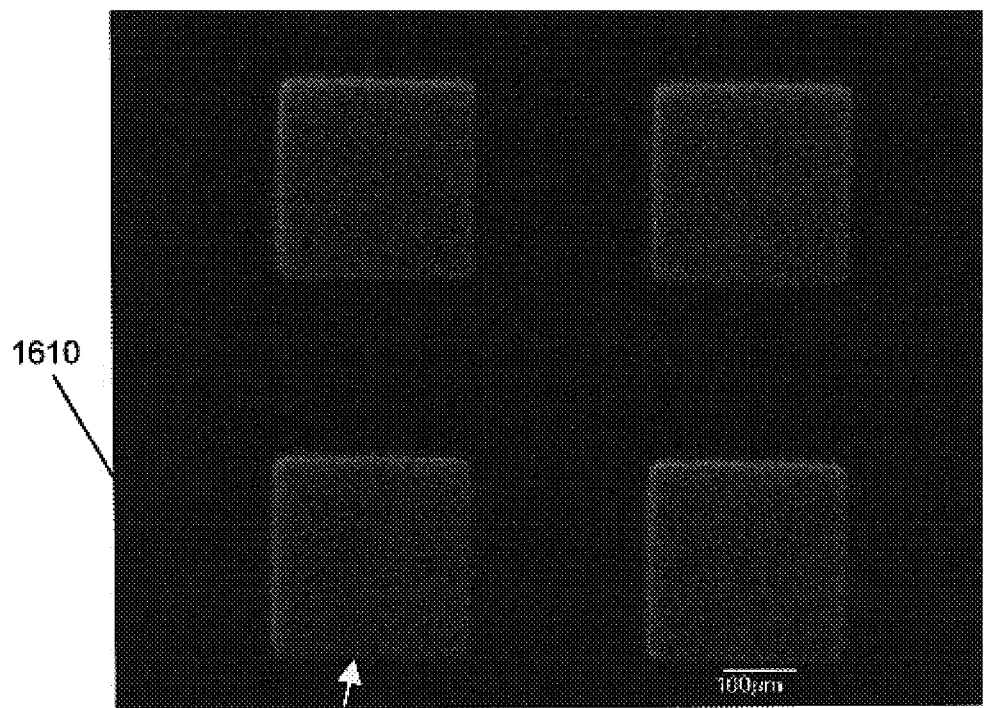
FIG. 16, Panels A and B, Displays an example of a nanofiber array of the invention.
Figure 16B:
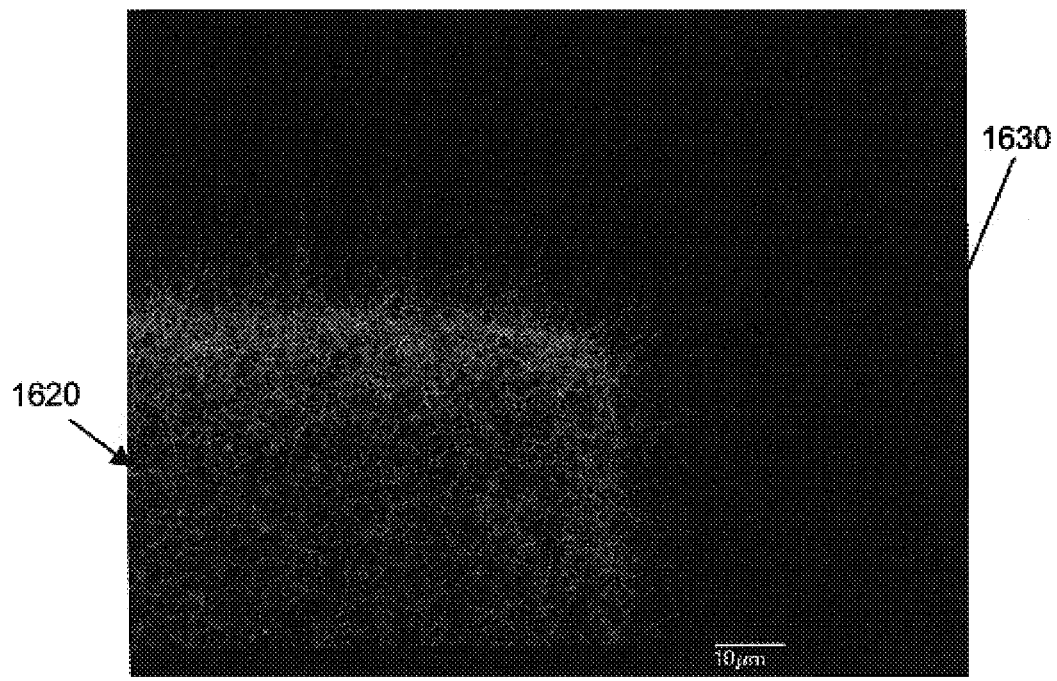

Another example of patterned nanofiber array of the invention is shown in Example 3, FIG. 15. The nanofiber array in FIG. 15 can be used as an improved substrate for DNA or protein arrays, etc. In the figure, nanofiber (here nanowire) features were pre-patterned on a silicon substrate. Again, it will be appreciated that nanofiber patterns of the invention can be created on many different substrate types depending upon the specific parameters involved. For example, silicon, quartz and glass are possible substrates for construction of nanofiber arrays of the invention. FIG. 16 in Example 3 shows SEM images (100× in Panel A and 1,000× in Panel B) of the unique nanostructured surface of another exemplary nanofiber array of the invention. It is contemplated that such patterning (and, indeed, typical patterning using any or all of the array construction techniques herein) be carried out on standard microscope slide formats (or other typical formats) for printing and analyzing with conventional instrumentation.

Other embodiments herein contemplate encompassing the broad capabilities of the nanofiber enhanced substrates in detecting DNA hybridization under real assay conditions and detection of protein binding as well as providing a versatile platform upon which to develop a fully optimized, array based detection system incorporating multiplexed gene/protein expression analyses and genetic tests under clinically relevant conditions.

iii) Structural Factors and Surface Chemistry in Patterned Enhanced Surface Area Microarrays In some embodiments, an increased surface area of a substrate is accessed or utilized by adsorbing materials to it. Although adsorption of DNA is one example of an immobilization approach on spotted arrays, other embodiments comprise, e.g., covalent linkage chemistry that shares characteristics common to other current multiple array linkage strategies, thus, allowing fair comparison between substrates (i.e., substrates of the invention and other current microarray substrates).

In some typical embodiments, the primary chemical attachment approach of the microarrays herein is to coat the surface of a nanofiber enhanced substrate or planar glass array with silanes that provide active groups for the attachment of a heterobifunctional PEG linker. An example is to coat the silica surfaces with aminopropyltriethoxy silane (APTES) and link the PEG to that surface using an NHS ester modified PEG. Subsequent linkages to this surface can then be carried out on the leaving end of the PEG, typically with use of carbodiimide chemistry to link amine modified oligonucleotides to hydroxyl or carboxyl groups. The use of a PEG linker thus allows efficient hybridization by spacing the oligonucleotide probe away from the surface. In some embodiments, short (12 mer) capture oligonucleotides and complementary targets labeled with Cy5 or Cy3 (standard microarray fluorophores) are used. Of course, it will be appreciated that different embodiments will have optionally different surface chemistry, etc. Types of chemical groups used in assays and means of their attachment to substrates are well known to those of skill in the art. See below.

The benefits of the present array (i.e., on nanofiber enhanced substrates) are apparent when compared with conventional array substrates including, e.g., those on plain glass as well as commercially available slides coated in polymer gel. For example, parameters such as signal intensity per unit area, and binding kinetics are all comparable, or better, between the current invention and traditional microarray techniques.

iv) Substrate Optimization in Enhanced Surface Area Microarrays

The basic elements of typical enhanced nanofiber microarray substrates herein are silicon nanofibers, e.g., nanowires, grown on a substrate such as a silicon wafer or glass slide. Of course, as explained throughout, various embodiments herein can be comprised of a number of different components, etc. More information on basic construction of nanofiber enhanced surface area substrates in general is found throughout. However, in general, there are at least two major aspects to preparing optimal surfaces as described for microarrays. It will appreciated that such optimization of nanofiber enhanced surfaces is equally applicable to embodiments in addition to array structures (e.g., equally applicable to separation columns, etc.).

First, the physical characteristics of the nanofiber substrate (e.g., diameter, length, density, orientation and surface properties of the nanofibers) can be varied to optimize the performance of the material in microarray applications. These parameters can be varied to optimize surface area, improve surface robustness and provide the best material for chemical linkage and subsequent assay performance. For example, as will be apparent to those skilled in the art and as detailed elsewhere herein, several methods have been reported in the literature for the synthesis of silicon nanowires, including laser ablating metal-containing silicon targets, high temperature vaporizing of $Si/SiO_2$ mixture, and vapor-liquid-solid (VLS) growth using gold as the catalyst. See above. In typical embodiments herein, the approach to nanofiber synthesis comprises VLS growth since this method has been widely used for semiconductor nanowire growth for other applications. However, again, depending upon the embodiment, alternate construction methods can be used. In most studies the gold catalyst is introduced on the surface of a substrate as a thin uniform layer. The catalytic particles are activated during the growth initiation period through migration and agglomeration. One of the problems with this approach, however, is that it is very difficult to control the diameter and diameter distribution of the nanofibers produced. A significant improvement to this method has been made recently. See, Liebers et al., infra. By using size selected gold colloid particles instead of a gold thin film, high quality silicon nanowires with a narrow diameter distribution can be produced. Yang has also pioneered methods for synthesizing high quality nanowires that can be used to provide a suitable substrate for further optimization. See, Yang et al., infra. Such improvements are optionally used in construction of the enhanced nanofiber surface areas herein.

Optimization and scale-up of the process to produce silicon nanofibers (e.g., nanowires) coated with $SiO_2$ that have controlled diameter, density, length and surface properties (e.g. oxide thickness) are factors of the current invention. The primary approach typically comprises distribution of gold nanoparticles with known diameters on a silicon substrate by spin-coating. After removing solvents and organic residue, the substrate is placed in a growth furnace to grow silicon nanofibers. $SiH_4$ or $SiCl_4$ are typically used as the growth gases. After the growth, the substrate is removed from the furnace and used as the substrate for microarrays or other structures as described herein, or further characterized using the methods described below. The surface of the nanofibers (e.g., nanowires) can be critical for the stability, sensitivity and selection of chemistries for the attachment of specific biomolecules or chemistries to block non-specific interactions. Typically, silicon nanofibers (e.g., nanowires) are covered with a thin native oxide layer that is formed upon exposure of the nanofibers to air. Control of the thickness and the nature of this oxide layer is another useful factor for the fabrication of a robust and chemically compatible substrate. Oxide growth can be controlled by the removal of the native oxide layer followed by the growth of a new layer in carefully controlled environments, for example, use of plasma enhanced deposition to grow the oxide layer on nanofibers. Other modifications, such as growth of nitride layers or specific organosilanes can be used to provide further control of the surface, e.g., by straightforward linkage chemistries well known to those of skill in the art.

As explained throughout, main morphological features of the microarrays herein that can be varied comprise nanofiber length, diameter and density of the nanofibers on the substrate. As is appreciated by those of skill in the art, nanofiber length is controlled by, e.g., the synthesis time in a reactor. Density is controlled by, e.g., the concentration and distribution of gold colloids per unit area on the growth substrate and diameter is controlled by, e.g., the size of the gold colloids used.

Figure 17:
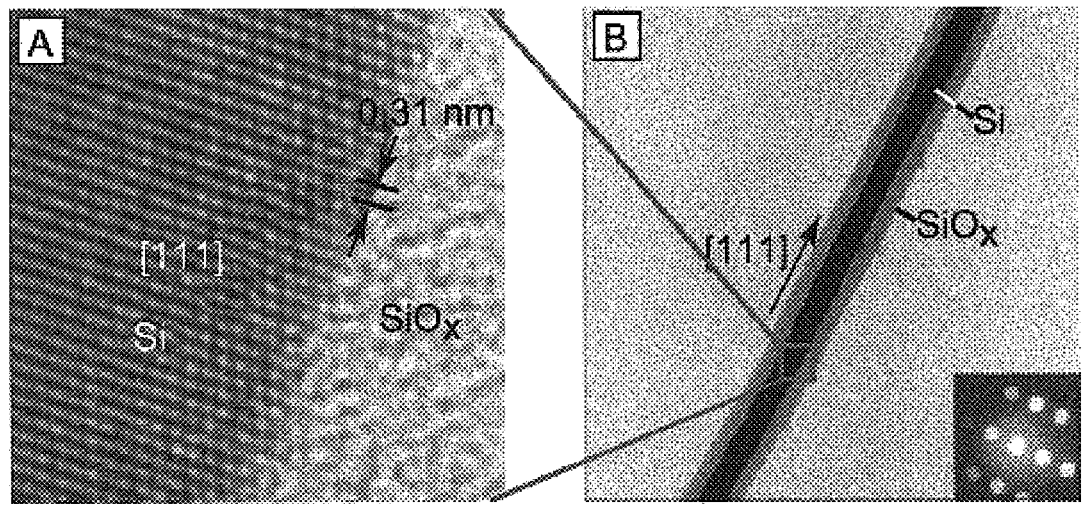
FIG. 17, Panels A and B, Displays electronmicrographs of nanofiber surfaces of the invention.

Throughout the process of optimization of microarrays herein and of developing synthetic control over the materials, a variety of characterization techniques are used to evaluate the quality of the materials produced. Fluorescent microscopy, for example, is often the initial tool to evaluate intensity improvements of the current invention over conventional surfaces. Such evaluations can be carried out on an array scanner. TEM and SEM are optionally used to evaluate overall nanofiber morphology. TEM can also be used to evaluate the quality and thickness of the oxide surface layer on nanofibers. FIG. 17 shows an example of a TEM image of a silicon nanowire and oxide surface. TEM analysis demonstrates that the nanowire consists of a crystalline silicon core encased in a sheath of amorphous silicon oxide.

A second major aspect to preparing optimal surfaces for microarrays as described herein involves methods for coating nanofibers on standard array format slides. In order for substrates to be evaluated on conventional array scanners it can be helpful to grow or construct the arrays on glass slides of standard size and thickness. Thus, some embodiments herein adapt the colloid coating methodologies from silicon wafers to, e.g., standard 1"×3" glass slides. This optionally allows reevaluation of approaches to optimizing fiber density and ensures all other parameters are stable on the substrate format using the methods described herein. Approaches to make the nanofiber surface more robust on the substrate (either by pre-treating the slide prior to nanofiber synthesis) are also involved. In terms of use in conventional scanning devices, etc., one useful aspect of some substrates herein is that they retain the dimensions (length, depth and width) of conventional glass slides and not the specific material. Hence in some embodiments it can prove beneficial to evaluate different substrates for fiber growth that are shaped into the appropriate size. The material optimization process provides a substrate that provides an increased signal intensity per unit area, e.g., 100-fold or more over conventional glass substrates with no significant change in assay kinetics.

The superior fluid wicking properties of the enhanced nanofiber substrates herein provide a more uniform surface for fabricating spotted arrays. However, unlike lithographically patterned arrays where the chemistry is present uniformly over the array and the spatial restriction is achieved by selectively activating small regions using UV light, spotted arrays require far more control over the spatial distribution of the chemistry. Thus, spot intensity, uniformity and size are all optionally optimized/controlled in embodiments of arrays herein.

For example, the amount of fluid spotted onto the hydrophilic nanofiber surface in various embodiments herein, with the available interstitial space for fluid to flow within the optimized surface can be calibrated. This allows the spotting of very precise and very uniform spots that have a high surface area. With this approach, a hypothetical enhanced surface area of 100 fold generated with 20 nm×10 um nanowires will have 180 wires per square micron and the deposition of about 80 pl of fluid will give a spot of 100 um in diameter. This type of precision is well within the capabilities of current ink-jet or piezoelectric printing technologies and can provide the basis for generating uniform spots that can be deposited at the lower end of what is currently achievable. This approach is limited by the amount of fluid that can easily be deposited accurately on the surface. Thus, to reduce spot sizes below 75 um (50 pl), new developments to the deposition of fluids e.g. acoustic drop ejection technologies that can supply a few picoliters of fluid are optionally utilized. In some embodiments, spotted microarrays of the invention are patterned using a low precision pin-printer to achieve spots of approximately 180 um in diameter and to quantitate uniformity and spot intensity compared to equivalent spots on a planar glass surface.

Figure 18:
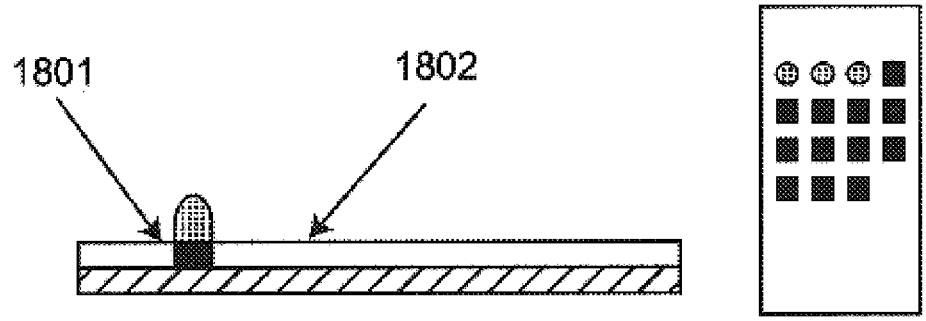
FIG. 18, Displays a schematic diagram of a hydrophobic/hydrophilic patterned nanofiber substrate.

Another means of optimizing spotted microarrays of the invention (specifically in reducing feature size) is to pattern the nanofiber substrate so that it consists of very hydrophobic and very hydrophilic regions of defined size where the chemistry is deposited (see, FIG. 18 for an exemplary schematic). FIG. 18 shows sample pre-patterned nanofiber substrates (with hydrophilic areas, 1801, and hydrophobic areas, 1802) used for spotting applications which provide a controllable uniform surface for applying chemistry. With such strategy, it is contemplated that 50 um spots are achievable (50 um spots at 100 um center-to-center (CTC) spacing equates with 10,000 spots/square centimeter). The nanofiber materials of the invention can be modified with, e.g., hydrophobic silanes to generate a surface that is more hydrophobic than any reported in the literature to date (see, FIG. 19 which shows a water droplet, 1910, on a super-hydrophobic nanofiber (here nanowire) substrate, 1920, and "Super-hydrophobic Surfaces, Methods of Their Construction and Uses Therefor," filed Apr. 28, 2003, U.S. Ser. No. 60/466,229 and Ser. No. 10/833,944 filed Apr. 27, 2004). By initially treating the surface in this manner and then lithographically removing the silane (e.g. by laser ablation) in a defined pattern to generate hydrophilic islands, any chemistry can be effectively restricted to very small regions of the spotted array at the stage of oligonucleotide deposition. Again, similar techniques can be used in a mirror-image fashion to create hydrophobic islands surrounded by hydrophilic areas (or, e.g., lipophilic/lipophobic or the like).

In some embodiments, 100 um spot sizes with CTC distances of 500 um are created. In other embodiments, 50 um diameter hydrophilic spots at 100 um CTC on a hydrophobic nanowire surface are predefined. Oligonucleotide probes can be effectively linked to such substrates and subsequently hybridized to fluorescent targets using various assays known to those of skill in the art.

As will be appreciated, for construction and optimization of many examples of arrays it is necessary to spot chemistries onto various pixels (i.e., discrete areas or spots of nanofibers) of arrays in a controllable fashion, e.g., so that the chemistries are unique to each pixel and remain in the appropriate pixel and not spread to adjoining pixels.

Yet another means of optimizing microarrays of the invention, which helps in controllably localizing chemistries to pixels, is to pattern the arrays with various hydrophobic/hydrophilic regions so that liquid chemistry deposited on a given pixel will not leak onto an adjoining pixel. In such embodiments, arrays comprising pixels, composed of nanofibers, are surrounded with "hedge" regions of nanofibers where the hedges are opposite in polarity (i.e., hydrophobicity/hydrophilicity) from that of the pixels. Additionally, in most such embodiments, a region of surface which contains substantially no nanofibers (or a greatly reduced number/concentration of nanofibers in comparison to the pixel/hedge areas) exists between the pixels and hedges. The hedges can be continuous so that liquid chemistry can be used to modify the polarity of the hedges by wicking throughout the hedges while not contacting the pixels (optionally starting from a "hedge loading pad" or similar area). See FIG. 20. As with many other array embodiments of the invention, the current embodiments can comprise nanofiber arrays for DNA and protein fluorescence binding assays as well as, e.g., MALDI surfaces for mass spectroscopy and the like. See below.

As described previously, many embodiments of nanofiber-coated surfaces tend to wick compatible fluids quite avidly. A surface having an array of patches of nanofibers (i.e., pixels) spaced apart by regions of surface that have a hydrophilicity similar to that of the nanofibers can allow fluids to wick to adjacent pixels if, e.g., even slightly too much fluid is added to a pixel or the surface were jarred, etc. To block such undesired wicking, in some of the current embodiments, the surface of the substrate between the pixels is not necessarily the opposite polarity of the surface of the nanofibers in the pixels; (although such embodiments do exist). Rather, "hedges" between the pixels are of opposite polarity in many embodiments. This embodiment comprises methods and structures that allow for placement of regions of different polarity (i.e., hedges) between pixels of nanofibers.

Figure 20:
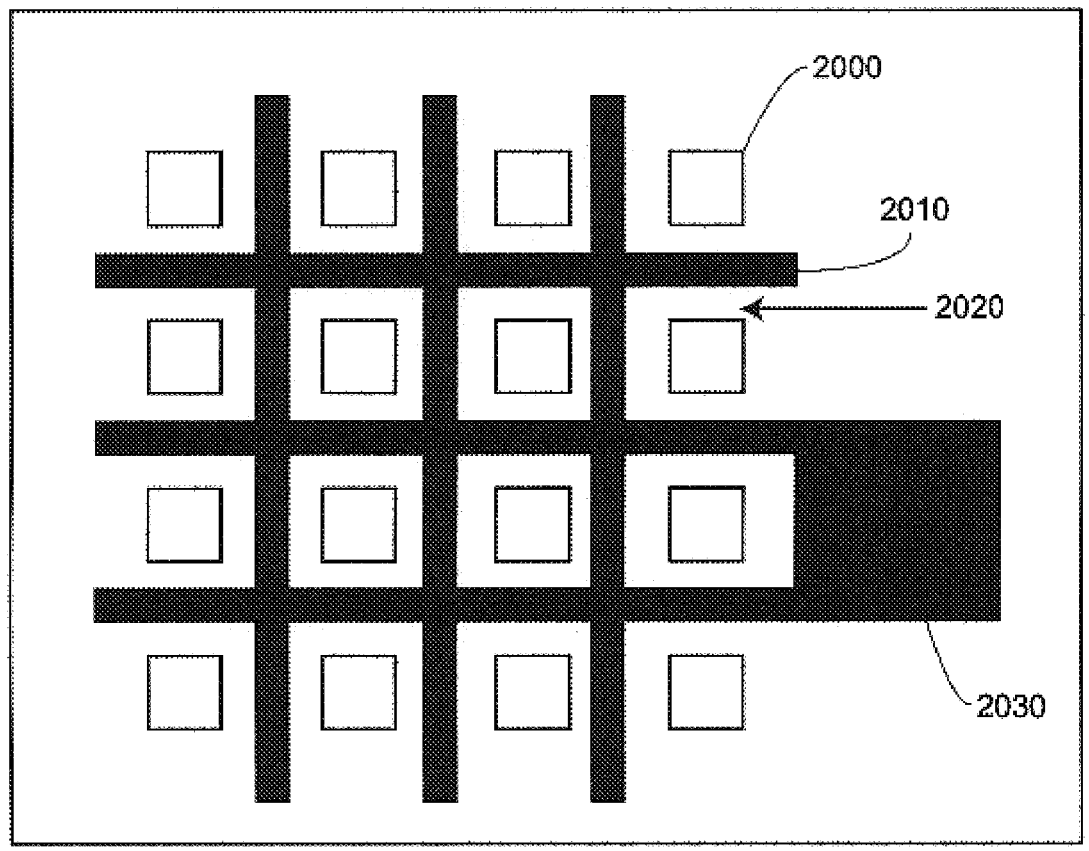
FIG. 20, Displays a schematic of an exemplary hedge/pixel arrangement of a nanofiber microarray of the invention.

As can be seen in FIG. 20, examples of this embodiment are composed of a continuous hedge of nanofiber covered surface area, 2010, which surround or enclose areas which contain substantially no nanofibers, 2020, which, in turn, surround pixel areas, 2000, that are composed of nanofiber areas that are of opposite polarity than the hedge areas. By opposite polarity here is typically meant hydrophobicity versus hydrophilicity (or optionally lipophobicity versus lipophilicity, etc.). Creation of such patterns is typically accomplished though removal of nanofibers in the emptied areas, thus, delineating the hedges and pixels. The patterning is optionally accomplished though any of a number of means, e.g., those described elsewhere herein such as photolithography, laser patterning, etc. In order to make the hedge nanofiber areas of a different polarity (typically hydrophobic) than the pixel areas (typically hydrophilic), a solution which conveys the hydrophobicity can be contacted with one or more area of the continuous hedge and allowed to wick throughout the hedge. Because the hedge areas and the pixel areas are separated by emptied regions, such hydrophobicity conveying solution will not wick into the pixel areas themselves. In some embodiments the solution can be applied to a specialized region, 2030, which can be described as a "hedge loading pad." Such loading pad area can be external to the main array area, but is fluidly connected to the continuous hedge, thus, allowing wicking of the deposited solution throughout the entire hedge area. Some embodiments can comprise multiple hedge areas located in various position upon the array formation. Addition of the hydrophobic solution to the hedge area is typically performed during manufacturing of the array rather than by an end-user of the array so that application can be more carefully controlled. Again, specific choices for coatings/moieties to add and/or enhance liquid repellency or attraction are very well known to those of skill in the art.

Once the hedge is made hydrophobic it will act as a barrier and prevent aqueous solutions applied to the pixels by the customer from migrating or spilling into other pixel areas. Thus, a solution that is meant for one pixel will not wick to an adjacent pixel, even if the first pixel is slightly overloaded with solution, etc. Those of skill in the art will appreciate that various aspects of this embodiment can be manipulated depending upon the specific parameters of the arrays to be constructed as well as the end use of such arrays. For example, the polarity (i.e., hydrophobicity/hydrophilicity) of the hedge and pixel areas can be reversed, with the pixels being hydrophobic and the hedges being hydrophilic. Additionally, pixel size and shape, hedge thickness, space between hedge and pixel, and hedge geometry are all optionally manipulated in various embodiments.

v) Characterization of Exemplary Nanofiber Enhanced Surface Area Microarrays Example 4 provides illustrative examples of NFS arrays of the invention. One of the largest growth areas in microarray technology is the application of DNA array substrates and analysis tools to proteomic applications. Protein arrays are analogous to miniaturized immunoassays, and like DNA arrays, can utilize fluorescence as a readout. Exemplary embodiments herein can involve, e.g., the chemical linkage of cytokine specific antibodies to an NFS array surface, the application of a target solution containing spiked cytokines and labeling with a fluorescently labeled secondary antibody. Arrays of the invention are optionally useful in, e.g., detection, such things as cytokines, etc. in tissue culture media or diluted plasma. Conventional fluorescent array scanners can be used for detection of the bound target and comparison of the signal intensity and dynamic range over conventional glass surfaces. Because of the importance of protein orientation for effective target binding it is believed that increasing the number of probes per square micron (e.g., as with the nanofibers of the invention herein) significantly improves the performance of protein arrays. In addition some embodiments contemplate further coating the nanowire surface to provide a polymeric matrix for the immobilized probes to improve array performance.

To illustrate a number of the concepts and embodiment descriptions above, several illustrative assays were performed using exemplary nanofiber enhanced surface area arrays of the invention. Results of such are provided in Example 5.

Another advantage of various embodiments of nanofiber enhanced area surfaces of the invention is that in many embodiments, the nanofiber containing areas can be isolated. In other words, islands of nanofiber areas (i.e., containing greatly enhanced surface areas) are surrounded by areas that do not have (or have much fewer) nanofibers (i.e., therefore such areas do not have an enhanced surface area or have a less enhanced surface area). Creation of such patterning is beneficial in many embodiments herein because numerous nanofiber surfaces display liquid wicking effects. With wicking effects, a liquid (e.g., a sample spotted onto a nanofiber surface) diffuses or wicks out from its point of contact. Patterning of nanofiber surfaces can, thus, stop such wicking activity. On planar surfaces spotting of samples also leads to "halo" or "doughnut" effects due to quick movement and drying of such small sample sizes typically used. The spot intensity profile of such halos/doughnuts shows a greater concentration of analyte encircling a region of lower concentration of analyte. Typical embodiments herein, however, can be constructed to display little or not such effect. See Example 5 and the figures therein.

The nanofiber arrays herein also display improved dynamic range and improved sensitivity as compared to substrates without nanofibers. Illustration of such is also shown in Example 5. See below for further discussion of increased dynamic range.

The figures and data herein (e.g., Example 5, etc.) demonstrate that embodiments of the invention comprising nanofiber enhanced surface area substrates can be modified with conventional chemistries and that in many embodiments, such surfaces display an almost 2 order of magnitude or more increase in signal intensity per unit area as opposed to planar substrates which do not have nanofiber enhanced area surfaces. Additionally, in many embodiments, it is seen that an at least 1 order of magnitude increase or more in dynamic range exists between nanofiber enhanced surfaces herein and planar $SiO_2$ surfaces without nanofibers. Also, the binding kinetics on dense nanofiber enhanced surfaces and planar surfaces are quite similar. Thus, nanofiber enhanced surface areas allow a reduced feature size, show an improved dynamic range, show improved spot uniformity, provide a generic platform for proteomics and genomics, and have reduced requirements for instrument sensitivity and reduced signal integration times as compared to planar surfaces (i.e., those without nanofibers).

vi) Use of Exemplary Enhanced Surface Area Microarrays with Mass Spectrometry As mentioned previously, various embodiments of the current invention can be used in creation of targets for mass spectrometry. Typically in such embodiments, various substances to be subjected to mass spectrometry are configured into microarrays of the invention. However, the enhanced nanofiber substrates of the invention can be used in construction of targets for mass spectrometry even without arranging a number of target substances into a microarray format. In other words, the enhanced surface area nanofiber surfaces can be used in construction of targets for single substances to be subjected to mass spectrometry, as well as for 2, 3, 5, 10, or more, etc. substances, substances in microarrays, etc.

MALDI, or matrix assisted laser desorption/ionization, commonly uses organic molecules capable of UV adsorption and energy transfer mixed with a sample and applied to a planar target for ionization mass spectrometry. However, the matrix, or organic additive, can cause interference in the technique and its elimination has been the target of research over the last ten years. Up to the present, the most promising matrix-free method involved etching silicon to create porous silicon. DIOS-MS, or matrixless desorption/ionization strategy for biomolecular mass spectrometry, is based on pulsed laser desorption from a porous silicon surface. For example, see, e.g., Lewis et al., *International Journal of Mass Spectrometry*, 2003, 226:107-116. Etched silicon has increased surface area and therefore can make contact with a large amount of sample. Silicon is UV absorbing and can also transfer energy to help ionize the sample. Because of these features, the etched silicon emulates an organic matrix. See, e.g., U.S. Pat. No. 6,288,390. However, poor reproducibility and flexibility of the etched silicon surfaces has prevented the commercial implementation of this method.

The use of nanofiber enhanced surface areas for MALDI, DIOS-MS and other similar mass spectrometry applications promises a highly controlled, patternable silicon surface having very high surface area. The non-tortuous open nature of the surfaces herein, the high purity of the materials involved, and the lack of restriction to a silicon substrate make the current enhanced surfaces ideal for various mass spectrometry applications.

Various embodiments of the invention comprise laser desorbtion mass spectrometry targets created by synthesizing or connecting nanofibers (e.g., semiconductor nanofibers) on a supporting substrate. The nanofibers are preferably silicon and most typically are synthesized on the surface by a CVD process using a gold catalyst. However, as explained throughout, nanofibers used in the various embodiments herein are optionally synthesized through any of a variety of means. See above. Furthermore, the substrate upon which the fibers are synthesized does not have to be silicon and, in some embodiments, is preferably a metallic surface. Also, in some embodiments, it is effective to deposit the nanofibers onto a surface without having them attached at the base. Again, see above. The high surface area, non-tortuous path morphology and UV absorbing characteristics of the semiconducting nanofiber surfaces of the invention make them ideal for construction of laser ionization targets.

In typical mass spectrometry target embodiments, the substances to be examined through MALDI, DIOS-MS, or the like are configured into a nanofiber enhanced surface array of the invention. Thus, for example, the substances to be examined are placed/contacted with various nanofiber pads, fields, or in the bottom of micro/nano-wells which comprise nanofiber surfaces. Most commonly, each separate pad, pixel, field, etc. (i.e., each separate discrete area of nanofiber surface) is contacted with, or has placed upon it, a different substance to be examined by mass spectrometry. Of course, depending upon the specific application, other configurations are equally possible. Greater description of exemplary arrays and array constructions, which are also applicable to the current embodiments, are described throughout.

As with the other embodiments herein, various aspects of the nanofiber enhanced area surfaces can be varied, e.g., in order to optimize the surfaces/methods for particular parameters. For example, the nanofibers can be varied in diameter, length, or density depending on the application requirements. Also, the fibers can be grown on silicon or on any other desired medium, e.g., metal, glass, ceramic, plastic, etc., and in any desired geometry, e.g., planar, in wells, in strips, etc. In the current embodiments, the nanofibers can be grown on silicon, but in many instances would more likely be produced on a dissimilar substrate such as glass, quartz or metal. Other possible materials for nanofibers and substrate surfaces are listed throughout. Additionally, those of skill in the art will be familiar with yet more possible construction materials. The fibers are also optionally coated or functionalized for optimum performance, e.g., as is described elsewhere herein.

Samples of the substances to be analyzed by mass spectrometry are optionally placed in contact with the nanofiber substrates by conventional dispensing means. Similar means are described elsewhere herein, e.g., pipetting, dot-printing, etc. Those of skill in the art will be familiar with various protocols to follow to dry the samples for analysis. Laser energy levels and pulse durations are also optionally optimized for analysis of the samples arrayed upon the nanofiber surfaces. Again, those of skill in the art will be familiar with ways of determining optimal parameters for laser energy, pulse time, etc. for mass spectrometry.

Various examples of use of nanofiber enhanced surfaces of the invention in mass spectrometry applications are shown in Example 6.

B) Quenching of Non-Specifically Bound Fluorescent Molecules by Proximity to Silicon in Enhanced Surface Area Substrates In embodiments herein comprising solid phase binding assays, where fluorescence is used for detection, the limit of detection is generally determined by non-specific binding of fluorescent molecules, while the maximum detection level is determined by saturation of the surface binding sites by the specific analyte. In general, modification of the solid phase surface with analyte capture molecules is not perfect and "holes" in the layer of capture molecules allow fluorophores to bind nonspecifically to the surface. Typically the capture molecules are large and tend to hold the fluorescent analyte at some distance from the surface.

In many embodiments herein, a mat of silicon nanofibers (e.g., nanowires) on a surface (e.g., a planar surface) is used as a means to increase the binding surface area for fluorescence binding assays. See, above. In typical embodiments, the silicon nanofibers are covered with a native oxide (about 2 nm thick) such that their surface properties are equivalent to those of glass. This surface would be expected to increase the maximum amount of analyte bound at saturation, but would also be expected to demonstrate an increased background fluorescence or non-specific binding (NSB). Both effects theoretically should be proportional to the total surface area, and thus the dynamic range of the assay (maximum fluorescence/background fluorescence) supposedly should be the same as that for an unmodified planar surface. Dynamic range is a limitation of solid phase binding assays, particularly those for DNA and RNA where the range of concentrations of different species of nucleotide can vary orders of magnitude in one sample. Quite surprisingly, binding assays performed on nanofiber enhanced surfaces demonstrated a greater dynamic range than their counterparts performed on planar glass substrates. Example 7 and the figures therein illustrate such ranges, etc.

Given these surprising points, for the purpose of performing fluorescence binding assays, various embodiments of the invention use a substrate that absorbs light in the spectral region where the fluorophore emits, and which has a chemistry attachment surface that is sufficiently close to the light absorbing part of the substrate such that energy transfer from molecules close to the surface is efficient.

It will be appreciated that material of the substrate can be changed in different embodiments as long as it absorbs light in the appropriate region of the spectrum. Those of skill in the art will be aware of materials (e.g., various inorganic semiconducting materials, metallic materials, etc.) which allow fluorescent molecules to non-radiatively transfer their energy to the materials. See, e.g., Chance, et al., in Advances in Chemical Physics, I. Prigogine and S. Rice (eds.) (Wiley, N.Y. 17978) Vol. 37, p. 1. Such materials, i.e., those to which energy from fluorescent molecules is non-radiately transferred, thus allowing fluorescent quenching, are selectively chosen to comprise nanofibers and/or substrates in the various embodiments herein. Thickness of the chemistry attachment layer (e.g., oxide for silicon) also can be modified to optimize depth into solution that fluorescence will be quenched. This will depend on the specific binding chemistry used (e.g., a long PEG spacer that keeps specifically bound fluorophores further away from the surface would allow for a thinner oxide that would quench nonspecifically bound molecules further form the surface).

As will be appreciated, embodiments of the invention (i.e., those involving self-quenching) can also optionally involve substrates in addition to those involving nanowires as well as those with nanofiber substrates to reduce NSB signal. For example, as will be understood from the above discussion, other enhanced surface area substrates (e.g., silicon substrates) of various conformations such as those involving microstructures (e.g., comprising structures which are too large to fall easily within the nanofiber parameters defined herein), myriad types of nanostructures (e.g., nanowires of various lengths/diameters, nanoposts, nanorods, nanopores, nanocrystals, etc.), as well as amorphous silicon surfaces can all utilize fluorescent quenching as shown herein, and are all contained within various embodiments of the current invention.

Thus, in some embodiments herein, an increased dynamic range of nanowire surfaces in contrast to glass or grown $SiO_2$ surfaces is achieved because background signal does not increase proportionally with enhanced surface area, whereas the saturated binding signal does increase in proportion to the enhanced surface area. A major contributing factor to this effect is the increased quenching of non-specifically adsorbed fluorescent material on native silicon dioxide surfaces (<2 nm oxide) as compared with grown oxide surfaces.

C) Separation Applications

Another exemplary area of use of the nanofiber enhanced surface area substrates of the invention concerns filtration/separation. Separation techniques such as HPLC are replete throughout academia and industry. In typical HPLC and other similar separations, various components in a liquid mixture are forced through a column (e.g., a capillary column) under pressure. Within the column is a packed bed of particles that selectively retains particular analytes within the liquid (e.g., due to specific physical properties such as electric charge, size, hydrophobicity, shape, etc.). Thus, separation of analytes is brought about by such interaction of particles with the various analytes which causes the analytes to pass through the column at different rates.

Figure 21:
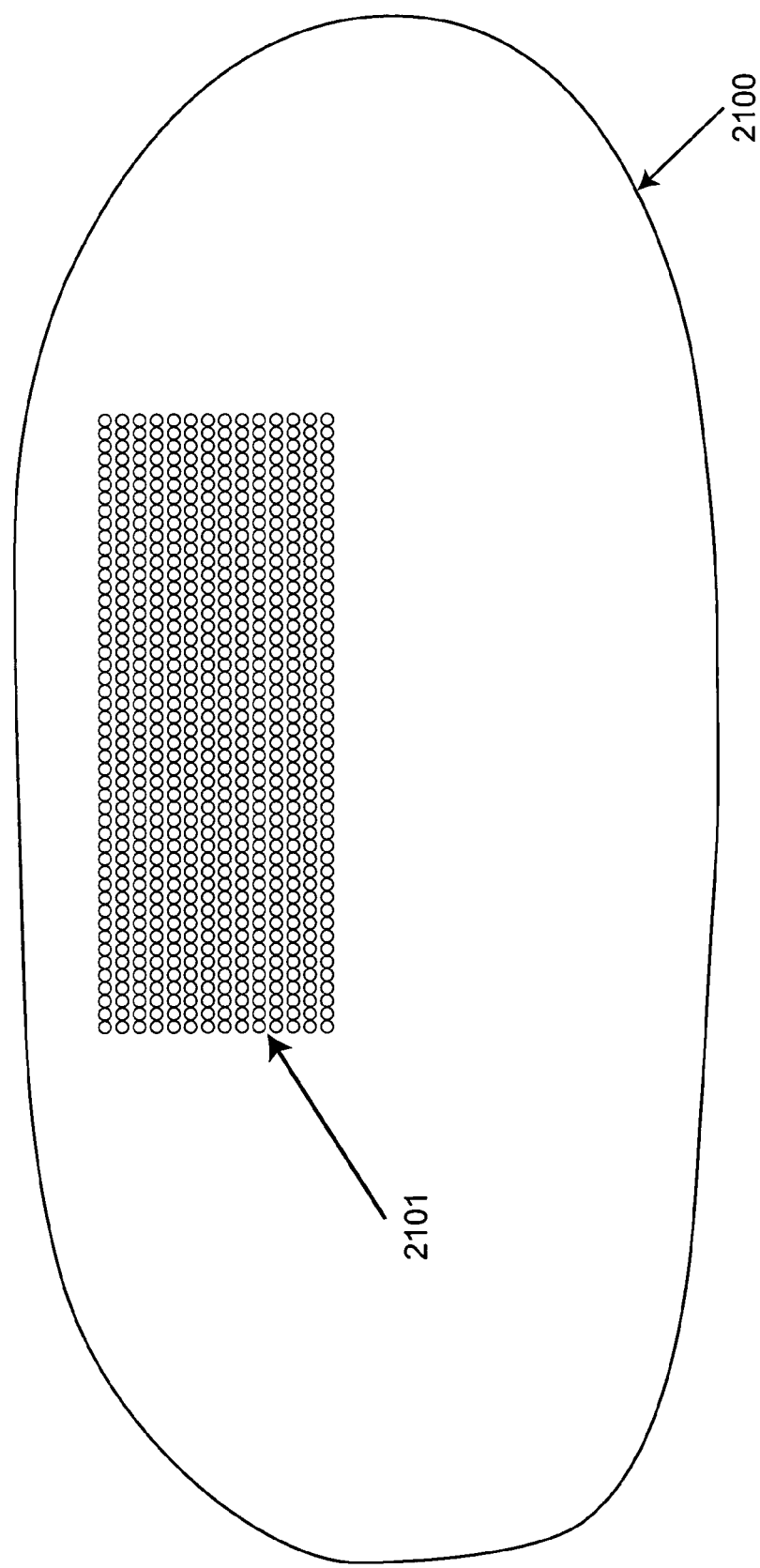
FIG. 21, Displays a schematic representation of nanofibers compared with a size representation of HPLC packing material.

In various embodiments herein, nanofiber enhanced surface area substrates are used in similar separation scenarios. For example, a packed bed of particles in a separation column can consist of particles (e.g., beads) that are coated with nanofibers, either through application or through growth on the beads. Thus, the beads are therefore nanofiber enhanced surface area substrates. The use of nanofibers benefits separations through several means. For example, the greatly enhanced surface area allows binding moieties, etc. to be present in a much higher concentration in a smaller overall volume. See, FIG. 21 for a comparison of nanofiber sizes, 2101 which represents vertical 40 nm nanofibers, to typical HPLC packing material, 2100 which represents an outline of a typical HPLC matrix bead. Thus, FIG. 21 shows a nanofiber grid superimposed over a typical 10 um HPLC column packing bead. Therefore, analytes passed through the column will not have to go through a tortuous path to encounter such moieties; less column volume needs to be provided to capture the desired analytes; and less pressure needs to be applied to the column to force the analytes through. Also, in some embodiments, cleaner bands of analytes are eluted from the column. Due to the enhanced surface area, a greater number of analyte capturing moieties exists in a smaller area, thus, a greater percentage/amount of the desired analyte is captured in the smaller area and will present a cleaner band when eluted from the column.

As will be appreciated by those of skill in the art, for numerous materials the surface properties provide a great deal of the functionality or use of the material. For example, in various types of molecular separations, the selectivity is provided by interaction of the surface of a column or packing material with the appropriate analytes. Thus, in many instances, increasing the surface area of such materials or columns can improve the separation efficiency and result in shorter analysis times and higher resolutions. For example, the current invention, by coating the walls of a capillary electrophoresis column or the beads in an HPLC packing matrix with nanofibers (e.g., metal terminated) that extend into the separation solution optionally creates a dramatic increase in surface area which can be in contact with the separation solution. In actuality, basically any type of column (e.g., capillary electrophoresis, HPLC, etc.) is optionally coated with the nanofibers of the invention. Of course, in different embodiments herein, the lumens of such tubes/columns have nanofibers grown within such areas, e.g., by coating the lumen with gold colloids, etc. See, below. In yet other embodiments, the nanofibers are used as "loose" packing material in tubes/columns or are attached to the wall of the lumen through a gold ball on the end of the nanofiber. In yet other embodiments, the nanofiber surfaces of the invention can provide "thin film" or other similar separation devices. Beneficially, in typical embodiments, the materials involved in separation devices, etc., are made from $SiO_2$ substrates. In many typical (but not all) embodiments herein, the nanofibers used to enhance surface area comprise silicon oxide(s) as well. Additionally, the non-tortuous path of the nanofiber separation media leads to lower required pressures and higher efficiency separations due to the lack of packing voids, etc. In many instances herein, conventional chemistry well known to those of skill in the art is optionally used to functionalize the nanofibers and, thus, tailor the enhanced surface area to specific uses.

In some embodiments herein, nanofibers are synthesized inside the lumen of a tube, e.g., a capillary tube. Such nanofibers coat the inside of the tube with a homogeneous layer of nanofibers and greatly increase the available surface area within the tube. In some such embodiments, the nanofibers are optionally treated (e.g., with a hydrophilic moiety to increase the wicking (capillary fluid transport) capability within the tube). Of course, in other embodiments herein the innate wicking action of particular nanofiber surfaces acts to wick fluids. Such embodiments can be used, for example, to increase the capillary pumping head in heat pipe structures and the like. The increased wicking capability can allow heat pipes to work more efficiently against gravity. Thus, the heat source can be located above, rather than below or level with, a cooling area. Similar embodiments can also be extend to refrigeration type systems and, in fact, to many other heat transfer systems. See below for discussion of construction of enhanced surface area nanofiber substrates within lumens of tubes.

Thus, the nanofiber enhanced surface area substrates of the invention are optionally used as, or within, numerous types of separation media. Their high surface to volume ratio and non-tortuous path structure lead to low flow resistance, high efficiency pressure driven separations. Additionally, since a number of embodiments are composed of silicon oxides, conventional functionalization is relatively straightforward as will be appreciated by those skilled in the art. Additionally, as is explained in greater detail below, solution phase growth allows growth of nanofibers inside separation devices (e.g., within various columns or capillaries, etc.). Also, tight spacing of vertical nanofiber surfaces can optionally allow biomolecular separations. Liquid separations done with the current invention are optionally useful in, e.g., reverse osmosis membranes, ion exchange systems, water treatment, and specialized applications in such areas as pharmaceuticals, fine chemicals, chemical processing, mining, catalysts, beverage and dairy processing, etc.

As described in more detail in various embodiments herein, hybridization substrates can benefit from similar nanofiber enhanced surface areas. For example, immunoassays and other similar assays are often set up on flow-through membranes. Such membranes typically have large pore sizes to allow rapid flow-through of analyte containing solutions. However, the large pore size limits the capture surface area of the membrane (i.e., there is less surface area available to capture the desired analytes). Further, increasing the available surface area by providing more, smaller pores, results in problems in the travel of molecules through the pores, e.g., back pressure is greater and diffusion is slower, thus, resulting in lower access to the added surface area resulting from the inclusion of such pores. In embodiments of the current invention, the effective surface area can be dramatically increased without compromising the strength of the membrane. This is due to end attachment of nanofibers functionalized with the capture antibody (or other moiety) to the surface material, e.g., which comprises the pores (i.e., the material in which the pores exist).

i) Variously Configured Separation Embodiments of Nanofiber Enhanced Surface Areas Several basic embodiment types of separation structures can be fabricated in the current invention from nanofibers and nanofiber processes. As explained throughout, embodiments can have utility, in particular, in the areas of separation, detection, catalysis, etc. In typical embodiments the utility of the nanofiber enhanced surface areas is based upon the basic porous structure formed from the nanofibers. Such nanofiber enhanced surface areas structures have such characteristics as, e.g., a porous profile formed by entangled or specifically arranged nanowires. Such pores or free spaces in the structure are between the nanofibers and typically are all connected one to another. Typical embodiments also present a profile free of micropores, dead end pores, etc. and a profile comprising mesoporous/macroporous pores with narrow size distribution. Embodiments herein also typically comprise a profile having high accessible surface area (with typically all surface sites being easily accessible), and optionally, a robust constitution (e.g., the nanofiber structures can take high pressure).

Figure 22:
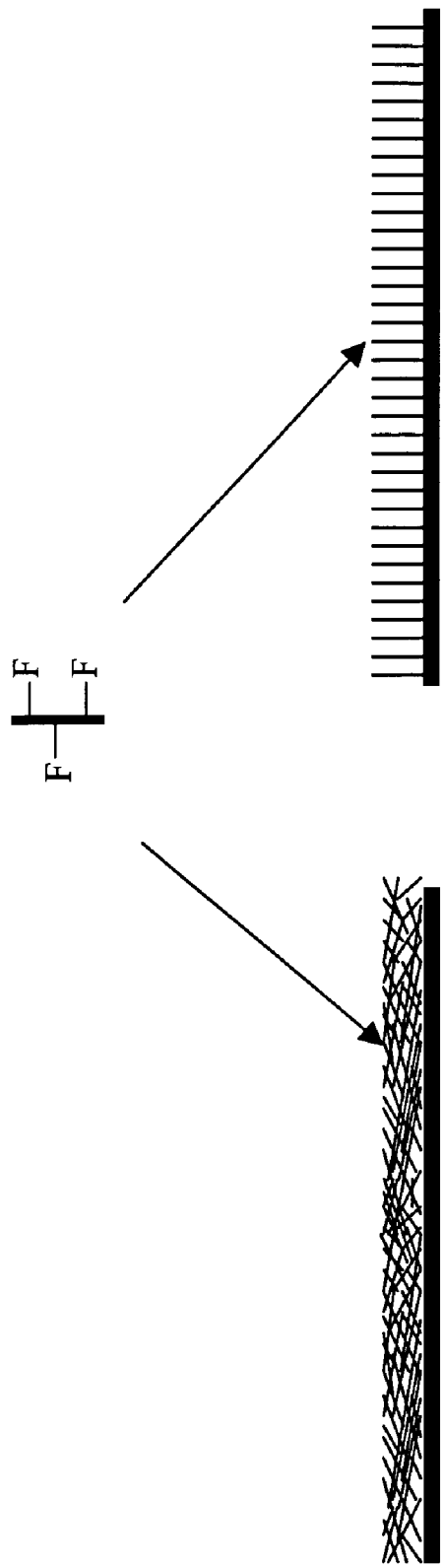
FIG. 22, Shows a schematic of substrates covered with thin nanofiber layers.
Figure 23:
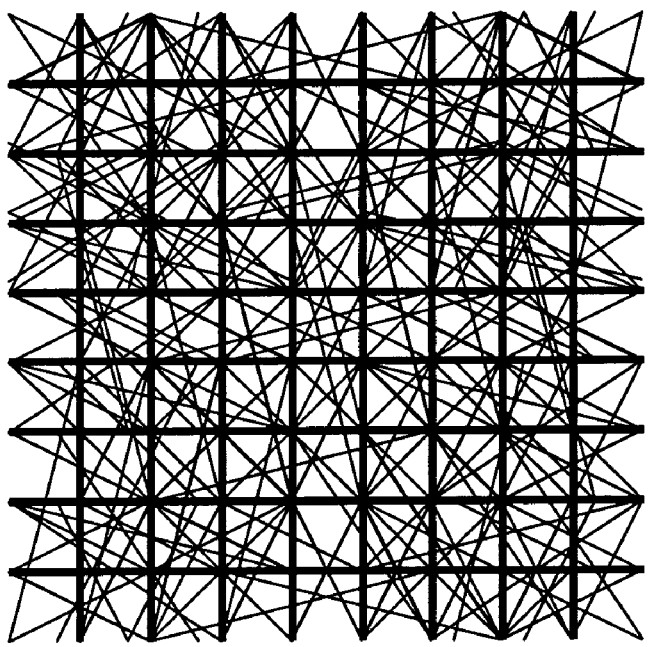
FIG. 23, Illustrates a membrane formed by coating a thin nanowire layer on a macroporous media.

The nanofiber thin film structures illustrated in FIG. 22 are similar to many embodiments herein. Typically, such nanofiber structures are of $SiO_2$, but as explained throughout, other substances are also possible. Panel A shows randomly oriented nanofibers producing a uniform mesoporous structure. The nanofibers can optionally be fused together at cross (contact points). Panel B shows vertically aligned nanofibers with a separation of, e.g., a few nanometers. In either configuration, the nanofibers can be functionalized, e.g., via —OH chemistry, etc. as is illustrated via the inset in FIG. 22 with "F" indicating functional groups. Such nanofiber surfaces can be utilized for, e.g., high resolution, high speed thin layer chromatography for protein/DNA separation, etc. Again, as explained throughout, however, such examples are but a few of the myriad possible embodiments herein. Such embodiments as shown in FIG. 23 (e.g., a $SiO_2$ nanofiber membrane (here nanowire) can be made into, e.g., high efficient TLC plates on glass, metal foils, or even plastics. One method to make a plastic supported plate includes, e.g., making a high nanofiber concentration polymer composite, making a composite sheet through compression/extrusion, then plasma etching to remove the polymer and expose the nanofibers on the surface. Such construction can be optionally followed by functionalizing the fibers with a chemical moiety.

Figure 24B:
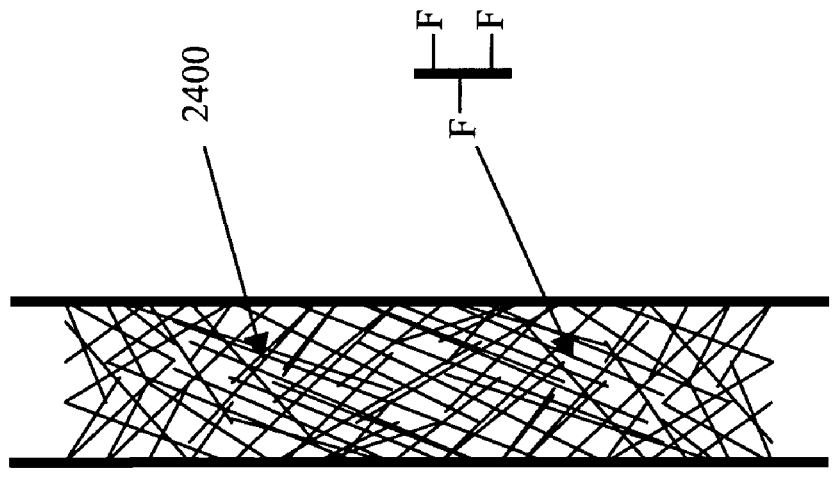
FIG. 24, Displays a schematic representation of nanofibers grown/deposited inside capillary tubes.
Figure 24A:
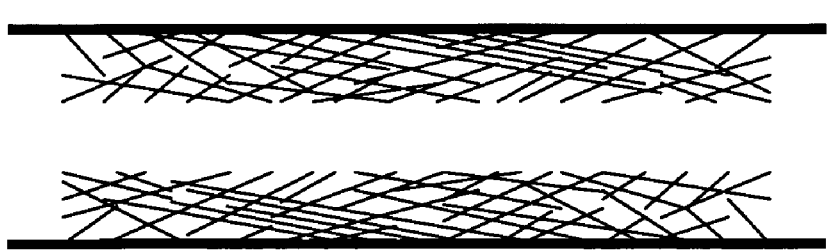
Figure 25:
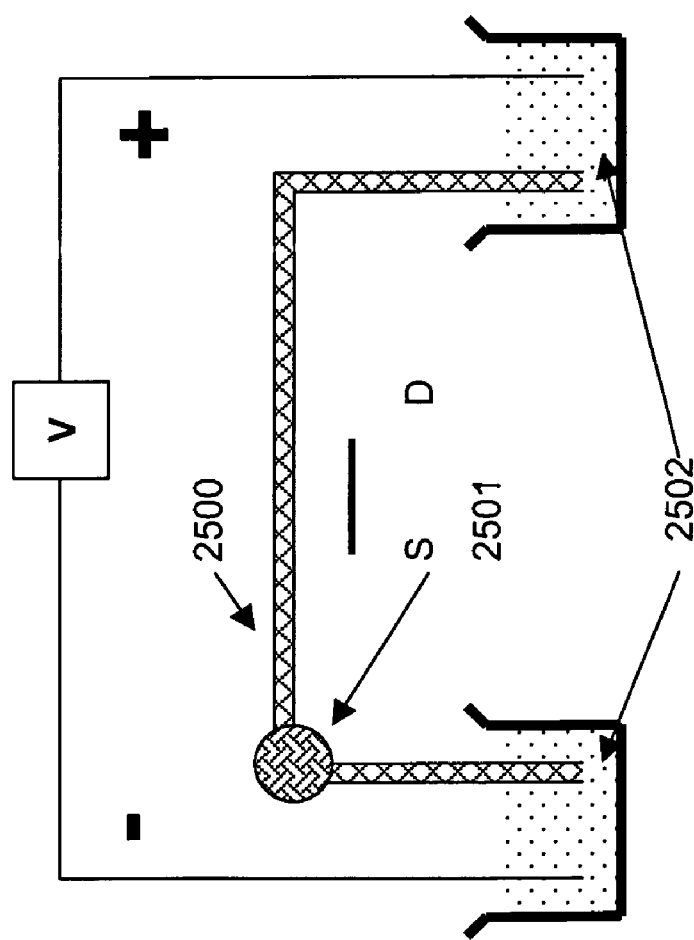
FIG. 25, Displays a schematic representation of a device comprising nanofibers grown/deposited inside capillary tubes.
Figure 27:
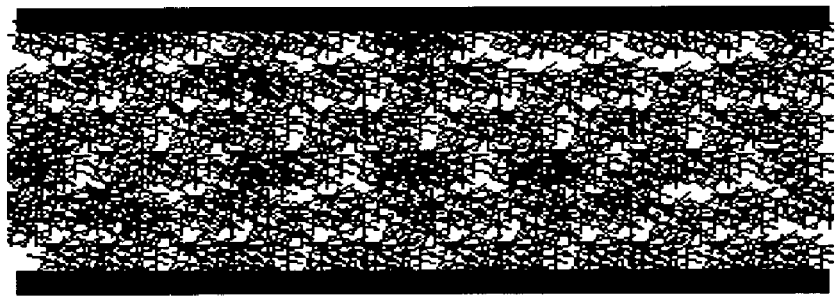
FIG. 27, Displays a sample chromatography column packed with particles made from nanofibers.
Figure 26:
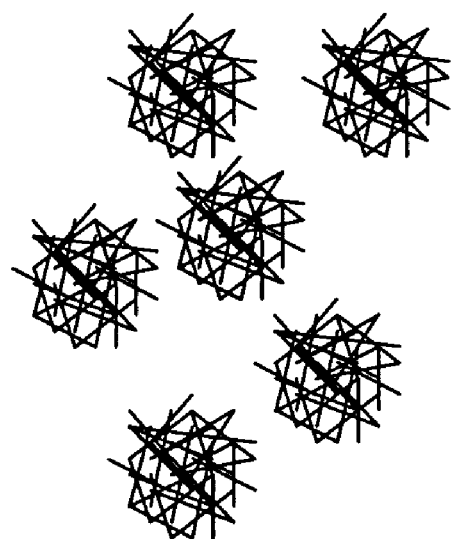
FIG. 26, Displays particles made from nanofibers.

Other embodiments herein, however, comprise nanofiber enhanced surface area structures comprised within the lumen of a tube, column, capillary, etc. For example, the schematics shown in FIGS. 24-27 can be made by directly growing nanofibers inside a capillary tube, such as a quartz/Pyrex® capillary. For example, FIG. 24 shows a schematic view of cross sections of possible nanofiber capillary columns (e.g., one with an open lumen and one wherein the nanofibers fill the entire or substantially the entire lumen). The nanofibers are optionally fused together where they cross (e.g., at 2400) and/or comprise functional groups (e.g., moieties to selectively bind molecules, etc.). Examples of such functional groups can include, e.g., chemical groups such as —OH, —COOH, $NH_3$, etc.; small molecules such as amino acids, protein and/or DNA segments, surfactants, etc.; polymer chains such as LPA, PDMA, PEO, PVP, PEG, AAP, HEC, etc. Again, "F" in FIG. 24 indicates functional groups. Those of skill in the art will be quite familiar with the wide range of possible functional groups that may be used in columns, etc. FIG. 25 shows a schematic diagram of an exemplary nanostructure enhanced electrophoresis device for, e.g., DNA separation. The device can combine a nanofiber engineered capillary, 2500, with a highly sensitive nanofiber FET detector, 2501, and buffer reservoirs, 2502. Nanofibers can be grafted with linear polyacrylamide chains and grafted polymer chains can be fixed on nanofibers, thus, suppressing electroosmotic flow. The nanofiber network can provide an additional separation factor. FIG. 26 shows exemplary mesoporous particles engineered with nanofibers (e.g., $SiO_2$ nanowires). The nanofibers can optionally be fused together at their cross points and/or can comprise functional groups (e.g., the nanofibers can be functionalized via —OH chemistry, etc. as described above). Such mesoporous particles present a unique porous structure, i.e., connected spaces in a three dimensional nanofiber network. The mesoporous structure presents uniform pore size distribution that is free of micropores, dead-end pores, etc. Such structures also present a high accessible surface area and a uniform surface site energy, and are free of extraneous binder. The structure can have a high strength (e.g., $SiO_2$ nanofibers can be fused at cross points with $SiO_2$) and can optionally be functionalized as exampled above. FIG. 27 presents an exemplary use of a nanofiber-enhanced column as a chromatographic column. The schematic view presents a cross section of a nanofiber-particle packed column that could be suitable for, e.g., high speed protein/DNA separation, chiral separation, etc. In many, but by no means all, embodiments, the nanofibers can comprise silicon nanofibers (e.g., nanowires) with a thin $SiO_2$ coating. As explained above, additional structure can be further fabricated in such nanofibers, e.g., through —OH chemistry. For example, chemical chains with specific functional groups are optionally attached. Embodiments comprising such tubular structure are especially useful for, e.g., chromatographic separation, such as micro-separation and chiral separation. Examples of nanofiber enhanced surface area substrates within capillaries is seen in Example 8.

In yet other embodiments herein, structures similar to those in FIGS. 24-27 can be made by fusing randomly packed nanofibers at contact points. In some optional embodiments, the nanofibers are not fused, or only a portion of the nanofibers are fused. The particles can be formed by grounding. These particles are optionally used for, e.g., packing large chromatographic columns for large scale, high throughput separations. A useful feature of such embodiments is that such columns have a bimodal pore structure (i.e., macro pores between particles (high throughput) and mesopores within the particles (high efficient separation)). Again, as with many embodiments herein the surface of nanofibers can be functionalized to suite, e.g., for various separation requirements. It will be appreciated that in order to realize such structures, a sometimes large quantity of nanofibers is required. Large scale fabrication can be accomplished through, e.g., supported powder catalyst methods and/or aerosol methods. Those of skill in the art will be familiar with other useful large-scale preparation methods.

Other embodiments herein optionally comprise structures similar to that illustrated in FIG. 23. Such embodiments comprise a membrane formed by a thin coating of nanofibers on the top of a macro/mesoporous sheet. See also, 60/541,463, filed Feb. 2, 2004. The pore size of such membranes is determined by the diameters of the nanofibers. Thus, membranes with pore size less than 10 nm can be made by using nanofibers with diameters less than 10 nm and so on. Such embodiments are optionally used for nanofiltration or to make water, air breathable suits, e.g., suitable for protection from bio-warfare agents (pores with less than 10 nm size will be sufficient to block viruses and bacteria). Furthermore, an absorbing function can be built in such structures by increasing the thickness of the nanowire layer (in addition to its block ability). The nanofibers also can optionally be specifically functionalized with specific surface chemistry.

Again, it will be appreciated that the illustrative embodiments shown herein are merely illustrative and should not be taken as necessarily limiting upon the current invention.

D) Interaction of Biomaterials and Nanofiber Enhanced Surface Area Substrates

In other embodiments, the nanofiber enhanced surface area substrates of the invention are used in various medical and medical product/device applications. For example, coatings on medical products for drug release, lubricity, cell adhesion, low bio-adsorption, electrical contact, etc. are included in the current invention. For example, the application of surface texture (e.g., as with the present invention) to the surfaces of polymer implants has been shown to result in significant increases in cellular attachment. See, e.g., Zhang et al. "Nanostructured Hydroxyapatite Coatings for Improved Adhesion and Corrosion Resistance for Medical Implants" Symposium V: Nanophase and Nanocomposite Materials IV, Kormareni et al. (eds.) 2001, *MRS Proceedings*, vol. 703. Other medical applications of the current embodiments include, e.g., slow-release drug delivery. For example, drugs can be incorporated into various pharmaceutically acceptable carriers which allow slow release over time in physiological environments (e.g., within a patient). Drugs, etc. incorporated into such carriers (e.g., polymer layers, etc.) are shielded, at least partially, from direct exposure to body fluids due to incorporation into the carrier layer (e.g., present interstitially between the nanofibers). Drugs, etc. at the interface between the body fluids and the carrier layer (at the top of the nanofiber layer) diffuse out fairly quickly, while drugs deeper within the carrier layer diffuse out slowly (e.g., once body fluid diffuses into the carrier layer and then diffuses back out with the drug). Such carriers are well known to those of skill in the art and can be deposited or wicked onto the surface of a nanofiber substrate (i.e., amongst the nanofibers).

Additionally, various embodiments herein can comprise semi-conducting or metal coated nanofibers used for imaging of surfaces or implants or electrical contact in uses such as pacemakers or the like. For example, such nanofiber substrates can reflect ultrasound rays back towards a transducer at angles almost parallel to an ultrasound beam, thus, allowing easy visualization of medical implants, etc. Tracking of devices such as amniocentesis and biopsy needles, stents (e.g., urinary, cardiovascular, etc.), pacemaker guide-wires, shunts, cannulae, catheters of numerous types, PICC lines, IUDs, cauterization loops, filters, etc. can be aided through addition of nanofiber enhanced surfaces. Those of skill in the art will be familiar with other similar devices capable of use of nanofiber substrates of the current invention. Other imaging applications can include, e.g., functional monitoring of such devices after they are implanted in a patient or tracking and retrieval of surgical devices accidentally left in patients. It will be appreciated that such imaging uses of nanofiber substrates are also optionally combined with antimicrobial or other benefits herein. Other medical uses and medical devices utilizing nanofiber substrates can be found in, e.g., U.S. Application No. 60/549,711, filed Mar. 2, 2004, entitled "Medical Device Applications of Nanostructured Surfaces."

Biofilm formation and infection on indwelling catheters, orthopedic implants, pacemakers and other medical devices represents a persistent patient health danger. Therefore, some embodiments herein comprise novel surfaces which minimize bacterial colonization due to their advantageous morphology. In contrast, yet other embodiments herein utilize the unique surface morphology of nanofiber enhanced surface area substrates to foster cell growth under desired conditions or in desired locations. The high surface area/non-tortuous aspect of the current invention allows greater attachment area and accessibility (in certain embodiments) for nutrients/fluids, etc. and initial attachment benefits over porous surfaces where growth, etc. is limited by space (both in terms of surface area and space within the pores for the cells to grow out).

The substrates of the invention, because of their high surface areas and ready accessibility (e.g., non-tortuous paths), are extremely useful as bioscaffolds, e.g., in cell culture, implantation, and controlled drug or chemical release applications. In particular, the high surface area of the materials of the invention provide very large areas for attachment of desirable biological cells in, e.g., cell culture or for attachment to implants. Further, because nutrients can readily access these cells, the invention provides a better scaffold or matrix for these applications. This latter issue is a particular concern for implanted materials, which typically employ porous or roughened surfaces in order to provide tissue attachment. In particular, such small, inaccessible pores, while providing for initial attachment, do not readily permit continued maintenance of the attached cells, which subsequently deteriorate and die, reducing the effectiveness of the attachment. Another advantage of the materials of the invention is that they are inherently non-biofouling, e.g., they are resistant to the formation of biofilms from, e.g., bacterial species that typically cause infection for implants, etc.

Without being bound to a particular theory or method of action, the unique morphology of a nanofiber surface can reduce the colonization rate of bacterial species such as, e.g., *S. epidermidis* by about ten fold. For example, embodiments such as those comprising silicon nanofibers (e.g., nanowires) grown from the surface of a planar silicon oxide substrate by chemical vapor deposition process, and which comprise diameters of approximately 60 nanometers and lengths of about 50-100 microns show reduced bacterial colonization. See below. It will be appreciated that while specific bacterial species are illustrated in examples herein that the utility of the embodiments does not necessarily rest upon use against such species. In other words, other bacterial species are also optionally inhibited in colonization of the nanofiber surfaces herein. Additionally, while examples herein utilize silicon oxide nanowires on similar substrates, it will be appreciated that other embodiments are optionally equally utilized (e.g., other configurations of nanofibers; nanofibers on non-silicon substrates such as plastic, etc; other patterns of nanofibers on substrates, etc.).

Catheters and orthopedic implants are commonly infected with opportunistic bacteria and other infectious micro-organisms, necessitating the implant's removal. Such infections can also result in illness, long hospital stays, or even death. The prevention of biofilm formation and infection on indwelling catheters, orthopedic implants, pacemakers, contact lenses, and other medical devices is therefore highly desirous.

It will be noticed that substrates herein that are covered with high densities of nanofibers (e.g., silicon nanowires) resist bacterial colonization and mammalian cell growth. For example, approximately 10× less (or even less) bacterial growth occurs on a nanowire covered substrate as compared to an identical planar surface. In various embodiments herein, the physical and chemical properties of the nanofiber enhanced surface area substrates are varied in order to optimize and characterize their resistance to bacterial colonization.

In contrast to prevention of bacterial colonization, other embodiments herein comprise substrates that induce the attachment of mammalian cells to the nanofiber surface, e.g., by functionalization with extra-cellular binding proteins, etc. or other moieties, e.g., hydroxyapatite coatings, etc., thus, achieving a novel surface with highly efficient tissue integration properties.

In some embodiments herein where NFS substrates are to be used in settings requiring, e.g., sterility, etc., the nanofibers are optionally coated with, or composed of, titanium dioxide. Such titanium dioxide confers self-sterilizing or oxidative properties to such nanofibers. Nanofibers which comprise titanium dioxide, thus; allow rapid sterilization and oxidation compared to conventional planar $TiO_2$ surfaces while maintaining rapid diffusion to the surface.

In embodiments herein which involve nanowires comprising titanium oxides (e.g., coated nanowires, etc.), such can optionally be achieved though any of a number of methods. For example, in some embodiments herein the nanowires can be designed and implemented through an approach which involves analytical monitoring of $(SiO_4)_x(TiO_4)_y$ nanowires by coating and a molecular precursor approach. The layer thickness and porosity are optionally controlled through concentration of reagent, dip speed, and or choice of precursor for dip coating such as tetraethoxytitanate or tetrabutoxytitanate, gelation in air, air drying and calcinations. Molecular precursors such as $M[(OSi(O^tBu)3]4$, where M=Ti, Zi, or other metal oxides, can be decomposed to release 12 equivalents of isobutylene and 6 equivalents of water to form mesoporous materials or nanowires. These precursors can also be used in conjunction with CVD or detergents in nanocrystal syntheses (wet chemistry) to produce dimetallic nanocrystals of desired size distribution. Materials can be made via wet chemistry standard inorganic chemistry techniques and oxidative properties determined by simple kinetics monitoring of epoxidation reactions (GC or GCMS) using alkene substrates. Porosity can be monitored by standard BET porosity analysis. Copolymer polyether templates can also be used to control porosity as part of the wet chemistry process.

Titanium oxide materials are well known oxidation catalysts. One of the keys to titanium oxide materials is control of porosity and homogeneity of particle size or shape. Increased surface area typically affords better catalytic turnover rates for the material in oxidation processes. This has been difficult as the kinetics of oxide formation (material morphology) can be difficult to control in solution.

As described, recent interest in $TiO_2$ for oxidative catalytic surfaces (self-cleaning surfaces) shows promise for marketing "green chemistry" cleaning materials. However, the self-cleaning efficiency of the material is dependent upon, e.g., the surface area and porosity. Nanowires have a much higher surface areas than bulk materials (e.g., ones with a nanofiber enhanced surface) that are currently used for self-cleaning materials. Thus, the combination of silicon nanowire technology coated with $TiO_2$ or $TiO_2$ nanowires or molecular precursors to form nanofibers can optionally provide access to previously unknown materials that are useful in self-cleaning, sterilizing, and/or non-biofouling surfaces.

In some embodiments, such sterilizing activity arises in conjunction with exposure to UV light or other similar excitation. Such factors are optionally important in applications such as, e.g., sterile surfaces in medical settings or food processing settings. The increased surface area due to the NFS of the invention (e.g., increasing area 100-1000 times or the like), therefore, could vastly increase the disinfection rate/ability of such surfaces.

i) Current Means of Preventing Bacterial Contamination of Medical Devices

Enhancement of resistance of biomaterials to bacterial growth and promotion of rapid tissue integration and grafting of biomaterial surfaces are both areas of research. However, despite advances in sterilization and aseptic procedures as well as advances in biomaterials, bacterial and other microbial infection remains a serious issue in the use of medical implants. For example, greater than half of all nosocomial infections are caused by implanted medical devices. These infections are often the result of biofilms forming at the insertion site of the medical implant. Unfortunately, such infections are often resistant to innate immune system responses as well as to conventional antibiotic treatments. It will be appreciated that such infections are problematic not just in treatment of humans, but also in treatment of a number of other organisms as well. For example, commercially important species such as horses, cattle, etc. are also capable of treatment with medical implants/devices which comprise the antimicrobial nanofiber surfaces herein.

A variety of methods have been used to combat surface colonization of biomedical implants by bacteria and other microorganisms as well as the resulting biofilm formed. Previous methods have included varying the fundamental biomaterial used in the devices, applying hydrophilic, hydrophobic or bioactive coatings or creating porous or gel surfaces on the devices that contain bioactive agents. The task of generating universal biomaterial surfaces is complicated by species' specificity to particular materials. For example *S. epidermidis* has been reported to bind more readily to hydrophobic than to hydrophilic surfaces. *S. aureus* has a greater affinity for metals than for polymers, while *S. epidermidis* forms a film more rapidly on polymers than metals.

Antimicrobial agents, such as antibiotics and polyclonal antibodies integrated into porous biomaterials have been shown to actively prevent microbial adhesion at the implant site. However, the effectiveness of such local-release therapies is often compromised by the increasing resistance of bacteria to antibiotic therapy and the specificity associated with antibodies. Recent in vitro studies have also explored the use of biomaterials that release small molecules such as nitrous oxide in order to non-specifically eliminate bacteria at an implant surface. Nitrous oxide release must, however, be localized to limit toxicity.

ii) Prevention of Biofilm Formation by Nanofiber Enhanced Area Surfaces

Results of the inventors have shown that silicon nanofiber (here nanowire) surfaces aggressively resist colonization by the bacteria S. epidermidis as well as the growth of CHO, MDCK and NIH 3T3 cell lines. This is found to be the case when the bacteria or cells were cultured in contact with a native hydrophilic nanowire surface or with a fluorinated hydrophobic nanowire surface. Since silicon oxide flat control surfaces and polystyrene flat control surfaces supported profuse growth of S. epidermidis and the three cell lines, it is inferred that the nanowire morphology renders the surface cytophobic. Of course, again, it will be realized that the utility of the current invention is not limited by specific theories or modes of action. However, surface morphology is thought to be basis for the antimicrobial activity. The nanofibers on such substrates are spaced tightly enough to prohibit the bacteria from physically penetrating to the solid surface below. The amount of presentable surface area available for attachment is typically less then 1.0% of the underlying flat surface. In typical embodiments, the nanofibers are approximately 40 nm in diameter and rise to a height about 20 uM above the solid surface. See, e.g., FIG. 2. Thus, unlike a typical membrane surface that would be found on a medical device, the nanowire surfaces herein are discontinuous and spiked and have no regular structure to aid in cell attachment. In fact, the current surfaces are almost the exact opposite of a conventional membrane; rather than a solid surface with holes, they are open spiked surfaces. It is thought that this unique morphology discourages normal biofilm attachment irrespective of the hydrophobic or hydrophilic nature of the nanofibers involved.

As detailed throughout, the nanofiber growth process can be conducted on a wide variety of substrates that can have planar or complex geometries. Thus, various substrates of the invention can be completely covered, patterned or have nanofibers in specific locations. However, for ease of focus herein, silicon nanofibers on silicon oxide or metallic substrates are discussed in most detail. Again, however, nanofibers from a wide variety of materials are also contemplated as is growing such on plastic, metal and ceramic substrates. The versatility of the nanofiber production process lends itself to the eventual scale-up and commercialization of a wide variety of products with nanofiber surfaces for the biomedical field.

Example 9 and its figures illustrate prevention of biological contamination of a nanofiber enhanced surface of the invention. As mentioned previously, it is thought that the primary means of biofilm prevention by nanofiber surfaces herein is due to the unique morphology of the substrate, however, it is also possible that such substrates comprise inherent cytophobicity activity.

The effect of surface hydrophilicity or hydrophobicity on growth is also optionally modified on the nanofiber substrates herein to specifically tailor biofilm prevention in different situations. Such functionalization goes along with variability in wire length, diameter and density on the substrate. In typical embodiments, the silicon oxide surface layer of the typical nanofiber substrates is quite hydrophilic in its native state. Water readily wets the surface and spreads out evenly. This is partially due to the wicking properties of the surface. Functionalization of the surface is facilitated by the layer of native oxide that forms on the surface of the wires. This layer of $SiO_2$ can be modified using standard silane chemistry to present a functional groups on the outside of the wire. For example the surface can be treated with gaseous hexamethyldisilazane (HMDS) to make it extremely hydrophobic. See above.

iii) Attachment of Extra-Cellular Proteins onto Nanofiber Surfaces

As shown herein, nanofiber surfaces do not readily support the growth of mammalian cells or bacteria. Yet, in other instances, the growth of mammalian cell lines on surfaces is advantageous. Thus, embodiments of the current invention, by attaching extra-cellular proteins or other moieties, e.g., hydroxyapatite coatings, etc., to nanofibers encourages such cell growth. The deposition of the proteins on the nanofibers can be through simple nonspecific adsorption. Proteins with known extra-cellular binding functions such as Collagen, Fibronectin, Vitronectin and Laminin are contemplated in use. Other embodiments contemplate covalent attachment of cells/proteins to a nanofiber surface. In embodiments where grafting and/or bonding of nanofiber substrates and, e.g., biological material such as bone or medical devices such as metal bone pins, etc. is to occur, different embodiments can have different patterns of nanofibers upon the substrate. Thus, for example, nanofibers can optionally only exist on an area of a medical implant where grafting or bonding is to occur. Again, standard protein attachment methods can be used to make the covalent linkage to the nanofibers.

Additionally various sol-gel coatings can be deposited upon nanofiber surfaces herein to encourage bio-compatibility and/or bio-integration applications. Previous work on devices concerned with bone integration has used porous materials on titanium implants to encourage bone growth. In some embodiments herein, the current intention utilizes addition of similar materials in conjunction with the nanofiber surfaces herein. For example, hydroxyapatite, a common calcium based mineral, can optionally be deposited on nanofiber surfaces to facilitate bone integration into/with the nanofiber surface. Common sol-gel techniques can optionally be used to produce the hydroxyapatite deposition and those of skill in the art will be familiar with such. Such hydroxyapatite coated nanofiber surfaces optionally could have the benefit of both promoting bone integration and displaying anti-biofouling properties, thus, resulting in a greater likelihood that proper bone growth/healing will occur.

Those of skill in the art will readily appreciate that the current invention also includes use of deposition of ceramic-type materials and the like through sol-gel techniques to produce a wide range of, e.g., compatibility applications (i.e., in addition to those involving hydroxyapatite and bone growth).

E) Kits/Systems

In some embodiments, the invention provides kits for practice of the methods described herein and which optionally comprise the substrates of the invention. In various embodiments, such kits comprise one or more nanofiber enhanced surface area substrate, e.g., one or more microarray, separation/filtration device, medical device, mass spectrometry device, heat exchanger, superhydrophobic surface or, one or more other device comprising a nanofiber enhanced surface area substrate, etc.

The kit can also comprise any necessary reagents, devices, apparatus, and materials additionally used to fabricate and/or use a nanofiber enhanced surface area substrate, or any device comprising such.

In addition, the kits can optionally include instructional materials containing directions (i.e., protocols) for the synthesis of a nanofiber enhanced surface area substrate and/or for adding moieties to such nanofibers and/or use of such nanofiber structures. Preferred instructional materials give protocols for utilizing the kit contents.

In certain embodiments, the instructional materials teach the use of the nanofiber substrates of the invention in the construction of one or more devices (such as, e.g., microassay devices, analyte detection devices, analyte separation devices, medical devices, etc.). The instructional materials optionally include written instructions (e.g., on paper, on electronic media such as a computer readable diskette, CD or DVD, or access to an internet website giving such instructions) for construction and/or utilization of the nanofiber enhanced surfaces of the invention.

F) EXAMPLES i) Example 1

Wicking on Nanofiber and Planar Substrates

Figure 28A:
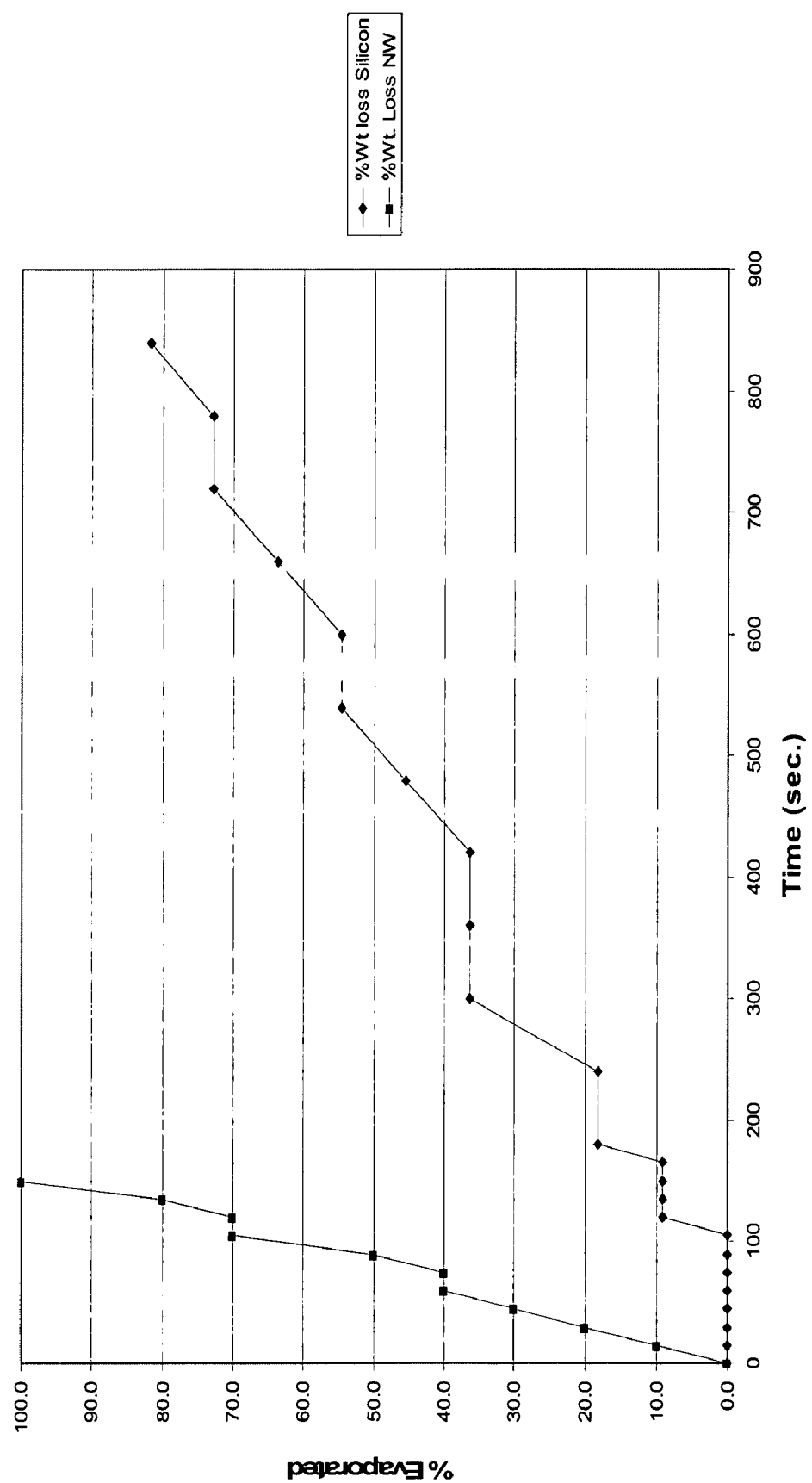
FIG. 28, Panels A and B, Displays data comparing the wicking ability of a planar substrate and a nanofiber enhanced substrate of the invention.

To illustrate comparative wicking of liquids (here water) between a planar silicon surface and a nanofiber enhanced area substrate of the invention, a 1 uL drop of water was placed upon each. FIG. 28A, displays a graph comparing the wicking of the water, (measured in FIG. 28 as comparative evaporation) between the planar silicon surface and the nanofiber enhanced surface area substrate of the invention. As can be seen, wicking (and hence, in FIG. 28, evaporation as displayed by "% water loss") occurs much more rapidly with the substrates of the invention. FIG. 28B displays the data for the graph in FIG. 28A.

ii) Example 2

Exemplary Flow Assays of Nanofiber Substrates

Figure 29:
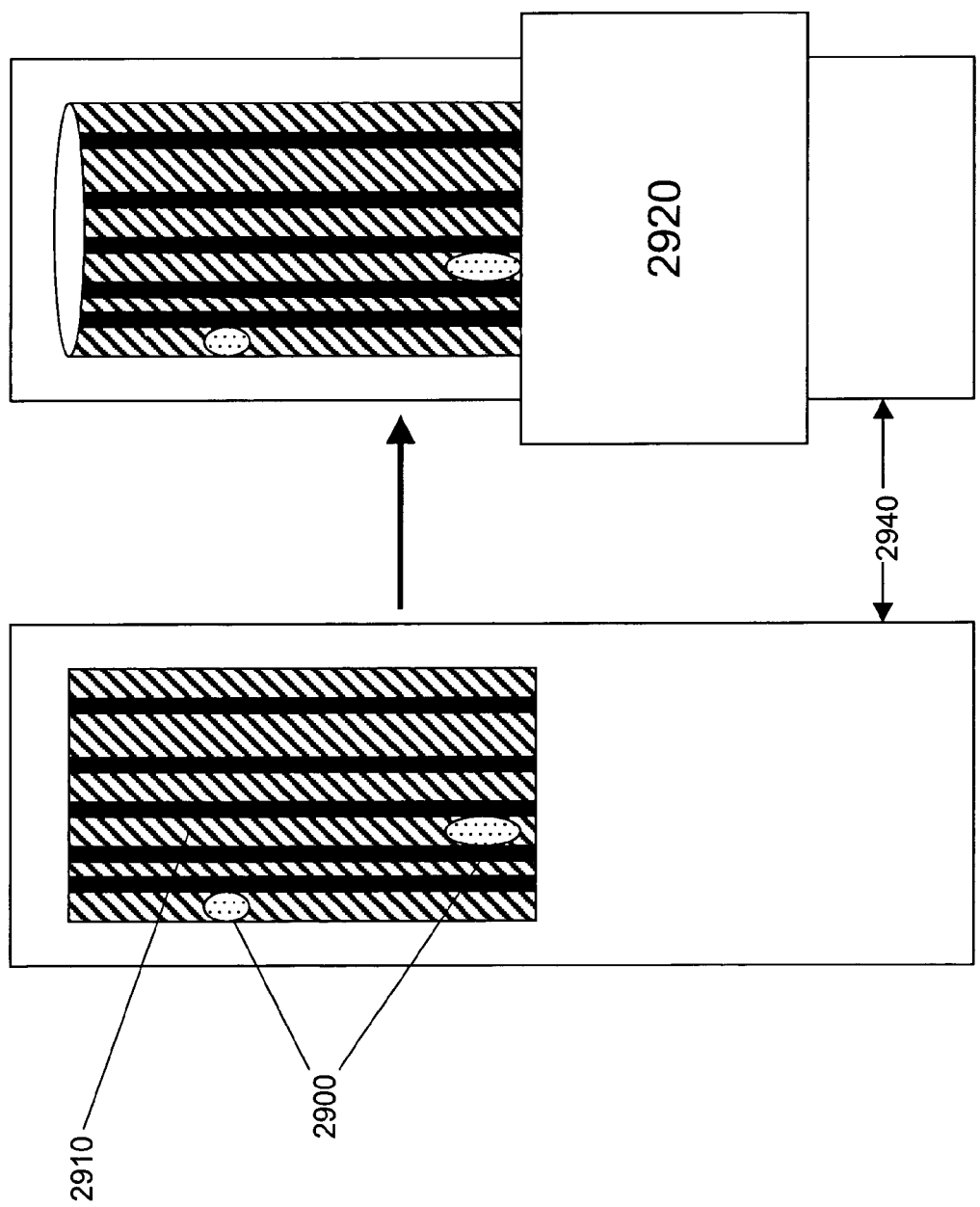
FIG. 29, Displays a schematic of an exemplary nanofiber wicking arrangement.

FIG. 29 shows a schematic of a nanofiber enhanced slide configured into a flow assay scheme. In FIG. 29, biotinylated BSA (i.e., a probe), 2900, was adsorbed at known positions along nanofiber tracks (in this instance nanowire tracks), 2910, on slide 2940. The tracks were generated by scraping the edge of a glass slide through a nanofiber field on a substrate. A solution containing fluorescently labeled streptavidin (i.e., a target) was applied to the tops of the tracks. 15 ul of SAv-647 in PBS/0.1% BSA was followed by a total of 300 ul PBS/0.1% BSA. The liquid, thus, wicked into the nanofiber tracks until it filled the interstitial space between the nanofibers. To continue the liquid flow and to wash through any unbound label, additional liquid was added at the top of the tracks and a filter paper wick, 2920, was placed at the bottom end of the tracks. The paper acted as a reservoir for the liquid that had traversed the track. See FIG. 29. After 20 volumes of label-free solution had traversed the track, the slide was allowed to dry and then scanned on a fluorescent array scanner to detect labeled streptavidin bound to the BSA immobilized at the specific positions on the tracks.

Figure 30:
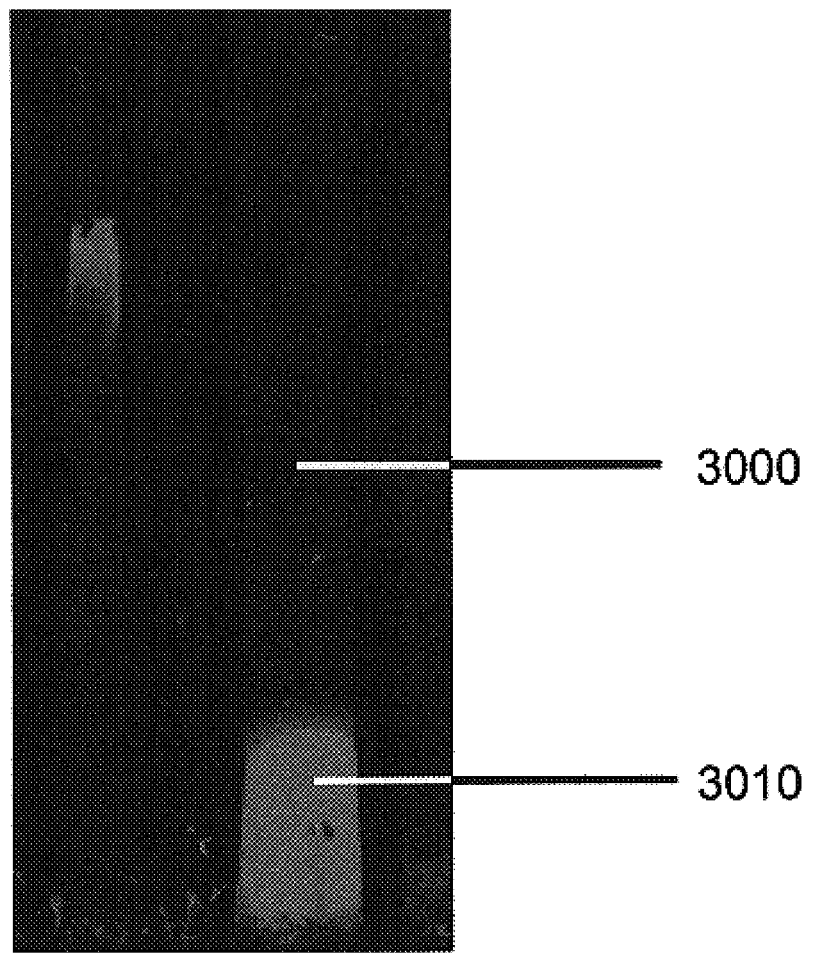
FIG. 30, Displays a fluorescent assay of a nanofiber wicking arrangement.

As can be seen from FIG. 30, the immobilized biotin-BSA was able to effectively capture and concentrate the labeled streptavidin (i.e., target) at the points where it was immobilized. A signal of 306 counts was seen at 3000, and a signal of 18,176 counts was seen at 3010 corresponding to the known positions of bound probe.

Figure 31:
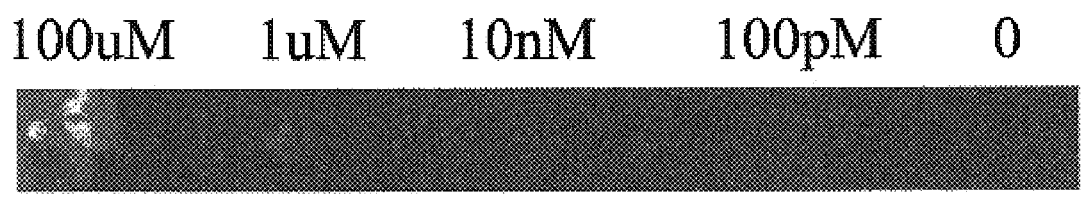
FIG. 31, Displays a fluorescent assay of a nanofiber wicking arrangement.

As another example of the current embodiment, 1 ul spots of varying concentrations of biotin-BSA were deposited onto specific nanofiber tracks carved out of a nanofiber lawn on a slide. The concentrations were 100 uM, 1 uM, 10 nM, 100 pM and 0 biotin-BSA. 10 ul of 100 ug/ml streptavidin was applied to the tracks and followed by 150 ul PBS/1% BSA. The tracks were dried and the image was taken on an Axon 4100A array scanner. FIG. 31 shows the clear distinction between the 100 uM through 1 uM spots. At the correct PMT settings 10 nM is also detectable above background.

iii) Example 3

Exemplary Nanofiber Array Patterning

The ability to grow nanometer scale wires of defined diameter and length on various surfaces is illustrated in FIG. 7. FIG. 7 shows an example of an "extreme" surface with very high surface to volume ratios and yet without the complex etched architecture of other more traditional strategies for increasing surface area to volume (e.g. etched silicon). FIG. 7 shows SEM views of top and side views of a typical nanofiber surface, both patterned and unpatterned. The silicon nanofibers were grown out from a silicon wafer and the surfaces were therefore compatible with standard glass modification chemistries, etc. Although discussion herein primarily focuses on silicon wafers as the substrate for nanowire growth, as explained further above, the process can potentially be conducted on a wide variety of substrates that can have planar or complex geometries.

Examples of nanofiber arrays produced by masking process can be seen in FIGS. 8 through 14. In the figures, a 150 um stainless steel mask having 200 um wide holes on a 400 um pitch was used with standard silicon/silicon oxide 4 inch wafers to produce a patterned nanofiber array. From 20 to 60 nm of gold was sputtered onto the silicon wafers through the mask to produce the defined nanofiber areas. The nanofibers (here nanowires) were grown to procedures standard in the art. FIG. 8 shows well-defined nanofiber pattern areas created using a shadow mask and 40 nm gold deposition. FIG. 9 shows side views of similar discrete nanofiber areas.

Based on fluorescent measurements, thinner deposits of gold film (e.g., 20 nm) typically can give thinner, more uniform diameter nanofibers with surface areas equivalent to other nanofiber growth methods (e.g., standard gold colloid deposition methods). For example, FIG. 10 displays nanofibers that are fairly uniform (e.g., 50 to 100 nm) that were created through use of a 20 nm gold film deposit. Additionally, FIG. 11 shows that gold film thickness of between 30 and 60 nm generates a wide nanofiber size distribution with many nanofibers within the 50 um range.

Figure 12A:
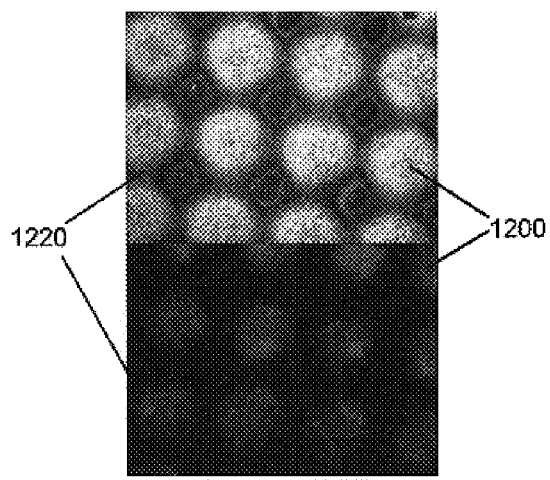
Figure 12B:
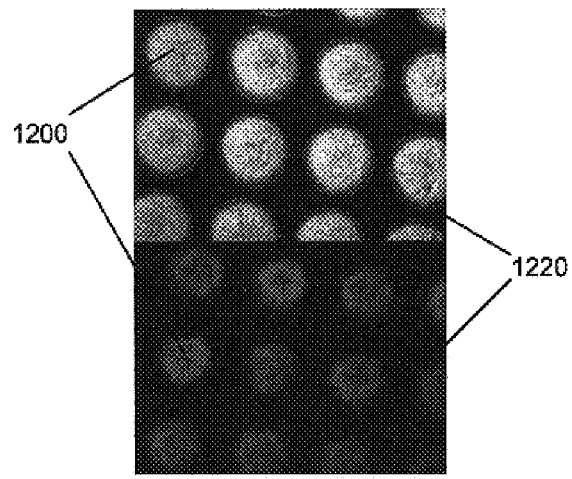

The difference between nanofiber areas and substrate background of nanofiber arrays produced by shadow-mask was examined via fluorescent intensity and light microscopy. The features produced using a 20 nm gold film showed a 25-fold increase over planar areas (i.e., those areas without nanofibers). FIG. 12 displays light and FL-microscopy of two sample nanofiber arrays (both using 20 nm gold film). One example of FIG. 12 displays a light/FL-microscopy heterogeneity between nanofiber areas, 1200, and planar areas, 1220, of 8.2× while the other example shows a difference of 25.1×. FIG. 13 also shows exemplary possible variations achievable through manipulation of gold film thicknesses in regard to feature homogeneity. For example, panels A-D show nanofiber array features constructed form increasing thicknesses of gold film and line profiles showing intensity/fluorescence within such different nanofiber features. FIG. 14 displays that through manipulation of the gold film used in nanofiber construction, nanofiber features on a substrate can produce "doughnut" intensity profiles (e.g., similar to the effect seen with analyte drops in traditional microarray technologies) which are believed to be due to large, thick nanofibers in the central portion of the features, 1400. Thus, as shown in FIG. 14, (panel A—FL intensity, panel %—high magnification dark field microscopy) nanofibers constructed from 60 nm gold film can comprise thicker nanofibers than those that could result from use of thinner gold films. Cf. FIGS. 13 and 14.

Another example of a patterned nanofiber array of the invention is shown in FIG. 15. In the figure, nanofiber (here nanowire) features were pre-patterned on a silicon substrate. A dark-field image (50×) shows the patterns of 250×250 um nanofiber features, 1500, on the silicon substrate, 1510, with a center to center distance of 500 um between the features. FIG. 16 shows SEM images (100× in Panel A and 1,000× in Panel B) of the unique nanostructured surface of another exemplary nanofiber array of the invention. Such nanofiber features, 1600 and 1620, were patterned on the entire surface of silicon or quartz 4 inch round wafers, 1610 and 1630.

iv) Example 4

Visualization of Binding with Exemplary Nanofiber Arrays

Figure 32:
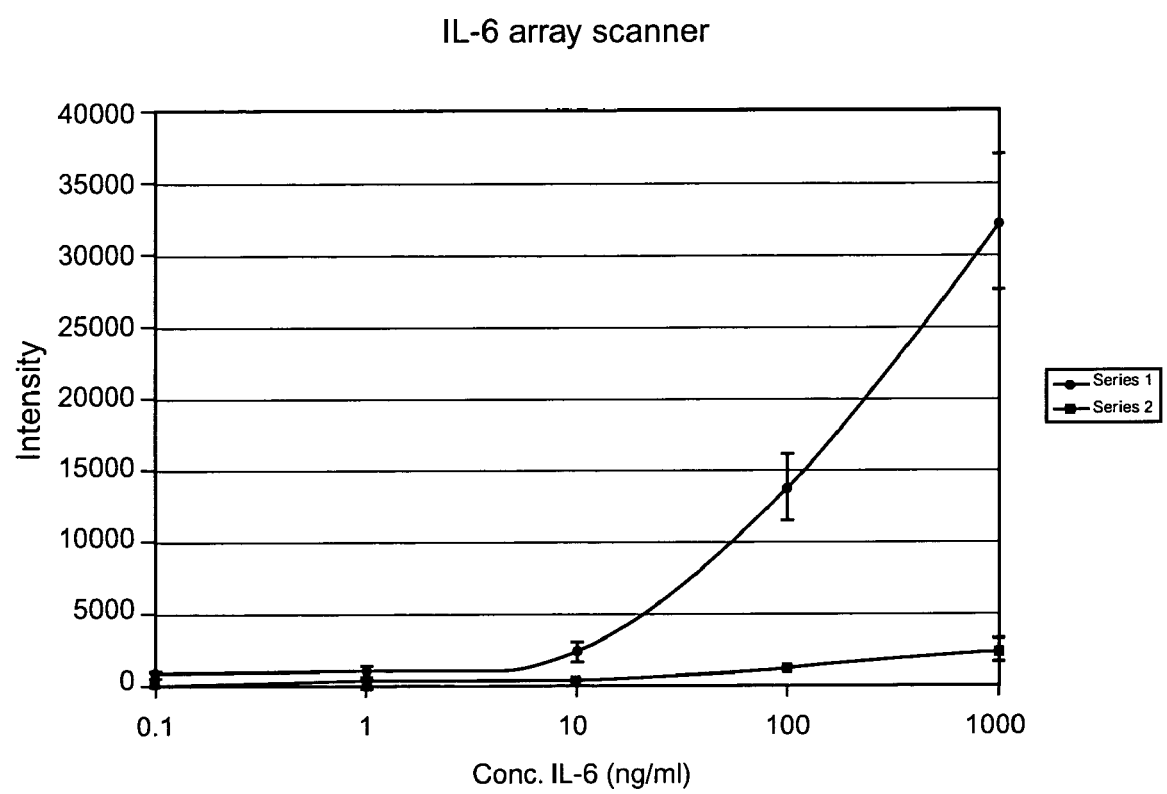
FIG. 32, Displays a graph produced through analysis of a nanofiber array by a conventional array scanner.
Figure 33A:
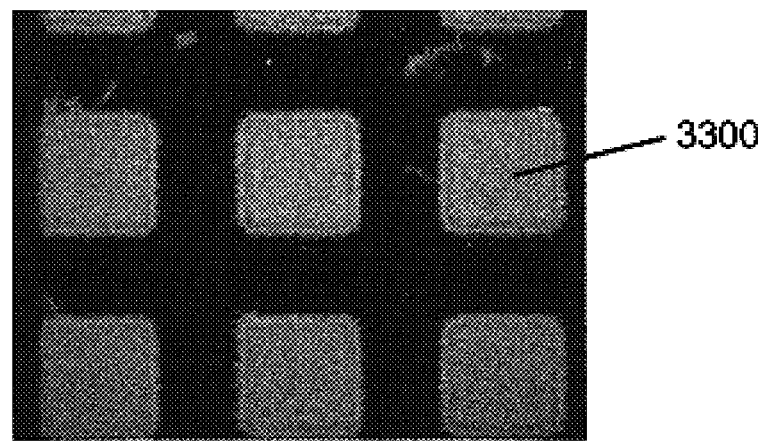
FIG. 33, panels A and B, Shows dark-field and fluorescent images of exemplary nanofiber arrays of the invention.
Figure 33B:
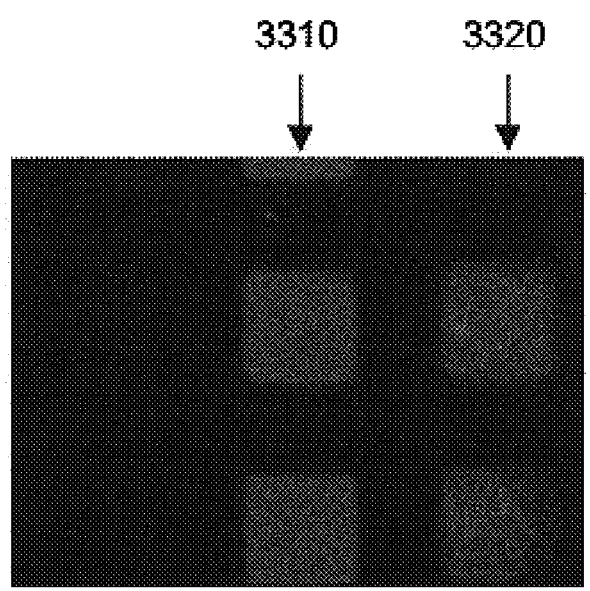

To show sample nanofiber arrays of the invention, standard mRNA preparations from eukaryotic cell cultures or pre-purchased RNA samples (e.g., from Clontech) were optionally used as a template to synthesize Cy3 or Cy5 labeled cDNA for hybridization on the array formats. Oligonucleotide probes can be generated against a select panel of well characterized genes known to be expressed in the appropriate samples and the relative performance of the nanofiber enhanced substrates can be compared against conventional glass arrays. Analysis can be done on a conventional fluorescent array scanner widely used for the analysis of spotted microarrays (e.g. Perkin Elmer ScanArray or the like). FIGS. 32 and 33 display analysis/measurement of nanofiber arrays of the system on a typical microarray scanner used for current commercial arrays as well as a 2 color assay with nanofiber arrays of the system. As can be seen from FIG. 32, nanofiber arrays of the invention can be read on conventional array scanners. The data shown was read with an Axon 4100A. Other similar array scanners (e.g., Perkin Elmers ScanArray) could also be used. The laser power of the scanner can be significantly attenuated from that used in typical planar analysis, thus, creating less photobleaching of the array. FIG. 32 shows that slides can be scanned on an array scanner and that the data is comparable to fluorescent microscope/CCD analysis; but with an order of magnitude improvement in detection limit. In FIG. 32, series 1 refers to scanning of a nanofiber surface, while series 2 refers to scanning of a planar surface. FIG. 33 shows a 2-color assay using nanofiber arrays of the invention. The nanofiber arrays were directly hand-spotted and different probes were adsorbed onto the distinct features and then exposed to a multiplex (2 color) assay. Panel A shows a dark field image of visible nanofiber areas, 3300, while Panel B shows a fluorescent image of the nanofiber array. The arrays were spotted with either BSA, biotin BSA or mouse IgG on the nanofiber features. Detection was carried out following simultaneous labeling with alexa 647 (red, 3310)-labeled streptavidin and alexa 488 (green, 3320) labeled anti-mouse IgG.

v) Example 5

Exemplary Patterned Nanofiber Assays

Figure 34:
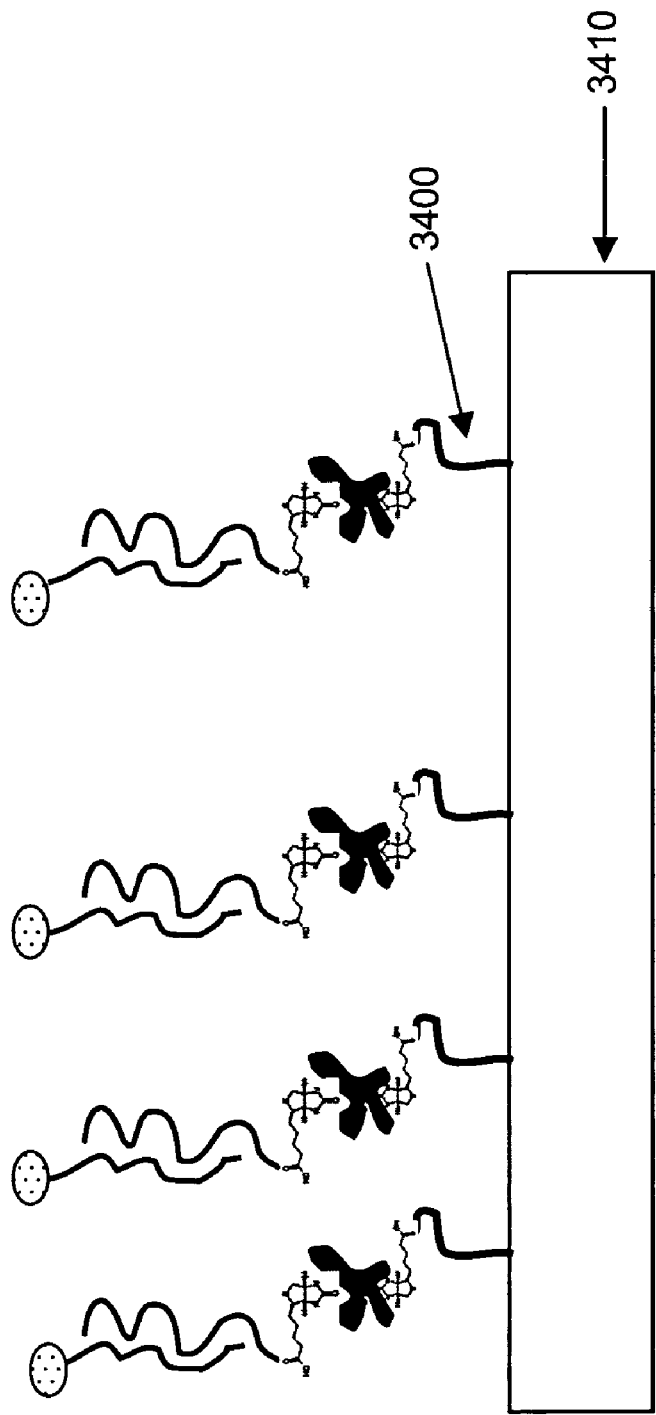
FIG. 34, Shows a schematic of a sample nanofiber hybridization assay system.
Figure 36A:
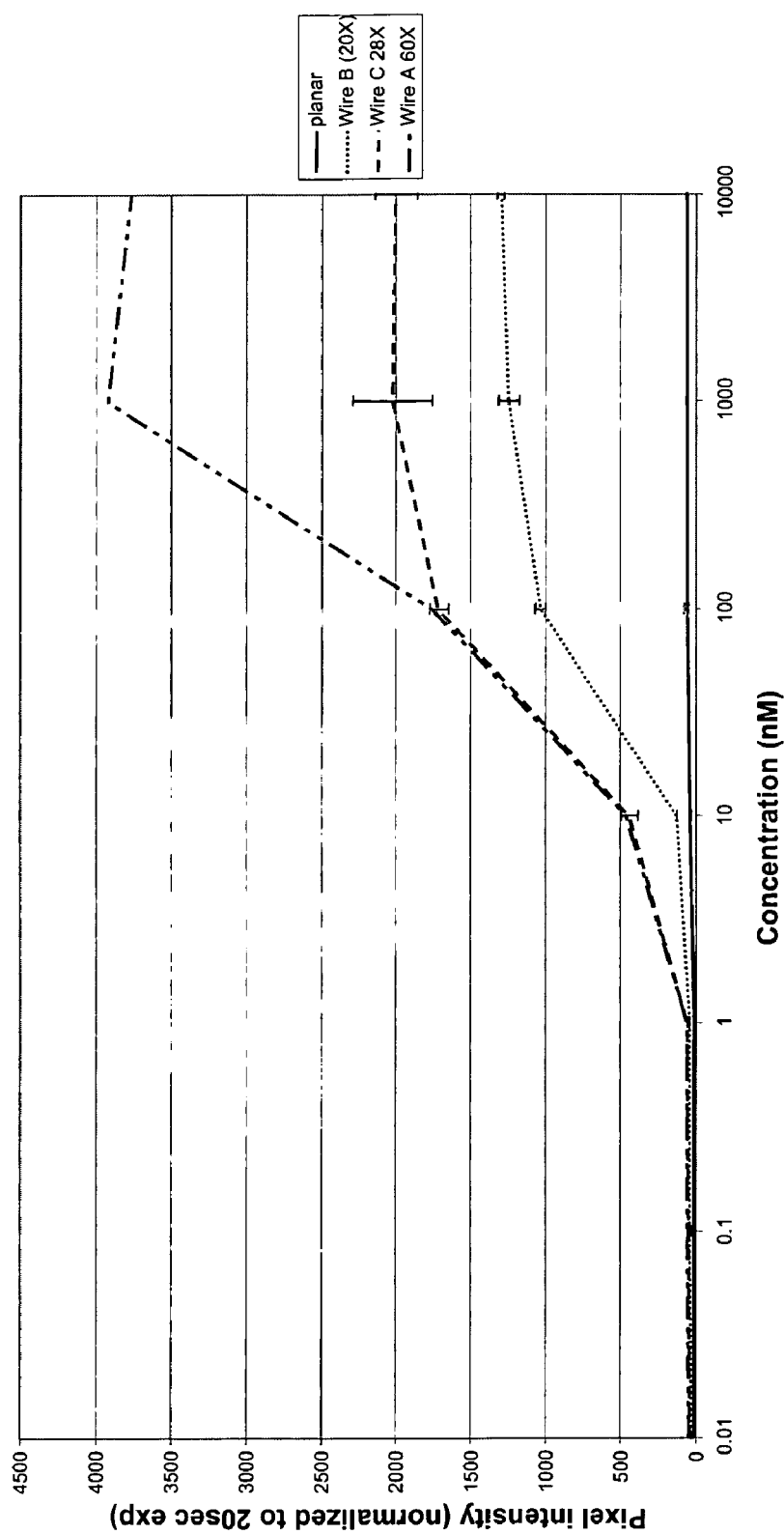
FIG. 36, panels A and B, Shows graphs comparing dynamic range of nanofiber versus planar surfaces.
Figure 36B:
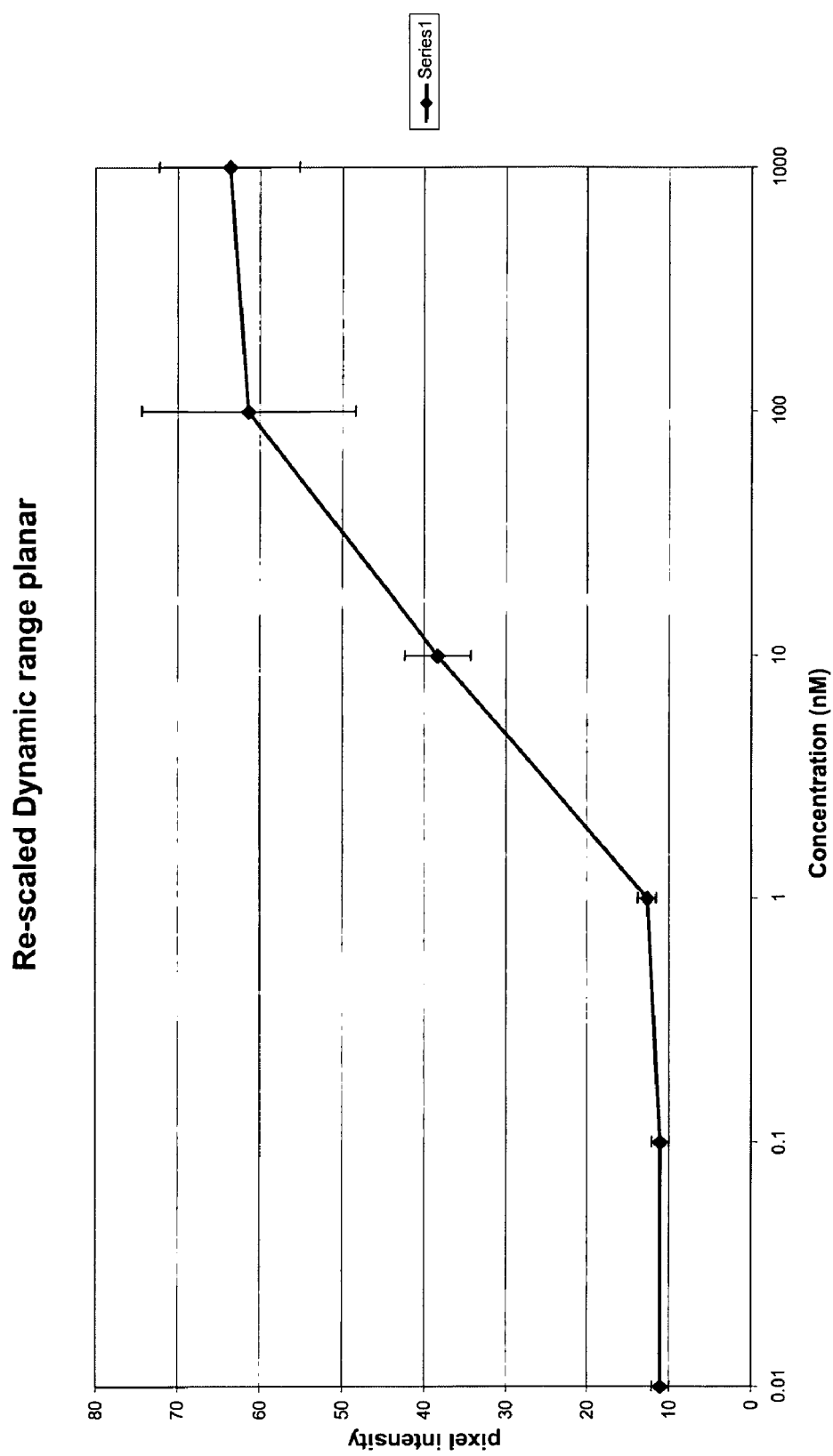

To illustrate concepts of nanofiber enhanced surface area microarrays, a number of illustrative, but not limiting, assays were performed. The results of such illustrative assays are shown in FIGS. 34-37. FIG. 34 shows a schematic of a sample hybridization assay system representative of assays that can be performed using the methods and devices of the invention. In FIG. 34, nanofibers, 3400, attached to a substrate, 3410, have been modified to comprise a target/probe system which allows fluorescent monitoring of binding. For FIG. 34, the probe was 5'-Biotin-TTTTGCCTACGATCA-3' (SEQ ID NO: 1) while the Target was 5'-CY5-TTGATCGTAGGCA-3' (SEQ ID NO:2) For FIG. 34 a flow-scheme showing sample steps involved in the illustrative assay can optionally include, APTES modified $SiO_2$ surface (plane or with nanofibers) followed by NHS-PEG-biotin, followed by Streptavidin, followed by Biotin-oligo probe (i.e., link probe) followed by Cy-5-oligo target (i.e., hybridize) followed by wash and determination of bound fluorescence by epifluorescent microscopy. Similar systems were utilized in the other figures illustrating this Example and the related section above concerning characterization of exemplary nanofiber enhanced surface area microarrays. In the present figures, "nanofiber" indicates a nanofiber enhanced surface area substrate while "planar" indicates that the surface does not comprise nanofibers. FIG. 35 compares signal intensity between nanofiber substrates and planar substrates. It should be noted that the fold increase of increase in fluorescence (thus, indicating increase in binding) is normalized amongst the various substrates in the figure (i.e., intensities shown in parentheses are saturated binding normalized to 20 second exposure time). Such normalization was necessary due to the differences in brightness between the samples and the corresponding differences in exposure time. As can be seen, NFS surfaces (i.e., ones comprised of nanofiber enhanced surface areas) show a marked increase in fluorescent intensity over planar $SiO_2$, which does show some general non-specific binding of probe, and the glass slide. As will be appreciated, the differences in intensity can optionally be correlated with differences in nanofiber density on the various substrates since the more nanofibers per unit area, the greater the enhanced surface, and the more probe that can bind. FIG. 36 illustrates the signal intensity and dynamic range between nanofiber substrates and planar surface substrates. Panel B is an enlargement of the bottom line of panel A (i.e., the line indicating the planar surface). As can be seen from the panels, the nanofiber surfaces show a greater dynamic range than does the unadorned planar surface. The dynamic range can be taken as an indication of the range between the lower level of fluorescent intensity (occurring at very low levels of probe) and the highest level of fluorescent intensity (occurring when all, or substantially all, possible binding/interaction sites for the probe are full). Thus, increased dynamic range can be useful in reactions needing greater sensitivity or which occur over a wide range of values. The nanofiber surfaces, since they have an enhanced surface area allowing for greater binding of probe per footprint area, can therefore be used over a greater range of experimental conditions, etc. than can planar non-enhanced surfaces. See below for further details on dynamic range in relation to fluorescent quenching.

Figure 37A:
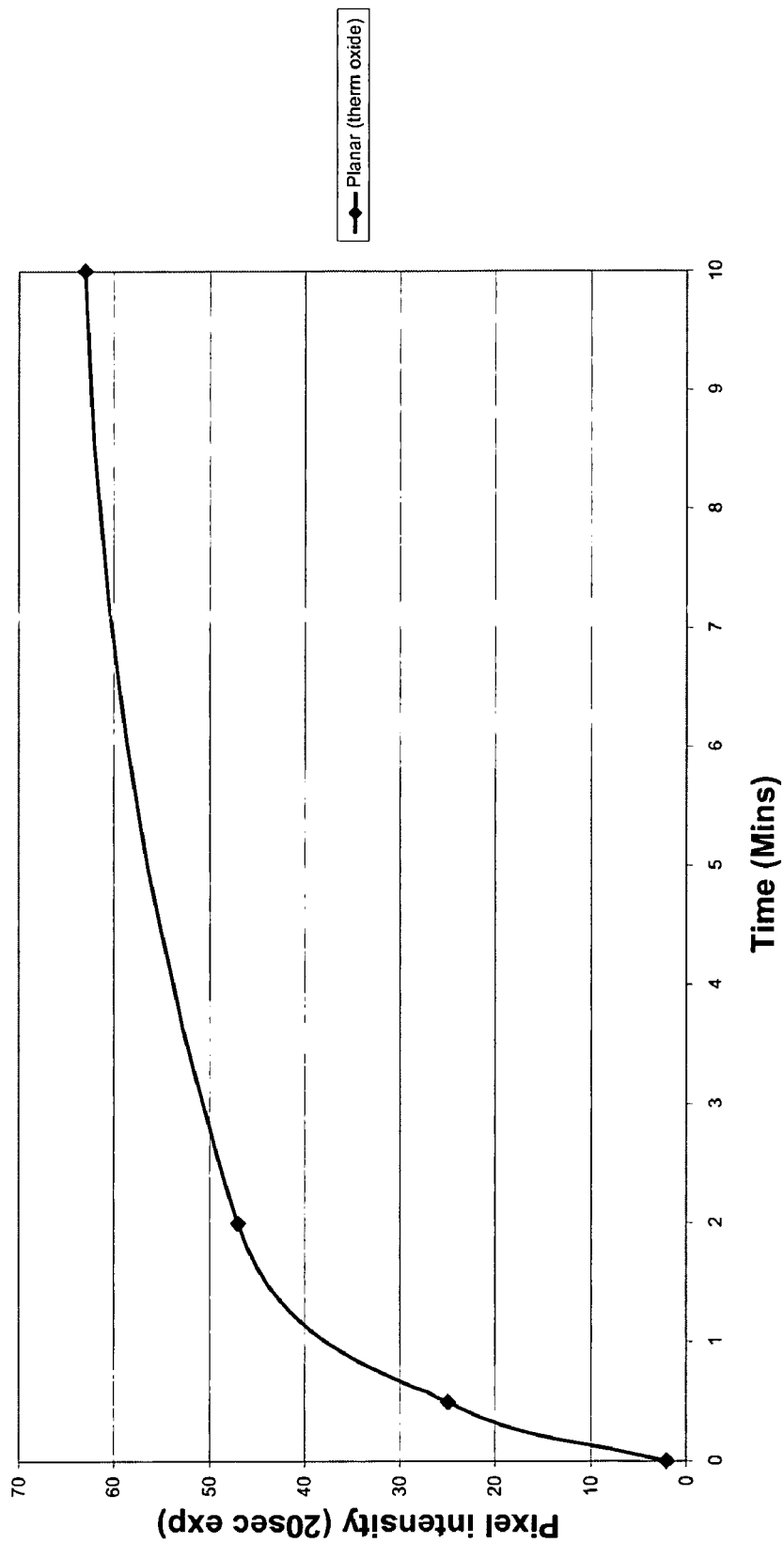
FIG. 37, panels A and B, Shows graphs comparing binding kinetics of nanofiber versus planar surfaces.
Figure 37B:
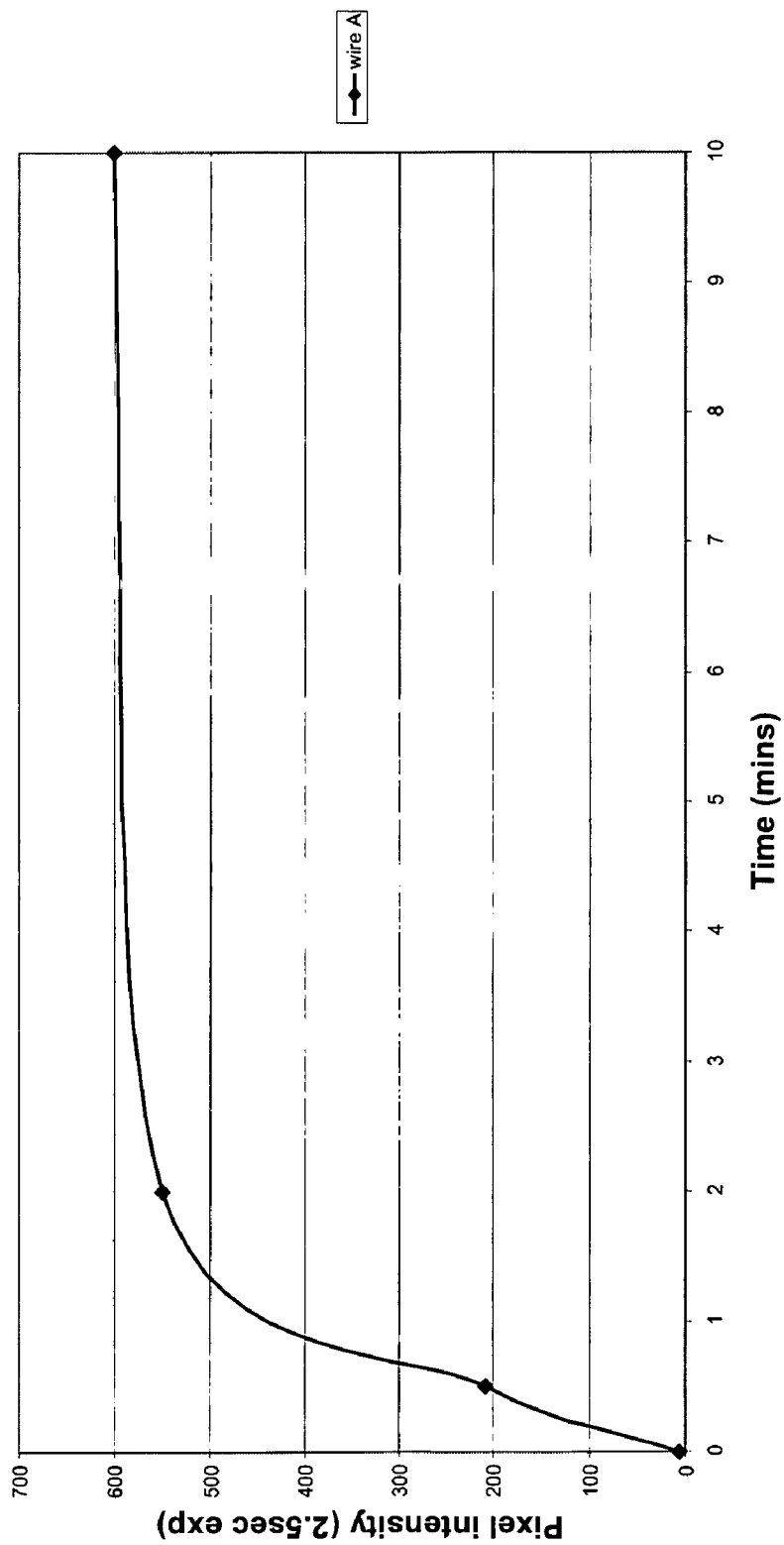

FIG. 37 illustrates time constants (i.e., binding kinetics tracked by fluorescent measurement) for both planar substrates, FIG. 37A, and nanofiber (here nanowire) substrates, FIG. 37B. Some prior attempts to create modified substrate surfaces (e.g., with various packing matrices, etc.) resulted in creation of tortuous pathways for analytes to follow in order to bind with the proper moiety. The tortuous pathways, thus, lead to interferences with kinetics, etc. However, the current invention does not experience such problems. As can be seen from FIG. 37, the kinetics of the nanofiber substrate and the planar substrate are substantially similar. Kinetics, and indeed most aspects of nanofiber surfaces discussed in terms of arrays, are also applicable to other nanofiber methods/devices herein, e.g., kinetic benefits also accrue in separation applications, etc. See below.

Figure 38A:
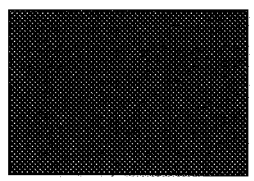
FIG. 38, panels A and B, Shows comparison of protein binding to nanofiber and planar substrates.
Figure 38B:
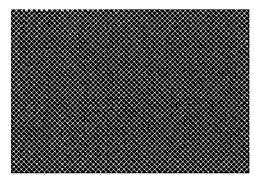
Figure 39A:
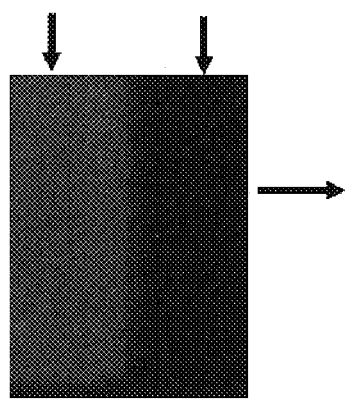
FIG. 39, panels A and B, Shows signal intensity and dynamic range comparison between nanofiber substrates and planar surface substrates.
Figure 39B:
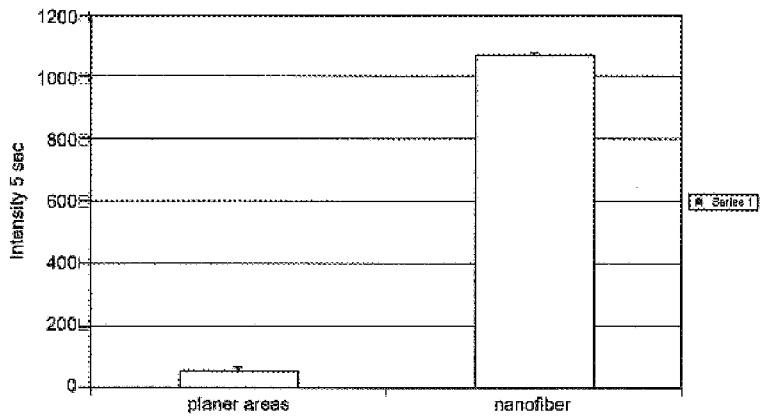

Comparison of protein binding to nanofiber and planar substrates is illustrated in FIGS. 38 and 39. FIG. 38 demonstrates that nanofiber surfaces are compatible with protein binding. Mouse IgG was adsorbed to both surfaces (A=planar surface, B=nanofiber surface) and was then detected with ALEXA 647 labeled anti-mouse IgG. A 20× increase in signal intensity was seen between the planar surface and the nanofiber surface. FIG. 38 also demonstrates again that the greatly enhanced surface area of the nanofiber substrate allows for a much greater protein binding as illustrated by a much greater fluorescent intensity. FIG. 39 demonstrates a typical signal intensity difference between a nanofiber surface (here nanowire) and adjacent planar surface that has been treated the same way. In FIG. 39, biotin-BSA was adsorbed to the surfaces followed by labeling with alexa 647-Streptavidin. It will be appreciated that patterned nanofiber features and planar (i.e., areas without nanofibers or with comparatively greatly fewer numbers of nanofibers, e.g., "alleys" between nanofiber features on arrays) were modified and labeled in an identical manner. As can be seen, a dramatic increase in fluorescent intensity of the nanofiber feature exists. In FIG. 39B, the intensity increase was 21.5 times. Typical intensity increases can be at least 20 times greater, however, some embodiments have increases of from 20 times to 50 times or more greater, from 30 times to 40 times greater, or about 50 times greater intensity for the nanofiber areas.

Figure 40:
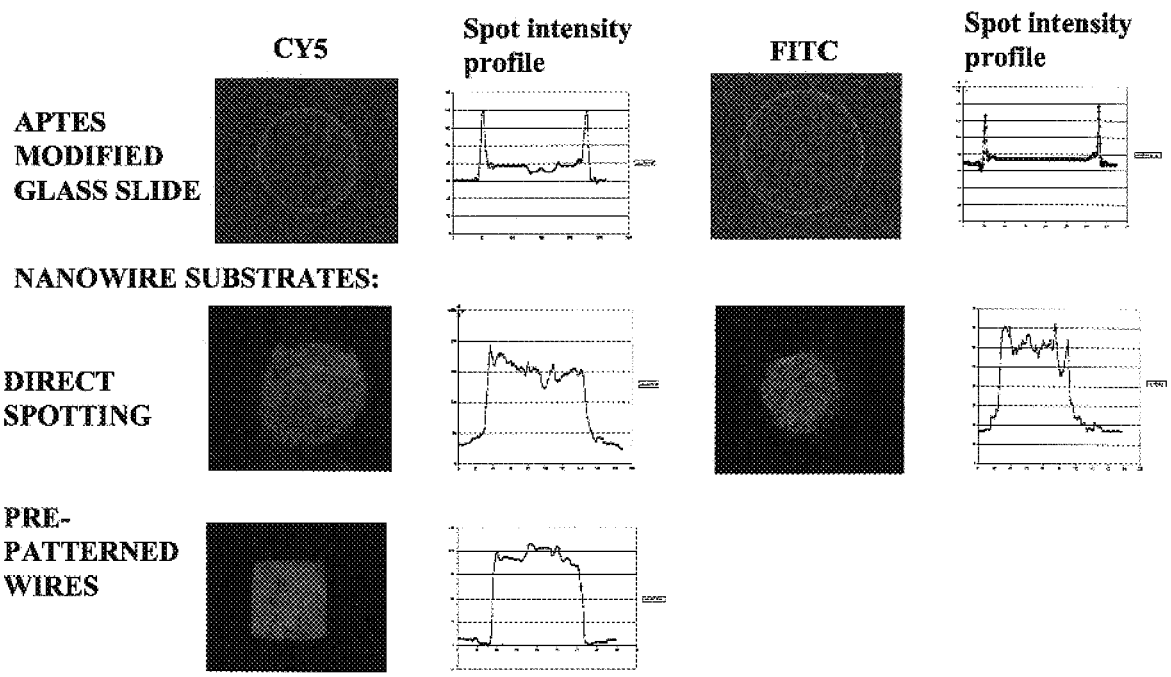
FIG. 40, Compares direct spotting of fluorescent protein on planar substrates and nanofiber (nanowire) substrates.
Figure 41:
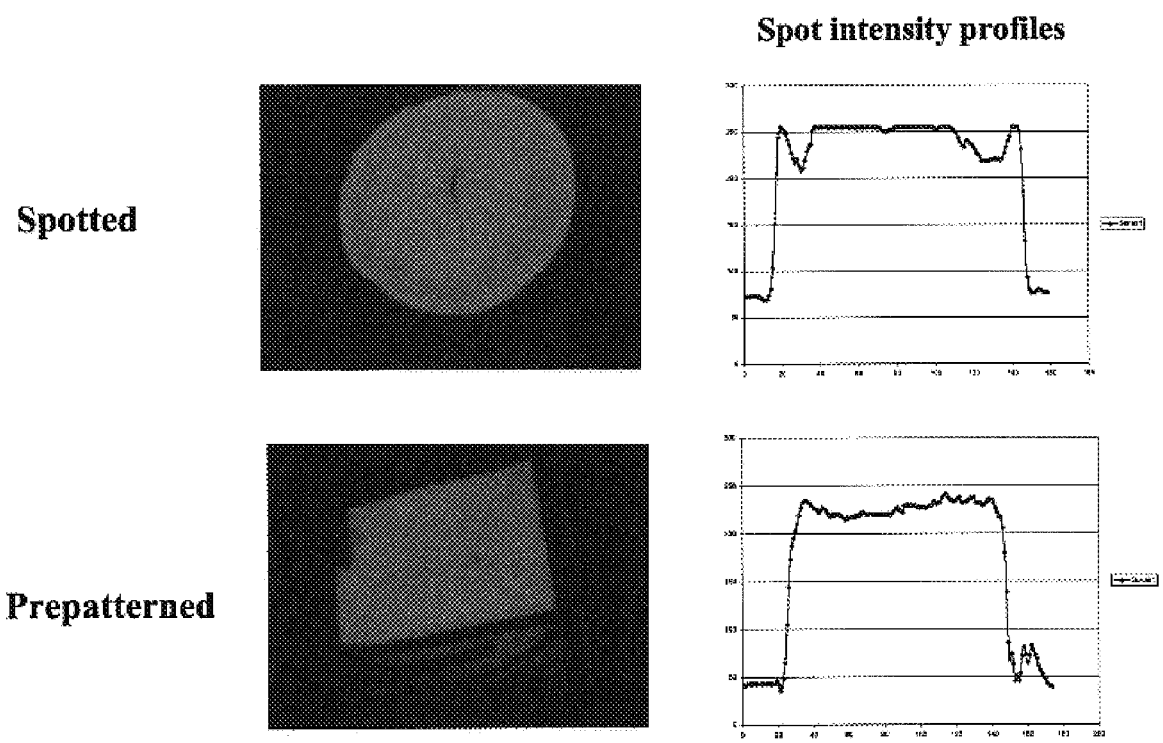
FIG. 41, Shows spotting of chemistry followed by incubation with a fluorescent target.
Figure 42A:
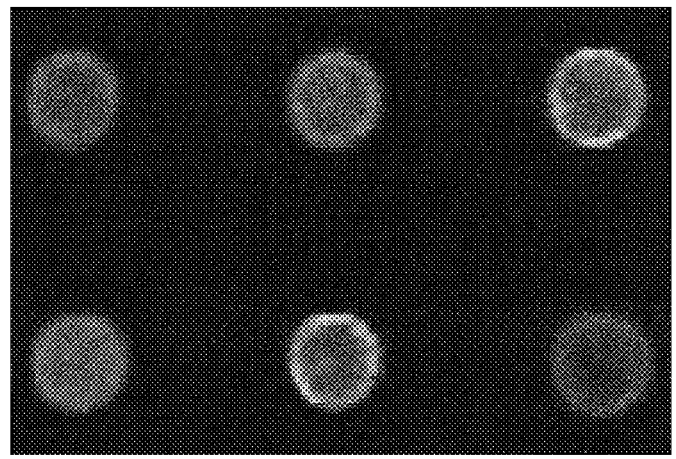
FIG. 42, panels A-D, Show intraspot and interspot variability for traditional arrays and nanofiber arrays of the invention.
Figure 42B:
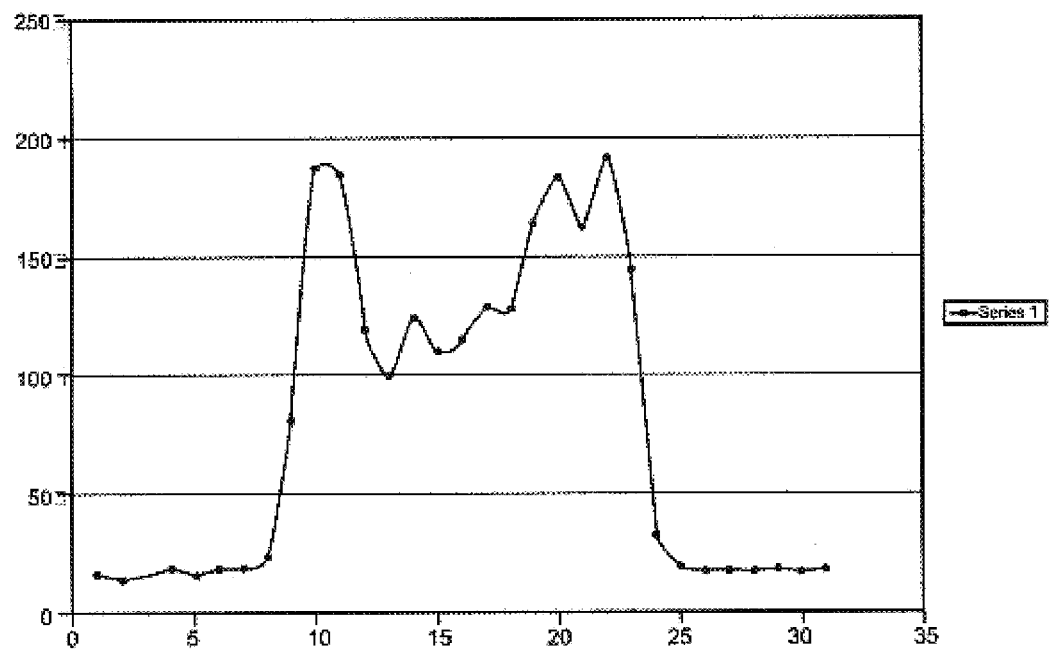
Figure 42C:
Figure 42D:
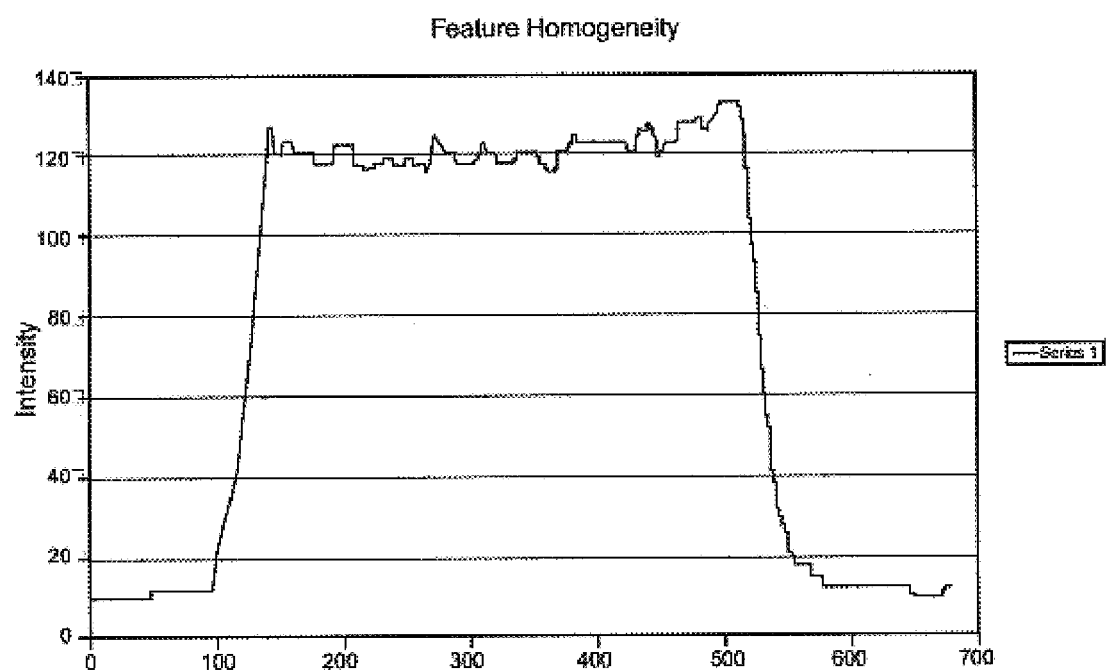
Figure 43A:
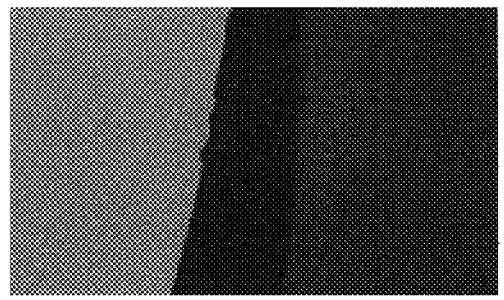
Figure 43B:
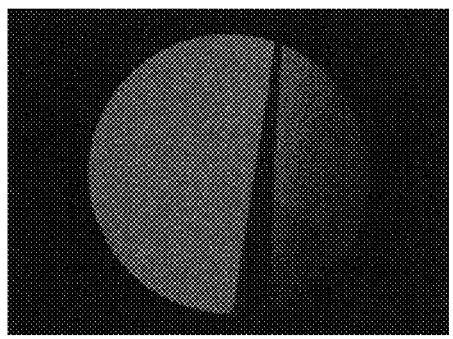
Figure 43C:
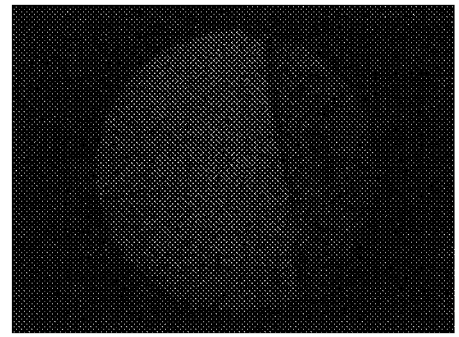
Figure 44A:
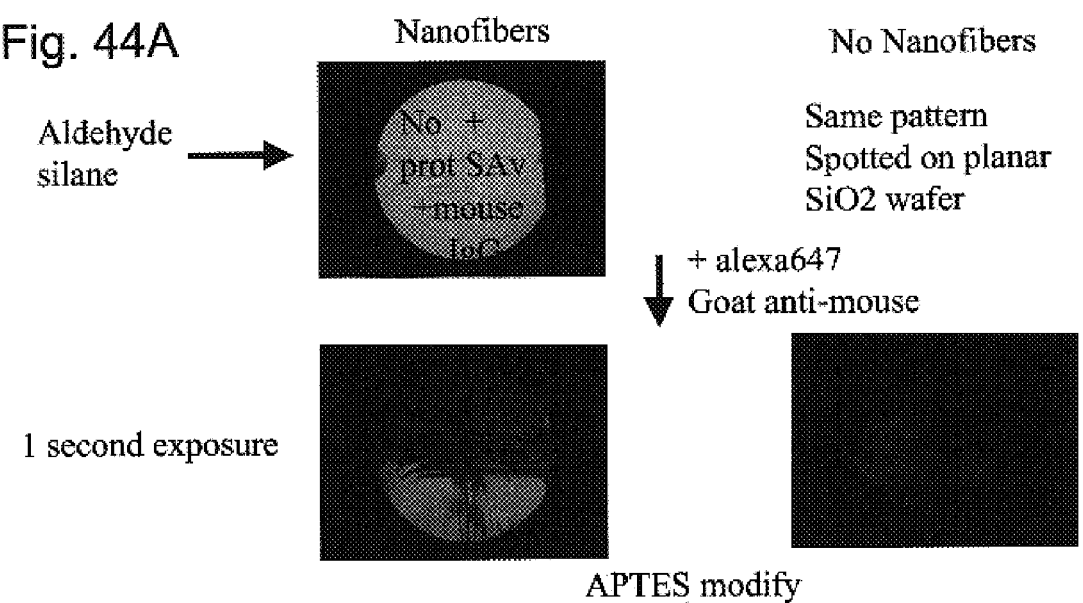
Figure 44B:
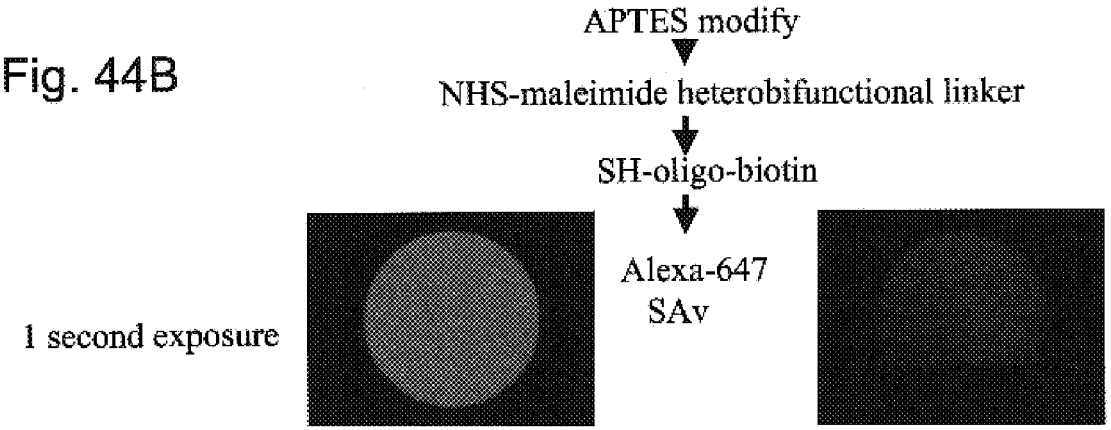
Figure 46:
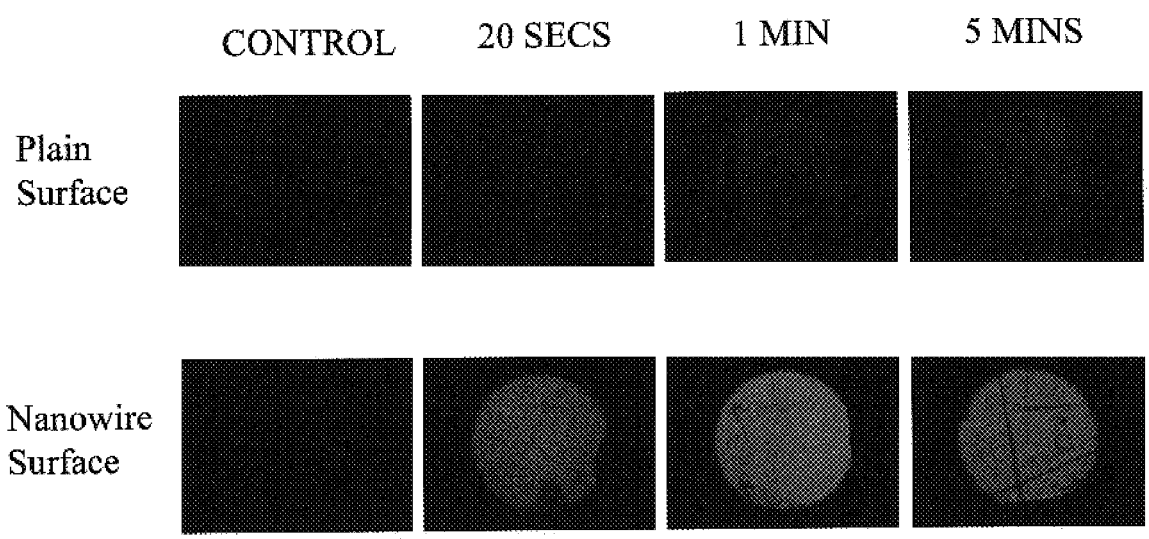

FIG. 40 shows comparisons of intraspot consistency of spots on planar substrates and spots (either direct spotting or pre-patterned spotting) on nanofiber substrates. As can be seen, the spot intensity on nanofiber substrates shows a much less pronounced halo effect. Traditional means to prevent halos have included, e.g., addition of surfactants, control of humidity, etc. Yet another benefit of embodiments of the current invention is that halo effects are eliminated or greatly reduced. Without being bound to a particular mode of action, it is thought that the increased wicking of the nanofiber surface quickly and evenly spreads the spotted solutions within an island of nanofibers. Thus, the solution is thought to fill up the interstitial spaces between the top of the nanofiber tips and the substrate surface. The end result is that nanofiber islands on substrates do not typically display pronounced halo/doughnut effects. FIG. 41 shows spotting of chemistry followed by incubation with a fluorescent target. FIG. 42 also illustrates the differences (e.g., in feature homogeneity and intrafeature uniformity) between a commercially spotted array and a nanofiber array of the invention. In FIG. 42, a commercially available planar glass spotted array (panels A and B) was compared against a nanofiber (here nanowire) patterned array (panels C and D). As can be seen, the distribution of fluorescence across the nanofiber features is much more even than the doughnut shaped pattern seen in the conventional array. Cf, FIGS. 42A and 42C. Also, the interspot variability is lower on selected regions of the patterned nanofiber wafers. Panels A and B (i.e., the commercial array) used a purchased prespotted slide (spotted with 70 mer oligos) which was hybridized to Cy3 labeled complement. Panels C and D (i.e., the nanofiber array) comprised monoclonal anti-IL-6 adsorbed overnight, followed by the addition of IL-6, biotin EL-6 and alexa 647 streptavidin. The feature intensity of the commercial spotted array was 146 (±32.3) with a CV of 22%. The feature intensity of the nanofiber array was 122 (±4) with a CV of 3.3%. FIGS. 42 through 46 also show comparison of intensity of protein or nucleic acid between nanofiber surfaces and planar surfaces as well as uniformity of spotting and kinetics. FIG. 43 shows increased intensity per unit area. In 43A biotin BSA was adsorbed onto the surfaces (planar and nanofiber, here nanowire), and visualized with alexa 488-labeled streptavidin. Both wafer fragments were treated identically (1 second exposure). In 43B and 43C, the wafers were APTES modified, NHS-biotin coated, with alexa 647 at 100 nM (left wafer) and 10 nM (right wafer). Both were exposed for 1 second. FIG. 44 shows linkage chemistries—protein attachment in 44A and DNA attachment in 44B. Chemistries added and exposure times are listed on the figure. Thus, in 44A, wafers with nanofibers and those without nanofibers were treated with aldehyde silane and protein SAv and mouse IgG followed by alexa 647 and goat anti-mouse antibodies. While in 44B, the wafers were APTES modified followed with an NHS-maleimide heterobifunctional linker, SH-oligo-biotin, and alexa-647 SAv. FIG. 45 displays the uniformity of probe deposition onto nanofiber surfaces as compared with plain (i.e., without nanofibers) wafers. Biotin-BSA was spotted onto wafers, blocked, and visualized with SAv-alexa 488. FIG. 46 displays binding kinetics between a "plain" surface, i.e., one without nanofibers and a "wire" surface, i.e., one with nanofibers (here nanowires). Briefly, mouse IgG was adsorbed to the surface of wafer slices. Unbound areas were blocked with BSA. For the control, only BSA was present. The wafers were then incubated with alexa 647-goat anti-mouse Ab (100 nM).

Figure 47:
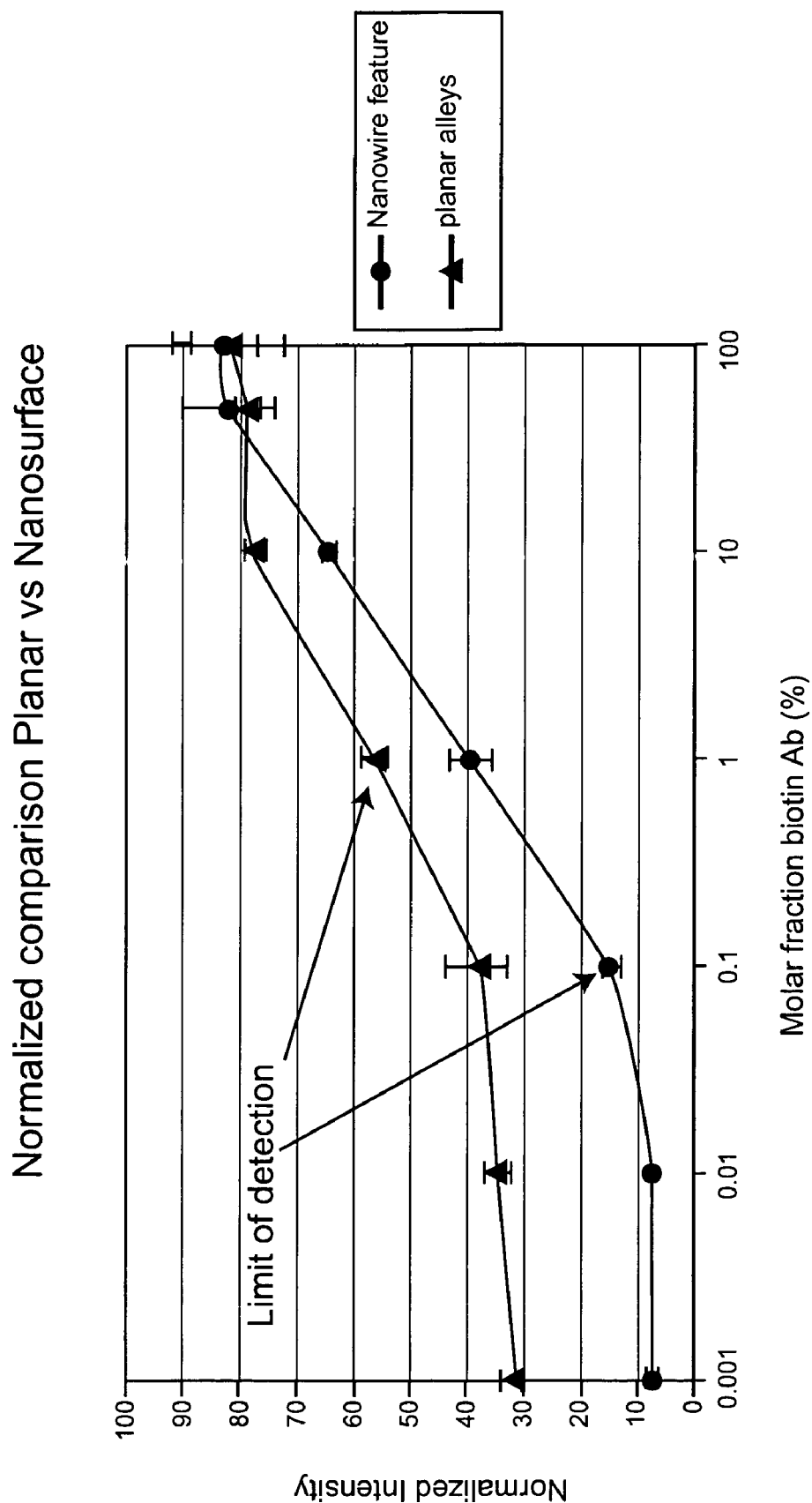
FIG. 47, Shows a normalized comparison indicating limits of detection of a planar versus a nanofiber surface.

FIG. 47 demonstrates the improved assay performance parameters in a simple assay system with a normalized comparison between planar and nanofiber (here nanowire) surfaces. The probe (biotinylated antibody diluted into non-biotinylated antibody at the indicated fractions) was adsorbed directly to the slide surface prior to detection with fluorescently labeled streptavidin. The graph in the figure shows the side-by-side detection limit, linear assay range and background signal from nanofiber versus planar surfaces when they are approximately normalized for surface area (e.g., for footprint area). Those of skill in the art will appreciate the reduced background and improved sensitivity on the nanofiber surface.

Figure 48:
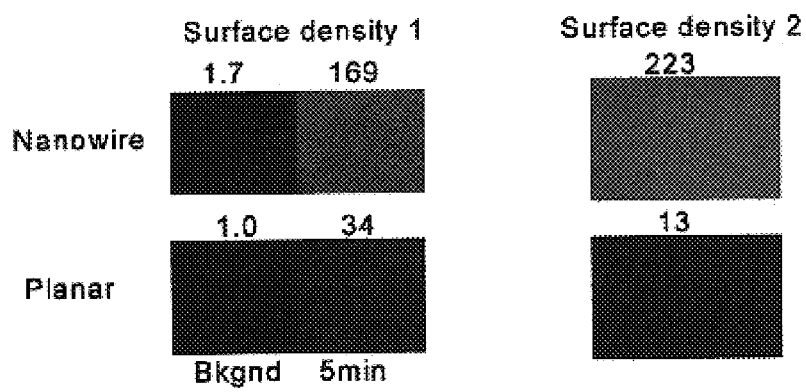
FIG. 48, Shows comparison of intensity per unit area of nanofiber substrate versus planar substrate.

As shown, FIG. 48 demonstrates the ability to functionalize enhanced area surfaces using preliminary chemistries and shows evidence of increased signal per unit area. These studies (using biotinylated BSA adsorption to the surfaces, followed by labeling with alexafluor labeled streptavidin) demonstrate that even without an attempt to optimize either density, wire diameter or surface properties, embodiments of the invention can achieve an almost 20 fold increase in intensity per unit area. Additionally, as shown in FIG. 48, the background fluorescence of both planar and nanofiber (here nanowire) enhanced substrates, exposed to labeled target in the absence of bound probe, are similar. This indicates that the lower end of the dynamic range for real assays was not significantly altered. FIG. 48 shows a comparison of intensity per unit area of nanofiber (here nanowire) versus planar $SiO_2$ surfaces. The surfaces were treated and imaged identically.

Figure 49:
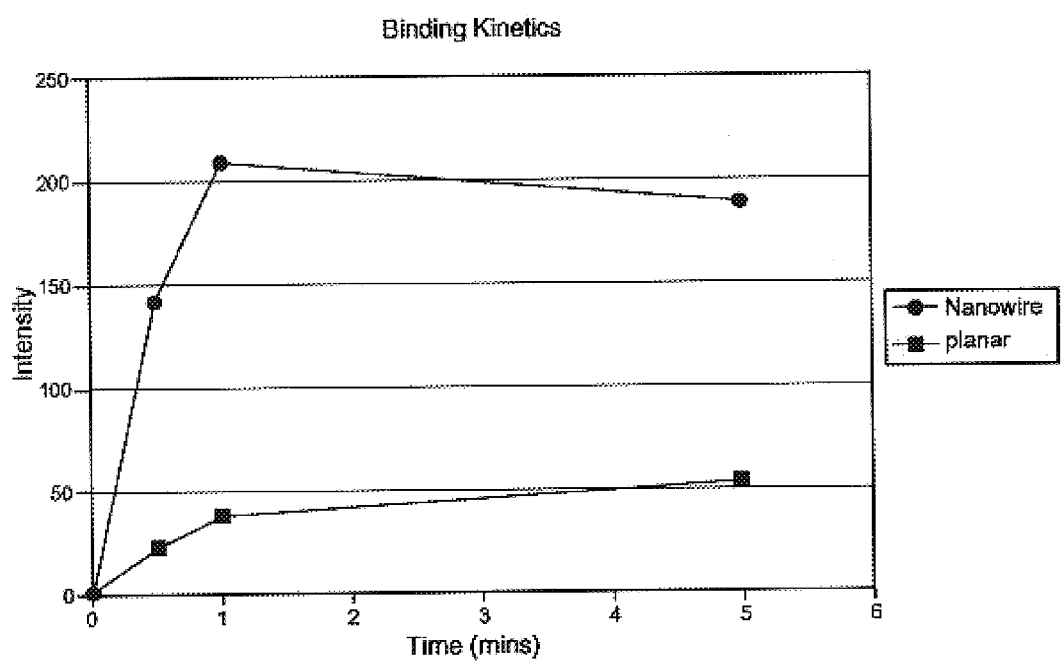
FIG. 49, Displays Initial assessment of binding rates to nanofiber versus planar surfaces.
Figure 50:
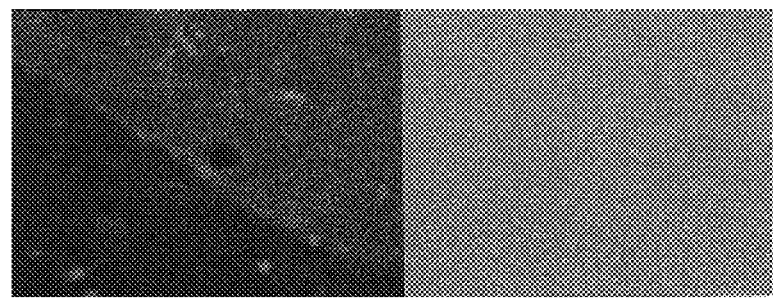
FIG. 50, Compares uniformity of signal on planar versus nanofiber substrates.

The numbers represent average pixel intensity. The panels on the left represent enhanced substrates with a lower density of nanofibers than those on the right. As will be appreciated, the background fluorescence of both substrates is similar (the controls were only exposed to the labeled target and did not have linked probe). FIG. 49 shows analyses of accessibility and binding kinetics of antibodies to immobilized target proteins on the substrate. The reactions measured binding of anti-mouse IgG to surfaces coated with mouse IgG. For both planar surfaces and nanofiber surfaces (here nanowire), binding appeared to be saturated in 1 minute under the given conditions. As shown, under these conditions there appears to be little difference in the time taken to reach saturated binding for either planar or nanofiber enhanced substrates indicating that surfaces of the invention do, in fact, behave like a non-tortuous high surface-area substrate. Finally, spotting analyses, using sections of wafer rather than patterned substrates, show that spotting material on a nanofiber enhanced substrate results in a more uniform distribution of capture probe than just spotting onto a planar surface. See FIG. 50. In FIG. 50, uniformity of signal on planar $SiO_2$ surface (left) is compared against a nanofiber-enhanced substrate (right). Each figure is an area of wafer at 200× magnification after equal volumes of biotinylated BSA solutions were spotted on the substrates followed by labeling with streptavidin alexa-488.

Figure 19:
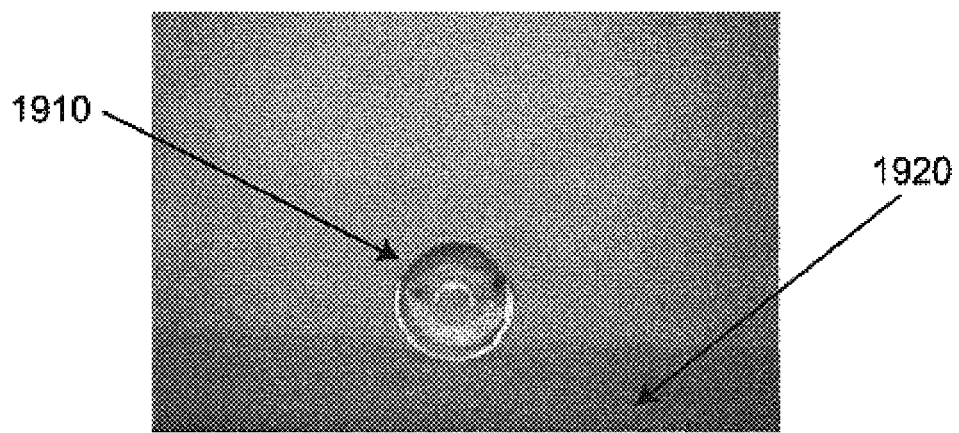
FIG. 19, Displays a photograph of a water droplet on a super-hydrophobic, enhanced nanofiber substrate.

In contrast to such highly wettable, high surface area quality of the nanowire substrate FIG. 19 demonstrates that the same material can be made super-hydrophobic. The contact angle on this surface is so high that it is almost impossible to measure, and thus, by taking advantage of these super hydrophilic or super hydrophobic properties, this material provides a unique platform for improving spotted arrays.

vi) Example 6

MS with Nanofiber Substrates

Figures 53A, 53B:
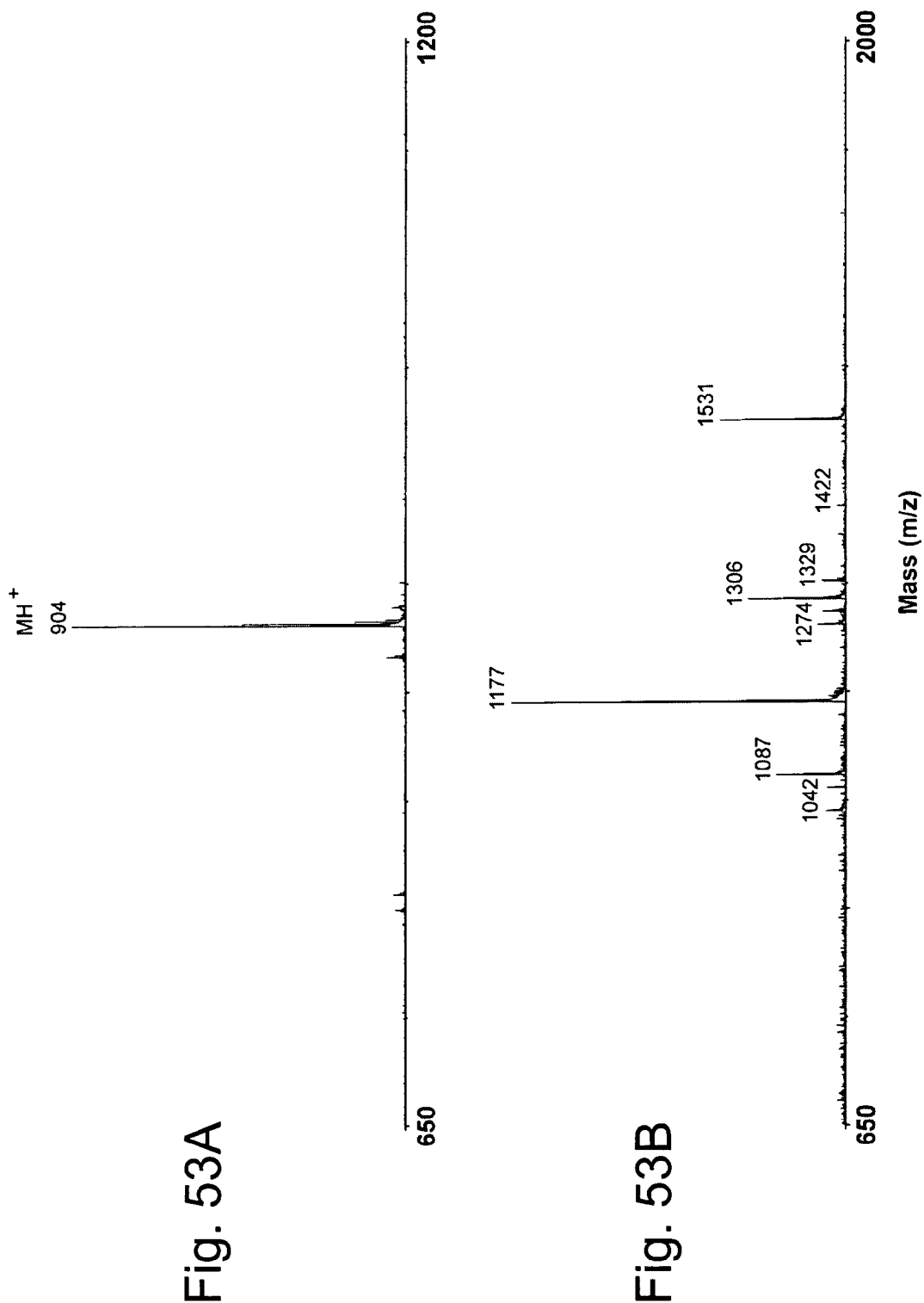
Figures 54A, 54B, 54C:
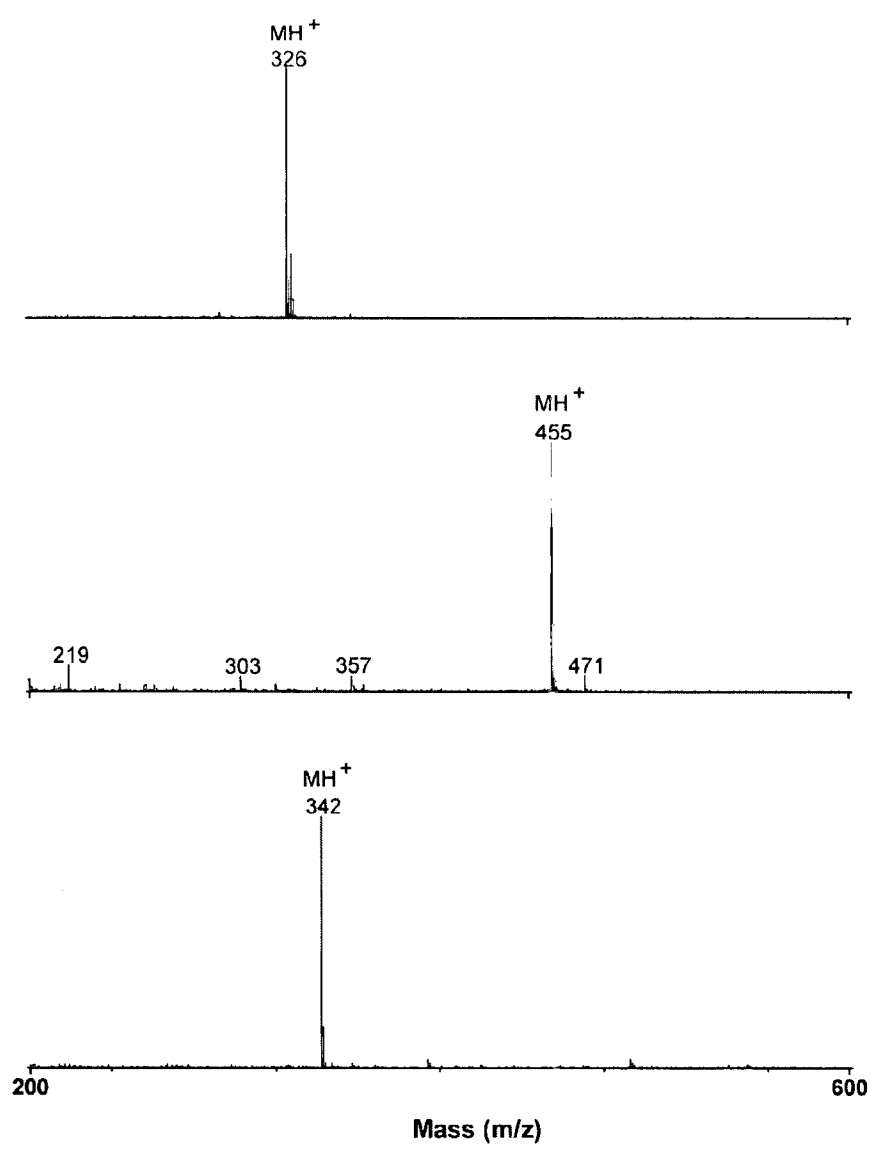
Figure 55:
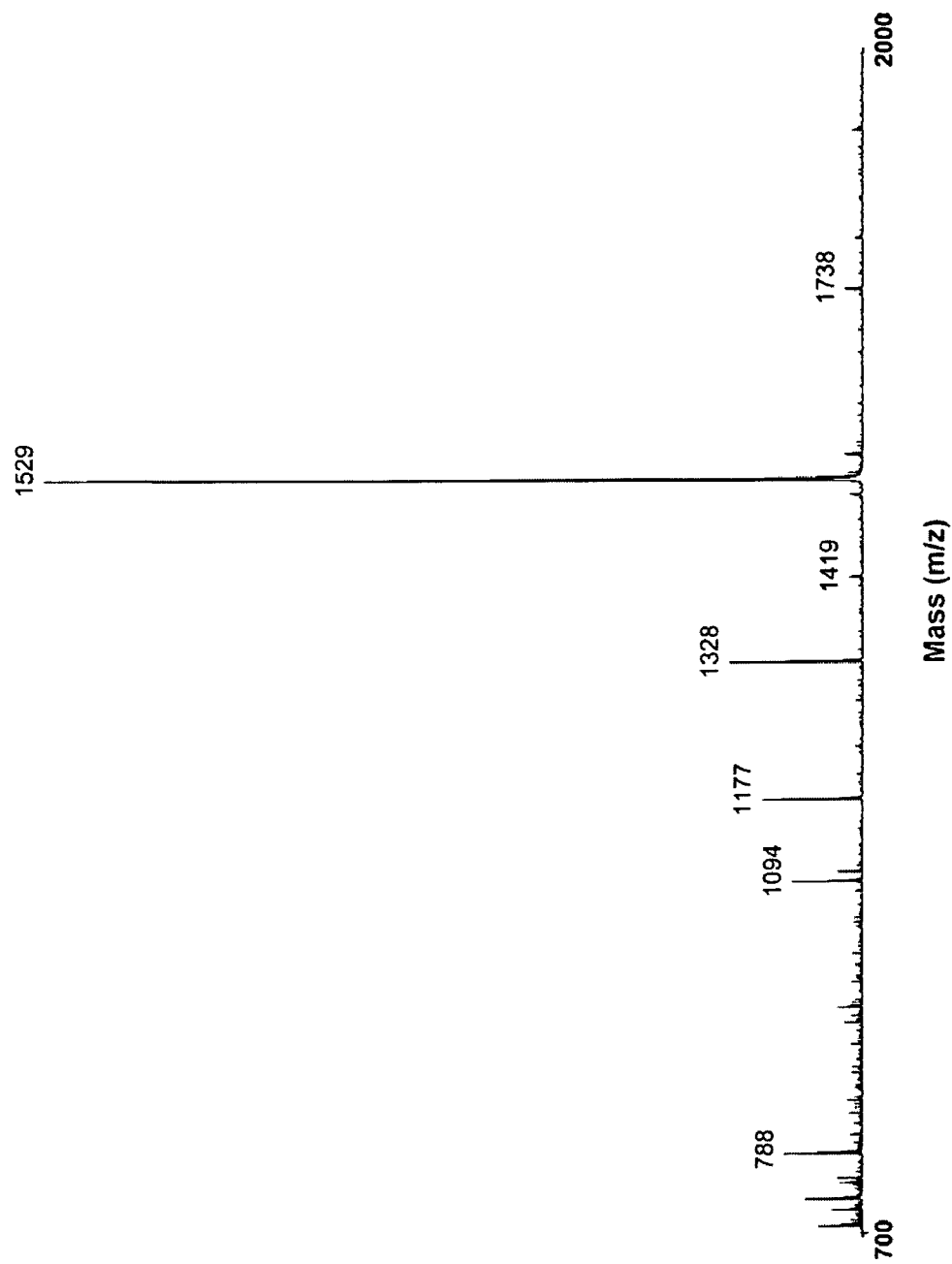
Figure 56A:
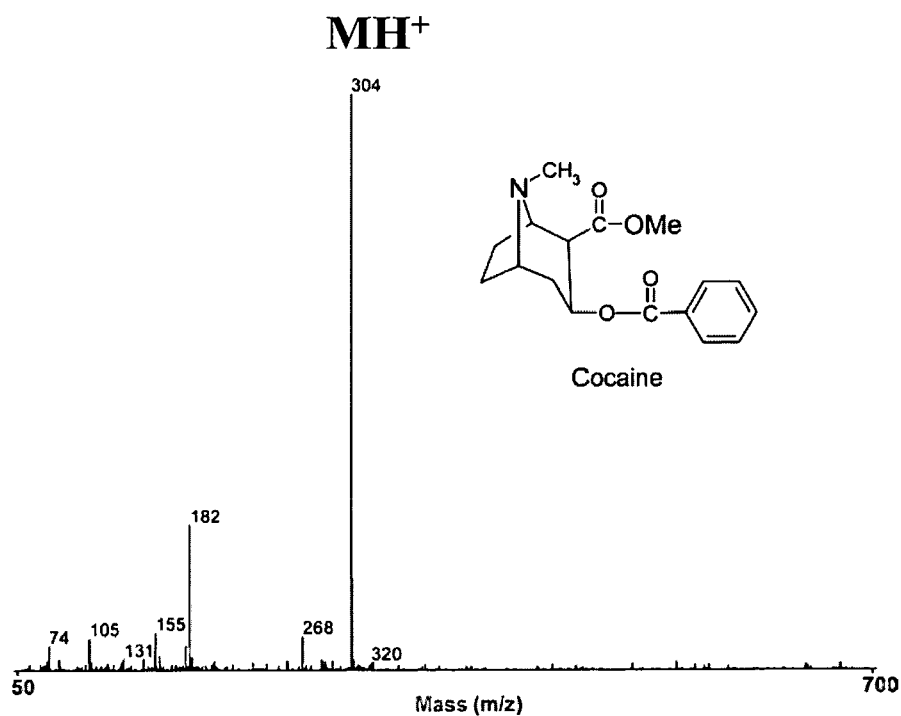
FIG. 56, Panels A-D, Display mass spectroscopy analysis of exemplary compounds on nanofiber surfaces.
Figure 56B:
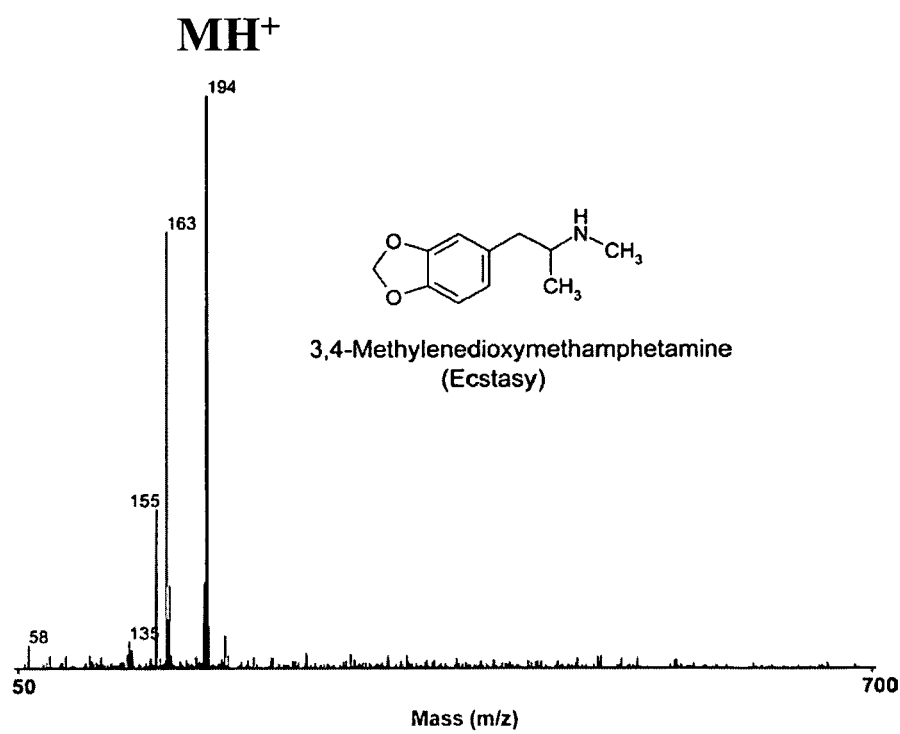
Figure 56C:
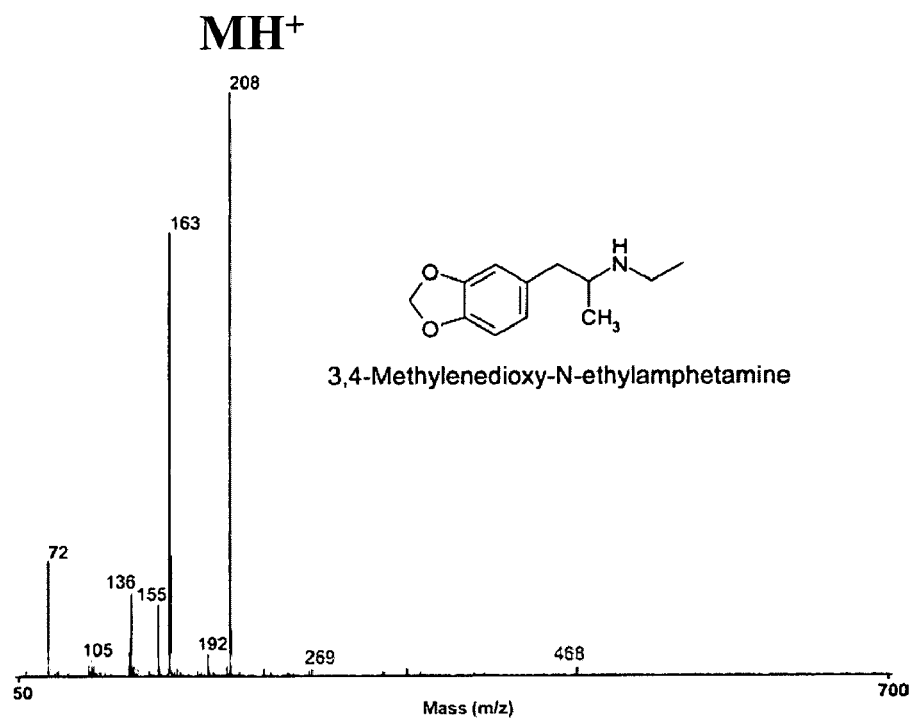
Figure 56D:
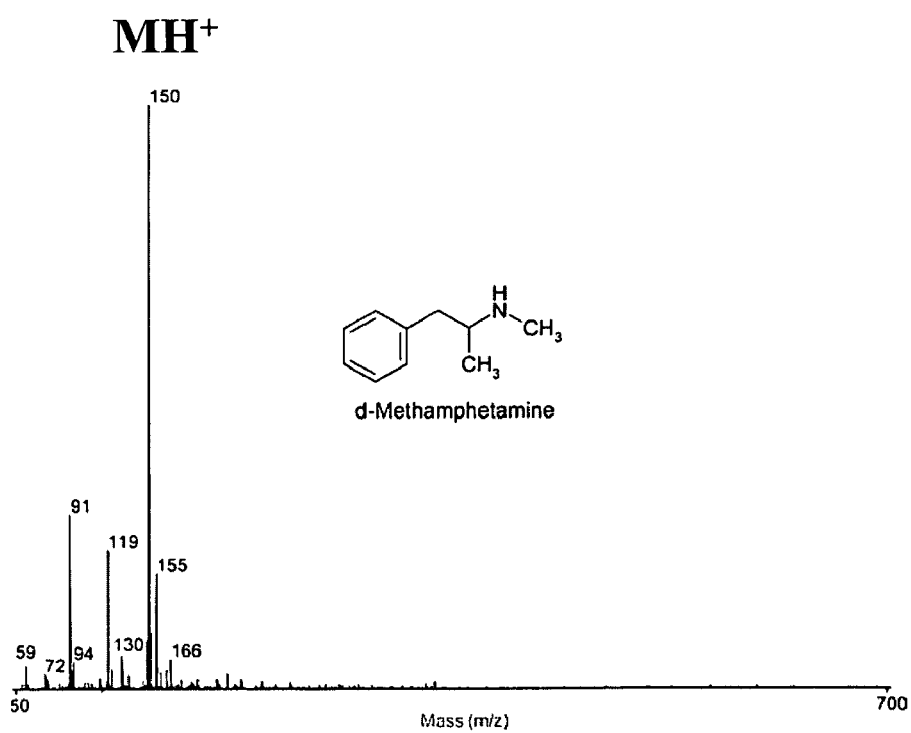

To illustrate various concepts herein concerning nanofiber enhanced surface areas used with mass spectrometry, nanofiber enhanced surfaces (in the example, nanowire surfaces) were tested and optimized for DIOS-MS activity under a variety of different conditions. The surfaces used comprised patterned nanowire surfaces (in 200 um square conformations), compressed and pulled nanowires (i.e., precrushed nanowires), and low density nanowires surfaces (i.e., monolayer nanowire surfaces). In typical embodiments of such, the nanofibers comprise a fairly high density of short fibers. Such nanofibers can be grown in situ or deposited on the surface. In some aspects, pre-crushing the fibers produces a similar surface as growing shorter fibers. The nanowire surfaces were derivatized (see, above for additional details on derivatization and functionalization) with BSTFA, (3,3,4,4,5,5,6,6,6-nonafluorohexyl)chlorosilane, and (3-pentafluorophenyl)propyldimethylchlorosilane (each tested separately). FIG. 51 shows the chemical structures of such compounds. The nanowire surfaces were patterned and precrushed compressed with a microscope slide, were oxidized with ozone, and were chemically modified with the reagents listed above. Analytes used for mass spectrometry analysis consisted of 3 small molecules, 2 standard peptides (MRFA and Bradykinin), and two protein digest (hemoglobin and BSA). FIG. 52 shows the chemical structure of the 3 small molecules analyzed. FIGS. 53A and 53B show mass spectrometry results for 5 fmol Bradykinin and 50 fmol hemoglobin, respectively, on perfluorinated patterned nanowire surfaces. FIGS. 54A through 54C show mass spectrometry results for 500 fmol midazolam, 500 fmol verapamil, and 2.5 pmol propafenone, respectively, on the perfluorinated patterned nanowire surfaces. Finally, FIG. 55 shows mass spectrometry results for 5 fmol hemoglobin digest on a perfluorinated monolayer nanowire surface. As can be seen from such results, the nanofiber enhanced surfaces of the invention are useful in mass spectrometry (here DIOS-MS) analysis of compounds. Conjugated perfluorinated nanowire surfaces apparently allow good DIOS-MS performance. Of course, use of such conjugated surfaces should not be taken as limiting. Thus, other surfaces are also optionally and/or alternatively used. Additionally, monolayer nanowire surfaces produce a higher level of sensitivity in mass spectrometry analysis (see, e.g., results in above figures for 5 fmol peptide amounts and 25 fmol small molecule amounts). In some embodiments for very high sensitivity, short nanofibers or monolayers of such are typically preferred. However, if extreme sensitivity is not required, thicker layers can optionally be used. Also, in other embodiments, deep wire sections are particularly valuable for doing thin layer chromatography prior to mass spectrometry analysis. In other embodiments of the invention used with various mass spectrometry applications, the different parameters are optionally modified depending upon, e.g., the specific molecules being detected, etc. For example, the laser energy used can optionally be adjusted (e.g., higher laser energy levels for peptides as opposed to small molecules, etc.). Again, those of skill in the art will be familiar with typical modifications and optimizations for various mass spectrometry techniques. FIGS. 56A-D show further examples of mass spectroscopy on nanofiber substrates and illustrate one of the myriad possible uses of the methods/devices of the invention (here to detect and/or identify controlled substances, e.g., cocaine, 3,4-methylenedioxymethamphetamine, 3,4-methylenedioxy-N-ethylamphetamine, d-methamphetamine, etc.). The concentrations of the drugs detected/characterized in FIG. 56 were 5 pmol for all but cocaine, which was 500 fmol.

Figure 57:
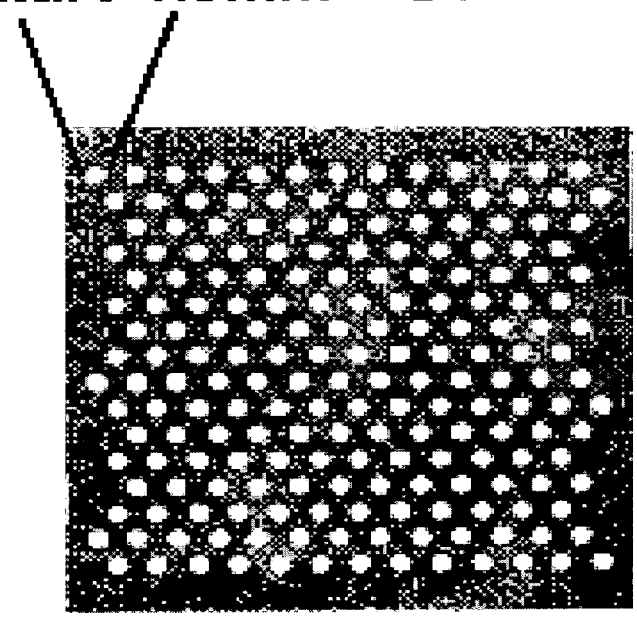
FIG. 57, Shows a shadow mask for generating alumina pattern for a nanofiber enhanced substrate used for mass spectrometry.

Further samples for mass spectrometry analysis were prepared on nanofiber enhanced substrates (here nanowire enhanced substrates). A plate was cleaned by 3 minute sonication in toluene, 3 minute sonication in acetone, blown dry under argon and then plasma cleaned (200 W 10 min). Alumina was evaporated onto the clean plate in 1.5 mm circles (see FIG. 57 for the pattern which had features of 1.5 mm with center-to-center distance of 3 mm). The plate was then boiled for 5 minutes and then soaked in 20 nm gold colloid for 20 minutes. After colloid deposition, the plate was plasma cleaned again (200 W, 10 mins) and then placed into a furnace and nanowire growth allowed to take place for 6 minutes.

Figure 58A:
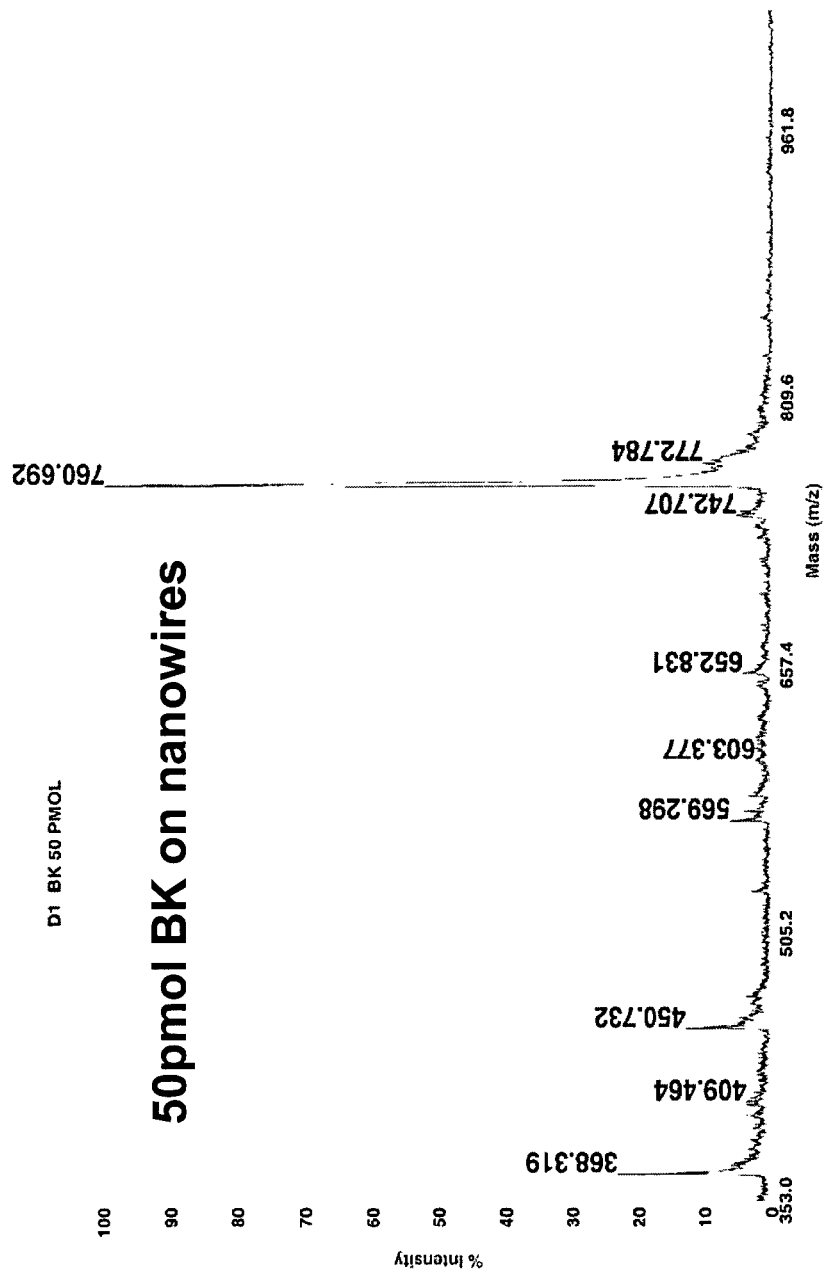
FIG. 58, Shows results from mass spectrometry analysis of samples on a nanofiber enhanced substrate of the intention.
Figure 58B:
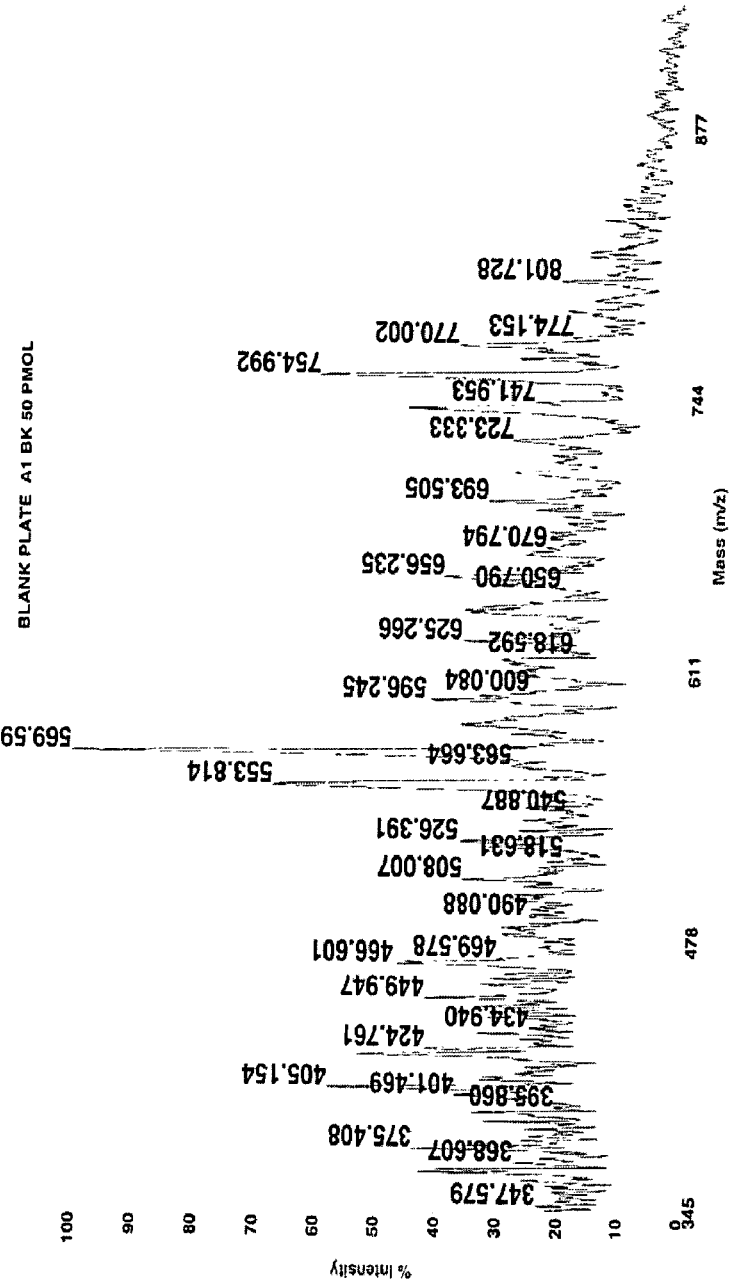

Following nanowire growth, the plate was plasma cleaned (200 W 30 seconds) and then covered with 100 μl of neat pentafluorophenylpropyldimethylchlorosilane (Gelest, Morrisville, Pa.) for 15 minutes at 65° C. The plate was washed in methanol and blow dried with argon. Bradykinin fraction 1-7 (MW 757.4) was dissolved in 50% acetonitrile/0.05% TFA at 100 pmol/μl and subsequently diluted into 20% acetonitrile prior to spotting onto the nanowire spots (0.75 μl volumes). The samples were allowed to dry and then analyzed on an ABI Voyager-DE mass spectrometer. FIGS. 58A and B show the signals obtained from 50 pmoles bradykinin on nanofibers (here nanowires) and on a similar spot on stainless steel with no nanofibers (at the same laser power). It will be appreciated that the bradykinin peak only appears on the nanofiber surface.

A further example of use of nanofiber substrates herein in conjunction with mass spectrometry took advantage of the usefulness of the substrates herein to perform separation reactions as well. See above. Thus, an integrated chromatographic separation and desorption/ionization mass spectrometry (on silylated silicon nanofibers, here nanowires) was performed. Dense arrays of single crystal silicon nanowires (SiNWs) can be used as a platform for laser desorption/ionization mass spectrometry of small molecules, peptides and protein digests. Again, however, other embodiments herein can use other nanofiber types/constructions, etc. Sensitivity down to the attomole level can be achieved on the nanowire surfaces by optimizing laser energy, surface chemistry, nanowire diameter, length, and growth orientation. An interesting feature of the nanowire surface is that it requires relatively low laser energy (1 to 5 µJ/pulse) to desorb small molecules therefore reducing background ion interference. Taking advantage of their high surface area and fluid wicking capabilities, SiNWs were used to perform thin layer chromatography (TLC) followed by mass analysis of the separated molecules providing a unique substrate that can integrate separation and mass spectrometric detection on a single surface. Surface-based mass spectrometry approaches have been widely applied to problems in protein identification, small molecule metabolite characterization, and synthetic organic chemistry. Among the most established techniques is matrix-assisted laser desorption/ionization (MALDI), which provides for soft ionization and high sensitivity analysis. See, e.g., Tanaka, et al., "Protein and polymer analysis up to m/z 100,000 by laser ionization time-of-flight mass spectrometry" *Rapid Commun. Mass Spectrom.* 2:151 (1988) and Karas, et al. "Laser Desorption Ionization of Proteins with Molecular Masses Exceeding 10000 Daltons" *Anal. Chem.* 60:2299-2301 (1988). However, MALDI is typically limited to the analysis of molecules above a mass range of 700 m/z. Porous silicon (pSi) was developed as a matrix-free desorption/ionization approach, where the absence of matrix related ions extends the observable mass range to small molecules. It is believed that its high surface area, low thermal conductivity, and high UV absorptivity of pSi enabled its successful application to desorption/ionization on silicon mass spectrometry (DIOS-MS). See, e.g., Wei, et al., "Desorption-ionization mass spectrometry on porous silicon" *Nature* 399: 243-246 (1999); Shen, et al., "Porous silicon as a versatile platform for laser desorption/ionization mass spectrometry" *Anal. Chem.* 73:612-619 (2001); Cuiffi, et al., "Desorption-ionization mass spectrometry using deposited nanostructured silicon films" *Anal, Chem.* 73:1292-1295 (2001); and, Kruse, et al., "Experimental factors controlling analyte ion generation in laser desorption/ionization mass spectrometry on porous silicon" *Anal. Chem.* 73:3639-3645 (2001).

SiNWs have been the subject of extensive research in electronics, photonics, optoelectronics, sensing, and other novel device applications. See, e.g., Cui, et al., "Nanowire nanosensors for highly sensitive and selective detection of biological and chemical species" *Science* 293;1289-1292 (2001); Cui, et al., "Functional nanoscale electronic devices assembled using silicon nanowire building blocks" *Science* 291:851-853 (2001); Huang, et al., "Integrated optoelectronics assembled from semiconductor nanowires" *Abstracts of Papers of the American Chemical Society* 224:U308 (2002); Zhou, et al., "Silicon nanowires as chemical sensors" *Chem. Phys. Lett.* 369:220-224 (2003); Duan, et al., "Single-nanowire electrically driven lasers" *Nature* 421:241-245 (2003); Hahm, et al., "Direct ultrasensitive electrical detection of DNA and DNA sequence variations using nanowire nanosensors" *Nano Lett.* 4:51-54 (2004) as well as references cited above. They share a number of the same basic properties of pSi and, e.g., as illustrated herein, appear to be an ideal platform for surface-based mass spectrometry. In contrast to pSi, and as explained throughout, SiNWs are catalyzed and grown on the surface of a substrate and their physical dimensions, composition, density, and position can be precisely controlled at the nanoscale level thus offering even greater potential for designing mass spectrometry active surfaces.

As explained above, SiNWs can be prepared through chemical vapor deposition, laser ablation of Si targets, liquid crystal templating methods, laser-assisted catalytic growth, vapor-liquid-solid (VLS) growth mechanism, and supercritical fluid methods as well as others. See, e.g., Morales, et al., "A laser ablation method for the synthesis of crystalline semiconductor nanowires" *Science* 279:208-211 (1998); Lieber, C. M., "One-dimensional nanostructures: Chemistry, physics & applications" *Solid State Commun* 107:607-616 (1998); Cui, et al., "Diameter-controlled synthesis of single-crystal silicon nanowires" *Appl. Phys. Lett.* 78:2214-2216 (2001); Gudiksen, et al., "Diameter-selective synthesis of semiconductor nanowires" *J. Am. Chem. Soc.* 122:8801-8802 (2000); Duan, et al., "Laser-assisted catalytic growth of single-crystal compound semiconductor nanowires" *Abstracts of Papers of the American Chemical Society,* 219:U874-U875 (2000)' Lyons, et al., "Tailoring the optical properties of silicon nanowire arrays through strain" *Nano Lett.* 2:811-816 (2002)' Wu, et al., "Inorganic semiconductor nanowires: rational growth, assembly, and novel properties" *Chem.* 8:1260-1268 (2002); and, Ma, et al., "Small-diameter silicon nanowire surfaces" *Science* 299:1874-1877 (2003) as well as previously cited references. In this example, surface deposited Au colloid with a defined diameter was used as a growth catalyst. This method is very flexible and allows the control of multiple growth parameters such as length, diameter and density as well as being compatible with growing SiNWs on a variety of substrates including silicon, glass, ceramics, and metals, etc. In addition, SiNWs can be grown in continuous fields or patterned using lithographic methods to provide precise positional control of the nanostructured surface at the micro- to millimeter scale or below. Typically, SiNWs are grown from 10 to 60 nm in diameter and up to 100 µM in length and the nanowire density can also be controlled by varying the density of the catalyst deposited onto the growth surface (typical densities for this application are between 1 and 10 wires/µm$^2$).

Figure 59:
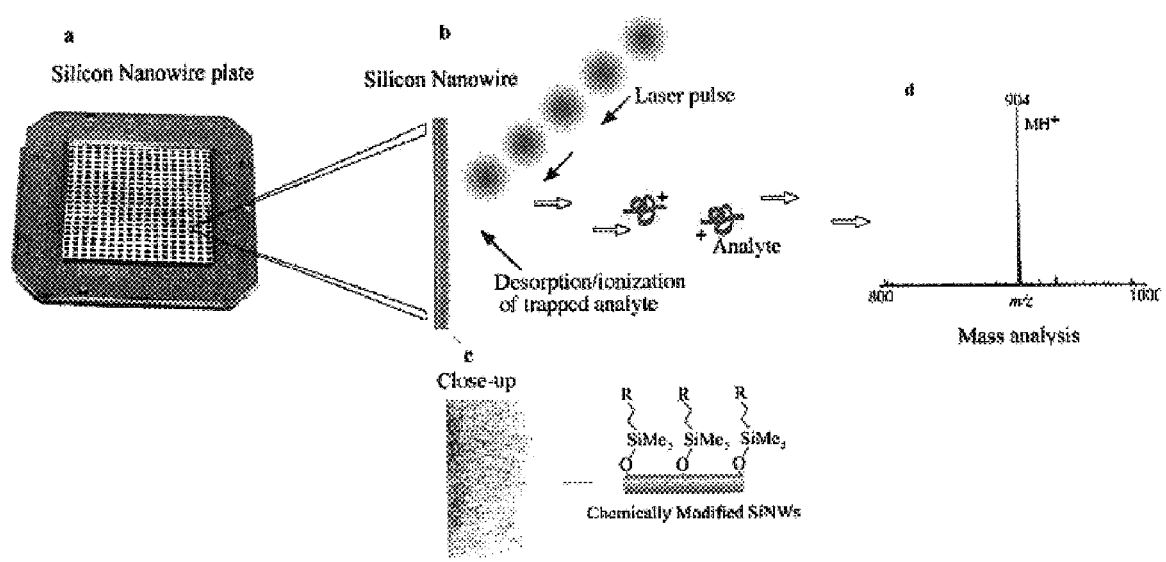
FIG. 59, Shows a configuration of an exemplary laser desorption/ionization MS set-up.

This example examines the effect of laser energy, nanowire density, nanowire size, and growth orientation on the SiNW performance as a platform for matrix-free mass spectrometry using peptides and small drug molecules as model compounds. Recently developed chemical modification on ozone-oxidized pSi has also been employed on the SiNWs, a feature that has proven essential to achieve high sensitivities. See, e.g., Trauger, et al. "High Sensitivity and Analyte Capture with Desorption/Ionization Mass Spectrometry on Silylated Porous Silicon" *Submitted* (2004). In addition, as explained above, it is observed that this surface has dramatic wicking properties driven by capillary action generated in the interstitial spaces between SiNWs. This property is exploited in TLC separation and subsequent MS analysis of small drug molecules. The application of silylated SiNWs to laser desorption/ionization mass spectrometry was examined as a function of nanowire diameter, length, density, and growth orientation. See FIG. 59 which shows a configuration of the laser desorption/ionization mass spectrometry experiment showing (a) patterned SiNWs grown on a silicon substrate attached to a modified MALDI plate, (b) a schematic of laser desorption/ionization of trapped analytes within the Si nanofiber mesh, (c) a close-up SEM image of SiNWs and an illustration of the functionalities by silylation, and (d) mass spectra of 500 amol des-Arg$^9$-bradykinin illustrating the sensitivity of Si nanofibers (here nanowires). The measured signal-to-noise in this example was 600 to 1. BSA and FHV tryptic digests, small drug molecules (midazolam, MH$^+$ 325, propafenone, MH$^+$ 342; verapamil, MH$^+$ 455), and a standard peptide (des-Arg$^9$-bradykinin, MH$^+$ 904) were used as model compounds to examine desorption/ionization properties of SiNWs. In the initial set of experiments the ability of silylated 40 nm diameter SiNWs to generate ion signals was investigated and further the optimal material characteristics in terms of SiNW length and density were determined. Using the growth methods, e.g., described herein, the nanowire growth orientation randomly varies from horizontal to vertical and is independent of wire density and diameter. The initial observation reveals that optimal performance was dependent on both the layer thickness (wire length) and wire density. Optimized mass spectral data were obtained reproducibly with nanowire densities of less than 10 wires/μm$^2$ and wire length of less than 5 μm. Mass spectral data obtained from silylated SiNW surfaces gave signal-to-noise levels and mass ranges very similar to the silylated pSi surface. Silylated planar silicon substrate (with no SiNWs) gave no detectable signal for peptides at 5 μM. FIG. 59 shows a scanning electron micrograph of the structured surface we investigated, the length of the wires were varied from 0.5 to 10 μm and the wires were deposited at various densities from 1 to 50 wires/μm$^2$.

Because the electrical and optical properties of the SiNWs are dependent on the nanowire length and density, the effect of the diameter on the laser desorption/ionization performance was also examined. SiNWs with approximately 1 μm and diameters of 10, 20, and 40 nm were tested for the analysis of small molecules and peptides. In contrast to the dependence on wire length and density, a clear difference in the performance of the nanowire surfaces with varying diameter was not observed. MS analysis of small molecules and protein digests were obtained reproducibly on SiNWs with diameters between 10 and 40 nm and 1 μm in length with sensitivity at the picomole to the attomole level. The data obtained from the digest could be searched against a protein sequence database using Mascot to identify BSA and FHV with a score greater than 99% confidence level. See FIG. 60. FIG. 60 shows laser desorption/ionization from silylated silicon nanofibers (here nanowires) of (a) 50 fmol Flock House Virus (FHV) and (b) 5 fmol BSA digests showing the cleavage peptides that have been identified. The data were searched with Mascot to identify the proteins with a confidence level of greater than 99%. Typically, MS analysis on the 10 to 40 nm diameter SiNWs provided a detection limit of 50 fmol for small molecules while 40 nm diameter SiNWs provided a detection limit of 500 amol for peptides. See FIG. 59. It is contemplated that with further optimization of SiNW fabrication and surface treatment, the detection limit can optionally be improved.

The minimum laser energy requirement to desorb/ionize analytes from SiNWs was also examined. Interestingly, SiNWs required lower energy than pSi or MALDI, FIG. 61, and, as a result, very little surface related background ions were observed from the SiNWs. This characteristic is especially useful in the analysis of small molecules wherein desorption/ionization can be performed with laser energy as low as 0.3 μJ. FIG. 61 shows (a) a plot of laser energy per pulse vs. MALDI instrument settings used in a laser desorption/ionization analysis using silicon nanowires (yellow shaded region on the left) and porous silicon (light blue shaded region on the right) as platforms;

(b) shows a comparison of the laser energy requirement to desorb/ionize small molecules (midazolam, m/z 326; propafenone, m/z 342; verapamil, m/z 455, 500 fmol) on the two platforms.

Figure 62:
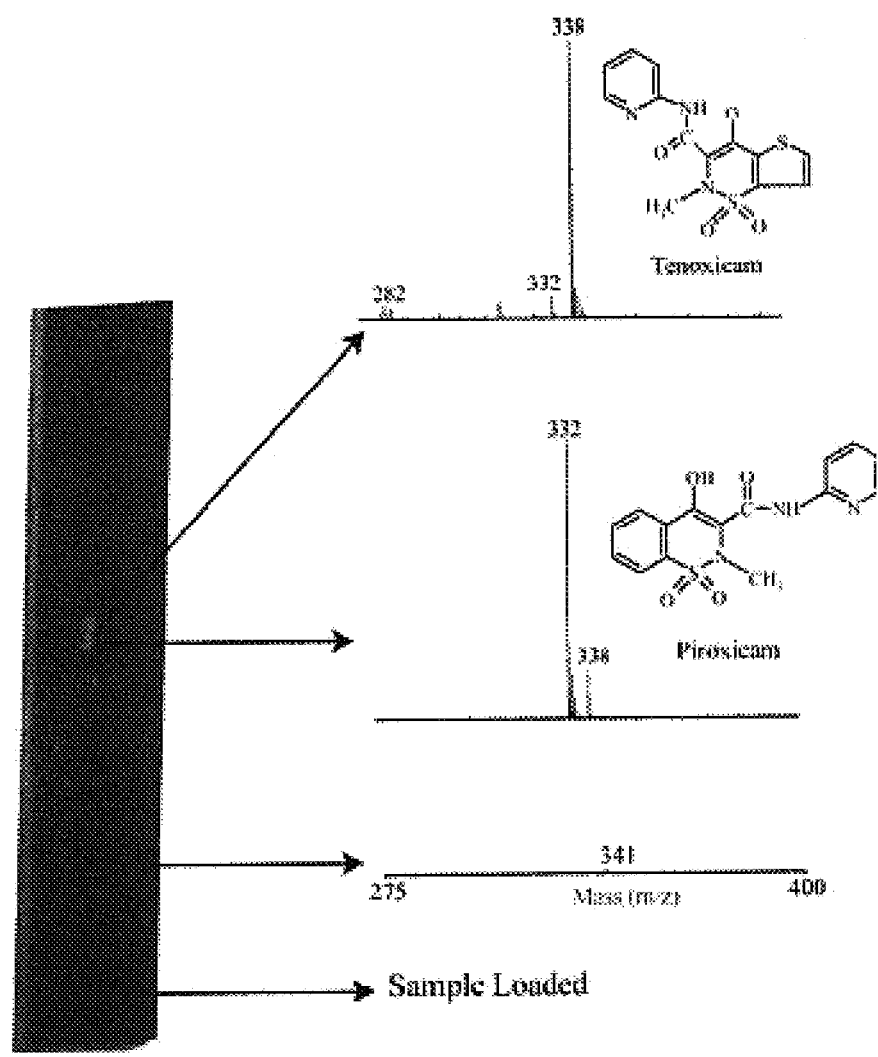
FIG. 62, Shows silicon nanowires as a platform for chromatographic separation of an exemplary mixture and mass spectrometry of such separation.

As explained above, one of the useful applications of SiNWs is in the area of chromatography since SiNWs can be employed as a platform for TLC. In TLC, capillary forces are employed to transport the analytes in the mobile phase allowing analytes applied on the stationary phase to move at different rates ultimately allowing separation. See, e.g., Sherma, J., "Thin-Layer and Paper-Chromatography" *Anal. Chem.* 60:R74-R86 (1988), see also, above. The capability of SiNWs to separate a simple sample mixture lies in its high surface to volume ratio. When combined with its ability to support laser desorption/ionization mass spectrometry, TLC-MS with SiNWs provides a simple, inexpensive, rapid and qualitative means to separate and analyze sample mixtures. This example demonstrates TLC with SiNWs in the analysis with a mixture of two small drug molecules (tenoxicam m/z 338; piroxicam m/z 332). See FIG. 62. The silylated nanowire silicon surface allowed for the migration and separation of the sample mixture ($R_f$=0.69, 0.56 for tenoxicam and piroxicam, respectively) as demonstrated by fluorescence of the drug molecules when irradiated with 254 nm UV light. MS scanning the SiNW TLC plate along the sample track revealed that two strong signals appearing at m/z 332 and m/z 338 corresponding to piroxicam and tenoxicam were observed, respectively. It should be noted that mass spectra were only observed from the two adjacent spots and analysis above and below those spots generated no signal. It is contemplated that changes in nanowire size and the effect of different silylating reagent can effect separation and extraction efficiency. FIG. 62 shows silicon nanowires as a platform for chromatographic separation of a mixture of small drug molecules (tenoxican, m/z 338; piroxican m/z 332). The sample was deposited 0.5 cm from the edge of the plate and allowed to separate using methanol:water mixture as mobile phase.

The results described here demonstrate the use of silylated SiNWs for direct biomolecule analysis. It is shown that the dimensionality, size, high surface area, and fluid wicking properties play an important role for its application in mass spectrometry and chromatographic separation. This example also demonstrates that SiNWs require lower laser energy for analyte desorption/ionization compared to MALDI or pSi-DIOS. Furthermore, the analysis of a wide range of molecules with good sensitivity was achieved, and the material could serve as a platform for the TLC-MS analysis. The ability to pattern SiNWs on a wide variety of substrates can lead to straightforward commercial developments. It is contemplated that significant improvement in sensitivity and chromatographic properties can result from tailoring the surface properties through additional chemical and structural modifications.

In this example, SiNWs were synthesized using Au nanocluster catalyzed vapor-liquid-solid (VLS) growth mechanism. Size selected Au colloid particles were deposited on silicon wafers to produce high-quality SiNWs with a narrow diameter distribution. Briefly, this method employs Au nanoparticles with diameters of 10, 20, and 40 nm distributed on a silicon substrate by spin-coating. Colloids were deposited at densities of 1 to 10 wires/μm$^2$ which was verified by SEM. After removing solvents and organic residues, the substrates were placed in a 480° C. chemical vapor deposition (CVD) furnace to grow SiNWs with silane (SiH$_4$) as the vapor phase reactant. SiNWs were etched in 5% HF solution to remove the oxide layer and subsequently oxidized with ozone. The surfaces were then modified with a silylating reagent. Surface derivatization involved the modification of OH groups present on the ozone-oxidized SiNWs by silylation with (pentafluorophenyl)propyldimethylchlorosilane (PFPPDCS). This modification generated a perfluorophenyl-derivatized SiNW surface. The silylation reaction was performed by adding 15 μL of the PFPPDCS on the oxidized SiNW which was placed in a glass Petri dish and incubated in an oven at 90° C. for 15 minutes. The chemically modified SiNW surface was rinsed thoroughly with methanol and dried in a stream of $N_2$. This simple procedure produced perflurophenyl silylated SiNW surfaces as verified by infrared (IR) spectroscopy. Nanowire diameter, length and densities were measured using a JEOL 6460LV SEM. The samples were mounted on the stage with brass clips and analyzed in their native condition. DIOS-MS measurements were performed with an Applied Biosystems (Framingham, Mass.) Voyager STR time-of-flight reflectron mass spectrometer. The SiNW surfaces were attached to a modified MALDI target plate using conductive carbon tape and samples were irradiated with a nitrogen laser operated at 337 nm at 5 Hz (3 ns pulse duration) and attenuated with a neutral density filter. Ions produced by laser desorption were energetically stabilized during a delayed extraction period of 25-250 ns and then accelerated through the linear time-of-flight reflectron mass analyzer with a 20 kV pulse. The MS spectra were generated by averaging between 50-500 laser pulses. The laser intensity was set to optimize the signal-to-noise ratio and the resolution of the mass spectral data of the analyte. For TLC separation, perfluorophenyl-derivatized SiNW surfaces were used as TLC plates. Prior to separation, the plates were heated at 90° C. for 15 minutes and were allowed to cool at room temperature. A 5 μL aliquot of the sample mixture containing tenoxicam and piroxicam at 1 mg/mL each was deposited on the plate. The separation of the sample was performed using methanol: water (8:2 v/v) mixture as the mobile phase. The separation was done in a beaker covered with transparent plastic film. The chromatogram was developed for 30 minutes. The SiNW surface was dried and spots were visualized by illuminating the surface with 254-nm UV light. Aqueous stock solutions of verapamil (MW 454 Da), propafenone (MW 341), midazolam (MW 324 Da), des-bradykinin (MW 904) were prepared by reconstituting lyophilized samples in deionized water at 1 mg/mL followed by subsequent serial dilution were done as needed. Stock solutions of tenoxicam and piroxicam were prepared at 2 mg/mL in dichloromethane. Bovine serum albumin (BSA) and flock house virus (FHV) proteolytic digests were prepared with trypsin (1:30 enzyme to protein ratio by mass). The proteins were denatured at 90° C. for 20 minutes. FHV was reduced and alkylated with dithiothreitol (DTT) and iodoacetamide (IAA), respectively. The tryptic digests were incubated overnight at 37° C. in 5 mM ammonium citrate buffer (pH 7.5). The enzymatic reaction reached completion within 18 hours, yielding a final BSA and FHV concentration of 1 μM, respectively. Samples (0.5 μl) were pipetted directly onto the chemically modified SiNW surfaces. High purity grade reagents were all obtained from Sigma except for PFPPDCS and trypsin which were obtained from Gelest, Inc. and Promega, respectively.

vii) Example 7

Fluorescence Quenching with Nanofiber Substrates

Figure 64:
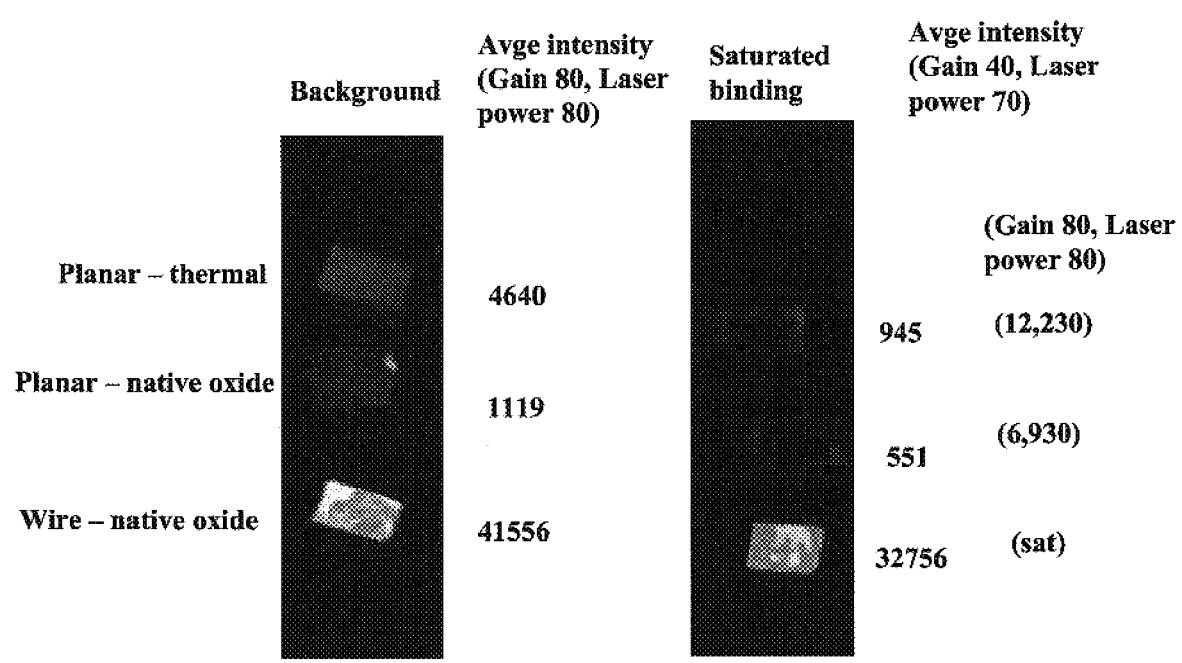
FIG. 64, Shows quenching of non-specifically bound fluorescence on native versus grown oxides on silicon (planar and nanofiber, nanowire, surfaces).

Quenching of non-specifically bound fluorescence compared between native oxides and grown oxides on nanofiber surfaces (here nanowire) is shown in FIG. 63. The figures show the quenching effect of silicon with native oxide surfaces. The two wafer segments that were oxidized had approximately 5-fold higher background signal, but only about 2.3 fold increase in specifically bound signal. The increase in specific signal is thought to likely be due to a higher nanofiber density. The fluorescence of the surfaces in FIG. 63 was detected on a Perkin Elmer ScanArray express scanner equipped with a 633 nm laser. The background intensity (measured as average intensity with gain of 45 and laser power of 70) of native oxide was 4080, of thermal oxide (part) was 21523 and of thermal oxide (total) was 18396. The saturated binding intensity (measured as average intensity with gain of 33 and laser power of 70) was 23245 for the native oxide and 54245 for the thermal oxide (part) and 51783 for the thermal oxide (total). Similar surfaces were also analyzed using fluorescent microscopy with similar results (not shown). FIG. 64 details quenching of non-specifically bound fluorescence of native oxides and grown oxides on silicon (planar and nanofiber surfaces). As can be seen in FIG. 64, the background signal on thermal grown oxide planar surfaces is over 4× the signal on native oxide surfaces. In contrast, the specific signal is only 1.75× higher. Such difference indicates enhanced quenching of non-specific binding on the native oxide surface. Similarly, the nanofiber surface (here nanowire), which has a native oxide surface, has a 9× higher background over the planar thermal oxide surface, but a 35× increase in specific signal. The combination of increased surface area and enhanced quenching, thus, leads to an increased dynamic range. Without being bound to specific mechanisms, this is thought to be due to energy transfer of fluorescence from the fluorophores to the silicon substrate through the native oxide. If nonspecifically bound fluorophores are, on average, closer to the surface than specifically bound fluorophores, there will be a selective quenching of fluorescence from the nonspecifically bound fluorophores and therefore a greater dynamic range. In FIG. 64, the background intensity (measured as average intensity with gain of 80 and laser power of 80) was 4640 for the planar (thermal), 1119 for the planar (native oxide) and 41556 for the nanofiber (here nanowire native oxide). The saturated binding intensity (measured as average intensity with gain of 40 and laser power of 70) was 945 for the planar thermal, 551 for the planar with native oxide and 32756 for the nanofiber with native oxide. When measured with gain of 80 and laser power of 80, the planar thermal was 12,230, the planar with native oxide was 6,930 and the nanofiber (nanowire) with native oxide was (sat).

Figure 65A:
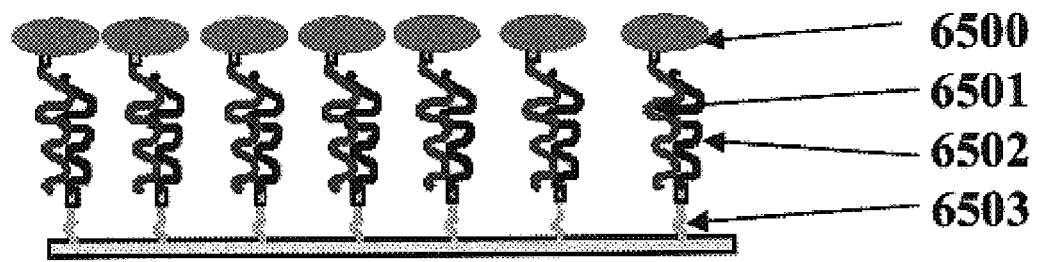
FIG. 65, Shows a schematic representation of DNA and protein hybridization to silicon substrates.
Figure 65B:
Figure 66:
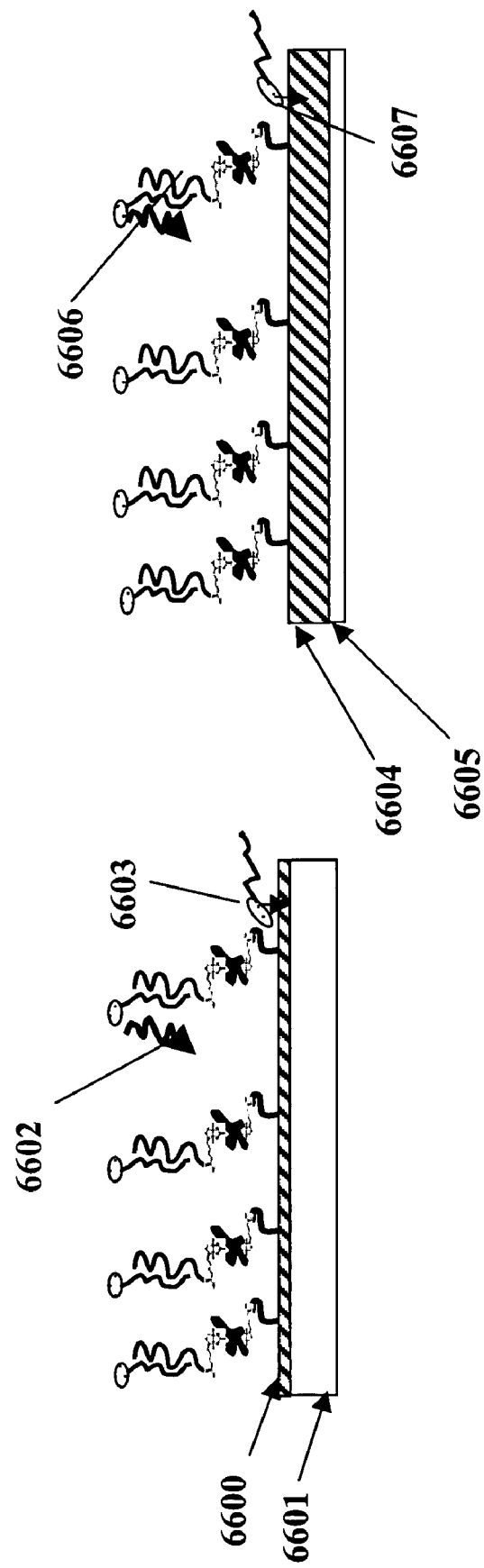
FIG. 66, Shows schematic representations of fluorescent quenching on nanofiber substrate assays.
Figure 67A:
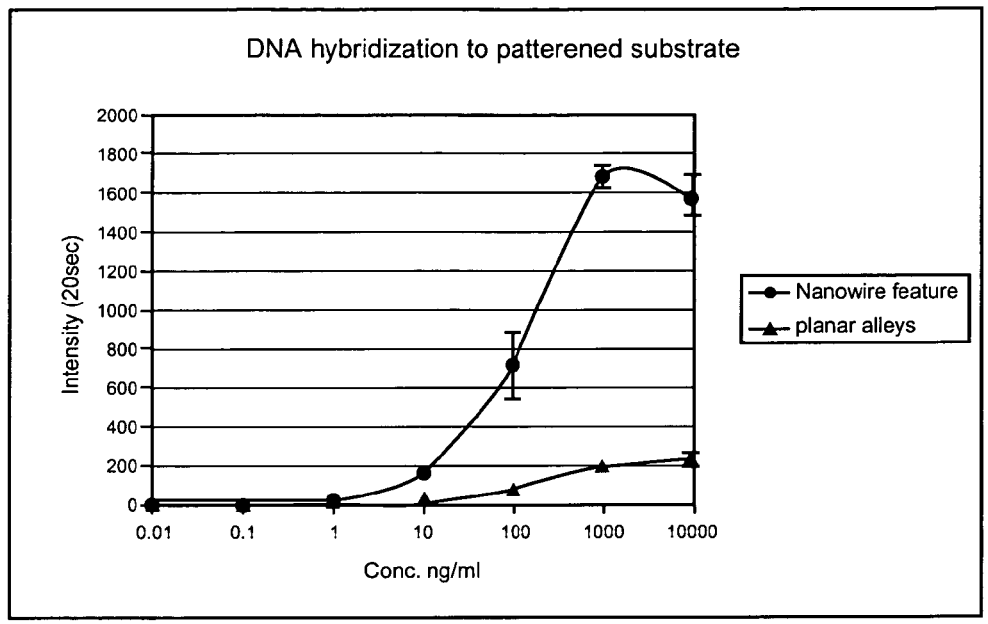
FIG. 67, Panels A and B, Shows comparison of dynamic intensity range for DNA and protein hybridization for nanofiber (here nanowire) surfaces and planar surfaces.
Figure 67B:
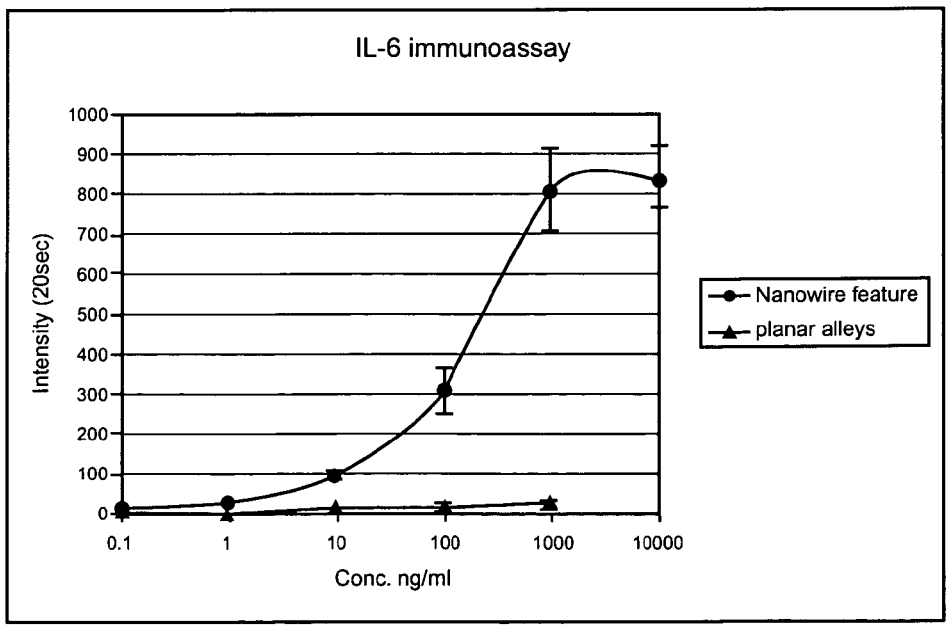

FIGS. 65 through 67 give additional support for the improved performance of protein and DNA arrays of the invention. FIG. 65 gives schematic representations of protein binding and DNA hybridization, while FIG. 66 shows schematics illustrating fluorescent quenching during the binding process. FIG. 65 illustrates reactions graphed in FIG. 67. In FIGS. 65A and 67A, DNA hybridization is shown by a Cy5, 6500, target oligonucleotide, 6501, being bound to an oligonucleotide probe, 6502, which is attached to a PEG linker to $SiO_2$, 6503. In FIGS. 65B and 67B, protein binding (IL-6) is shown by binding of fluorescent streptavidin, 6504, biotinylated secondary (polyclonal anti-IL-6), 6505, IL-6 (recombinant human), 6506, and adsorbed monoclonal anti-IL-6, 6507. FIG. 66 schematically shows quenching on a wafer of native oxide, 6600, on silicon, 6601. Specifically bound fluorescent light is not quenched, 6602, while NSB fluorescence is quenched. For substrates of grown oxide, 6604, on silicon layers, 6605, specifically bound fluorescent light is not quenched, 6606, and NSB fluorescence is not quenched, 6607. FIG. 67 illustrates representative binding data from both a DNA hybridization and a protein binding assay (sandwich immunoassay), comparing nanofiber (here nanowire) features with planar regions on the same chip. The features were modified and assayed identically. The data in FIG. 67 demonstrates the dramatically improved signal intensity and dynamic range of the nanofiber arrays of the invention. It will be noted that the limit of detection on array features is an order of magnitude lower for both assay formats.

viii) Example 8

Nanofiber Substrates in Capillaries/Tubes

Figure 68:
FIGS. 68-71, Show photographs of nanofibers grown within capillary tubes
Figure 69:
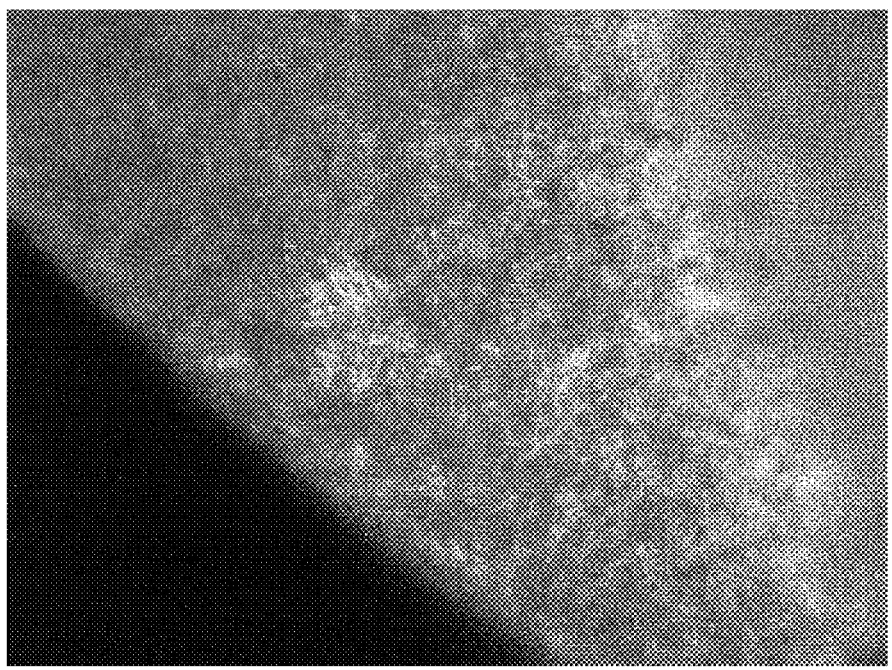
Figure 70:
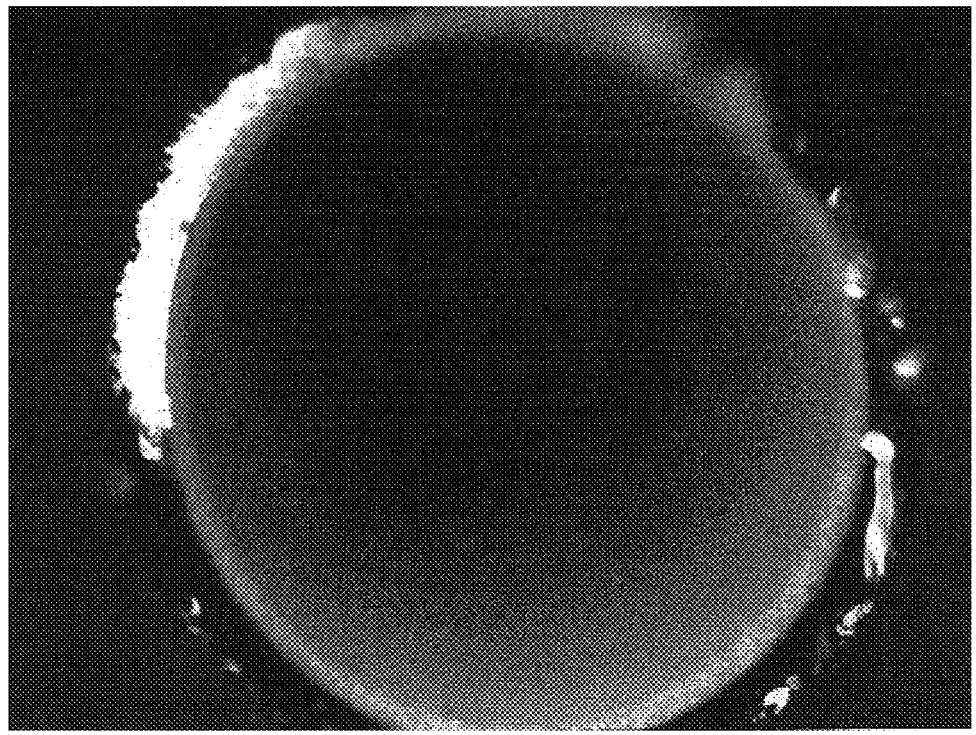
Figure 71:
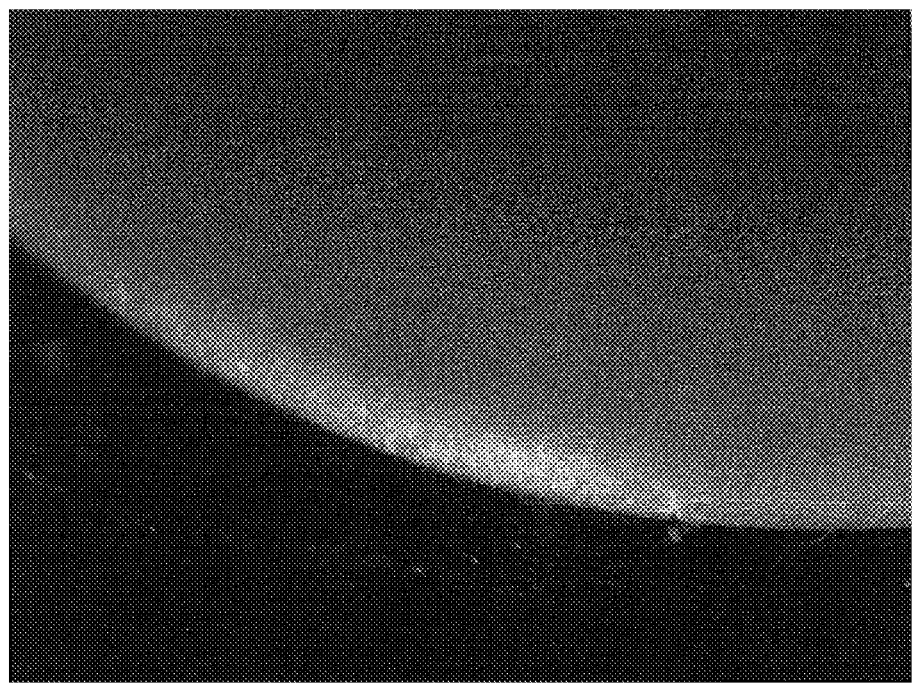

An example of an nanofiber enhanced surface area substrate within a capillary tube is illustrated in FIGS. 68 through 71. To produce such enhanced surface area capillaries, a quartz capillary tube was constructed with an internal diameter of approximately 1 mm and a length of approximately 50 mm. The tube was treated with 0.001% poly-L-Lysine for 20 minutes and blown dry with $N_2$. The tube was then heated at 150° C. for 30 minutes and cooled. Just the tip of the tube was placed into 40 nm gold colloid, which was drawn into the tube via capillary action. The colloid was allowed to attach to the inner wall of the tube for 15-20 minutes and blown dry with $N_2$. Nanofibers (in this instance nanowires) were grown at 470° C. for 30 minutes at 30 T and 1.5 T of $SiH_4$. Nanofiber growth extended throughout the length of the tube. FIGS. 68 and 69 show photographs of a piece of inside tube broken approximately 1.5 mm from the end of the tube. FIGS. 70 and 71 are top-down pictures taken from the end opening of the tube.

ix) Example 9

Prevention/Reduction of Cellular Growth on Exemplary Nanofiber Substrates

It is thought that, although absolute surface area is increased on substrates growing nanofibers, the low solid surface volume, lack of continuity and nanoscale aspect of the fibers discourages cellular attachment. The nanowire surfaces used in these illustrations herein was produced for an electronics application and was not optimized for this use, yet, as will be noted, such surfaces still reduced biofilm accumulation. The silicon wires utilized were ~40 nm in diameter and 50 to 100 um in length and were grown on a four inch silicon substrate. The nanowire preparation method is described below. In the current example, the nanowire pieces used in this experiment were about 0.25 $cm^2$. Immediately before introduction into the culture media they were soaked in 100% ethanol and blown dry with a stream of nitrogen. Silicon wafer controls (i.e., without nanowires) were also soaked in ethanol and blown dry. *S. epidermidis* was grown in LB broth for 6 hours at 37° C. with gentle shaking in 35 mm Petri dishes. Wafer sections were then placed in the culture and left for 24 hours at 37° C. in the original media. The wafer slices were removed after 24 hours incubation, washed briefly in fresh media, rapidly immersed in water and then heat fixed for 30 seconds prior to staining in a 0.2% crystal violet solution. The wafer segments were rinsed thoroughly in water. Any microbes attached to the wafers were visualized by conventional brightfield microscopy. Images were captured with a digital camera. The images in FIG. 72 show approximately a ten-fold decrease in bacteria on the nanowire substrate as compared to the silicon wafer control. Quantitation was performed on the microscope by focusing through the nanowires since the thickness of the nanowire layer was greater than the depth of field of the microscope. In FIG. 72, the pictures were taken at 1000× magnification. The black spots are stained *S. epidermidis*. The top left photograph is a nanofiber (here nanowire) surface after 24 hours. The bottom left photograph are the nanofibers after 72 hours. The top right picture is a flat silicon surface at 24 hours, while the bottom right photograph is the silicon at 72 hours. The 72 hour flat silicon is covered by a thick biofilm. Blurry areas on the nanofibers are due to the surface texture being greater than the depth of focus of the microscope.

To illustrate the nanofiber surfaces' repulsion of mammalian cells, CHO cells were maintained in culture in complete media (Hams F12 media supplemented with 10% fetal bovine serum) at 37° C. in a 5% $CO_2$ atmosphere. Wafer segments were placed in 35 mm cell culture treated Petri dishes. CHO cells were seeded into the dishes at a density of $10^6$ cell/ml in complete media after trypsinization from confluent culture. The cells were allowed to adhere overnight and were then observed microscopically every 24 hours. The surface of the 35 mm Petri dish was confluent at 48 hours when the first observation was made. No cell growth was observed directly on the nanowire surface. Where the nanowires had been removed by scratching the surface with a knife the cells adhered and grew. Silicon wafer controls became confluent with cells. The micrographs in FIG. 73 demonstrate this behavior. In FIG. 73, a scratched nanofiber surface is shown at 200× magnification through use of Nomarski optics. Dark brown areas are intact nanofibers (here nanowires), 7300, while orange areas are scratches with CHO cells growing along the scratch lines, 7301. In these experiments complete retardation of mammalian cellular growth and approximately a 10× reduction in bacterial growth was observed. The control surfaces were chemically identical to the nanowires so it is thought that reduction in cell and bacterial growth is due to the unique surface morphology of the nanofiber enhanced surface area substrates.

*S. epidermidis* was used in the illustrations herein because it is a representative bacteria involved in infections of medical devices. Additionally, *S. epidermidis* has been widely used in the evaluation of biomaterials and has been identified as a dominant species in biomaterial centered infections. Other bacteria implicated in biomaterial related infections such as *S. aureus, Pseudomonas aeruginosa* and B-hemolytic streptococci are also contemplated as being prohibited through use of current embodiments. In addition to CHO cells illustrated herein, other common tissue culture lines such as, e.g., MDCK, L-929 and HL60 cells are also contemplated as being prohibited through use of current embodiments. Such cell lines represent a wide diversity of cell types. The CHO and MDCK cells are representative of epithelial cells, L-929 cells participate in the formation of connective tissue and the HL60 line represents immune surveillance cells. Thus, the nanofiber enhanced surface areas herein are contemplated against these cell types and other common in vivo cell types. The nanofibers used in the in vitro illustration herein were made of silicon, and, as detailed throughout, several methods have been reported in the literature for the synthesis of silicon nanowires. For example, laser ablating metal-containing silicon targets, high temperature vaporizing of $Si/SiO_2$ mixture, and vapor-liquid-solid (VLS) growth using gold as the catalyst. See above. While any method of construction is optionally used, the approach to nanowire synthesis is typically VLS growth since this method has been widely used for semiconductor nanowire growth. Description of such method is provided elsewhere herein. FIG. 7 shows an example of a TEM image of a silicon nanowire and oxide surface typical of ones used in the current embodiment.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A drug delivery device for introduction of one or more substances into a subject, which device comprises a substrate made from a first material, which substrate comprises: at least a first surface, a plurality of semiconductor nanofibers attached to the first surface which nanofibers are made from a second compositionally different material from the first material, a reservoir of the one or more substances comprised between the members of the plurality of nanofibers, and the one or more substance incorporated into the reservoir such that said one or more substances is at least partially shielded from direct exposure to bodily fluids within the subject when the device is introduced into the subject.

2. The device of claim 1, wherein the reservoir further comprises one or more storage matrix.

3. The device of claim 1, wherein the storage matrix comprises one or more polymer.

4. The device of claim 1, wherein the plurality of nanofibers is grown on an at least second surface and transferred to the first surface.

5. The device of claim 1, wherein the plurality of nanofibers is grown on the first surface.

6. The device of claim 1, wherein the nanofibers are substantially parallel to the plane of the first surface.

7. The device of claim 1, wherein the nanofibers are substantially perpendicular to the plane of the first surface.

8. The device of claim 1, wherein the first surface and/or the nanofibers are independently selected from the group consisting of: silicon, glass, quartz, plastic, ceramic, metal, polymers, TiO, ZnO, ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, PbS, PbSe, PbTe, AlS, AlP, AlSb, $SiO_1$, $SiO_2$, silicon carbide, silicon nitride, polyacrylonitrile (PAN), polyetherketone, polyimide, an aromatic polymer, and an aliphatic polymer.

9. The device of claim 1, further comprising a plurality of nanoparticles dispersed among the plurality of nanofibers.

10. The drug delivery device of claim 1, wherein the nanofibers comprise nanowires comprising silicon.

11. The drug delivery device of claim 10, wherein the nanowires comprise a core made from silicon and one or more shell layers disposed about said core.

12. The drug delivery device of claim 11, wherein said one or more shell layers comprises a nitride or carbide coating.

13. A method of suppressing the formation of a biofilm on a medical device in a subject, the method comprising providing one or more surface of the medical device, growing a plurality of semiconductor nanofibers on at least a portion of the one or more surface of the medical device, which nanofibers have an external surface that is functionalized with one or more functional groups that render the external surface of the nanofibers hydrophobic and which surface of the medical device comes into contact with the subject, wherein members of the plurality of nanofibers comprise an average length of from about 1 micron to at least about 200 microns; an average diameter of from about 5 nm to at least about 1 micron, and an average density of from about 1 nanofiber per square micron to at least about 1000 nanofibers per square micron.

* * * * *

UNITED STATES PATENT AND TRADEMARK OFFICE
CERTIFICATE OF CORRECTION

PATENT NO.       : 7,579,077 B2                                              Page 1 of 1
APPLICATION NO. : 10/840794
DATED            : August 25, 2009
INVENTOR(S)      : Dubrow et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 591 days.

Signed and Sealed this

Fourteenth Day of December, 2010

David J. Kappos
*Director of the United States Patent and Trademark Office*

```
                       SEQUENCE LISTING

<160> NUMBER OF SEQ ID NOS: 16

<210> SEQ ID NO 1
<211> LENGTH: 15
<212> TYPE: DNA
<213> ORGANISM: Artificial
<220> FEATURE:
<223> OTHER INFORMATION: synthetic oligonucleotide

<400> SEQUENCE: 1
ttttgcctac gatca                                                  15

<210> SEQ ID NO 2
<211> LENGTH: 13
<212> TYPE: DNA
<213> ORGANISM: Artificial
<220> FEATURE:
<223> OTHER INFORMATION: synthetic oligonucleotide

<400> SEQUENCE: 2
ttgatcgtag gca                                                    13

<210> SEQ ID NO 3
<211> LENGTH: 9
<212> TYPE: PRT
<213> ORGANISM: flock house virus

<400> SEQUENCE: 3

Gly Met Asn Met Ala Ala Leu Thr Arg
1               5

<210> SEQ ID NO 4
<211> LENGTH: 9
<212> TYPE: PRT
<213> ORGANISM: flock house virus

<400> SEQUENCE: 4

Gly Ile Pro Asp Arg Phe Glu Gly Lys
1               5

<210> SEQ ID NO 5
<211> LENGTH: 10
<212> TYPE: PRT
<213> ORGANISM: flock house virus

<400> SEQUENCE: 5

Leu Ser Gln Pro Gly Leu Ala Phe Leu Lys
1               5                   10

<210> SEQ ID NO 6
<211> LENGTH: 14
<212> TYPE: PRT
<213> ORGANISM: flock house virus

<400> SEQUENCE: 6

Val Ser Ala Pro Glu Gly Ala Val Asn Ser Ala Ile Leu Lys
```

```
                1               5                   10

<210> SEQ ID NO 7
<211> LENGTH: 14
<212> TYPE: PRT
<213> ORGANISM: flock house virus

<400> SEQUENCE: 7

Cys Ala Phe Ala Pro Pro Asp Phe Asn Thr Asp Pro Gly Lys
1               5                   10

<210> SEQ ID NO 8
<211> LENGTH: 18
<212> TYPE: PRT
<213> ORGANISM: flock house virus

<400> SEQUENCE: 8

Val Val Val Thr Thr Thr Gln Thr Ala Pro Val Pro Gln Gln Asn Val
1               5                   10                  15

Pro Arg

<210> SEQ ID NO 9
<211> LENGTH: 6
<212> TYPE: PRT
<213> ORGANISM: Bos sp.

<400> SEQUENCE: 9

Cys Ala Ser Ile Gln Lys
1               5

<210> SEQ ID NO 10
<211> LENGTH: 7
<212> TYPE: PRT
<213> ORGANISM: Bos sp.

<400> SEQUENCE: 10

Leu Val Thr Asp Leu Thr Lys
1               5

<210> SEQ ID NO 11
<211> LENGTH: 7
<212> TYPE: PRT
<213> ORGANISM: Bos sp.

<400> SEQUENCE: 11

Tyr Leu Tyr Glu Ile Ala Arg
1               5

<210> SEQ ID NO 12
<211> LENGTH: 8
<212> TYPE: PRT
<213> ORGANISM: Bos sp.

<400> SEQUENCE: 12

Asp Leu Gly Glu Glu His Phe Lys
1               5

<210> SEQ ID NO 13
<211> LENGTH: 10
<212> TYPE: PRT
<213> ORGANISM: Bos sp.

<400> SEQUENCE: 13

Phe Lys Asp Leu Gly Glu Glu His Phe Lys
```

```
-continued

<210> SEQ ID NO 14
<211> LENGTH: 11
<212> TYPE: PRT
<213> ORGANISM: Bos sp.

<400> SEQUENCE: 14

His Leu Val Asp Glu Pro Gln Asn Leu Ile Lys
1               5                   10

<210> SEQ ID NO 15
<211> LENGTH: 13
<212> TYPE: PRT
<213> ORGANISM: Bos sp.

<400> SEQUENCE: 15

Leu Gly Glu Tyr Gly Phe Gln Asn Ala Leu Ile Val Arg
1               5                   10

<210> SEQ ID NO 16
<211> LENGTH: 15
<212> TYPE: PRT
<213> ORGANISM: Bos sp.

<400> SEQUENCE: 16

Lys Val Pro Gln Val Ser Thr Pro Thr Leu Val Glu Val Ser Arg
1               5                   10                  15
```